(12) United States Patent
Kim et al.

(10) Patent No.: US 11,456,422 B2
(45) Date of Patent: *Sep. 27, 2022

(54) COMPOUND AND ORGANIC ELECTROLUMINESCENT DEVICE COMPRISING SAME

(71) Applicant: SOLUS ADVANCED MATERIALS CO., LTD., Iksan-si (KR)

(72) Inventors: Tae Hyung Kim, Yongin-si (KR); In Hyuk Lee, Yongin-si (KR); Yong Hwan Lee, Seongnam-si (KR); Jin Yong Shin, Yongin-si (KR); Ho Cheol Park, Suwon-si (KR); Chang Jun Lee, Ansan-si (KR); Eun Jung Lee, Seoul (KR); Young Mi Beak, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 924 days.

This patent is subject to a terminal disclaimer.

(21) Appl. No.: 16/251,873

(22) Filed: Jan. 18, 2019

(65) Prior Publication Data

US 2019/0157567 A1 May 23, 2019

Related U.S. Application Data

(63) Continuation of application No. 14/421,488, filed as application No. PCT/KR2013/007265 on Aug. 13, 2013, now Pat. No. 10,297,759.

(30) Foreign Application Priority Data

Aug. 17, 2012 (KR) ........................ 10-2012-0090295

(51) Int. Cl.
| | | |
|---|---|---|
| H01L 51/00 | (2006.01) | |
| C07D 487/04 | (2006.01) | |
| C09K 11/06 | (2006.01) | |
| H01L 51/50 | (2006.01) | |
| C07D 403/14 | (2006.01) | |

(52) U.S. Cl.
CPC ........ *H01L 51/0061* (2013.01); *C07D 403/14* (2013.01); *C07D 487/04* (2013.01); *C09K 11/06* (2013.01); *H01L 51/006* (2013.01); *H01L 51/0052* (2013.01); *H01L 51/0059* (2013.01); *H01L 51/0067* (2013.01); *H01L 51/0072* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1059* (2013.01); *H01L 51/0058* (2013.01); *H01L 51/0081* (2013.01); *H01L 51/0085* (2013.01); *H01L 51/5012* (2013.01); *H01L 51/5056* (2013.01); *H01L 51/5088* (2013.01)

(58) Field of Classification Search
CPC .. C07D 487/04; C07D 487/14; C07D 487/22; C09K 11/06; C09K 2211/1011; C09K 2211/1014; C09K 2211/1022; H01L 51/0059; H01L 51/006; H01L 51/0061; H01L 51/0072; H01L 51/5012; H01L 51/5016; H01L 51/5056; H01L 51/506; H01L 51/5064; H01L 51/5088; H01L 51/5096

See application file for complete search history.

(56) References Cited

U.S. PATENT DOCUMENTS

| | | | |
|---|---|---|---|
| 9,761,813 B2 | 9/2017 | Kim et al. | |
| 9,837,618 B2 | 12/2017 | Park et al. | |
| 10,038,146 B2 | 7/2018 | Kim et al. | |
| 10,297,759 B2 * | 5/2019 | Kim | ................... H01L 51/0067 |
| 2011/0031483 A1 | 2/2011 | Kwak et al. | |
| 2011/0240979 A1 | 10/2011 | Kim et al. | |
| 2011/0263669 A1 | 10/2011 | Anizon et al. | |

FOREIGN PATENT DOCUMENTS

| | | | |
|---|---|---|---|
| CN | 101730681 A | 6/2010 | |
| CN | 102017220 A | 4/2011 | |
| CN | 102449106 A | 5/2012 | |
| JP | 11144867 A | 5/1999 | |
| JP | 2011037826 A | 2/2011 | |
| KR | 10-2010-0131629 A | 12/2010 | |
| KR | 10-2011-0105269 A | 9/2011 | |
| KR | 10-2011-0117549 A | 10/2011 | |
| KR | 10-2012-0009984 A | 2/2012 | |
| KR | 10-2012-0034140 A | 4/2012 | |
| WO | WO-2010110553 A2 * | 9/2010 | ......... H01L 51/0059 |
| WO | 2012/011756 A1 | 1/2012 | |

OTHER PUBLICATIONS

Isabel C.F.R. Ferreira et al., "Synthesis of New Methylated thieno [2,3-a] and [3,2-b] carbazoles by Reductive Cyclization of 6-(2'-Nitrophenyl)benzo[b]thionphenes Obtained by Palladium-Catalyzed Cross-Coupling", J. Heterocyclic Chem., 2001, pp. 749-754, vol. 38.

Vasudevan Dhayalan et al., "A Versatile Synthesis of Annulated Carbazole Analogs Involving a Domino Reaction of Bromomethylindoles with Arenes/Heteroarenes", Eur. J. Org. Chem., 2009, pp. 531-546, vol. 2009.

International Searching Authority International Search Report for PCT/KR2013/007265 dated Nov. 29, 2013.

State Intellectual Property Office of P.R.C., Communication dated Dec. 28, 2015 issued in Corresponding Chinese Application No. 201380053853.5.

(Continued)

*Primary Examiner* — Dylan C Kershner
*Assistant Examiner* — Elizabeth M. Dahlburg
(74) *Attorney, Agent, or Firm* — Sughrue Mion, PLLC

(57) ABSTRACT

The present disclosure relates to a novel compound having excellent hole injection capabilities and transport capabilities, light-emitting capabilities, and the like, and an organic electroluminescent device which includes the compound in one or more organic material layers thereof so as to improve characteristics such as light-emitting efficiency, driving voltage, and a service life.

8 Claims, No Drawings

(56) References Cited

OTHER PUBLICATIONS

Communication dated Jun. 1, 2016, from the Japanese Patent Office in counterpart application No. 2015-527366.

* cited by examiner

COMPOUND AND ORGANIC ELECTROLUMINESCENT DEVICE COMPRISING SAME

CROSS REFERENCE TO RELATED APPLICATIONS

This application is a Continuation Application of U.S. application Ser. No. 14/421,488 filed Feb. 13, 2015, which is a National Stage of International Application No. PCT/KR2013/007265 filed Aug. 13, 2013, claiming priority based on Korean Patent Application No. 10-2012-0090295 filed Aug. 17, 2012, the contents of all of which are incorporated herein by reference in their entirety.

TECHNICAL FIELD

The present disclosure relates to a novel compound and an organic electroluminescent device including the same, and more particularly, to a novel compound having excellent hole injection capabilities, hole transport capabilities, light-emitting capabilities, and the like, and an organic electroluminescent device which contains the compound as a material for an organic material layer so as to improve characteristics such as light-emitting efficiency, driving voltage, and a service life.

BACKGROUND ART

A study on an organic electroluminescent (EL) device (hereinafter, simply referred to as 'organic EL device') has continued from the start point of observing an organic thin film light emission by Bernanose in the 1950s to blue electric light emission using an anthracene single crystal in 1965, and an organic EL device having a lamination structure, which is divided into functional layers of a hole layer and a light-emitting layer, was proposed by Tang in 1987. Thereafter, the organic EL device has been developed in the form of introducing a characteristic organic material layer into a device in order to enhance efficiency and a service life of the organic EL device, and the development has also been led to the development of specialized materials used therein.

In the organic electroluminescent device, when voltage is applied between two electrodes, holes are injected into the organic material layer at the anode and electrons are injected into the organic material layer at the cathode. When the injected holes and electrons meet each other, an exciton is formed, and when the exciton falls down to a bottom state, light is emitted. Materials used as the organic material layer may be classified into a light-emitting material, a hole injection material, a hole transporting material, an electron transporting material, an electron injection material, and the like according to the function.

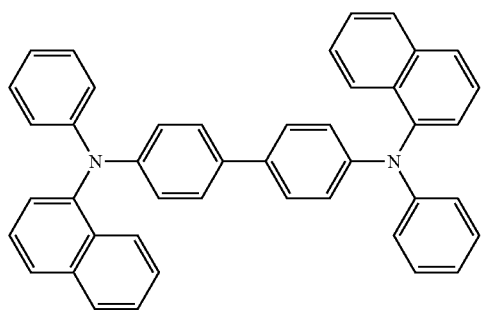

NPB

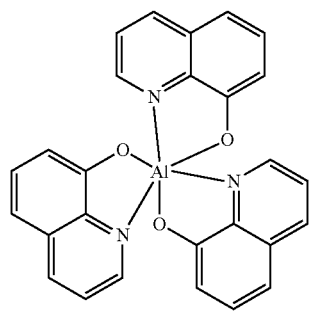

Alq3

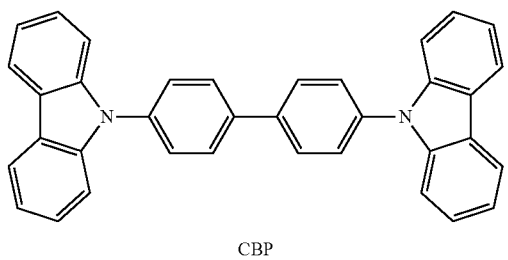

CBP

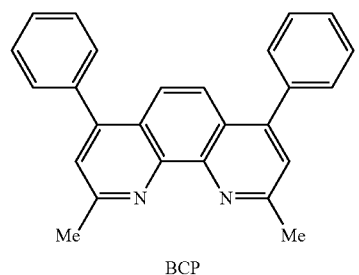

BCP

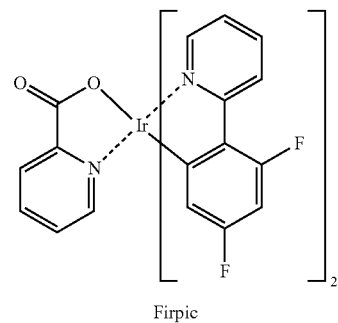

Firpic

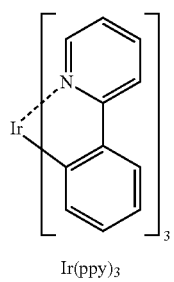

Ir(ppy)$_3$

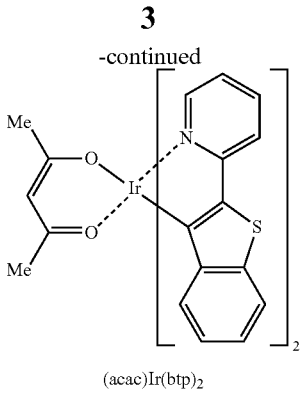

(acac)Ir(btp)$_2$

Meanwhile, in order to achieve practical application of the organic electroluminescent device and enhance characteristics thereof, the device needs to be formed of an organic material layer having the multi-layered structure as described above, and a material for the device, particularly a hole transporting material, needs to have thermally and electrically stable characteristics. This is because when voltage is applied to an organic electroluminescent device, heat is generated from the device, and molecules having low thermal stability are rearranged due to low crystal stability, and as a result, there occurs a local crystallization, and thus there exists an inhomogeneous portion, and an electric field is concentrated on the inhomogeneous portion, thereby degrading and destroying the device.

In consideration of these points, m-MTDATA [4,4',4"-tris (N-3-methylphenyl-N-phenylamino)-triphenylamine], 2-TNATA [4,4',4"-tris (N-(naphthylen-2-yl)-N-phenylamino)-triphenylamine], TPD [N,N'-diphenyl-N,N'-di(3-methylphenyl)-4,4'-diaminobiphenyl] and NPB [N,N'-di (naphthalene-1-yl)-N,N'-diphenylbenzidine], and the like were used in the related art as a hole transporting material.

However, since m-MTDATA and 2-TNATA have a low glass transition temperature (Tg) of about 78° C. and about 108° C., respectively, and many problems occur in the process of mass production, there has been a problem in implementing a full color. Meanwhile, TPD and NPB also have a low glass transition temperature (Tg) of about 60° C. and about 96° C., respectively, thereby causing deterioration in the service life of the device like m-MTDATA and 2-TNATA.

Therefore, there is a need for the development of a new hole transporting material which may increase thermal stability and has excellent hole transport capabilities, and thus may enhance the light-emitting efficiency and power efficiency of the organic electroluminescent device.

DISCLOSURE

Technical Problem

An object of the present disclosure is to provide a novel compound which has excellent hole injection capabilities, hole transport capabilities, light-emitting capabilities, and the like, and thus may be used as a material for a light-emitting layer, a material for a hole transporting layer, and a material for a hole injection layer.

Further, another object of the present disclosure is to provide an organic electroluminescent device which includes the novel compound, and thus has low driving voltage, high light-emitting efficiency, and enhanced service life.

Technical Solution

In order to achieve the objects, the present disclosure provides a compound represented by the following Formula 1.

[Formula 1]

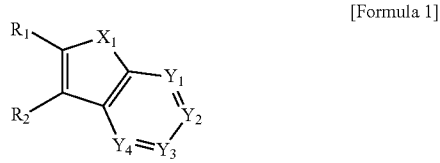

In Formula 1, $Y_1$ to $Y_4$ are each independently N or $CR_3$, and in this case, when $CR_3$ is present in a plural number, they are the same as or different from each other, and provided that at least one of $Y_1$ and $Y_2$, $Y_2$ and $Y_3$, and $Y_3$ and $Y_4$ is $CR_3$, and forms a fused ring represented by the following Formula 2;

[Formula 2]

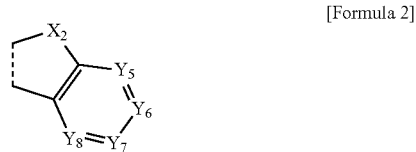

in Formula 2, $Y_5$ to $Y_8$ are each independently selected from N or $CR_4$, and in this case, when $CR_4$ is present in a plural number, they are the same as or different from each other, and provided that at least one of $Y_5$ to $Y_8$ is $CR_4$, and in this case, at least one $R_4$ is a substituent represented by the following Formula 3;

[Formula 3]

in Formula 3,

L is a single bond, or selected from the group consisting of a substituted or unsubstituted $C_6$ to $C_{60}$ arylene group, and a substituted or unsubstituted heteroarylene group having 5 to 60 nuclear atoms, in this case, one or more substituents each introduced into the arylene group and the heteroarylene group of L are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, and a $C_6$ to $C_{60}$ arylamine group, and provided that when the substituent is present in a plural number, these may be the same as or different from each other;

$R_a$ and $R_b$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, and a substituted or unsubstituted heteroaryl group having 5 to 60 nuclear atoms, in this case, one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other;

provided that L, $R_a$, and $R_b$ may combine with an adjacent substituent to form a fused ring;

$X_1$ and $X_2$ are each independently selected from the group consisting of O, S, Se, $N(Ar_1)$, $C(Ar_2)(Ar_3)$, and $Si(Ar_4)(Ar_5)$, and in this case, when $N(Ar_1)$ is present in a plural number, they are the same as or different from each other, when $C(Ar_2)(Ar_3)$ is present in a plural number, they are the same as or different from each other, and when $Si(Ar_4)(Ar_5)$ is present in a plural number, they are the same as or different from each other, and provided that at least one of $X_1$ and $X_2$ is $N(Ar_1)$;

$Ar_1$ to $Ar_5$ are the same as or different from each other, and are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ to $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these form or do not form a fused ring with an adjacent group; and one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ to $Ar_5$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other.

Further, the present disclosure provides an organic electroluminescent device including an anode, a cathode, and an organic material layer including one or more layers interposed between the anode and the cathode, in which at least one of the organic material layers including one or more layers includes the compound.

The organic material layer including one or more layers, which includes the compound, is selected from the group consisting of a hole transporting layer, a hole injection layer, and a light-emitting layer, and is preferably a hole transporting layer and/or a light-emitting layer, and is more preferably used as a material for a hole transporting layer.

Advantageous Effects

The compound according to the present disclosure has excellent heat resistance, hole injection capabilities, hole transport capabilities, light-emitting capabilities, and the like, and thus may be used as a material for an organic material layer of an organic electroluminescent device, preferably a material for a hole injection layer, a material for a hole transporting layer, or a material for a light-emitting layer.

In addition, an organic EL device including the compound according to the present disclosure in a hole injection layer, a hole transporting layer and/or a light-emitting layer may be enhanced greatly in terms of light-emitting performance, driving voltage, a service life, efficiency, and the like, and furthermore, the device may be effectively applied to a full-color display panel, and the like.

BEST MODE

Hereinafter, the present disclosure will be described.

A novel compound according to the present disclosure has a basic structure in which an arylamine moiety is bonded directly or through a linking group (for example, an arylene group, and the like) to an end of a moiety in which an indole-based moiety, and the like and an indole-based moiety, and the like are fused, in which various substituents are bonded to the basic structure, and the compound is represented by Formula 1. The compound represented by Formula 1 may enhance phosphorescent characteristics of a device, and simultaneously, may enhance hole injection/transport capabilities, light-emitting efficiency, driving voltage, service life characteristics, durability, and the like, and may also enhance electron transport capabilities, and the like according to the kind of substituent to be introduced. Therefore, the compound of Formula 1 may be used as a material for an organic material layer of an organic electroluminescent device, preferably a material for a light-emitting layer (a phosphorescent host material), a material for a hole transporting layer, and a material for a hole injection layer, and more preferably a material for a hole transporting layer.

Furthermore, the compound of Formula 1 may also be used as a material for an electron transporting layer, and the like by optionally introducing an appropriate substituent.

The compound represented by Formula 1 may include a moiety in which an indole-based moiety, and the like and an indole-based moiety, and the like are fused, thereby having the existing wide singlet energy level and a high triplet energy level. Further, an arylamine moiety is introduced directly or through a linking group (for example, an arylene group, and the like) into a moiety in which the indole-based moieties are fused, so that the energy level is effectively adjusted, thereby maximizing hole blocking capabilities and hole injection/transport capabilities. The compound of Formula 1 may be usefully applied as a material for a hole injection layer and a material for a hole transporting layer of an organic EL device.

In addition, the compound represented by Formula 1 may variously modify the linking group to enhance phosphorescent characteristics, and the compound may be used as a material for a light-emitting layer of a phosphorescent light-emitting organic EL device.

Furthermore, various substitution products, particularly, an aryl group and/or a heteroaryl group, are introduced into the compound represented by Formula 1 to significantly increase the molecular weight of the compound and enhance the glass transition temperature, and accordingly, the compound represented by Formula 1 may have thermal stability higher than that of the existing light-emitting material. Therefore, an organic electroluminescent device including the novel compound represented by Formula 1 according to the present disclosure may greatly enhance durability and service life characteristics.

Furthermore, when the compound represented by Formula 1 is adopted as a hole injection/transporting layer, a blue, green, and/or red phosphorescent host material of an organic electroluminescent device, much better effects may be exhibited in terms of efficiency and a service life compared to the NPB in the related art. Therefore, the compound according to the present disclosure may greatly contribute to the improvement of performance and the enhancement of service life, of the organic electroluminescent device, and furthermore, the enhancement of service life of the organic electroluminescent device may maximize the performance of a full color organic light-emitting panel.

In the compound represented by Formula 1 according to the present disclosure, $Y_1$ to $Y_4$ are each independently N or $CR_3$, and in this case, when $CR_3$ is present in a plural number, they are the same as or different from each other.

Provided that at least one of $Y_1$ and $Y_2$, $Y_2$ and $Y_3$, and $Y_3$ and $Y_4$ is $CR_3$, and forms a fused ring represented by the following Formula 2. For example, when both $Y_1$ and $Y_2$ of $Y_1$ and $Y_2$, $Y_2$ and $Y_3$, and $Y_3$ and $Y_4$ are $CR_3$ and are fused with each other to form the fused ring represented by Formula 2, a compound represented by the following Formula 4 or 9 may be formed.

In Formula 2, the dotted line means a site where condensation with the compound of Formula 1 occurs.

In Formula 2, $Y_5$ to $Y_8$ are each independently N or $CR_4$, and in this case, when $CR_4$ is present in a plural number, they are the same as or different from each other.

Provided that at least one of $Y_5$ to $Y_8$ is $CR_4$, and in this case, at least one $R_4$ is the substituent represented by Formula 3.

According to an example of the present disclosure, all of $Y_1$ to $Y_4$ may be $CR_3$, and all of $Y_5$ to $Y_8$ may be $CR_4$. In this case, a plurality of $R_3$ and a plurality of $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these may or may not form a fused ring with an adjacent group. Provided that at least one of the plurality of $R_4$ is the substituent represented by Formula 3.

In Formula 3, L is a single bond or selected from the group consisting of a substituted or unsubstituted $C_6$ to $C_{60}$ arylene group and a substituted or unsubstituted heteroarylene group having 5 to 60 nuclear atoms, or may form a fused ring with an adjacent group. In this case, one or more substituents each introduced into the arylene group and the heteroarylene group of L are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, and a $C_6$ to $C_{60}$ arylamine group, and provided that when the substituent is present in a plural number, these may be the same as or different from each other.

Preferably, L is a single bond, or may be selected from the group consisting of a phenylene group, a biphenylene group, a fluorenylene group, a naphthylene group, a pyridinylene group, a pyrimidinylene group, a quinolinylene group, and a carbazolylene group.

Further, $R_a$ and $R_b$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, and a substituted or unsubstituted heteroaryl group having 5 to 60 nuclear atoms, or may form a fused ring with an adjacent ring. In this case, one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other.

Preferably, $R_a$ and $R_b$ may be each independently selected from the group consisting of a phenyl group, a biphenyl group, a fluorenyl group, a naphthyl group, a pyridyl group, a pyrimidinyl group, a quinolyl group, and a carbazolyl group.

More preferably, Formula 3 may be selected from the group consisting of the following substituents U1 to U86, and is not limited thereto.
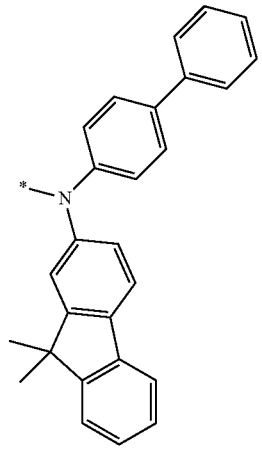
U1
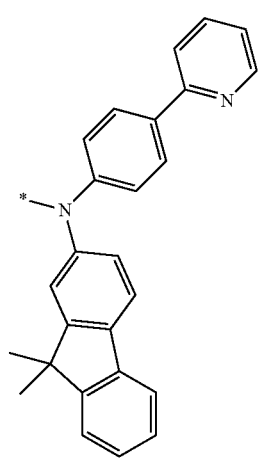
U2
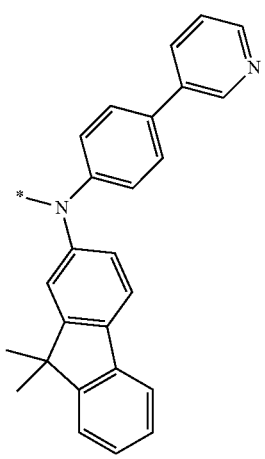
U3
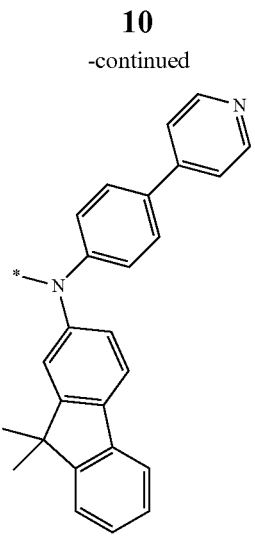
U4
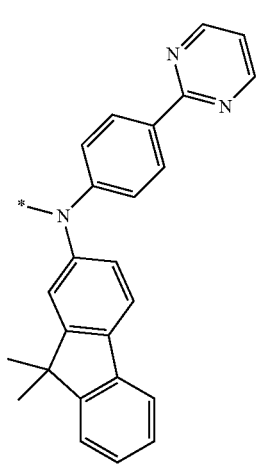
U5
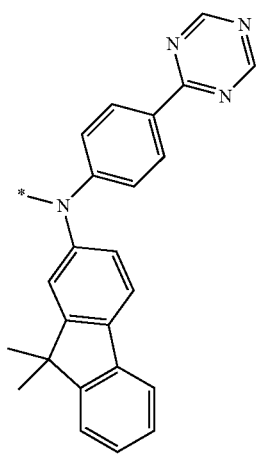
U6

U7
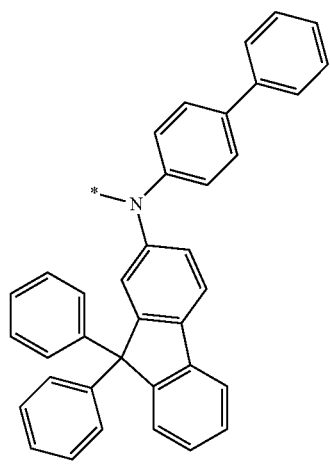
U8
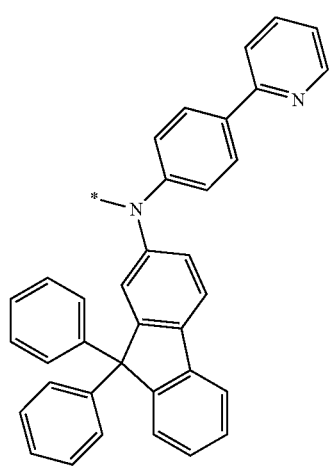
U9
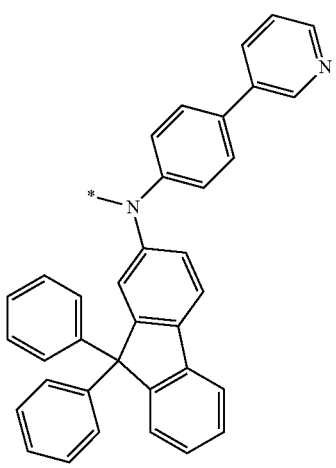
U10
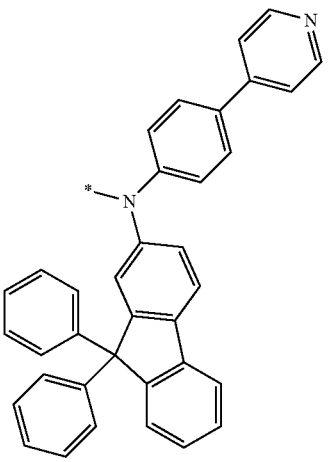
U11
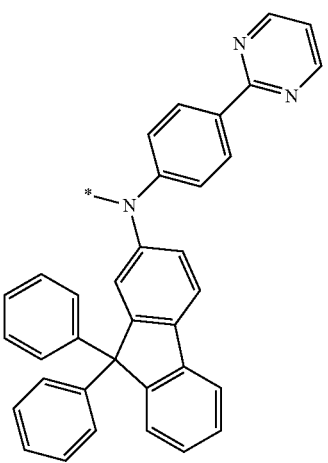
U12
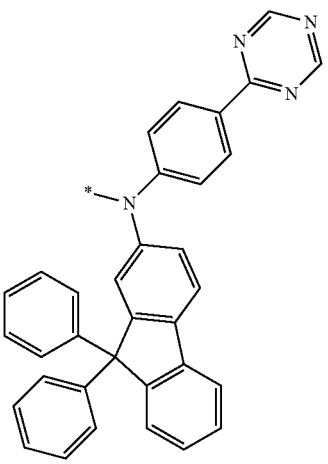

U13
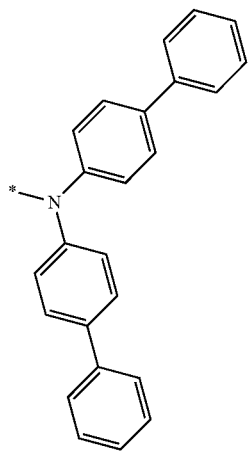
U14
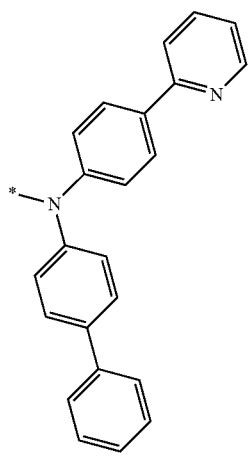
U15
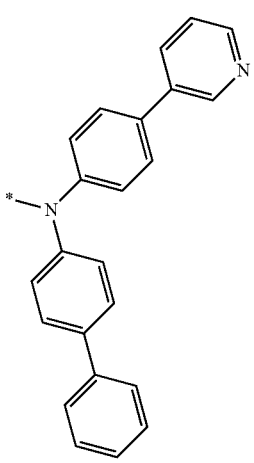
U16
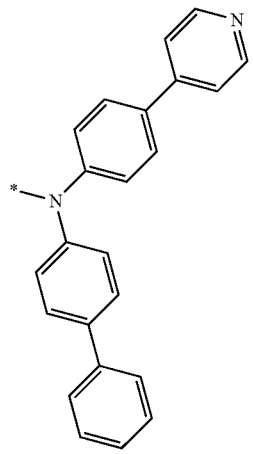
U17
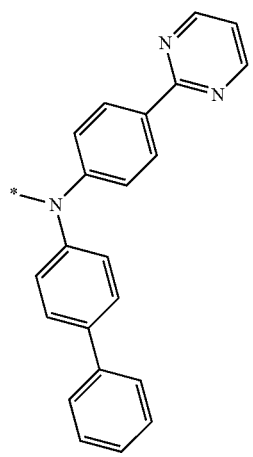
U18
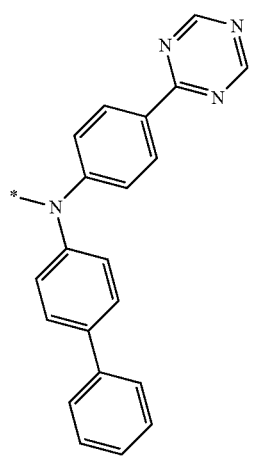

U19

U20

U21

U22

U23

U24

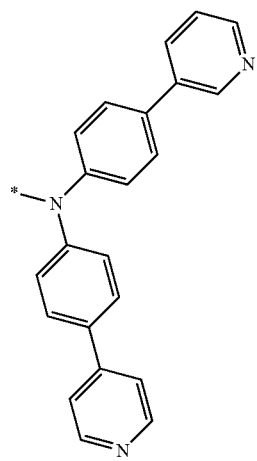
U25
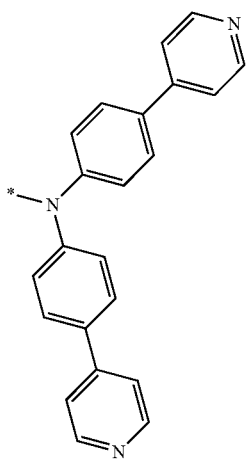
U28
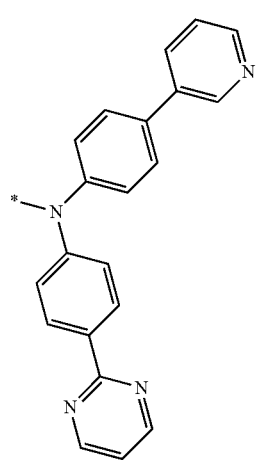
U26
U29
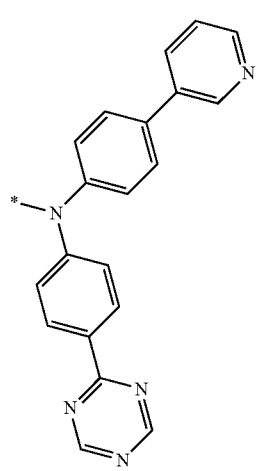
U27
U30

-continued
U31
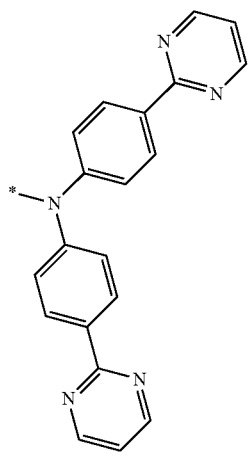
U32
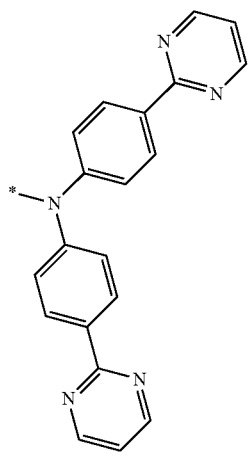
U33
U34
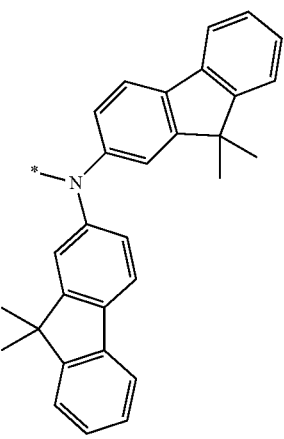
U35
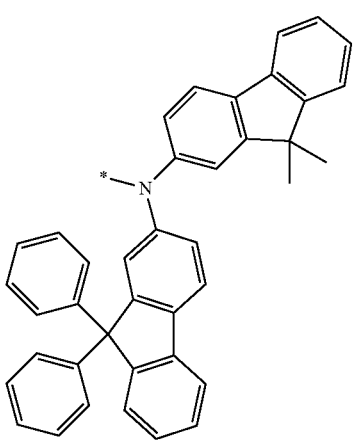
U36

U37
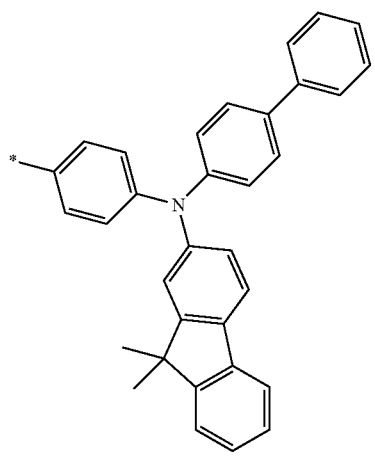
U38
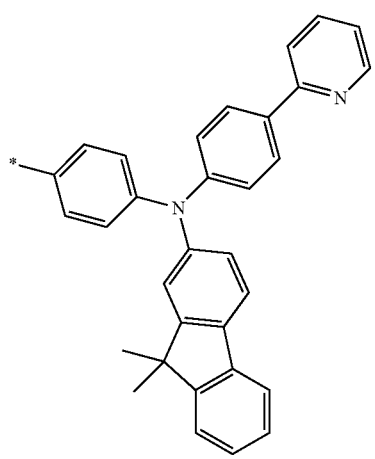
U39
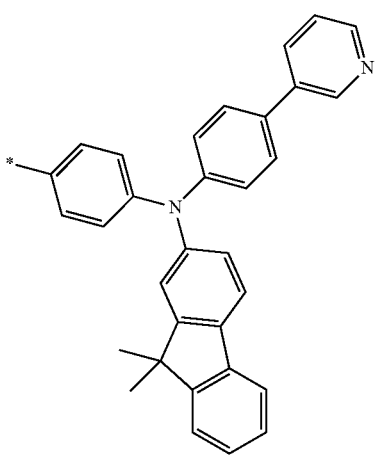
U40
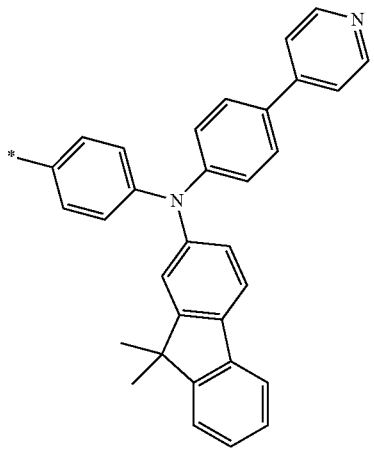
U41
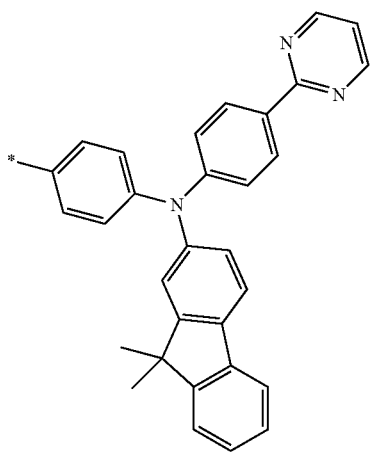
U42
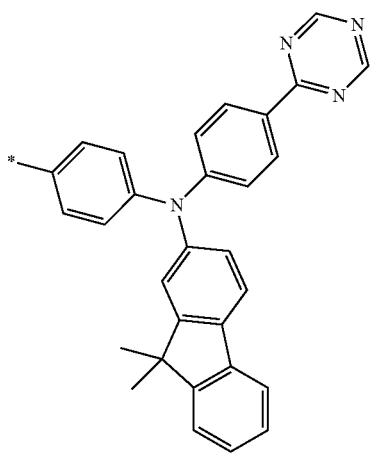

U43
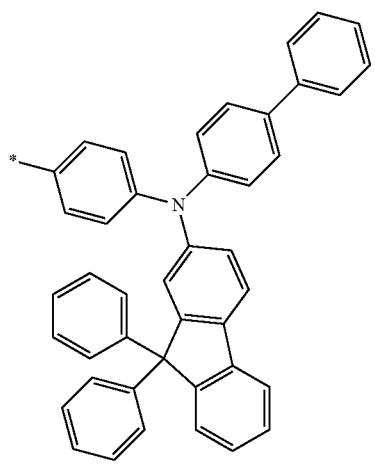
U44
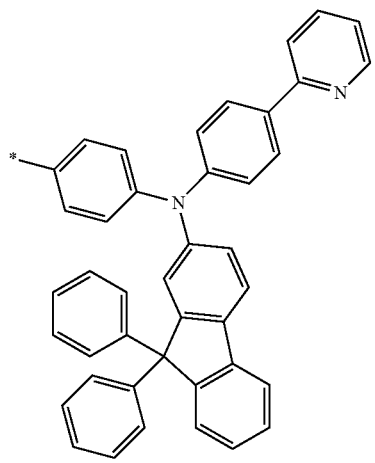
U45
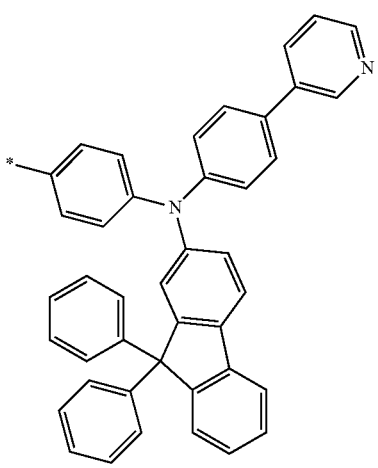
U46
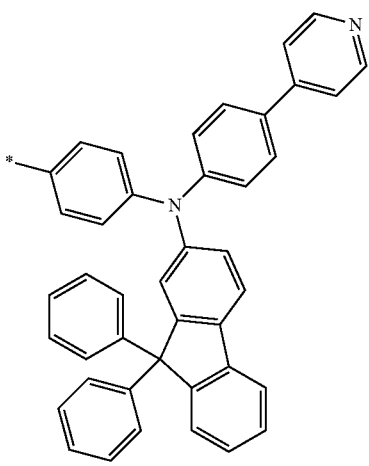
U47
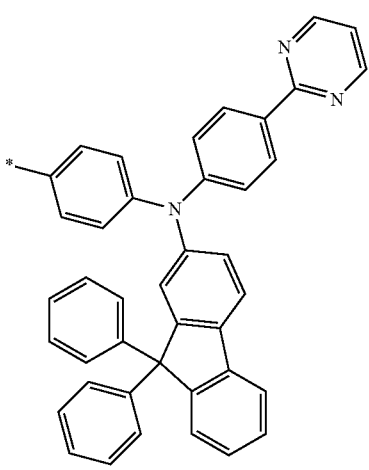
U48
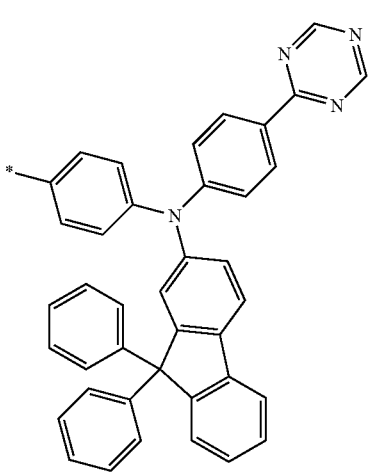

U49 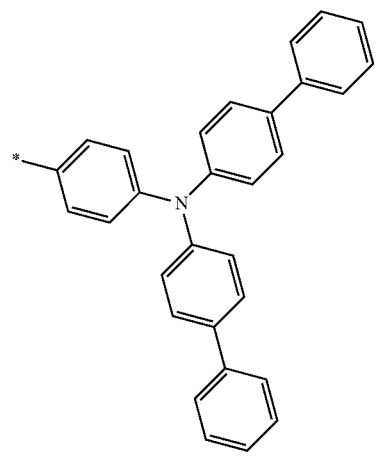
U52 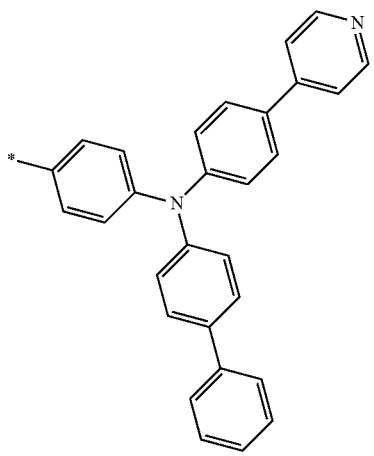
U50 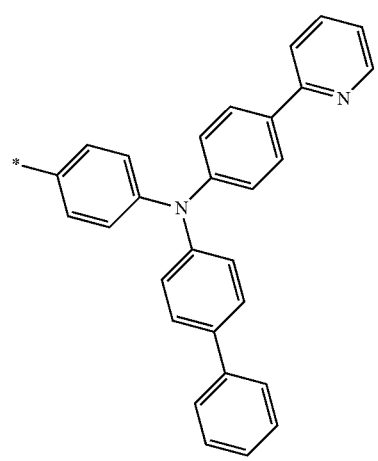
U53 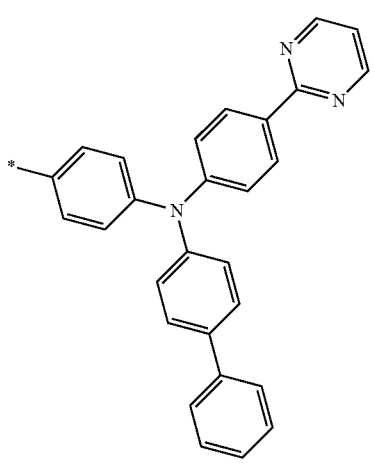
U51 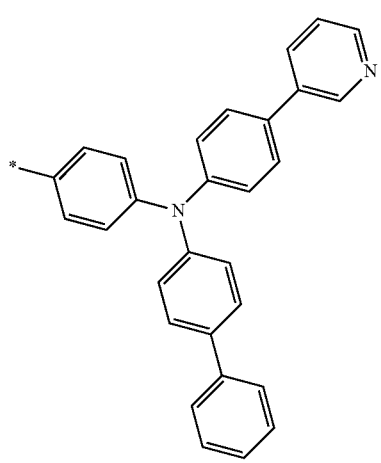
U54 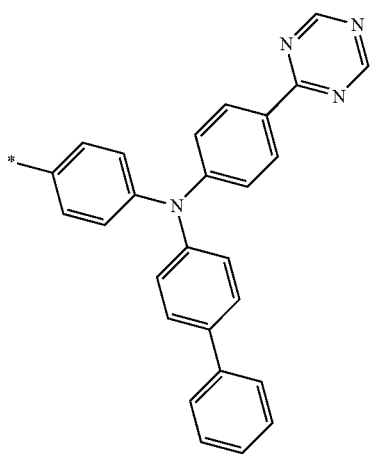

U55
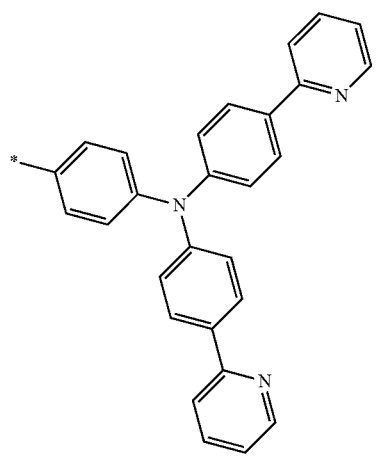
U56
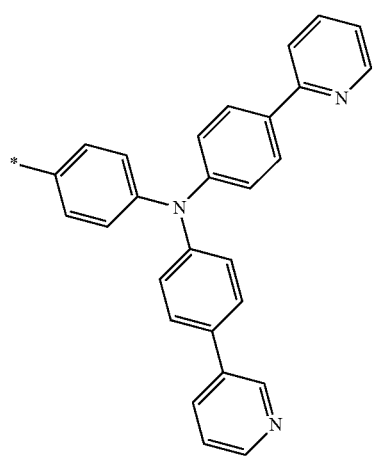
U57
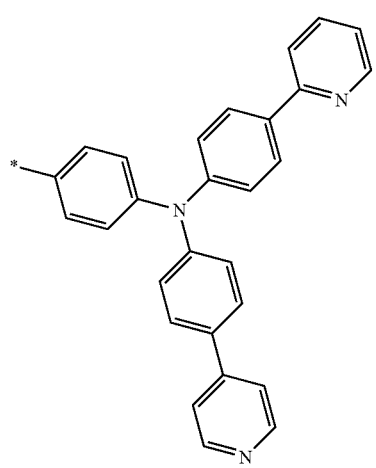
U58
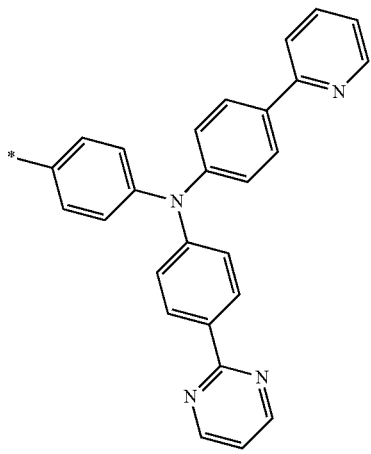
U59
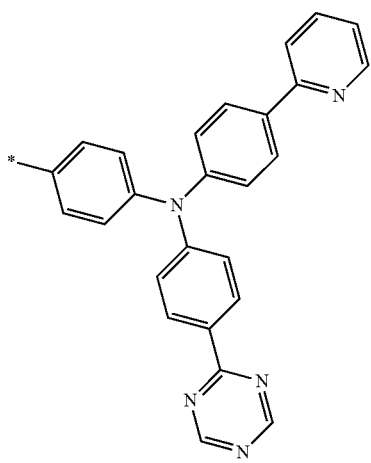
U60
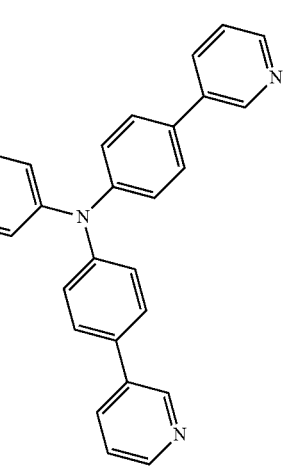

U61 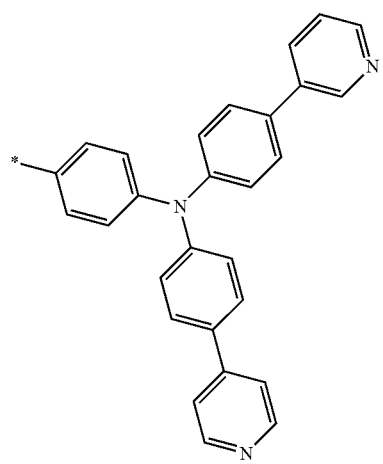
U62 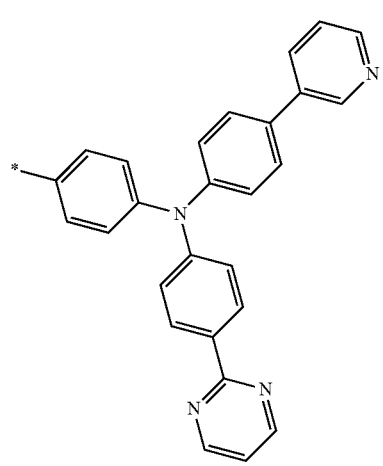
U63 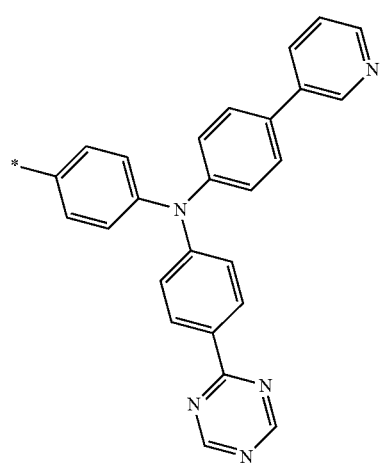
U64 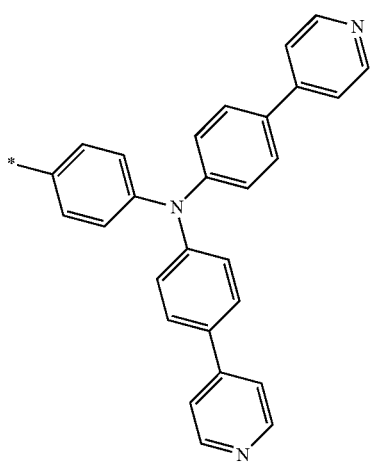
U65 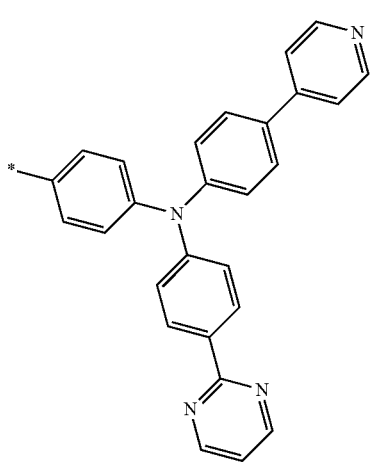
U66 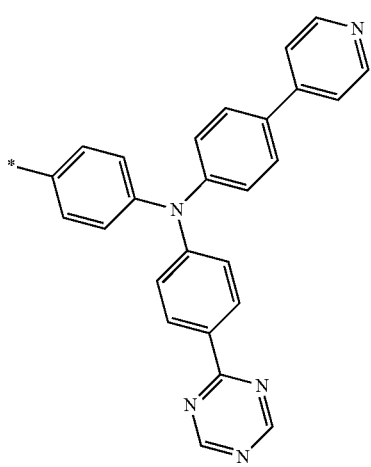

U67
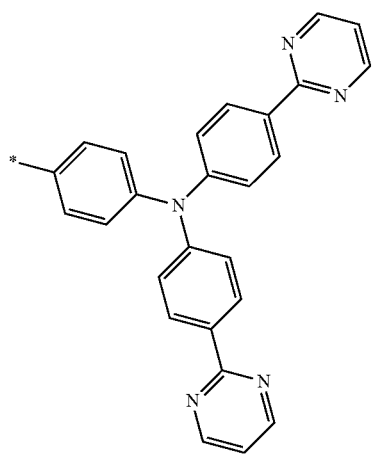
U68
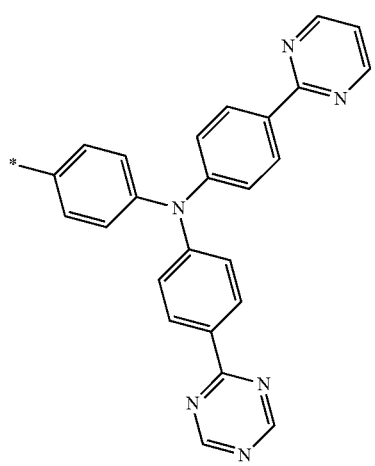
U69
U70
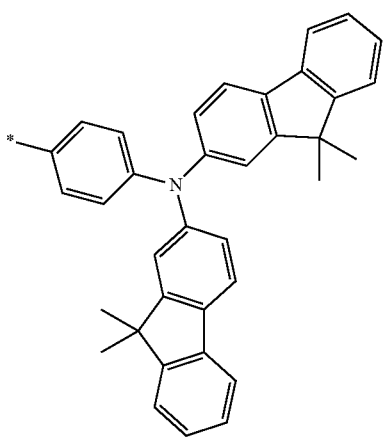
U71
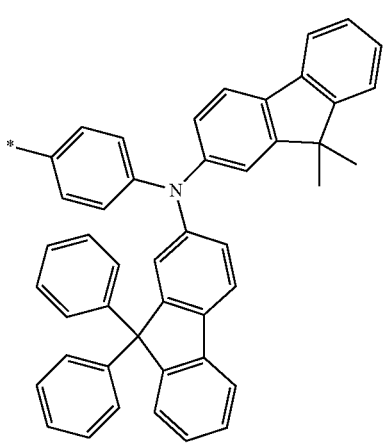
U72
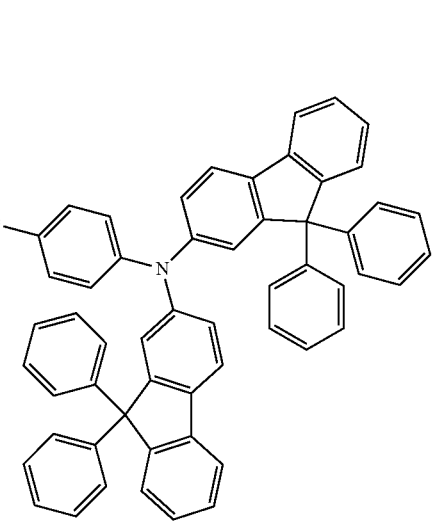

U73 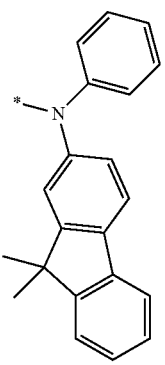
U74 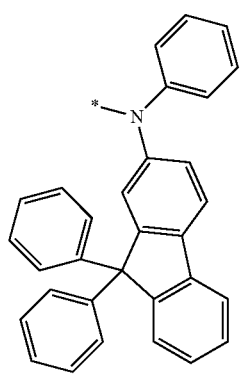
U75 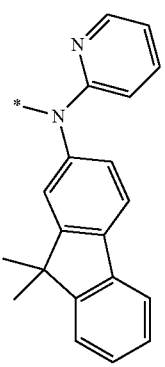
U76 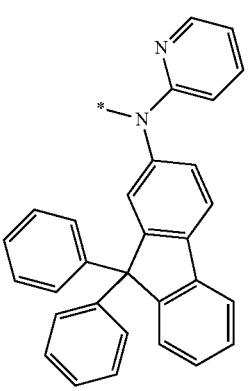
U77 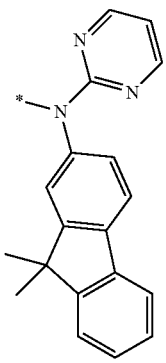
U78 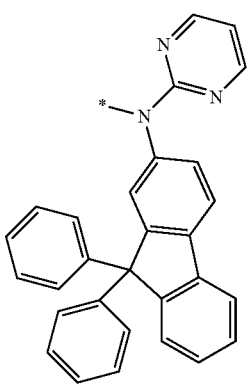
U79 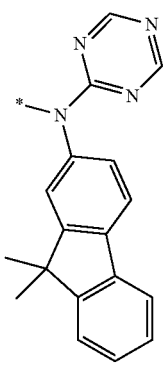
U78

U81
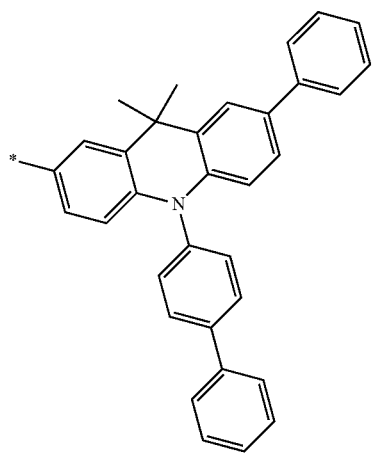

U82
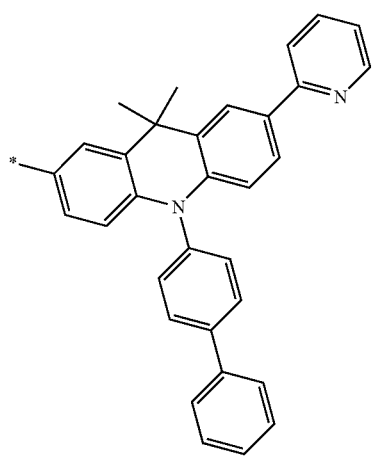

U83
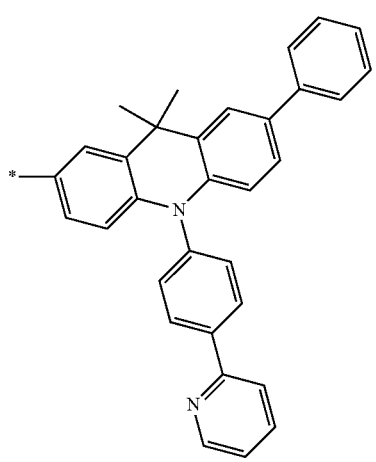

U84
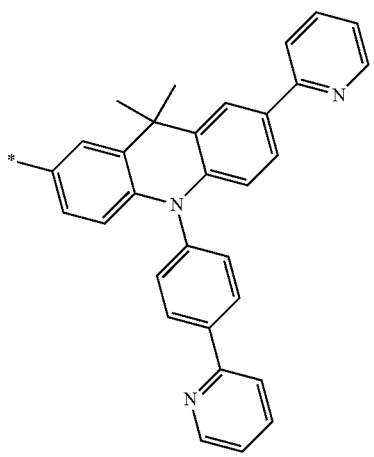

U85
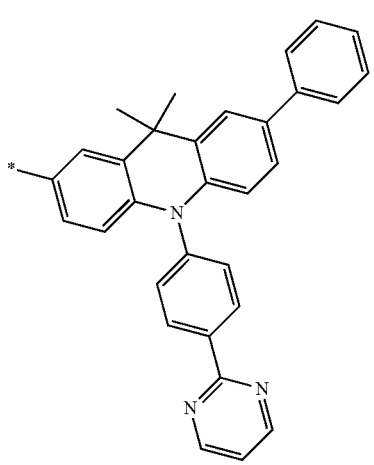

U86
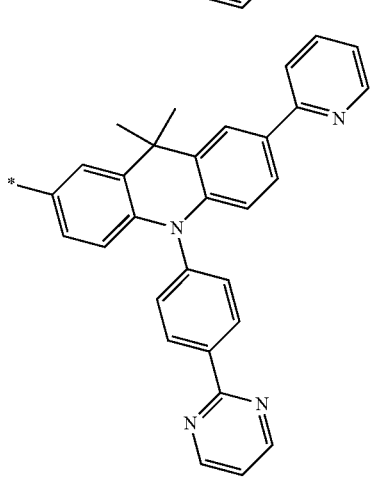

In the compound according to the present disclosure, $X_1$ and $X_2$ are each independently selected from the group consisting of O, S, Se, $N(Ar_1)$, $C(Ar_2)(Ar_3)$, and $Si(Ar_4)(Ar_5)$.

Provided that at least one of $X_1$ and $X_2$ is $N(Ar_1)$, and preferably, both $X_1$ and $X_2$ are $N(Ar_1)$.

In the compound according to the present disclosure, $R_1$ to $R_4$ and $Ar_1$ to $Ar_5$ may be each independently selected from the group consisting of hydrogen and the following S1 to S166, but are not limited thereto. Provided that when at least one of $Y_5$ to $Y_8$ is $CR_4$, at least one $R_4$ is the substituent represented by Formula 3.

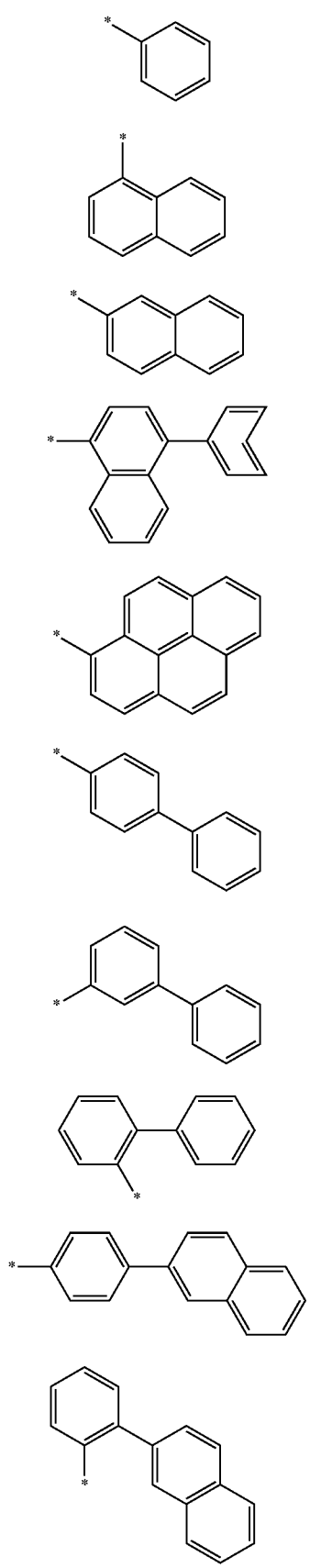
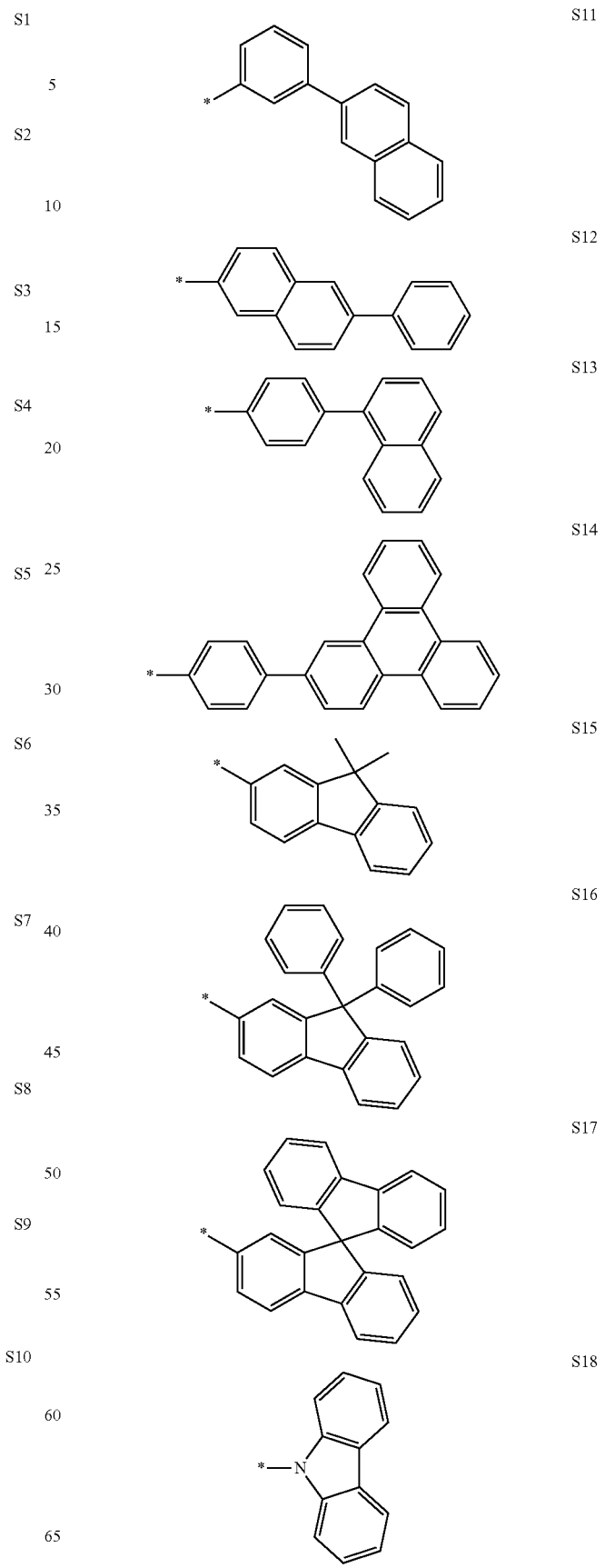

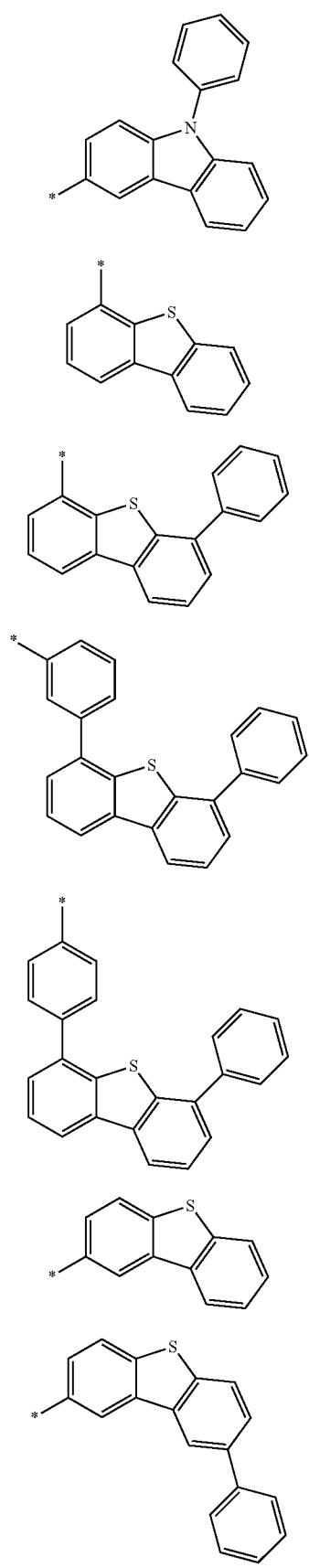
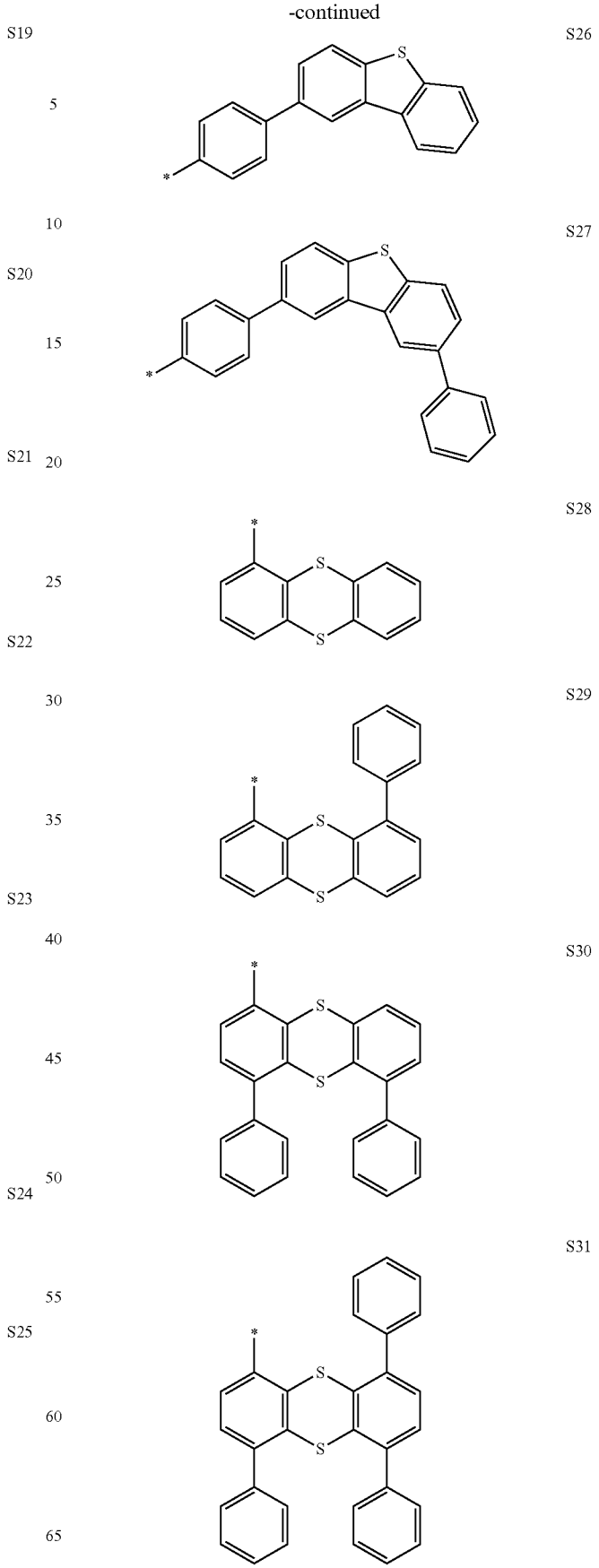

-continued
S32
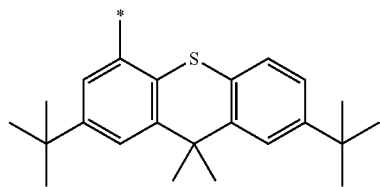
S33
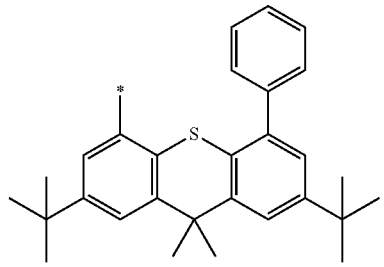
S34
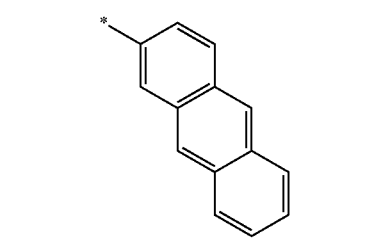
S35
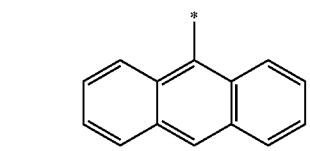
S36
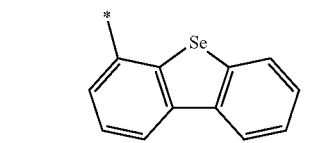
S37
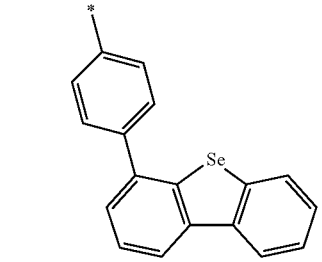
S38
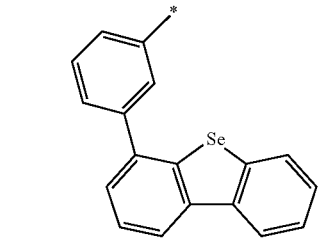
S39
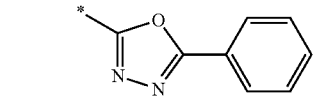
-continued
S40
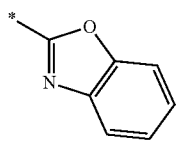
S41
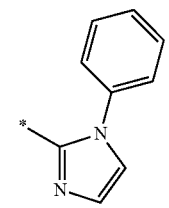
S42
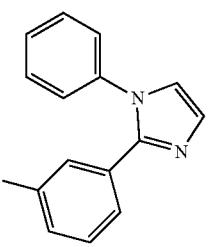
S43
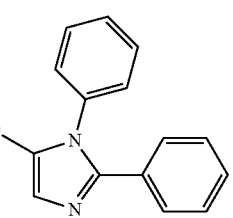
S44
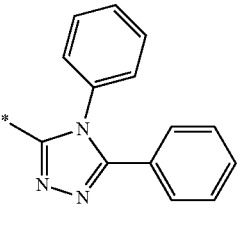
S45
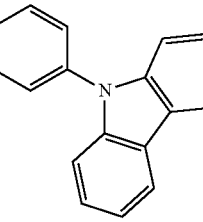
S46
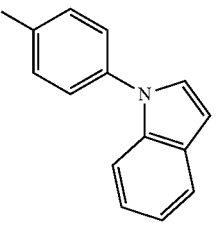

S47 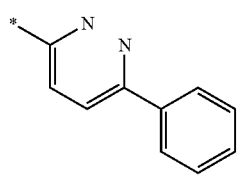
S48 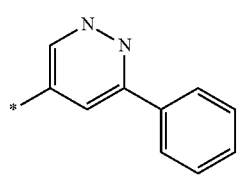
S49 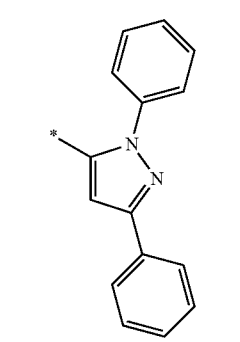
S50 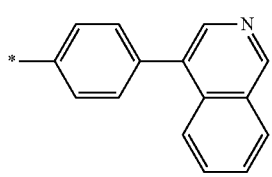
S51 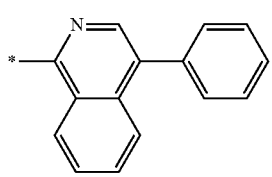
S52 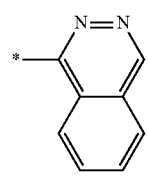
S53 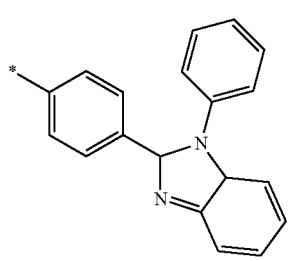
S54 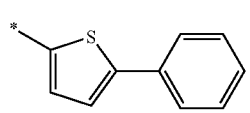
S55 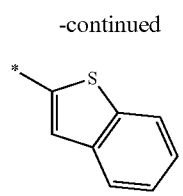
S56 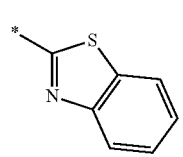
S57 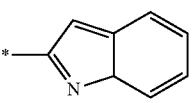
S58 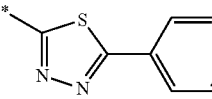
S59 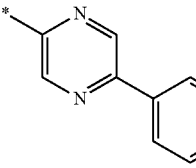
S60 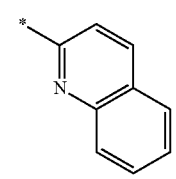
S61 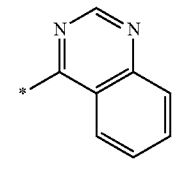
S62 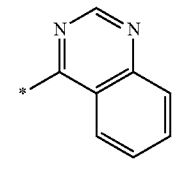
S63 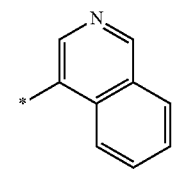
S64 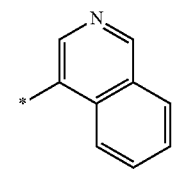

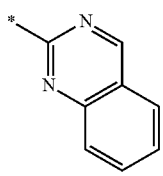 S65
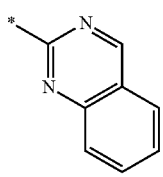 S66
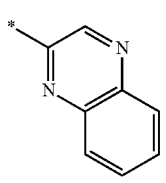 S67
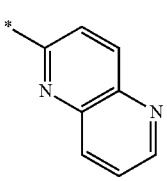 S68
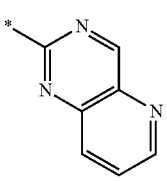 S69
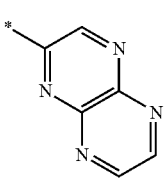 S70
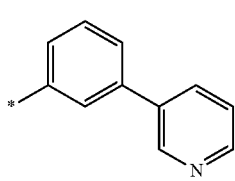 S71
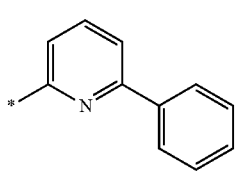 S72
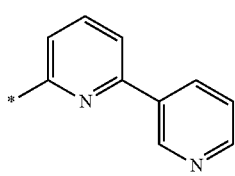 S73
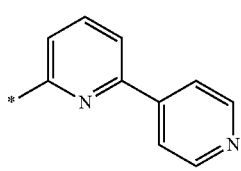 S74
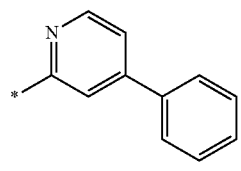 S75
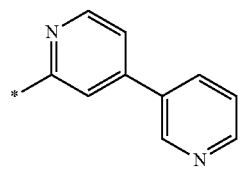 S76
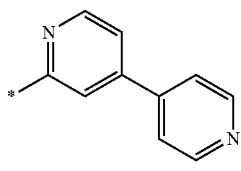 S77
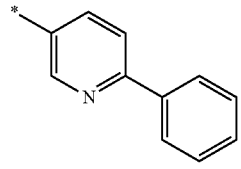 S78
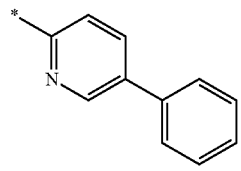 S79
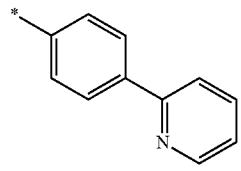 S80
 S81
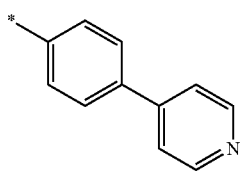 S82

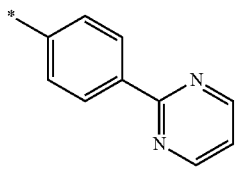 S83
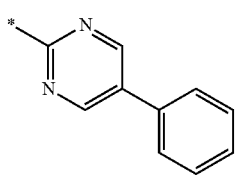 S84
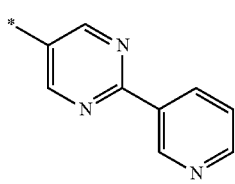 S85
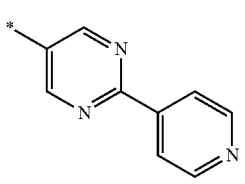 S86
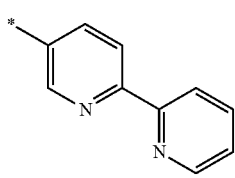 S87
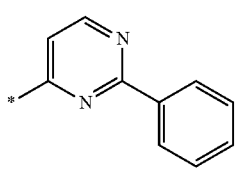 S88
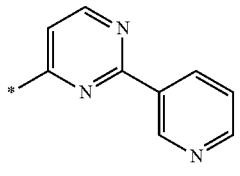 S89
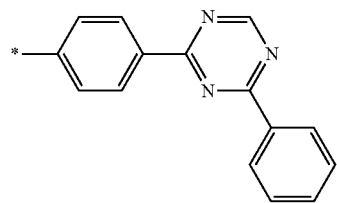 S90
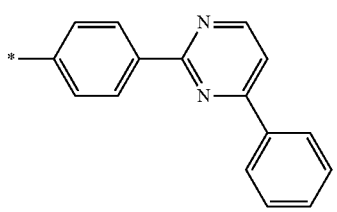 S91
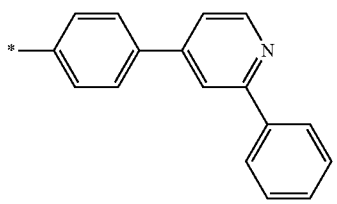 S92
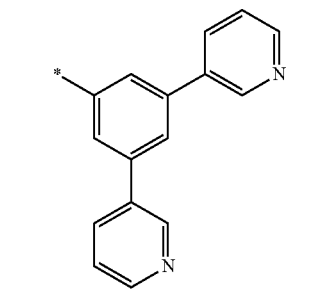 S93
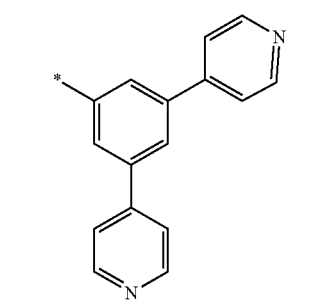 S94
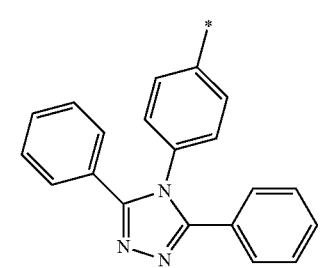 S95
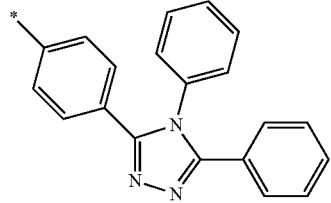 S96

S97 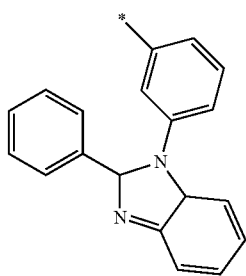
S98 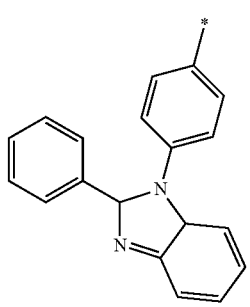
S99 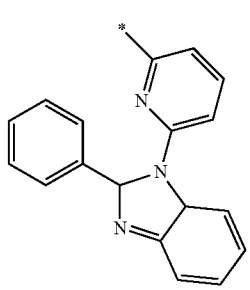
S100 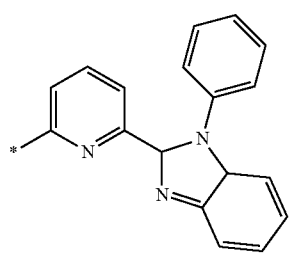
S101 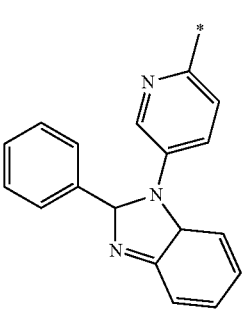
S102 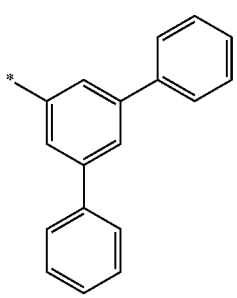
S103 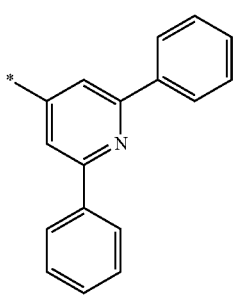
S104 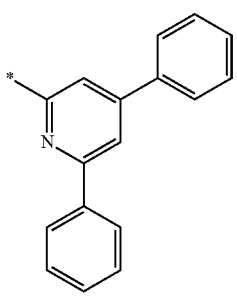
S105 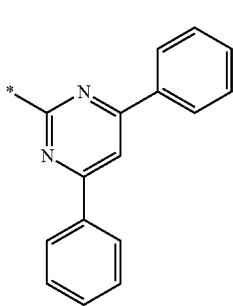
S106 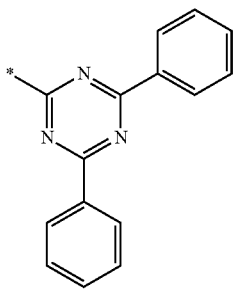

S107 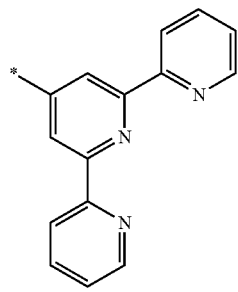
S108 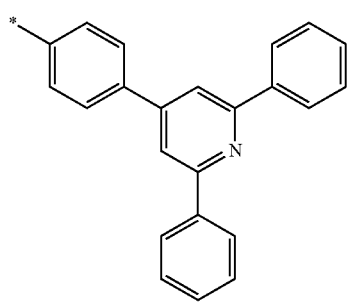
S109 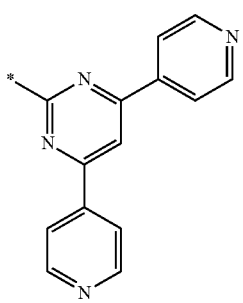
S110 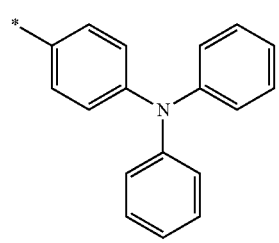
S111 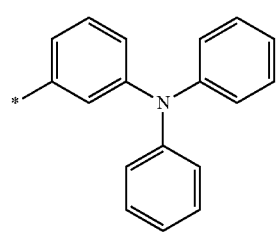
S112 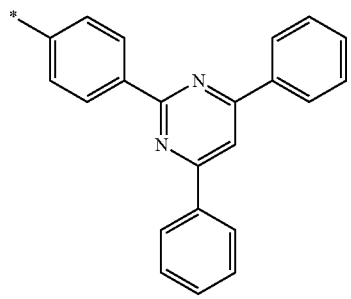
S113 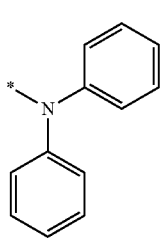
S114 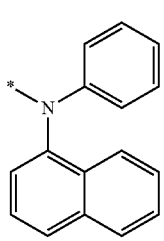
S115 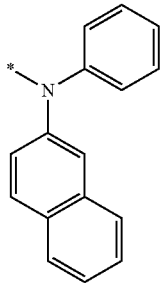
S116 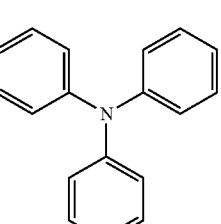
S117 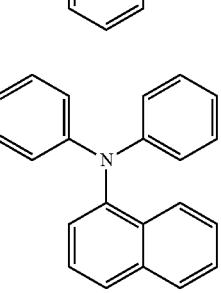

S118 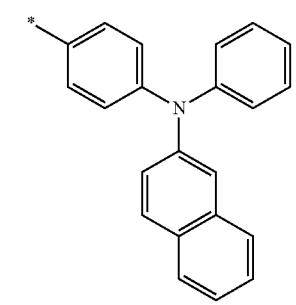
S119 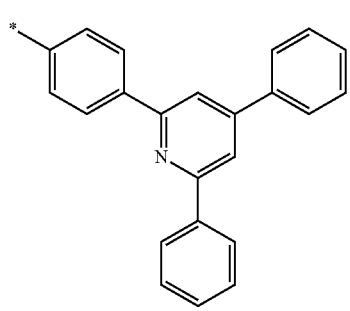
S120 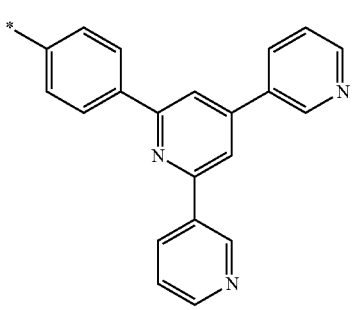
S121 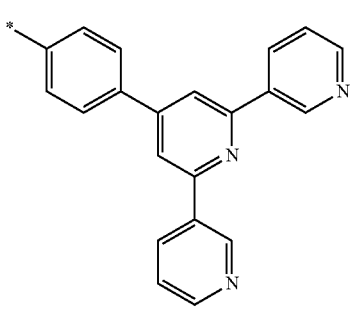
S122 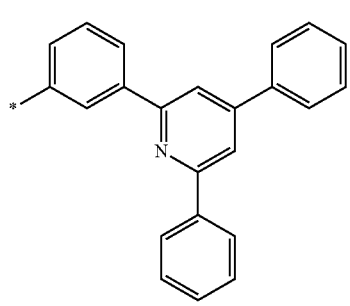
S123 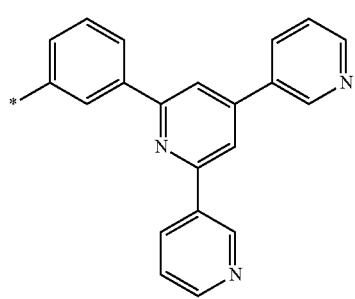
S124 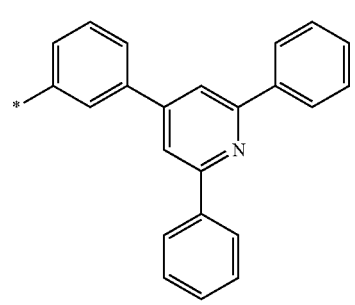
S125 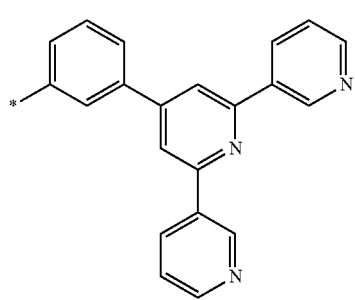
S126 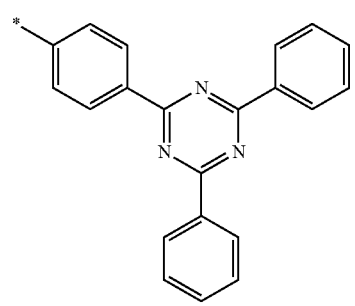
S127 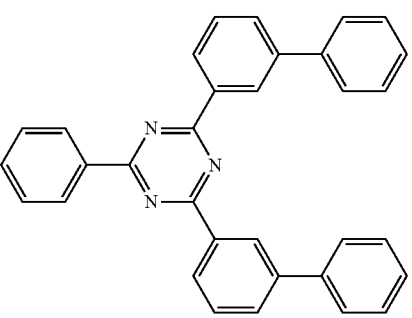

-continued
S128
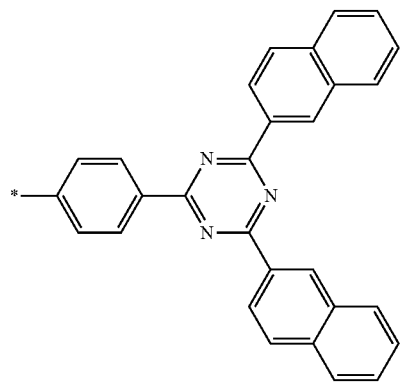
S129
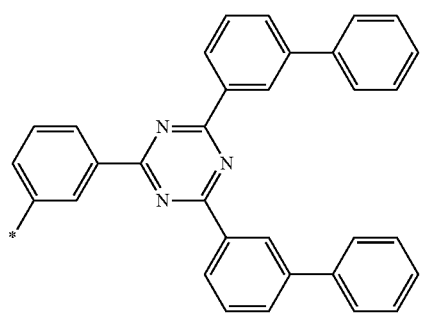
S130
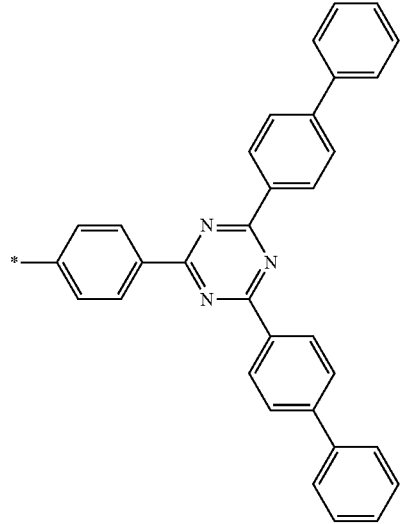
S131
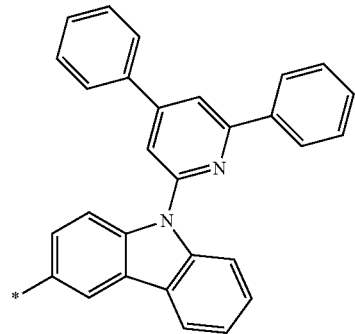
S132
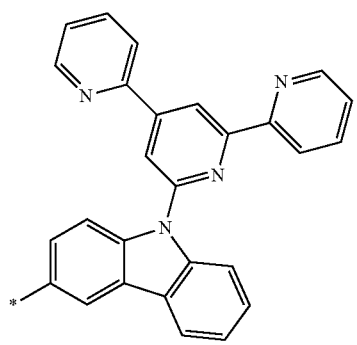
S133
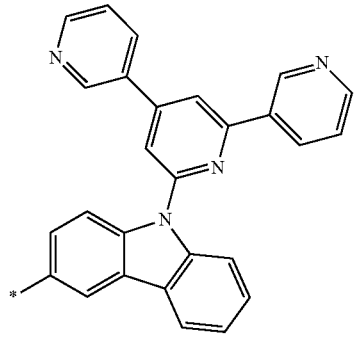
S134
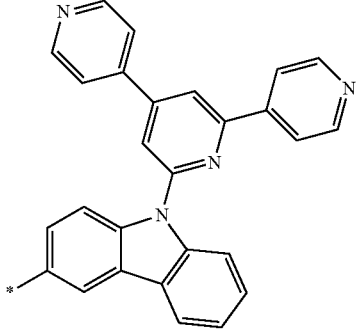
S135
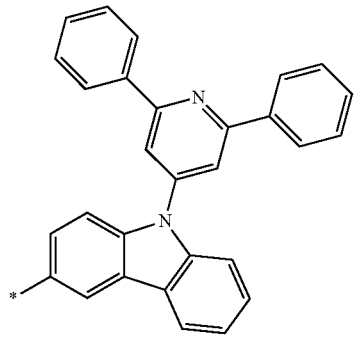

| | |
|---|---|
| 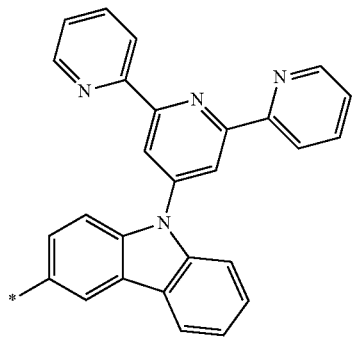 | S136 |
| 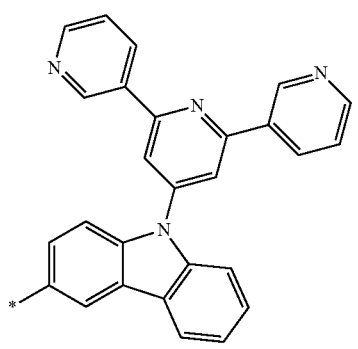 | S137 |
| 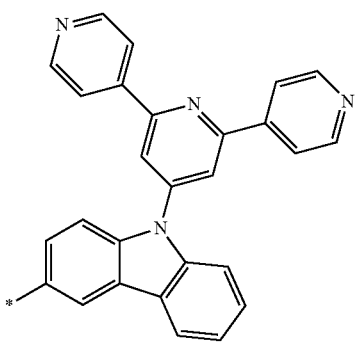 | S138 |
| 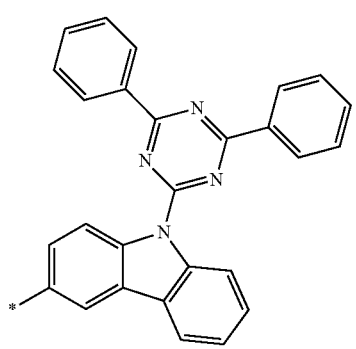 | S139 |
| 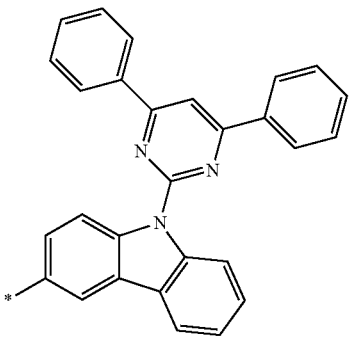 | S140 |
| 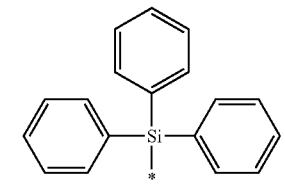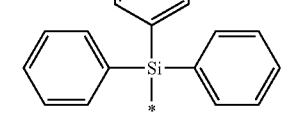 | S141 |
| 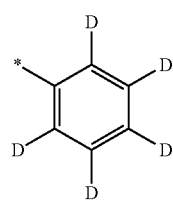 | S142 |
| 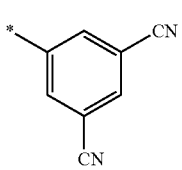 | S143 |
| 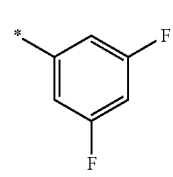 | S144 |
| 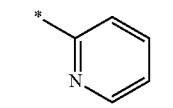 | S145 |
| 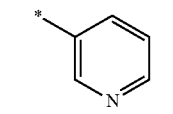 | S146 |
| 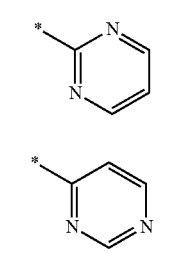 | S147 |
| | S148 |

S149 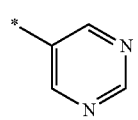
S150 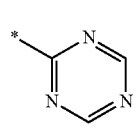
S151 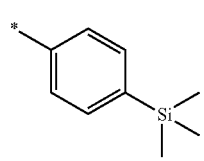
S152 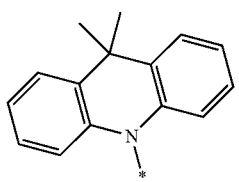
S153 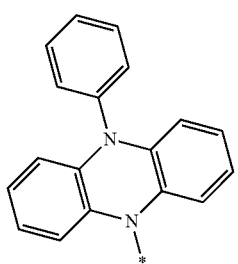
S154 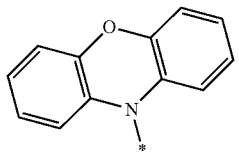
S155 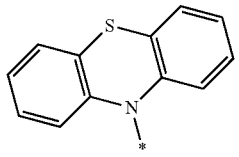
S156 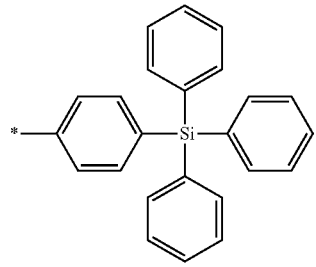
S157 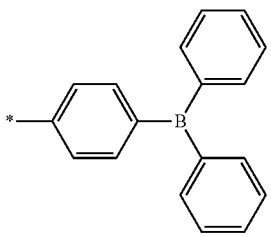
S158 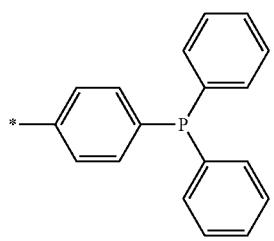
S159 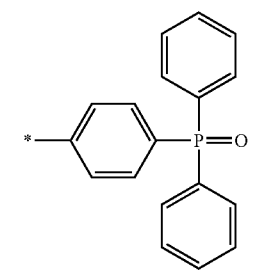
S160 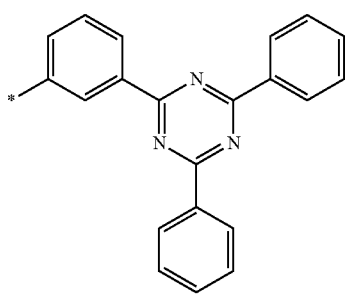
S161 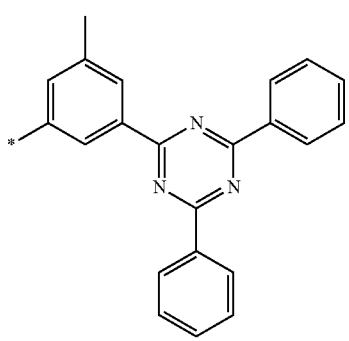

S162 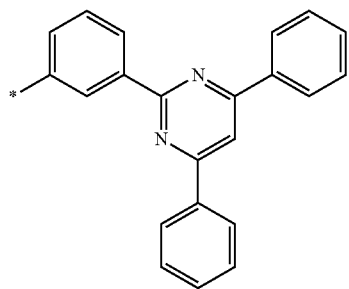
S163 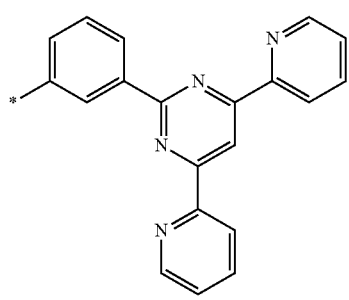
S164 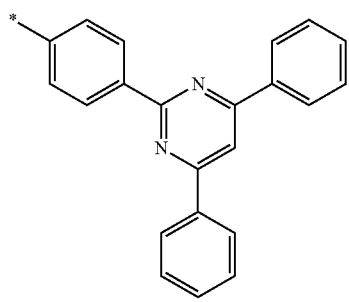
S165 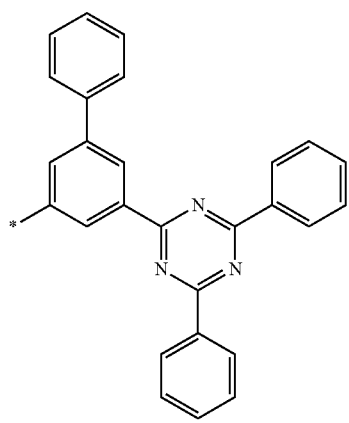
S166 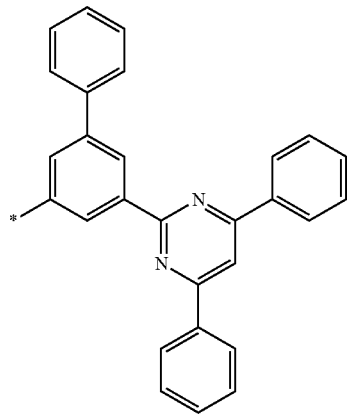
Examples of the compound represented by Formula 1 according to the present disclosure include compounds represented by the following Formulae 4 to 9, but are not limited thereto.
[Formula 4]
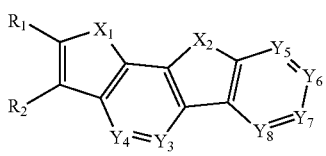
[Formula 5]
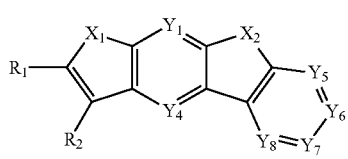
[Formula 6]
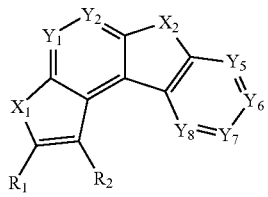
[Formula 7]
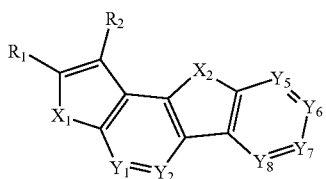
[Formula 8]
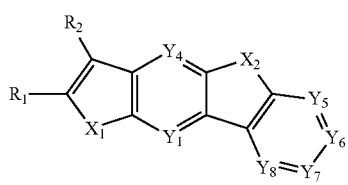

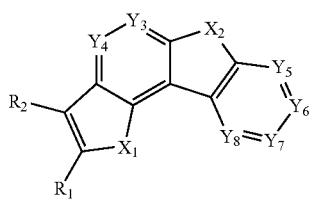 [Formula 9]

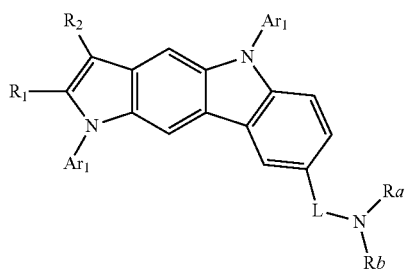 [Formula 14]

In Formulae 4 to 9, $Y_1$ to $Y_4$ are each independently N or $CR_3$, and in this case, when $CR_3$ is present in a plural number, they are the same as or different from each other; and $X_1$ and $X_2$, $Y_5$ to $Y_8$, $R_1$, $R_2$, and $R_3$ are each the same as those defined in Formula 1.

In addition, examples of the compound represented by Formula 1 according to the present disclosure include compounds represented by the following Formulae 10 to 15, but are not limited thereto.

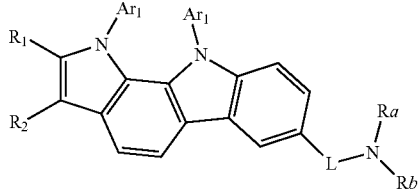 [Formula 10]

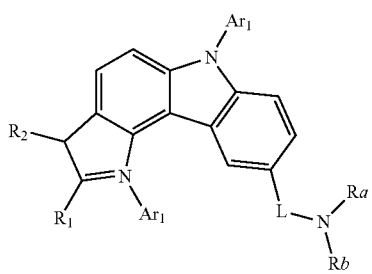 [Formula 15]

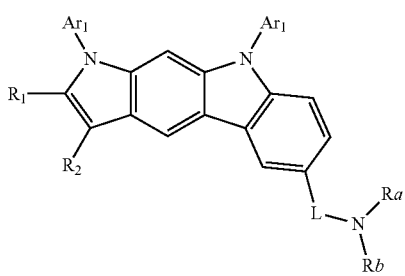 [Formula 11]

In Formulae 10 to 15, $R_1$, $R_2$, $Ar_1$, $R_a$, $R_b$, and L are each the same as those defined in Formula 1, and in this case, when $Ar_1$ is present in a plural number, they are the same as or different from each other.

Specific examples of the compound represented by Formula 1 include the following Compounds 1 to 489, and the like, but are not limited thereto.

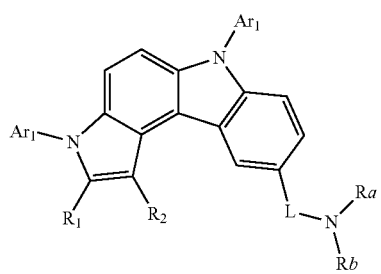 [Formula 12]

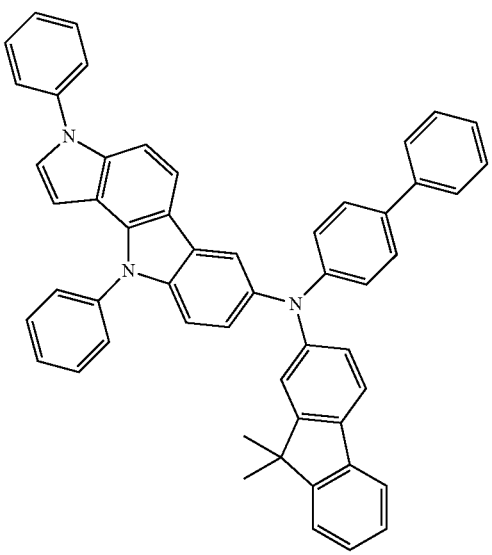

1

[Formula 13]

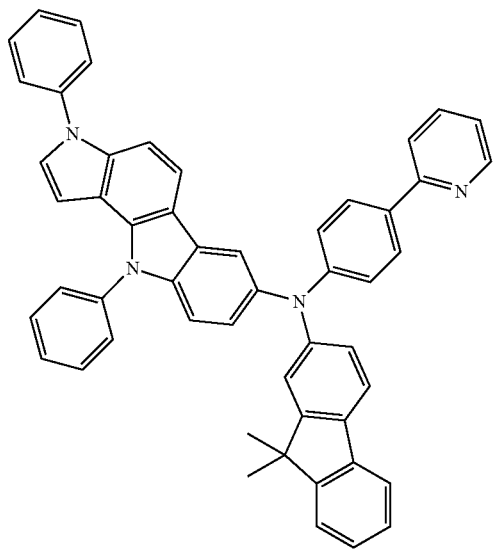
2
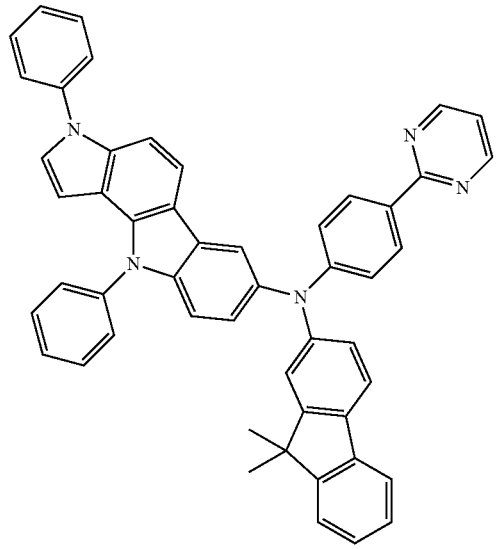
5
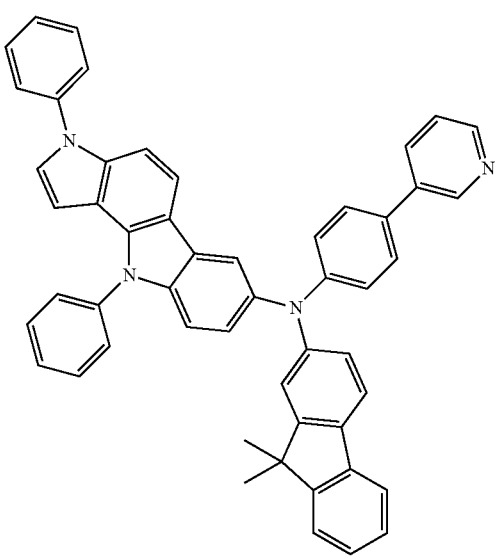
3
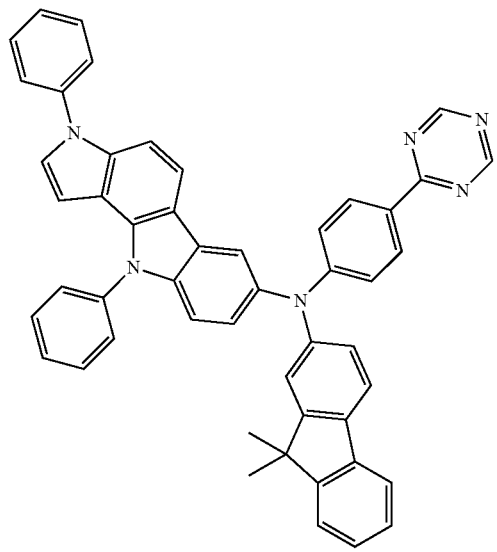
6
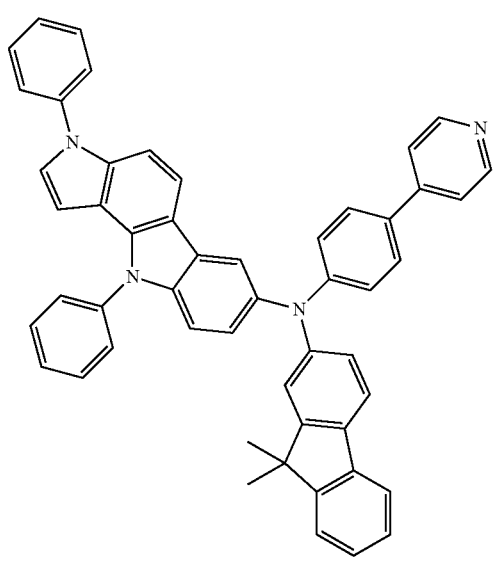
4
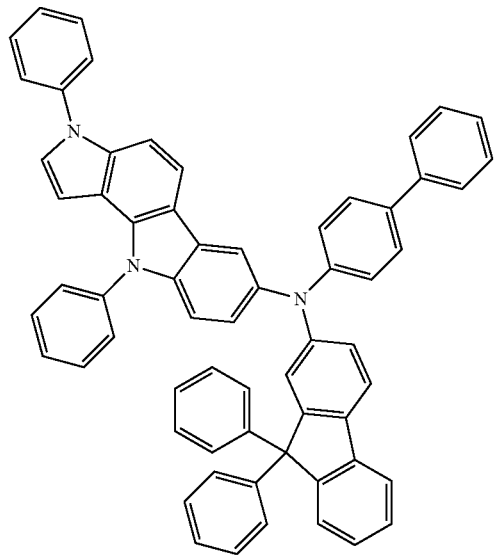
7

8
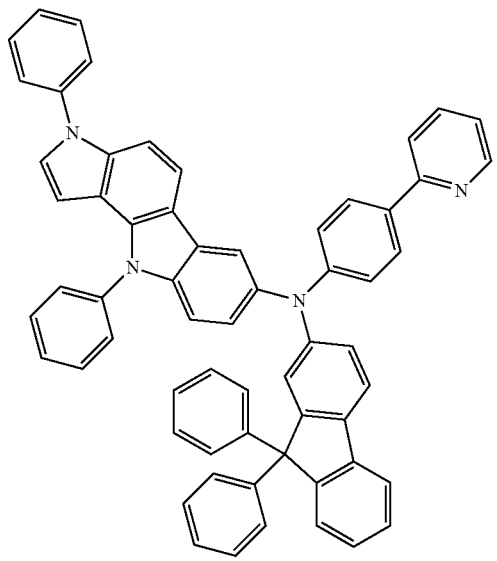
9
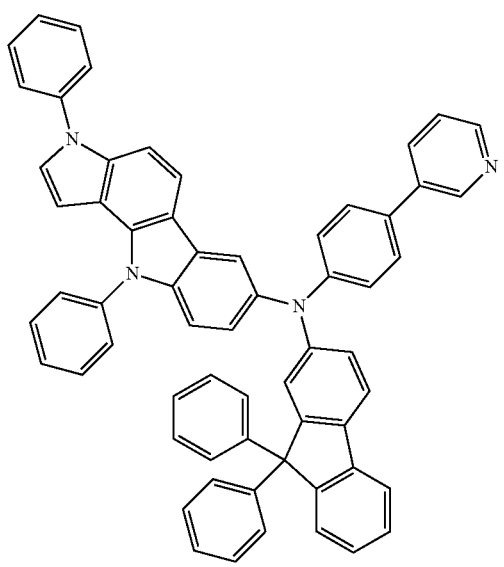
10
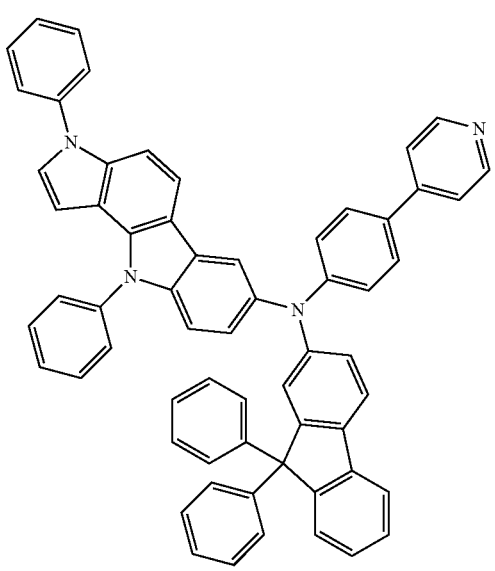
11
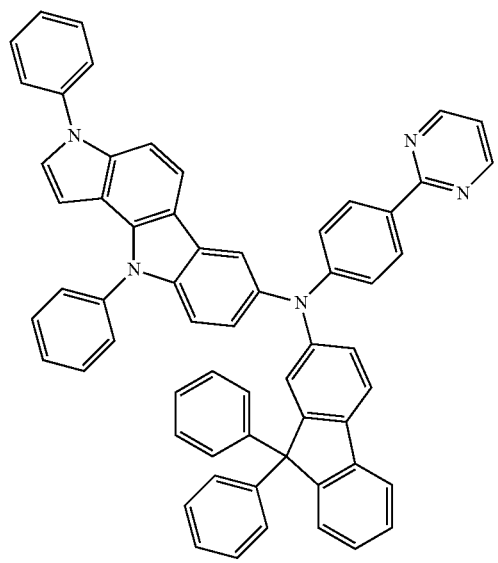
12
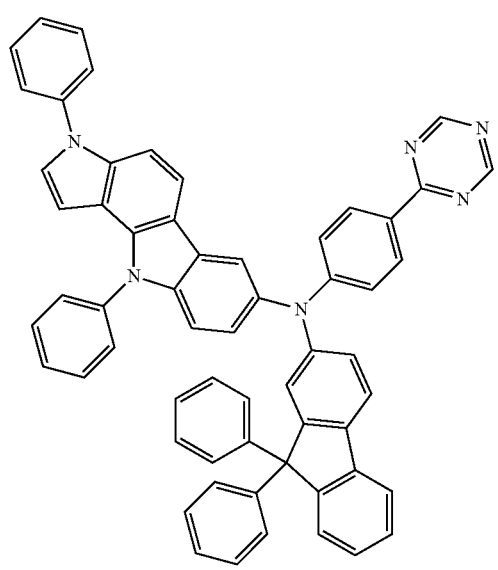
13
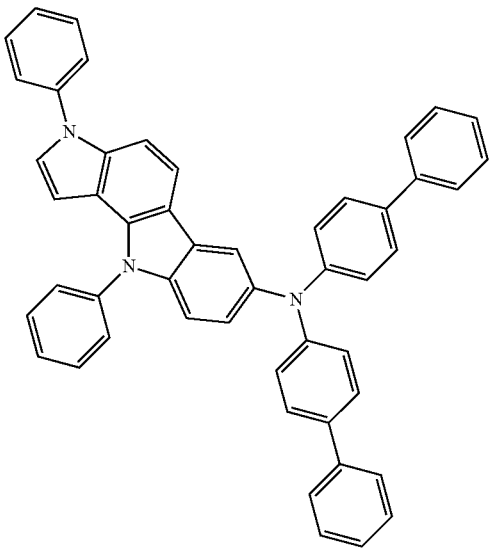

14
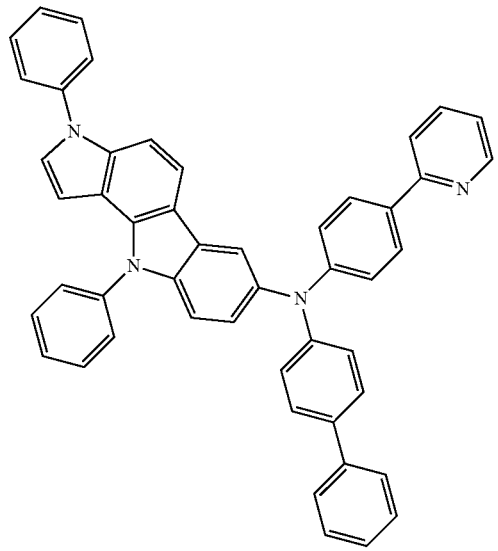
15
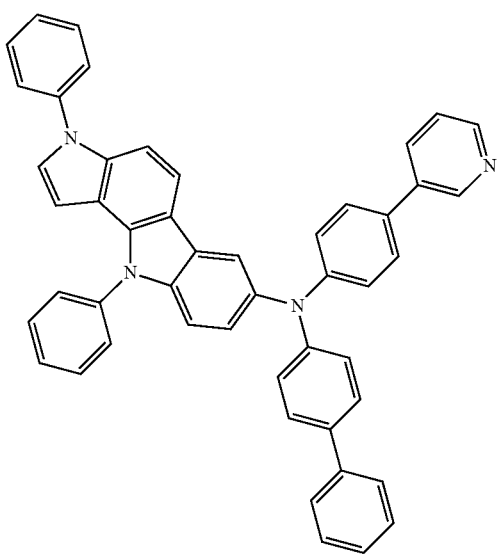
16
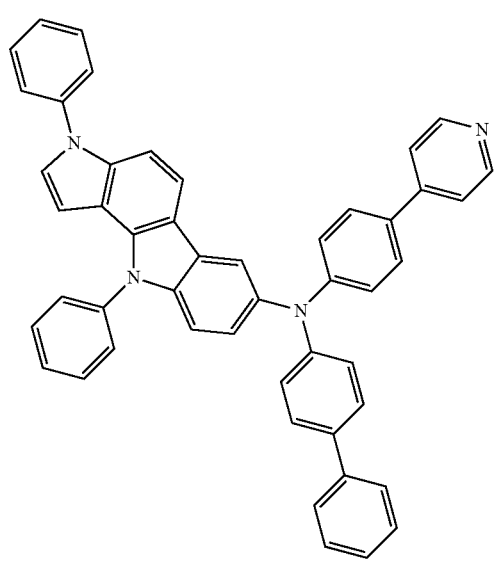
17
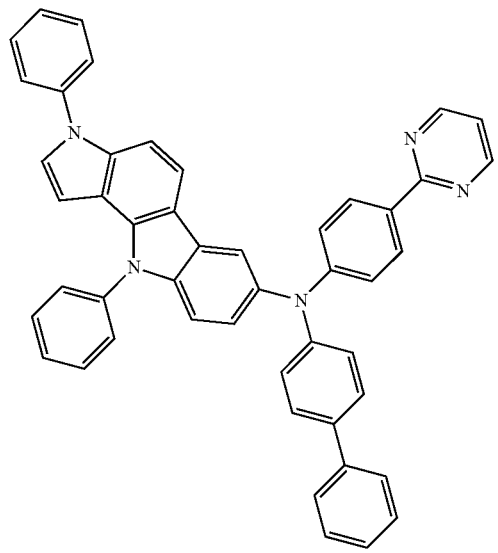
18
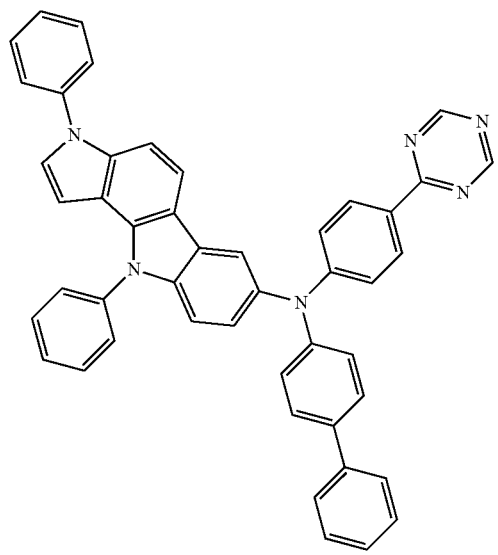
19
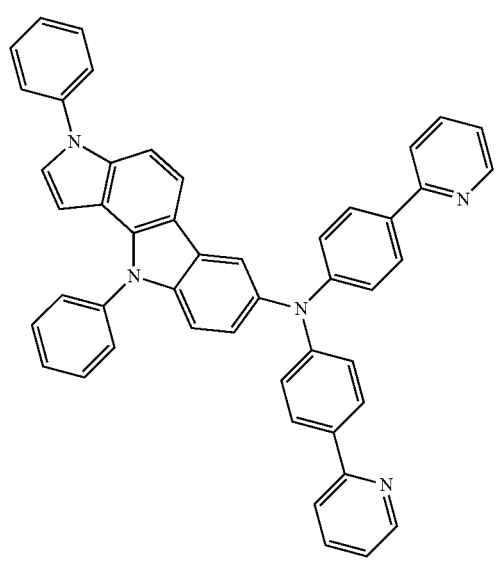

20
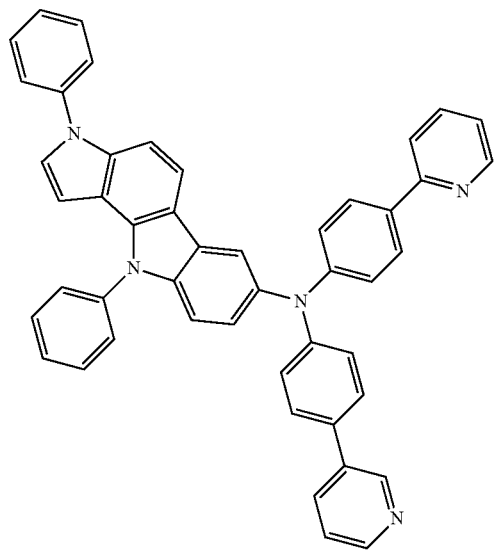
21
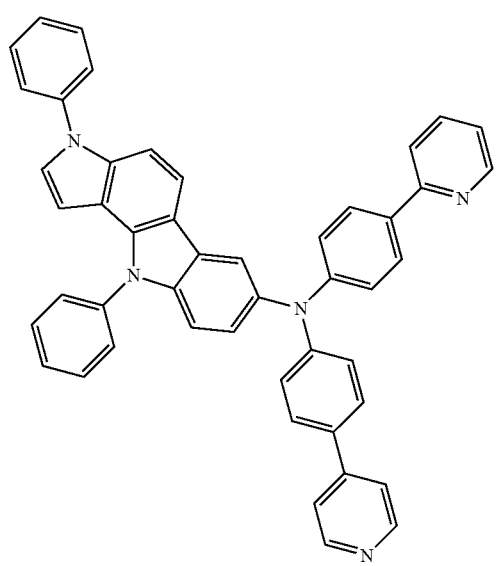
22
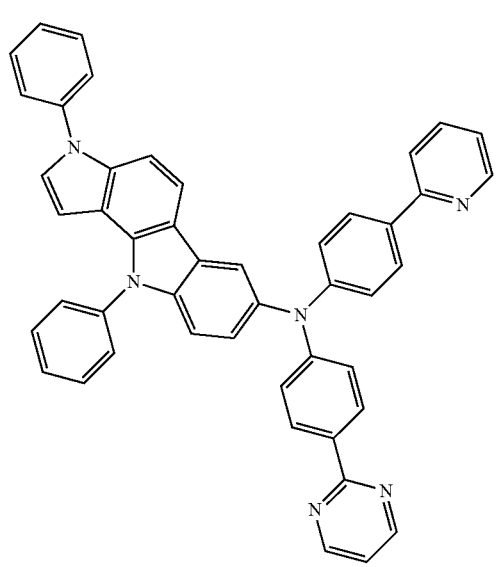
23
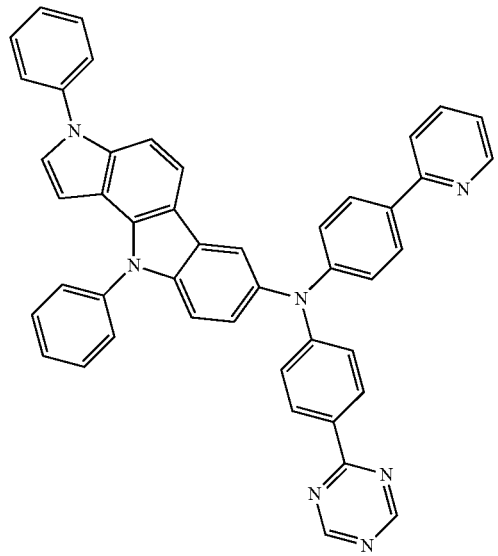
24
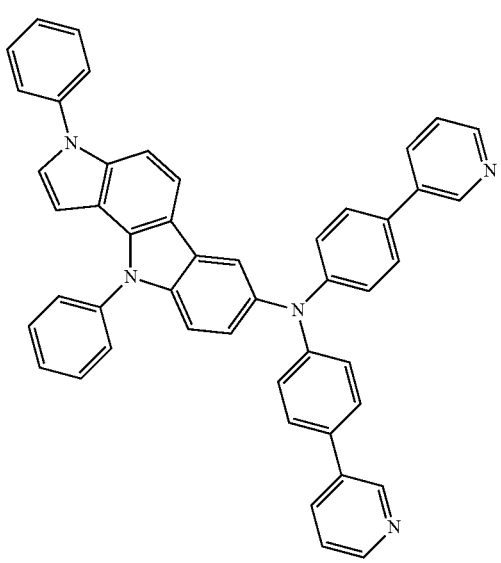
25
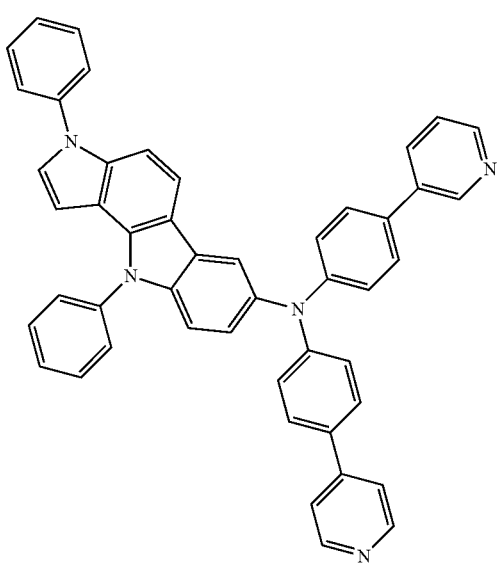

26
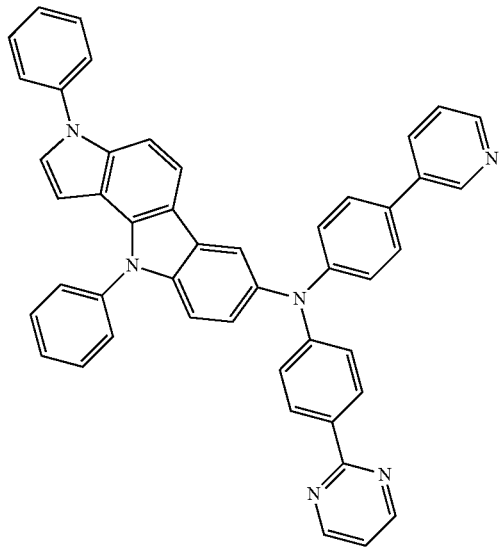
29
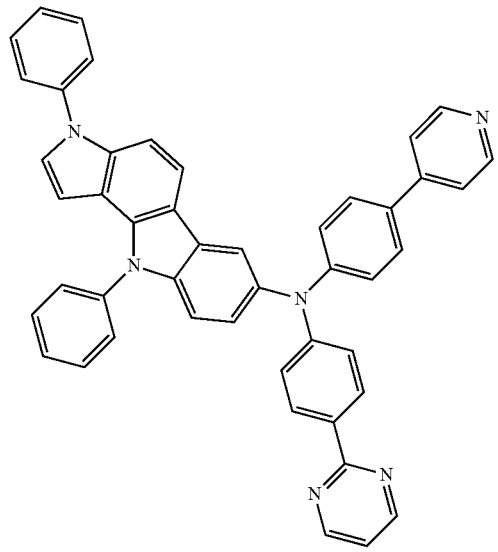
27
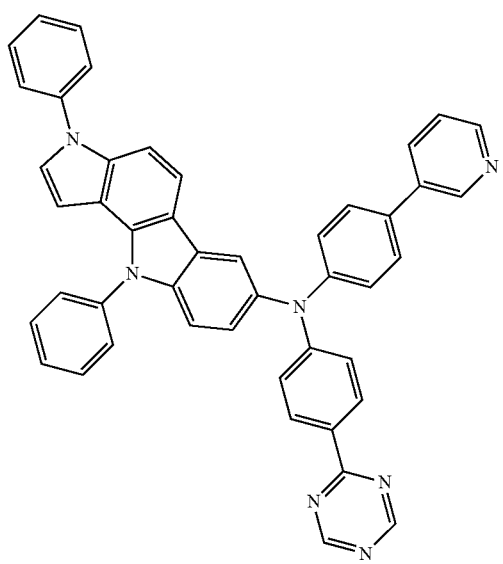
30
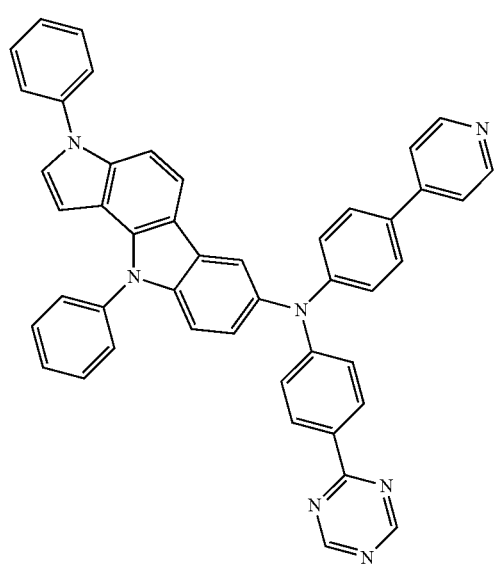
28
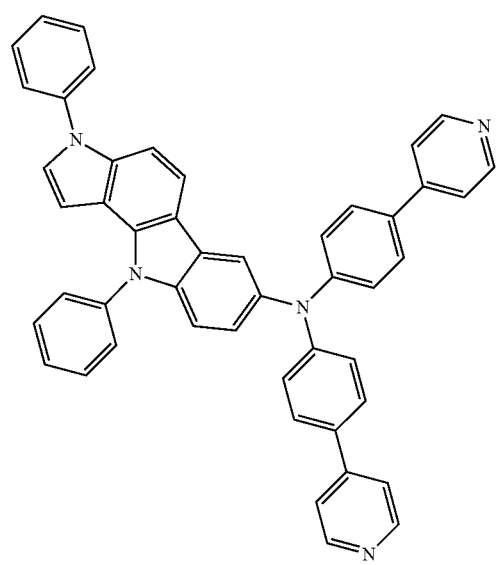
31
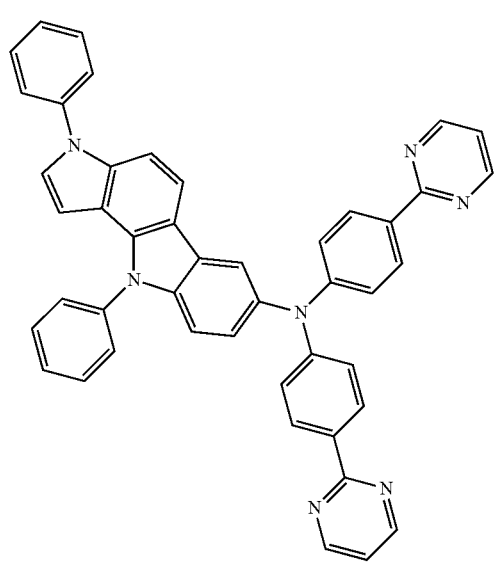

32
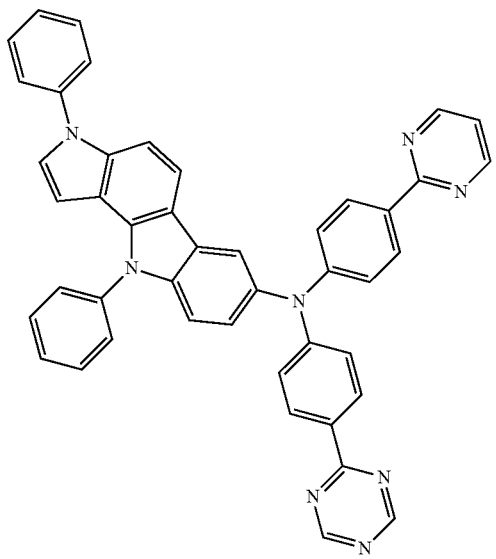
33
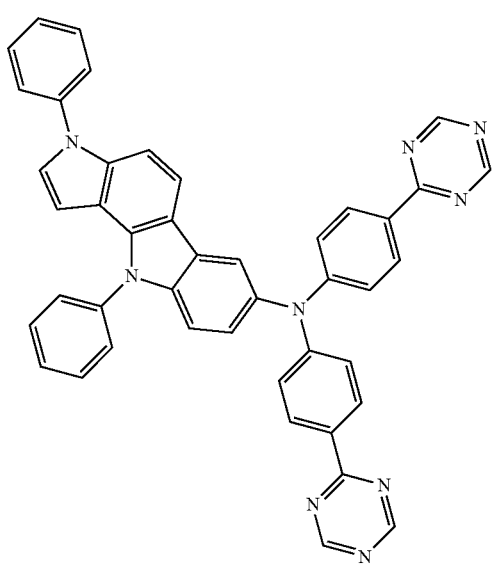
34
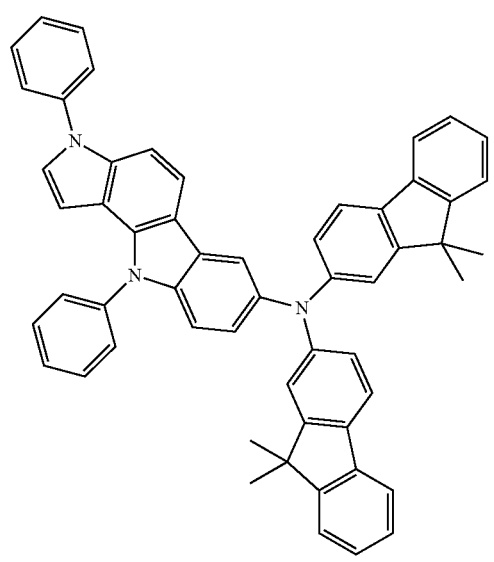
35
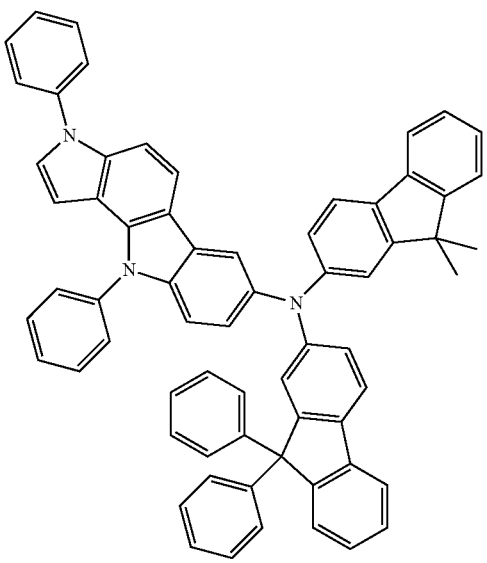
36
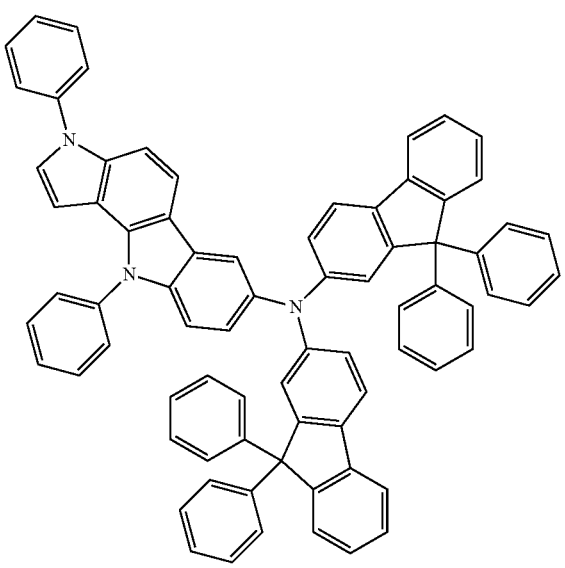

37
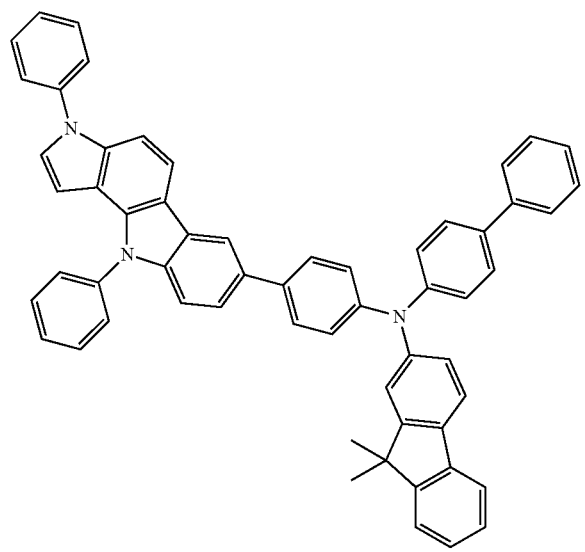
38
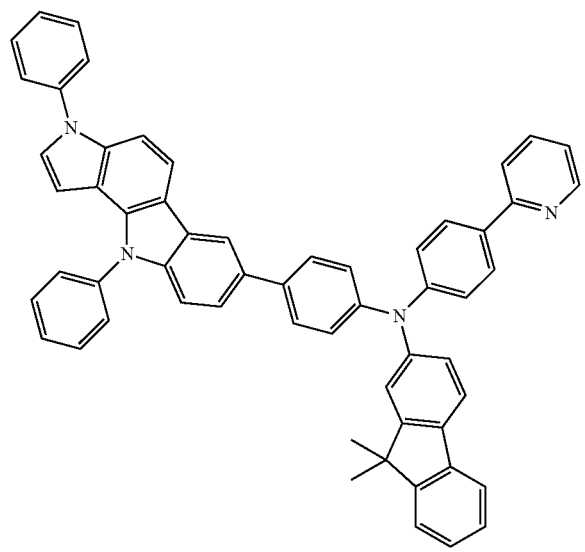
39
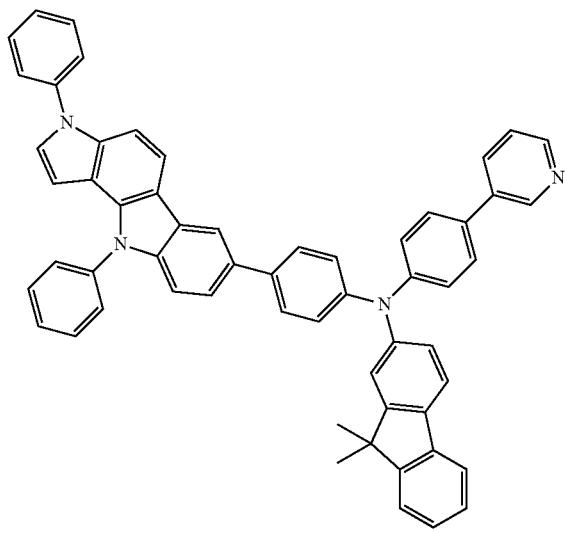
40
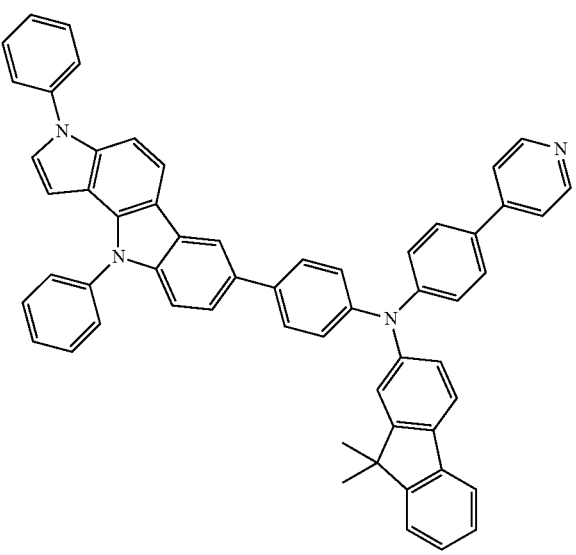

-continued
41
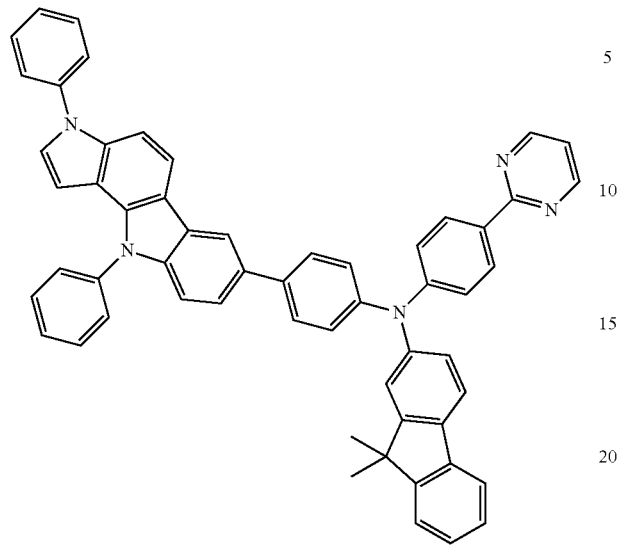
42
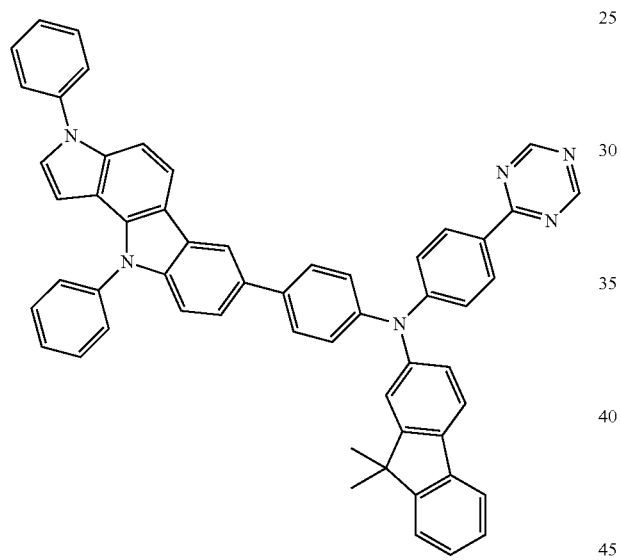
43
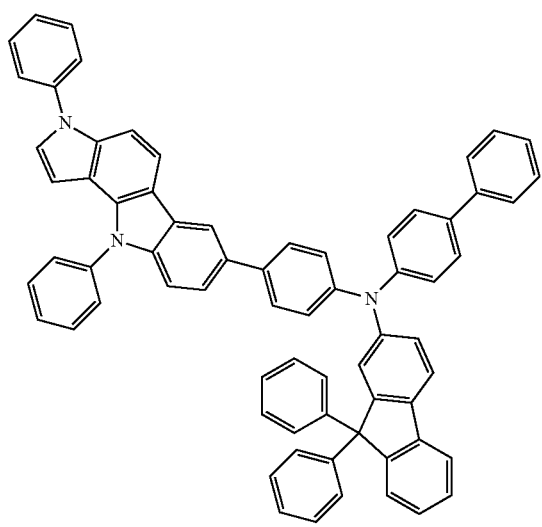
-continued
44
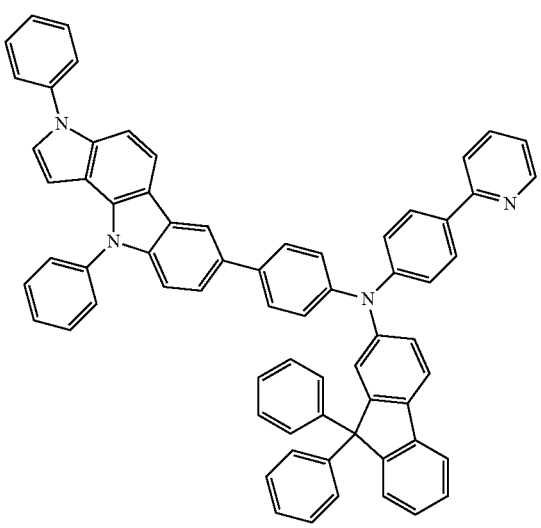
45
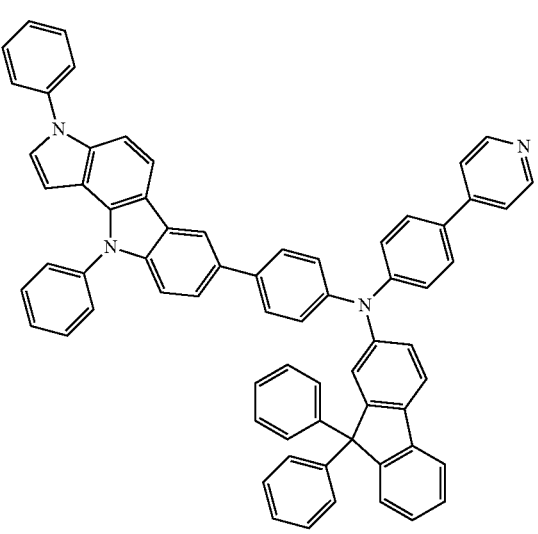
46
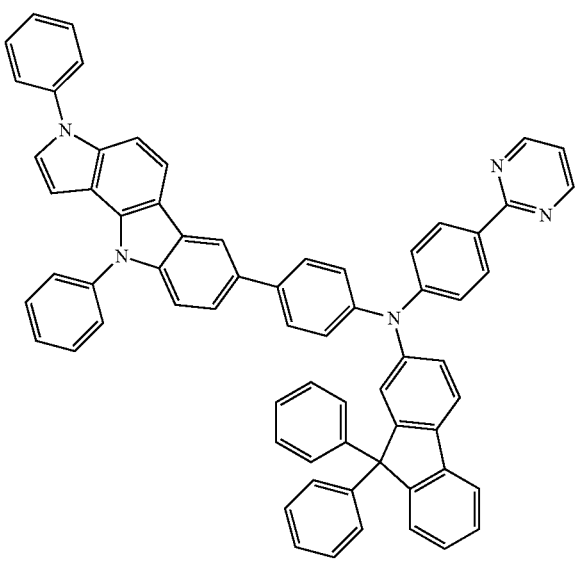

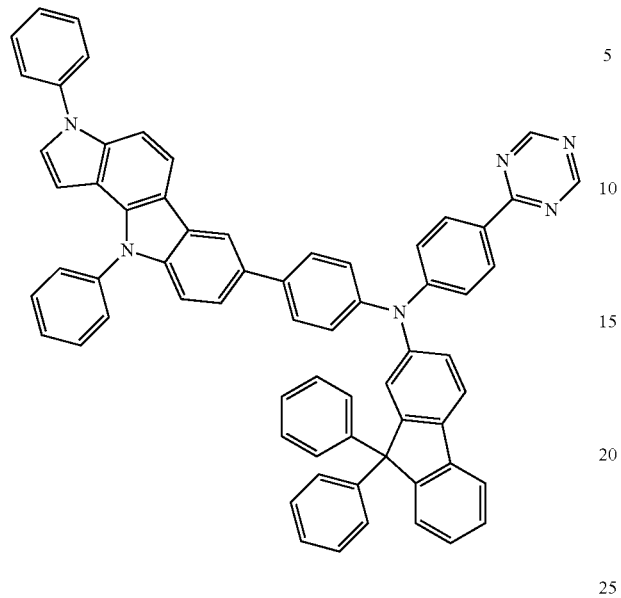
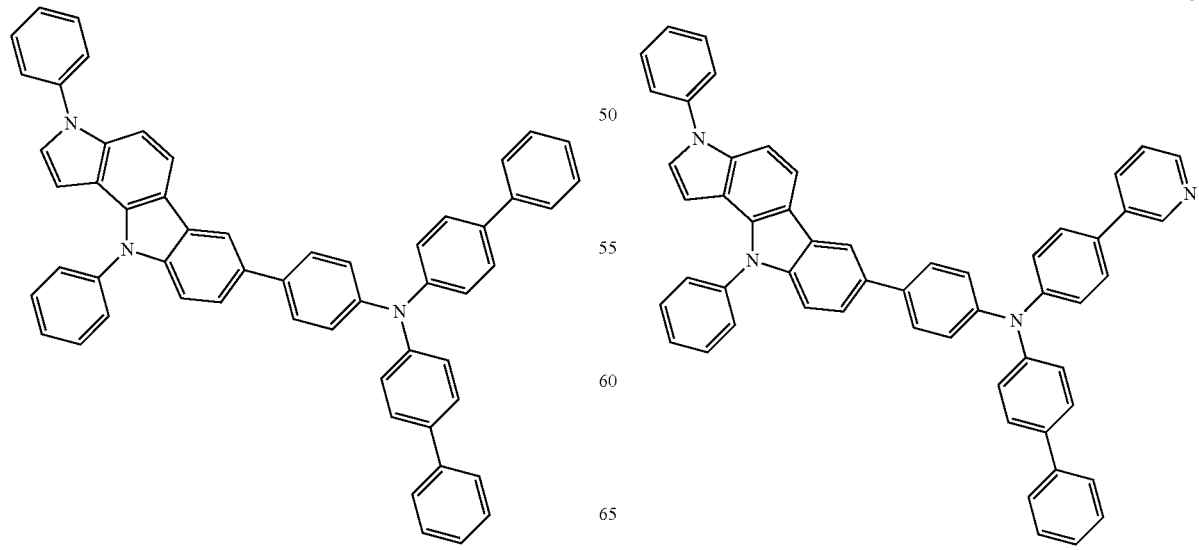

51
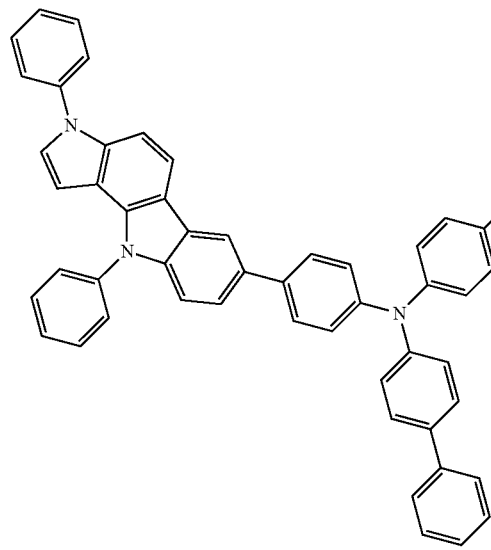
53
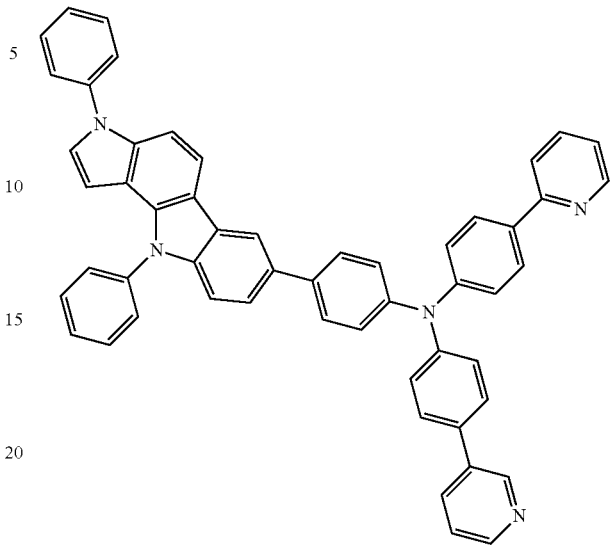
52
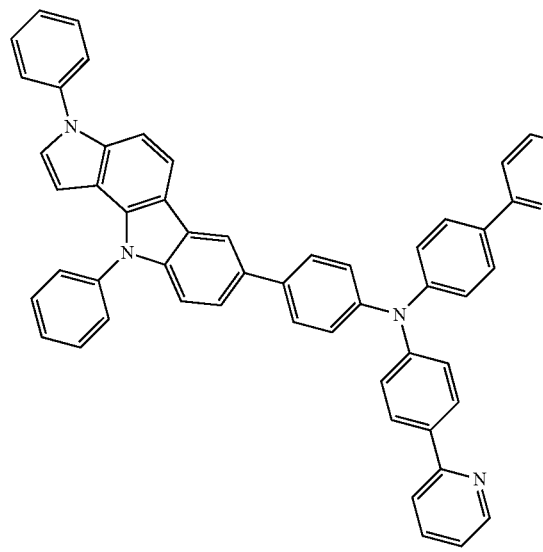
54
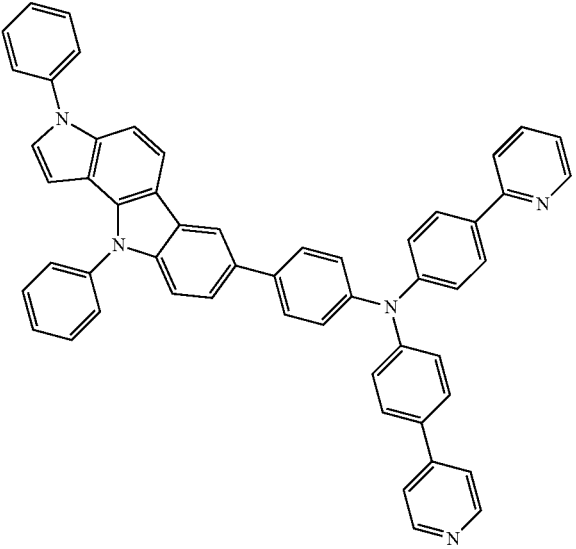

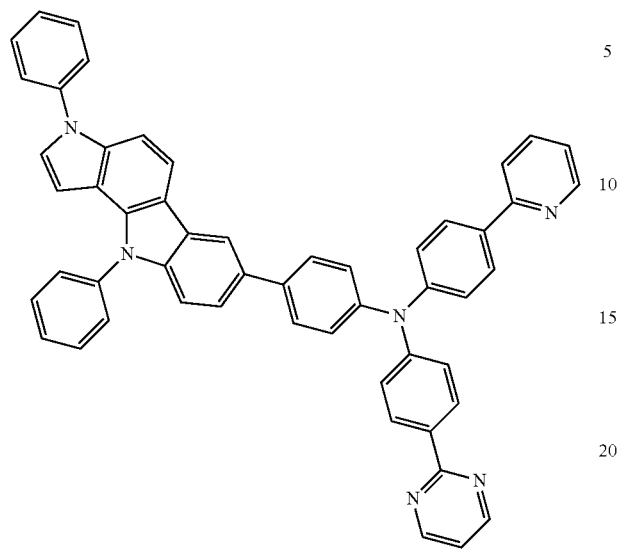
55
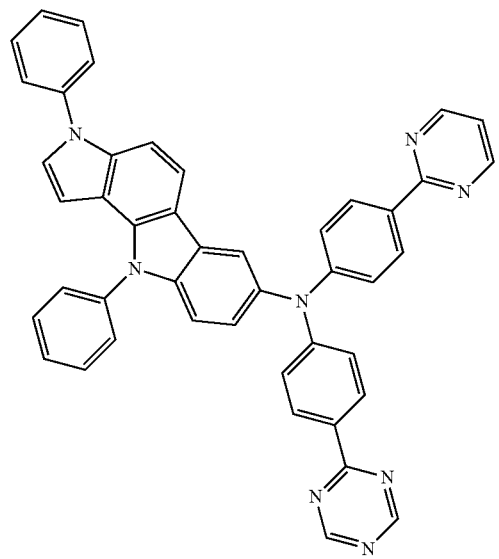
56
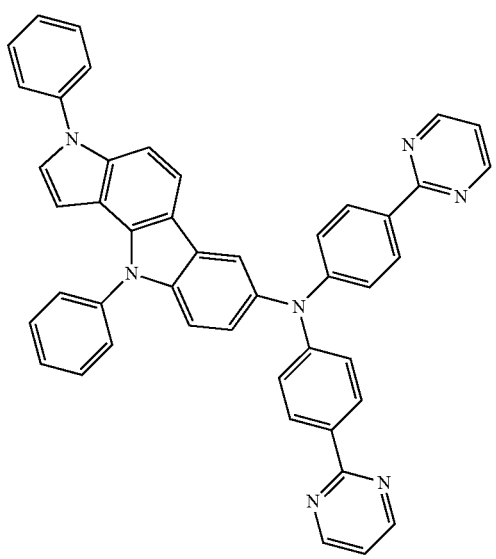
57
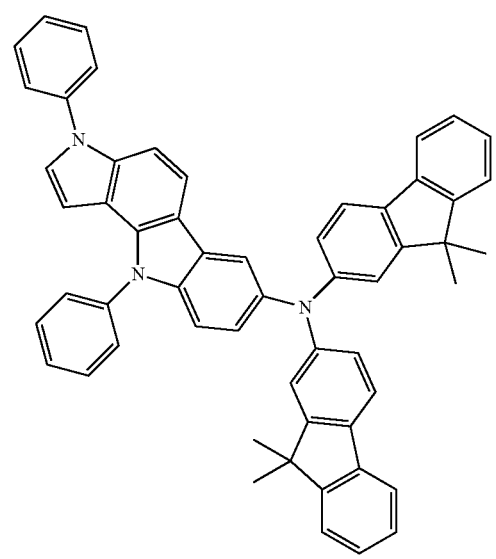
58
59

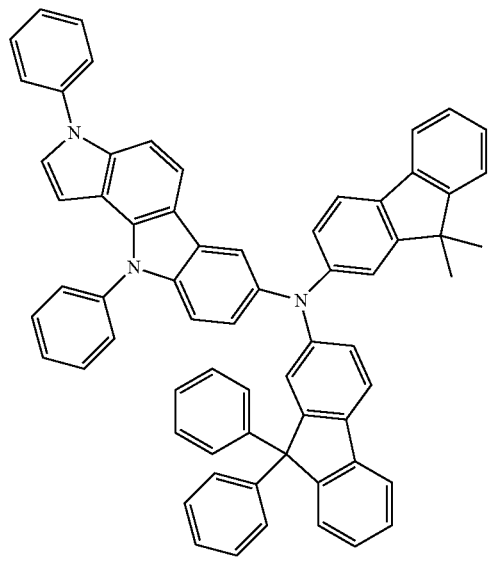
60
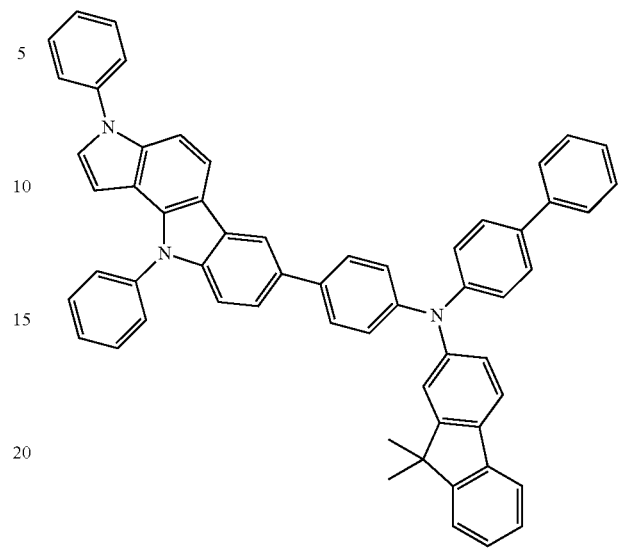
62
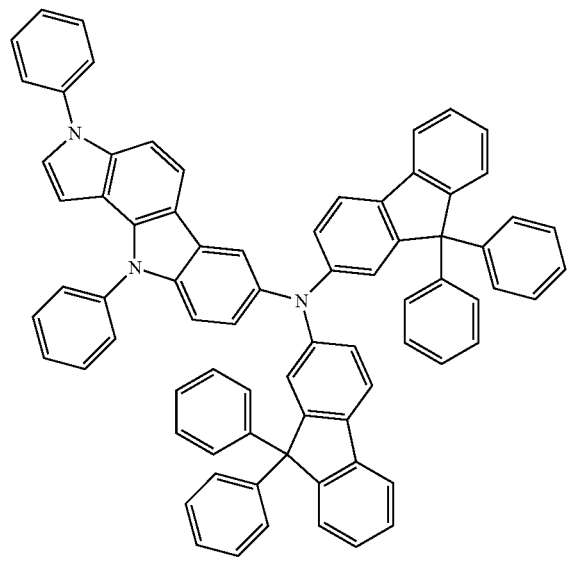
61
63

64
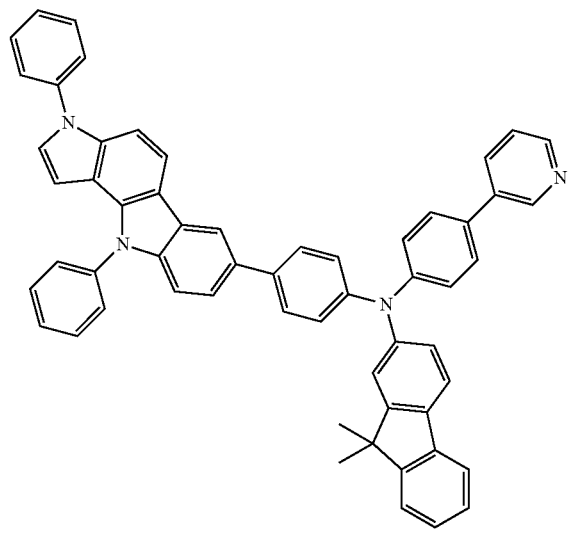
66
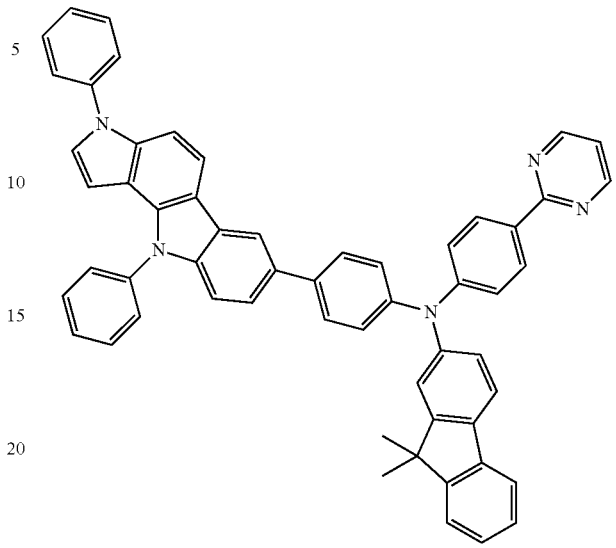
65
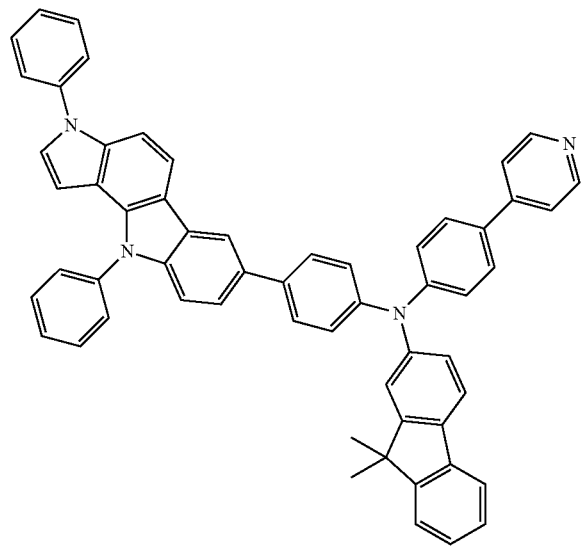
67
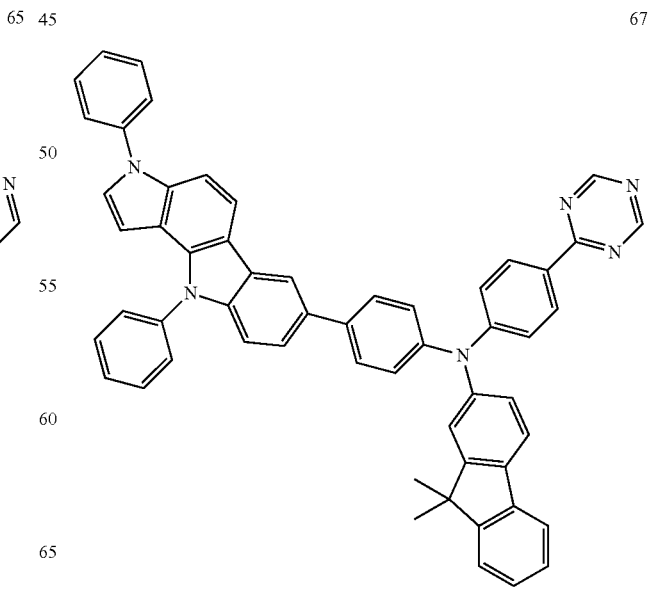

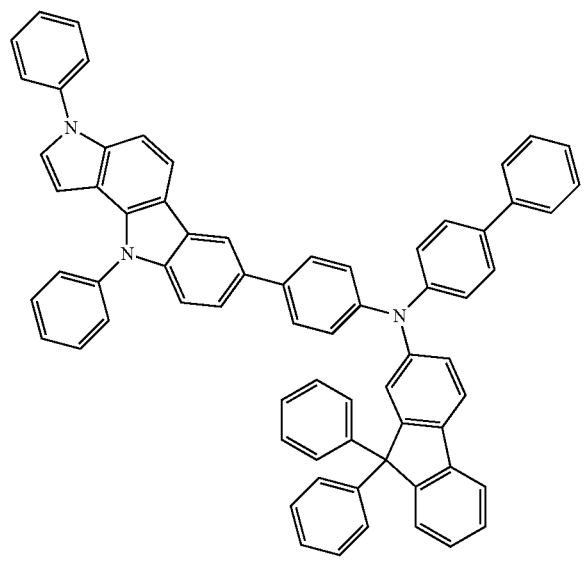
68
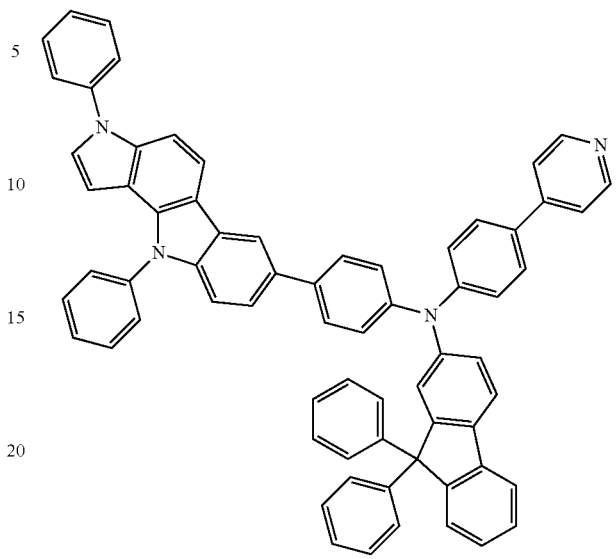
70
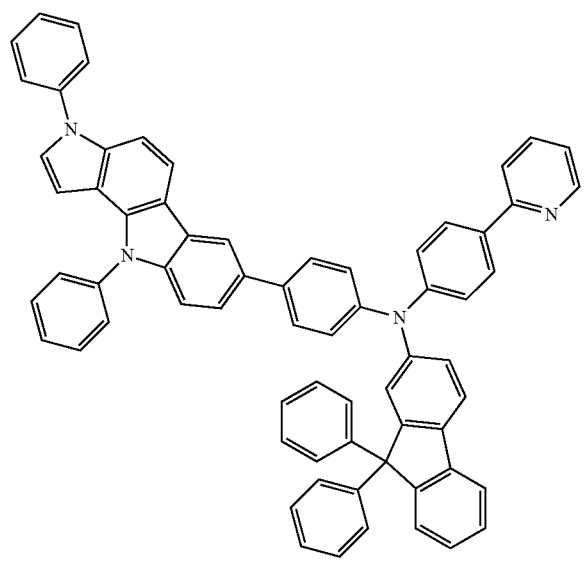
69
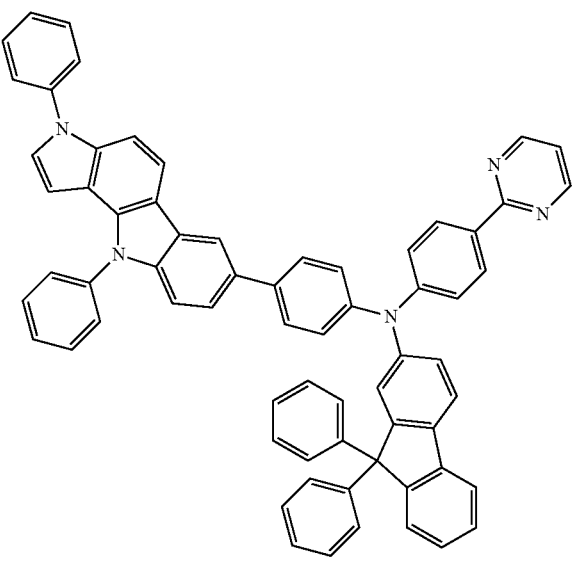
71

72
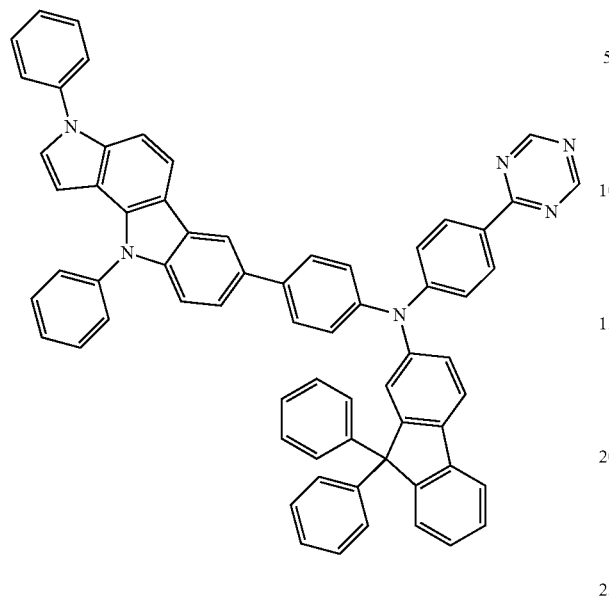
73
74
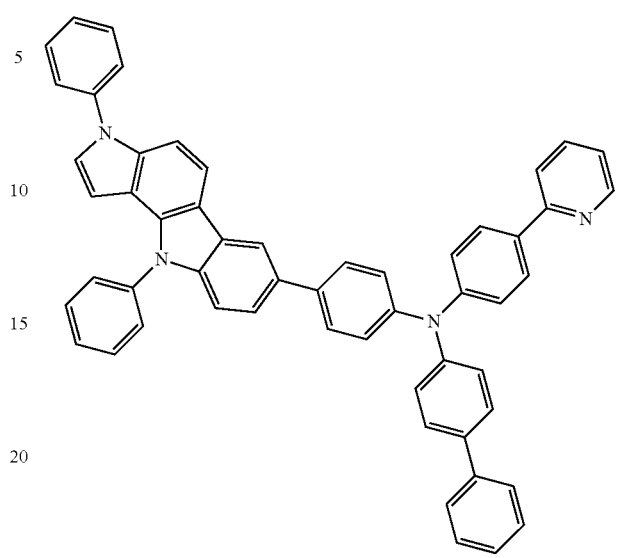
75
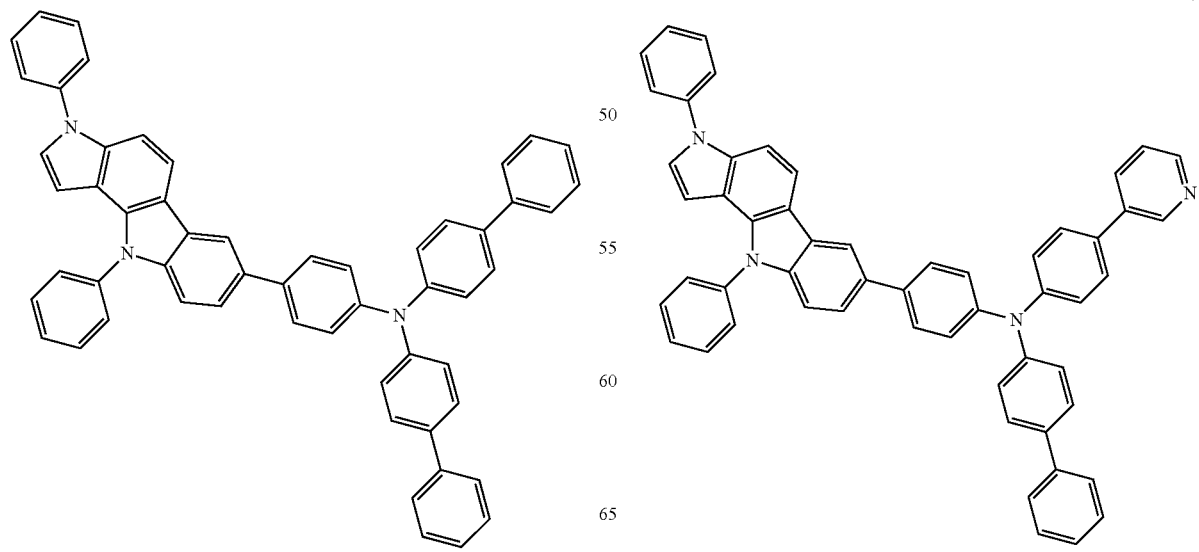

76
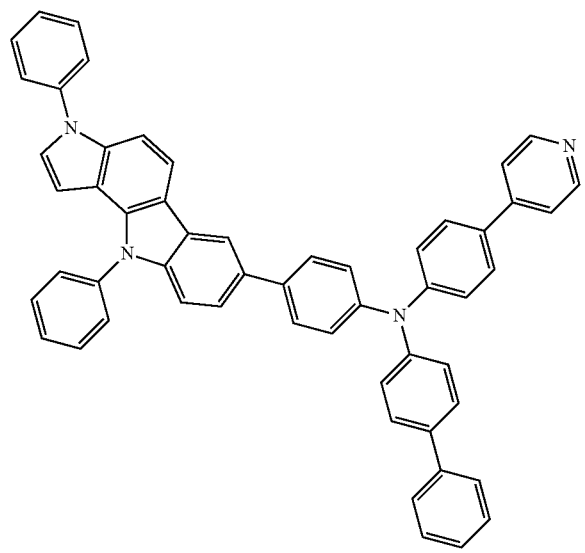
78
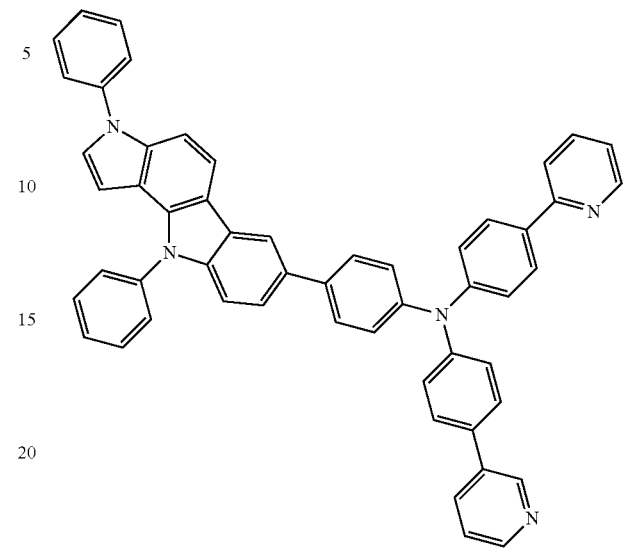
77
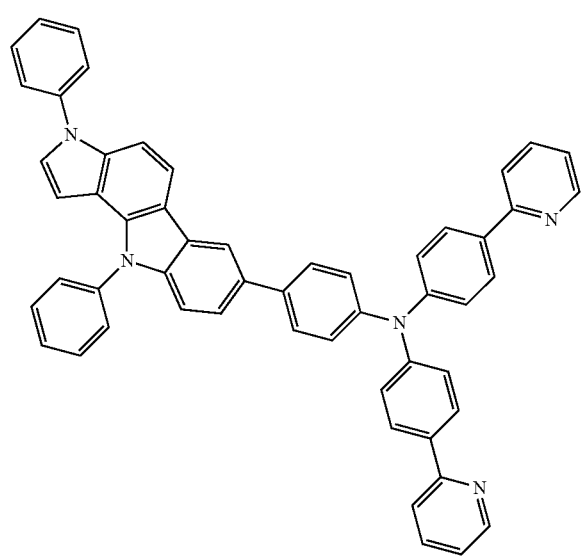
79
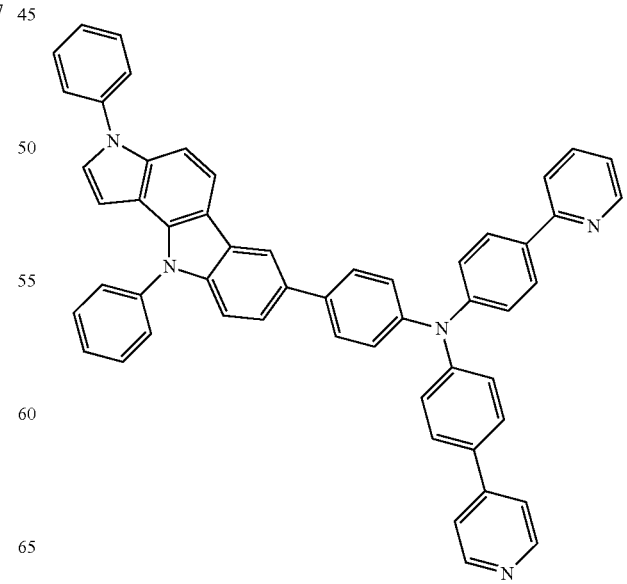

-continued
80
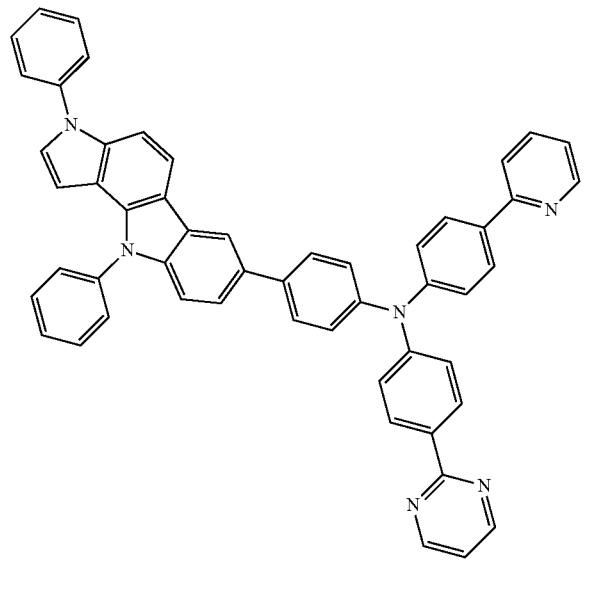
81
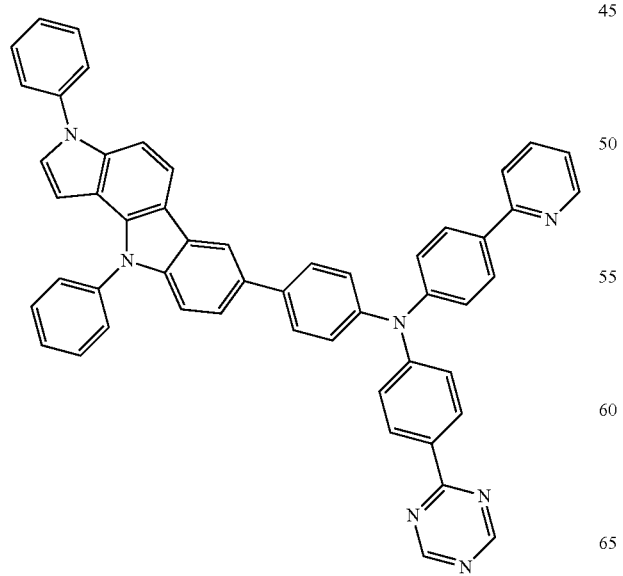
82
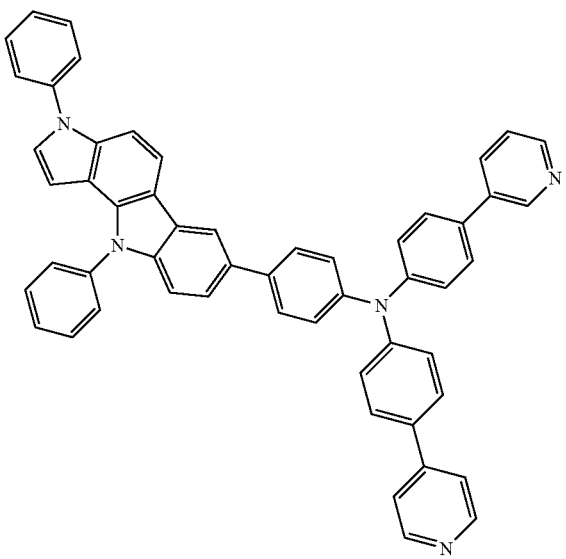
83
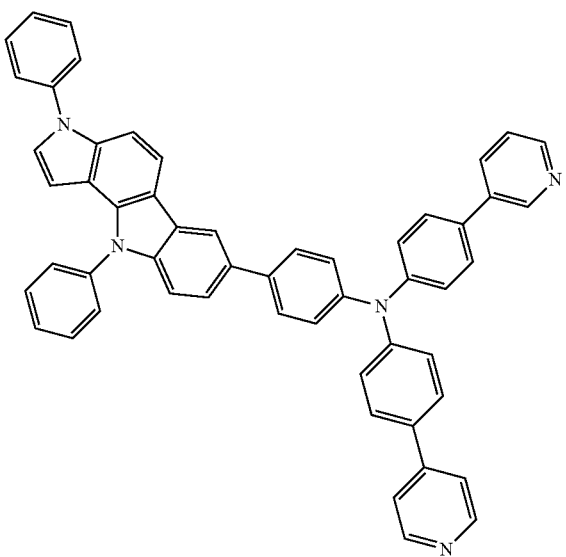

84
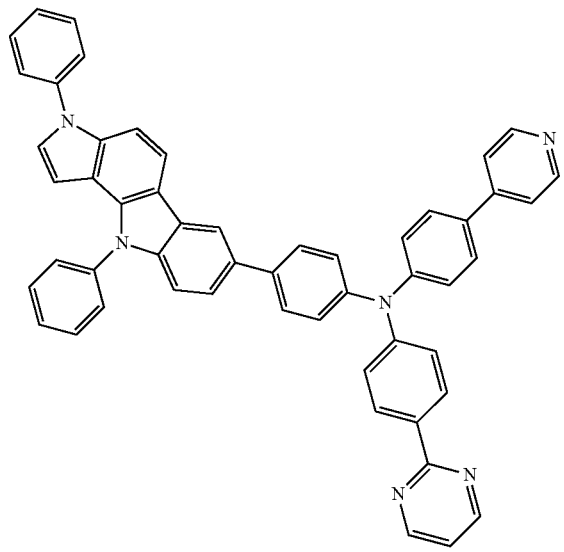
85
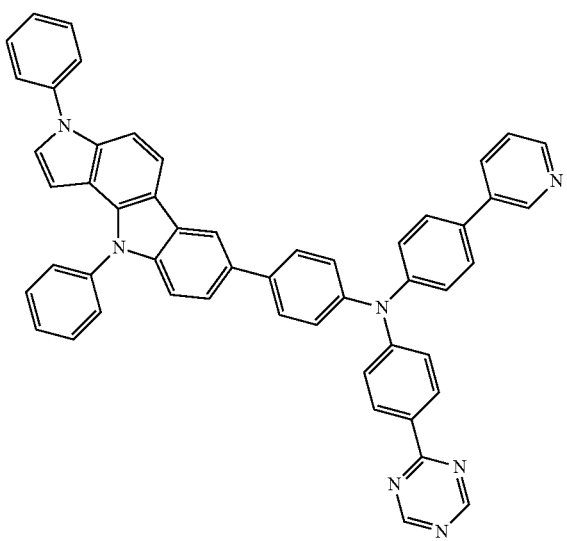
86
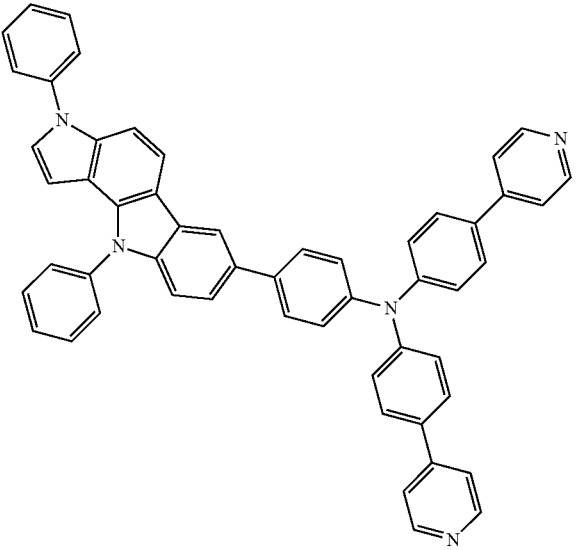
87

101
-continued
88
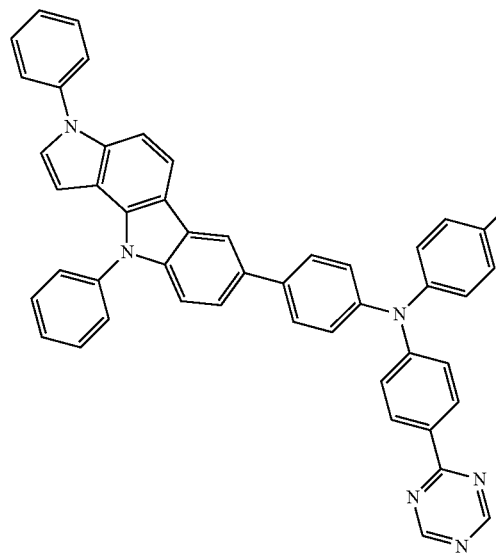
89
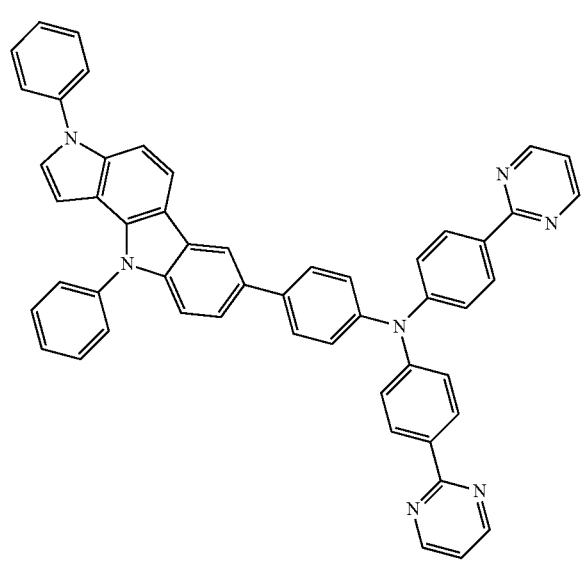
102
-continued
90
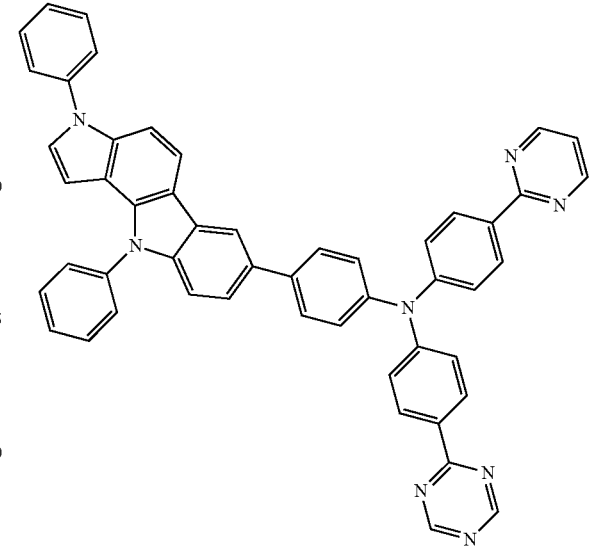
91
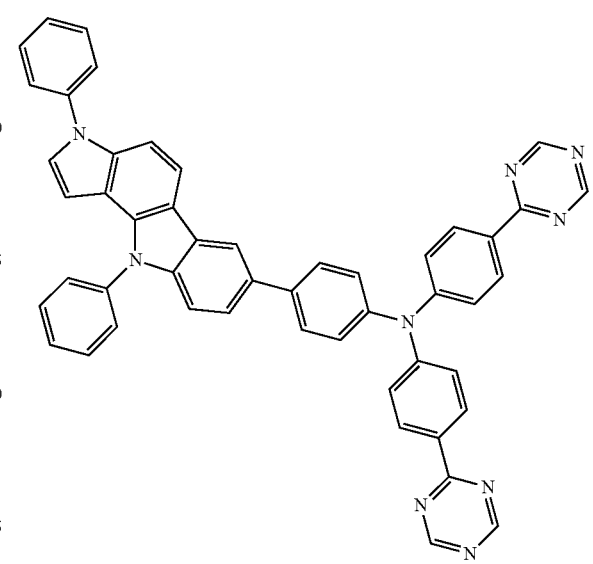

103
-continued
92
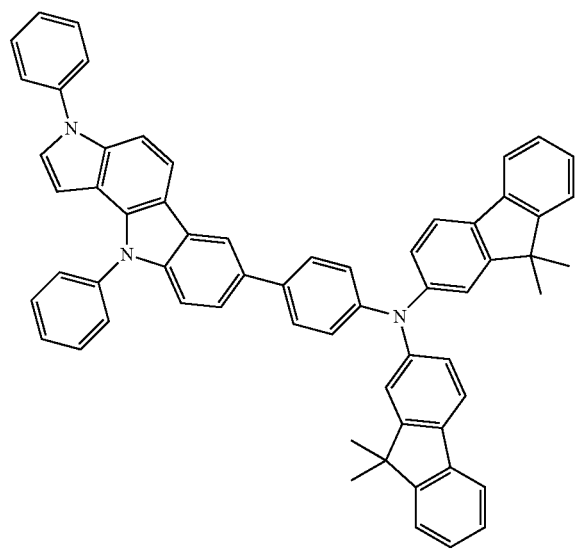
93
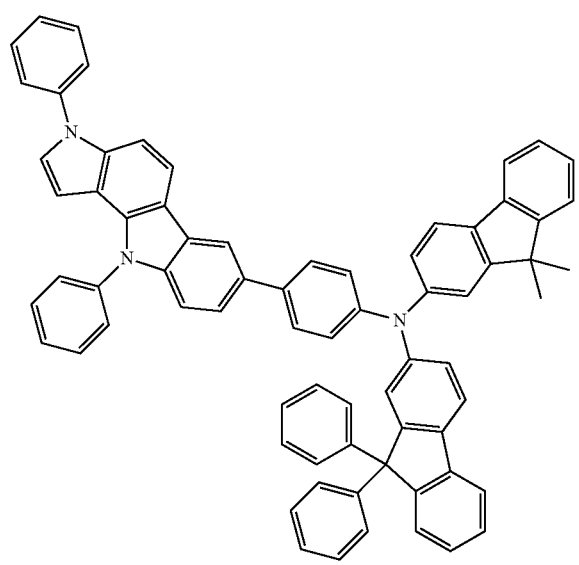
94
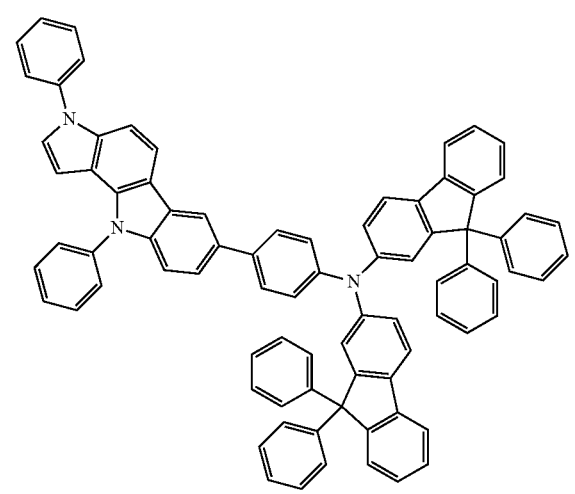
104
-continued
95
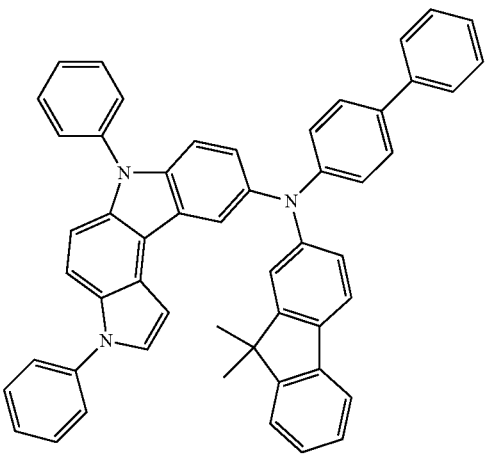
96
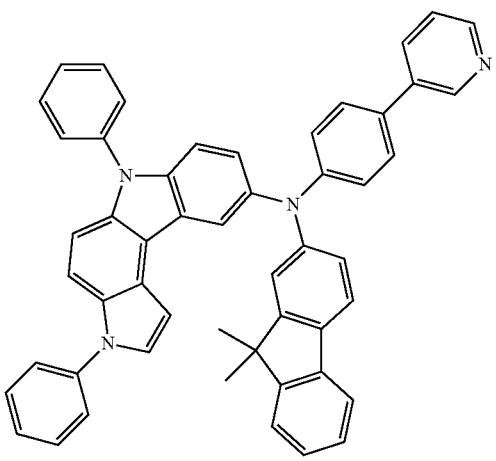
97
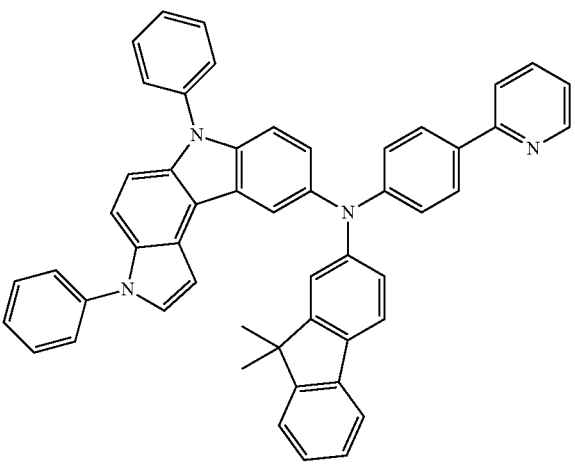

98
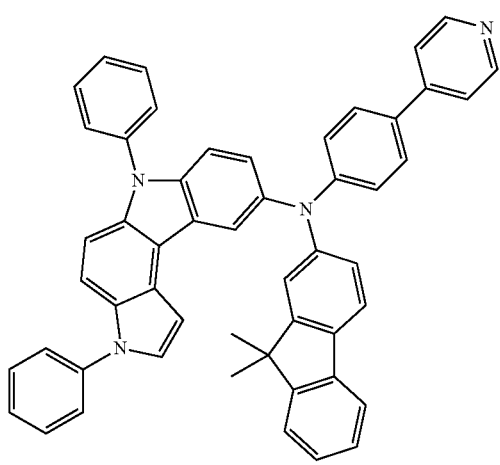
99
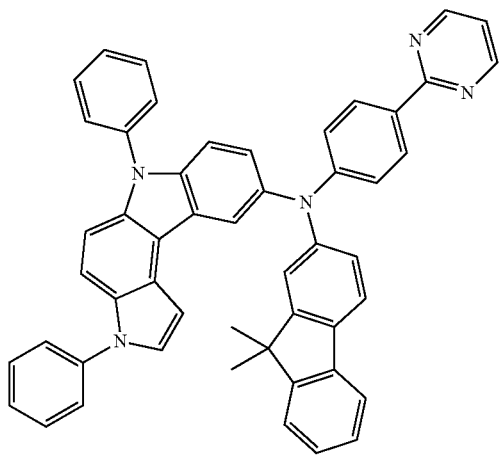
100
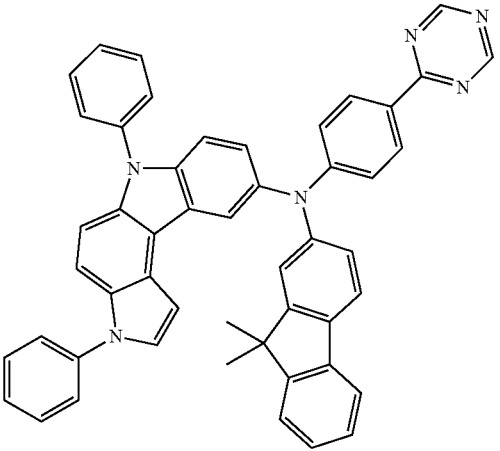
101
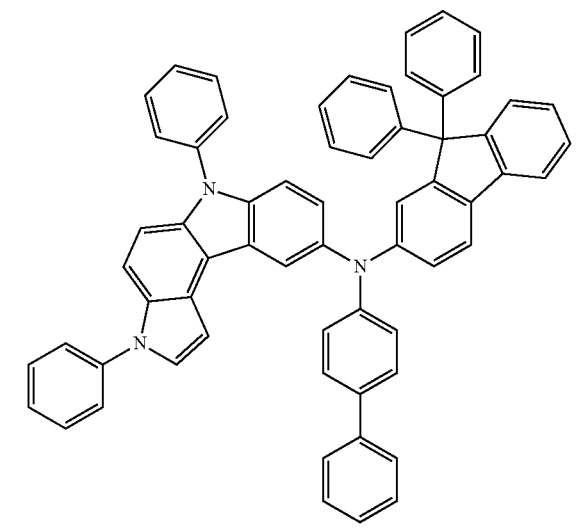
102
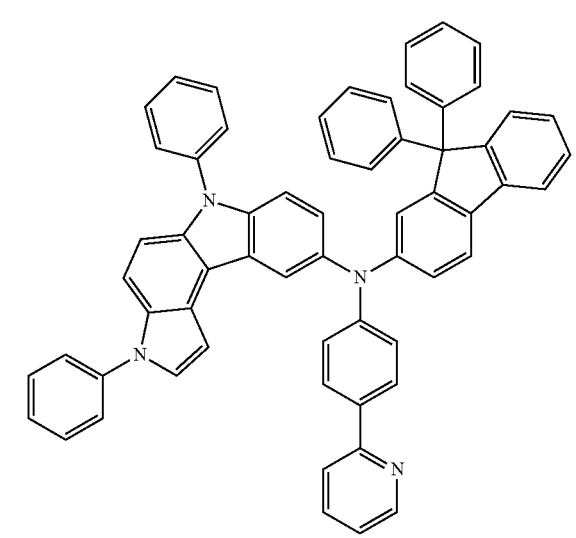
103
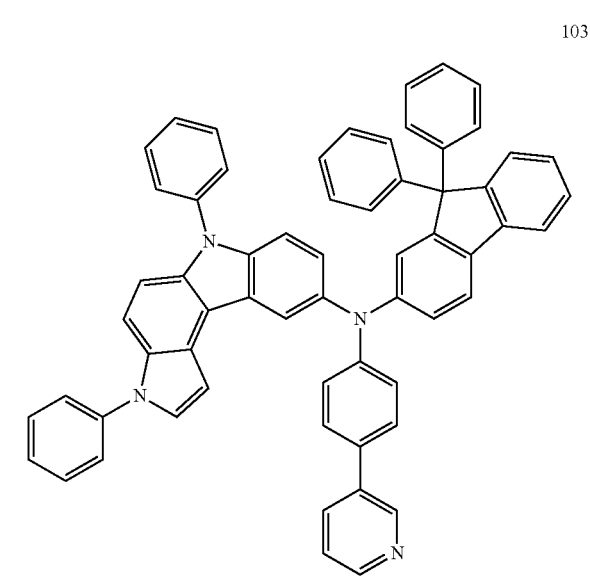

104
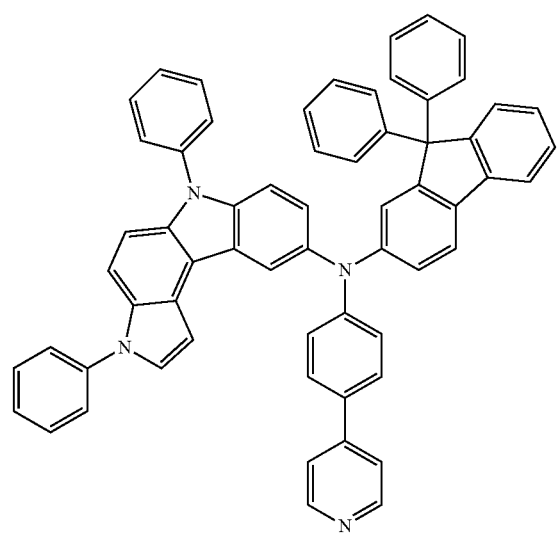
105
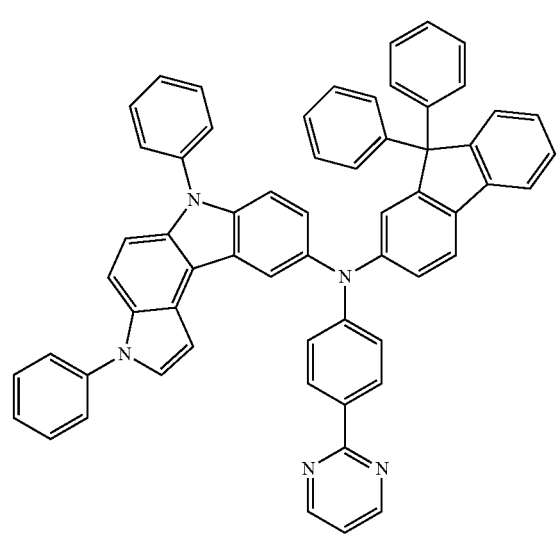
106
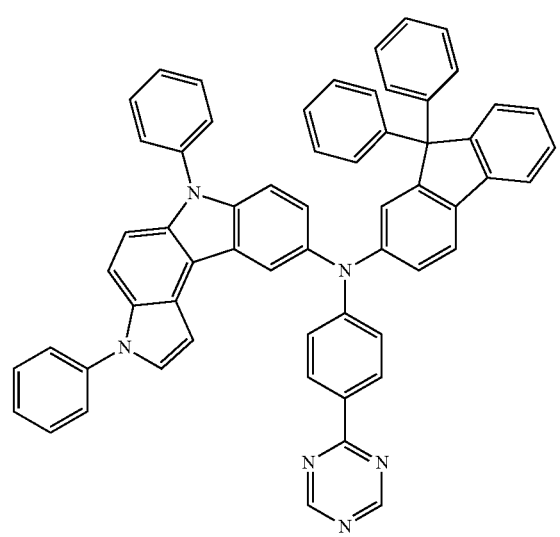
107
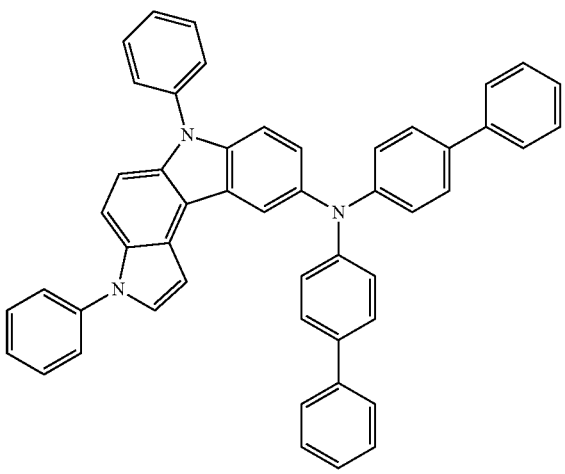
108
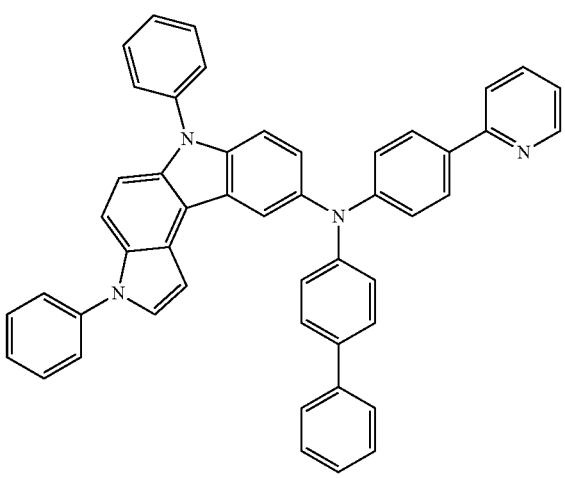
109
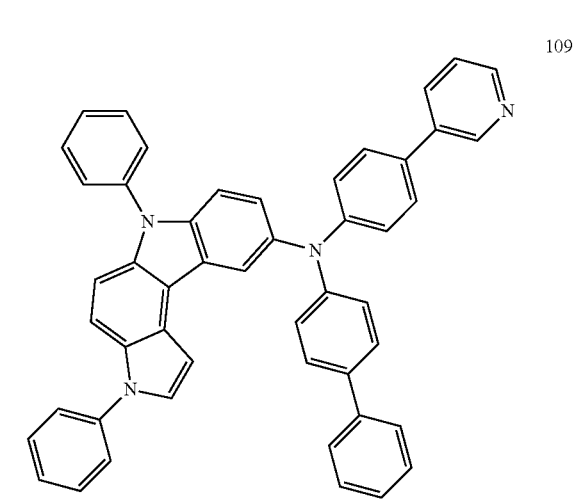

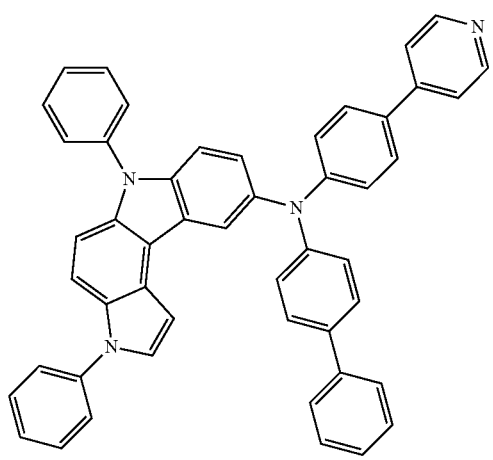
110
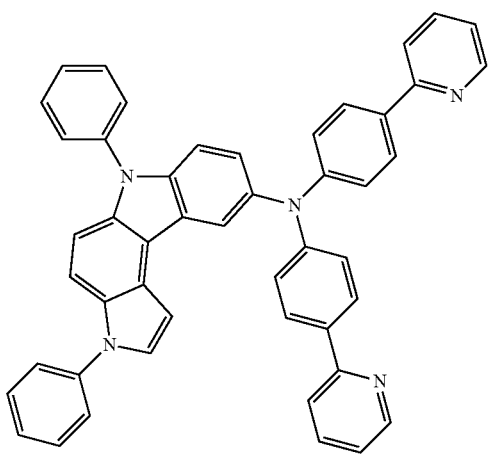
113
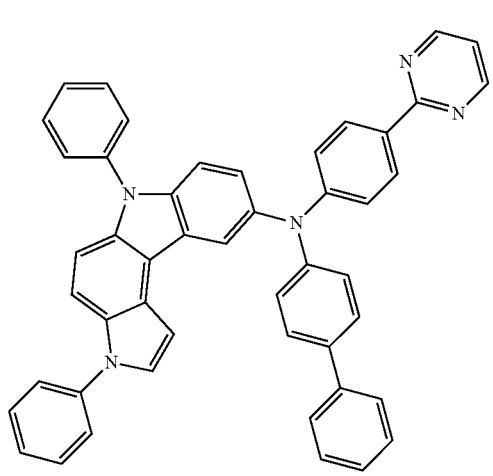
111
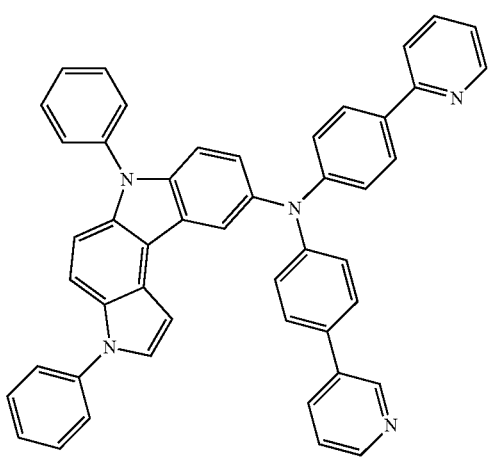
114
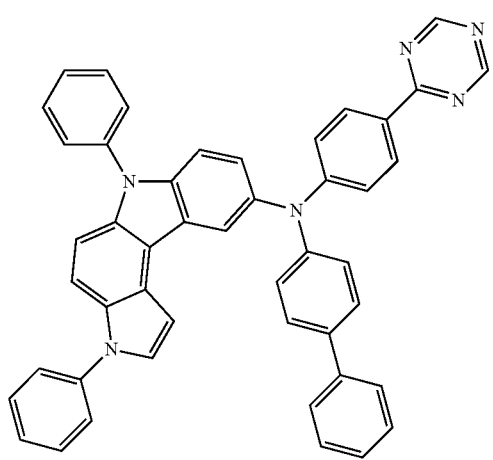
112

-continued
116
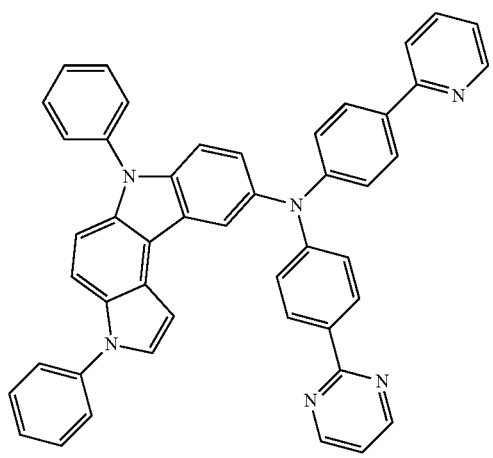
117
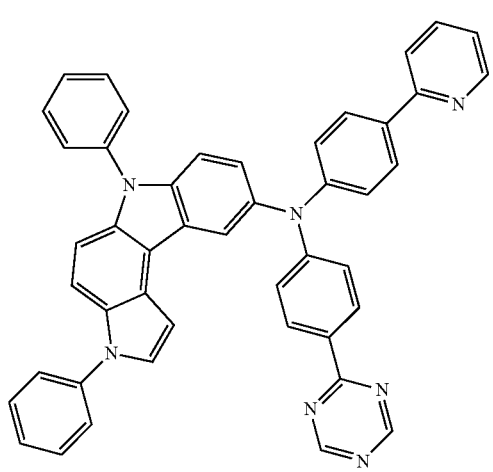
118
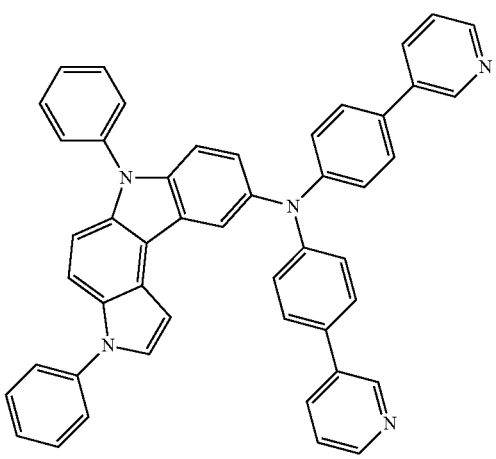
-continued
119
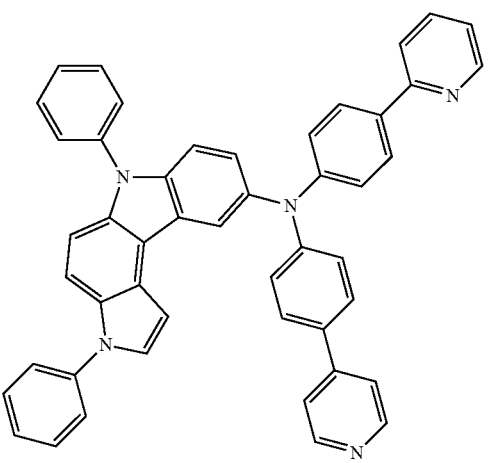
120
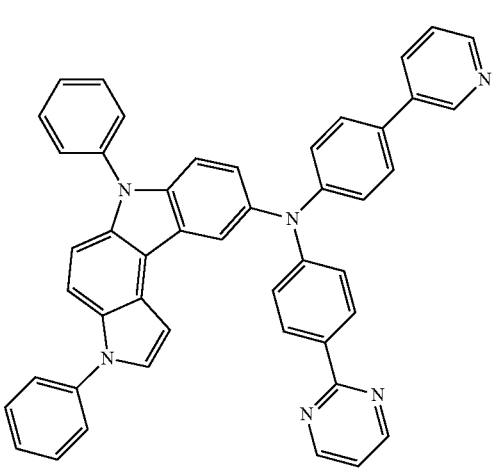
121
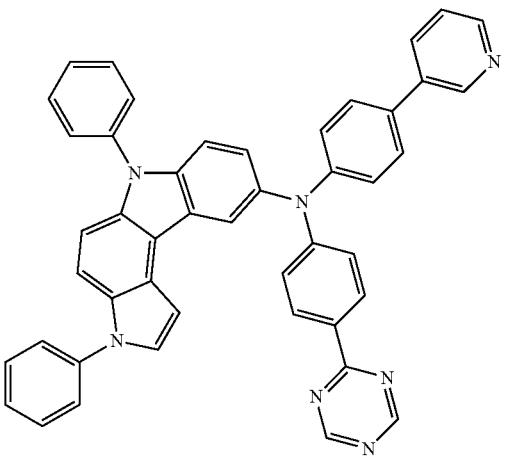

122
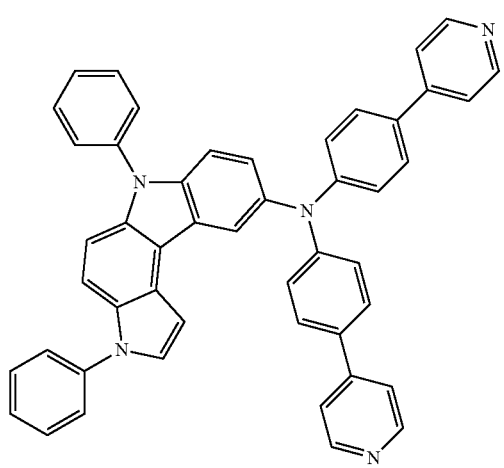
123
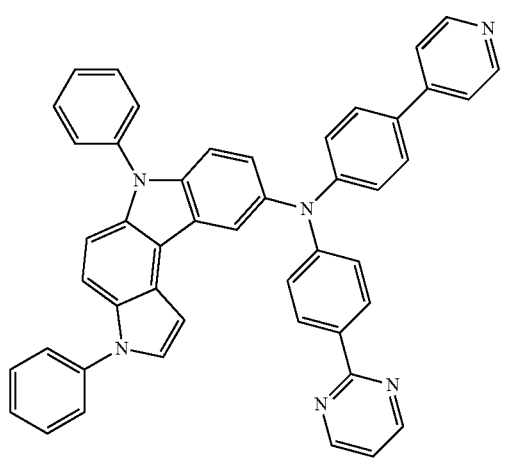
124
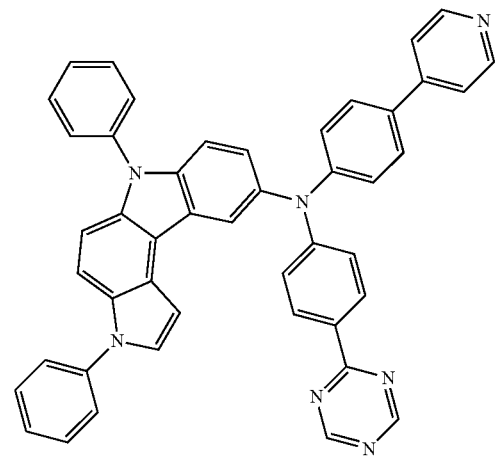
125
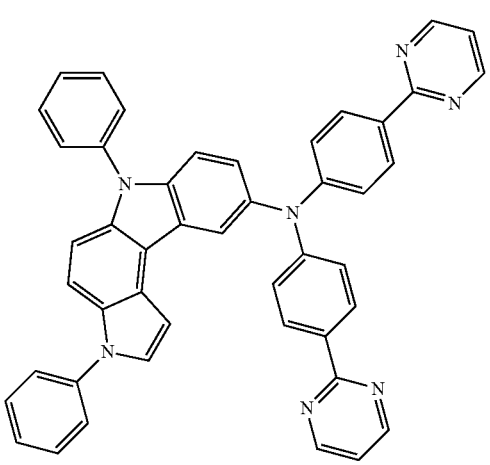
126
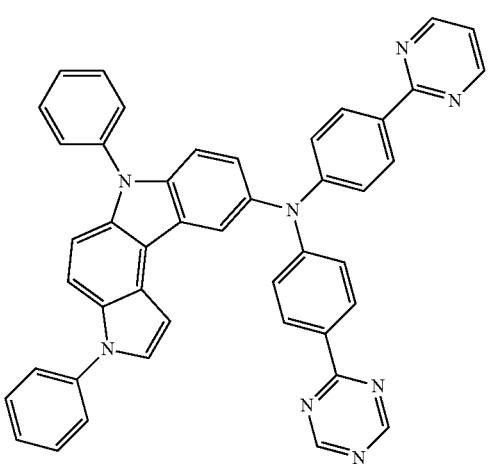
127
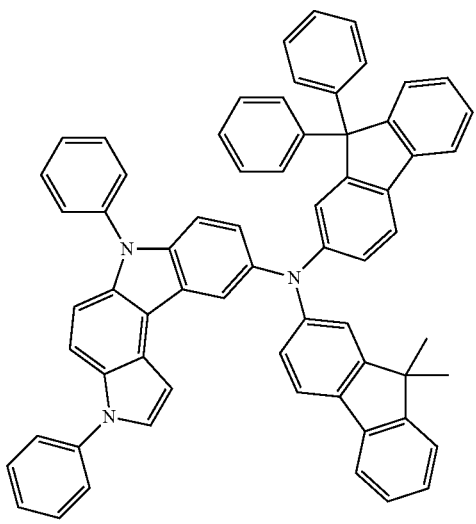

128
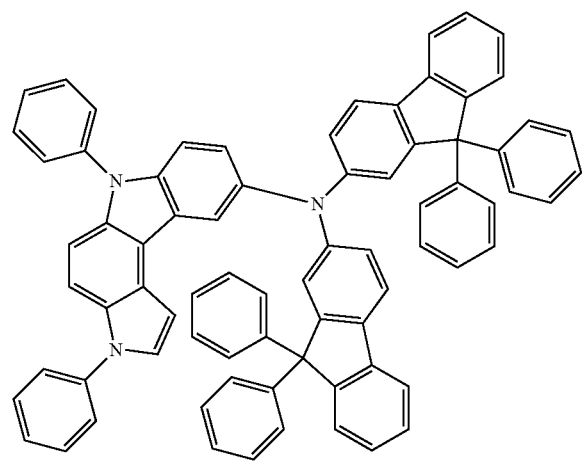
129
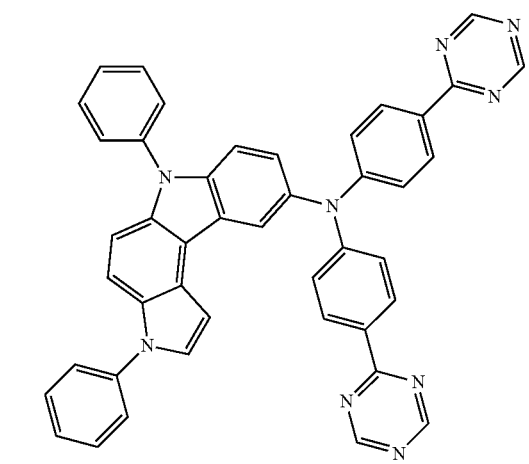
130
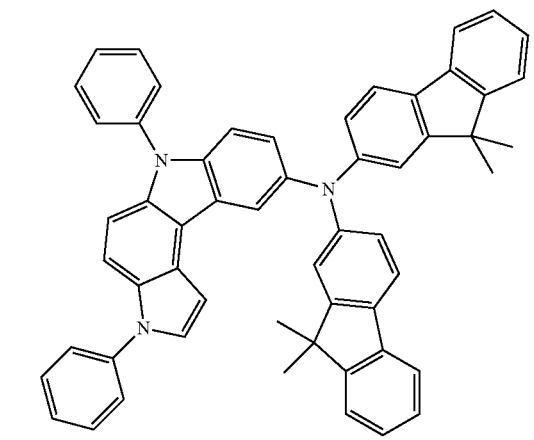
131
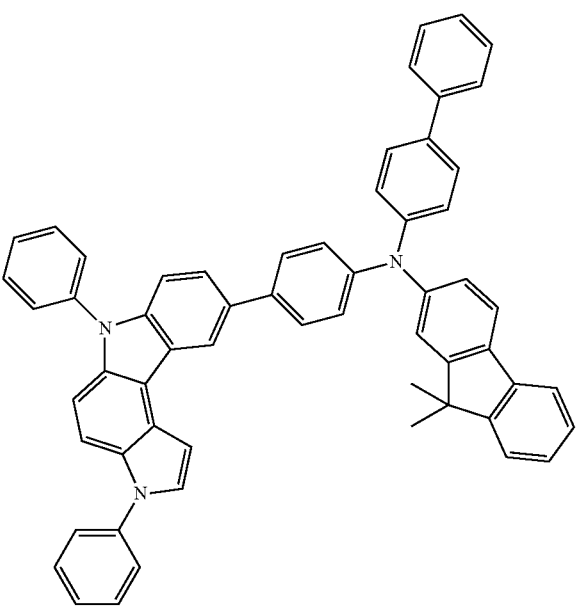
132
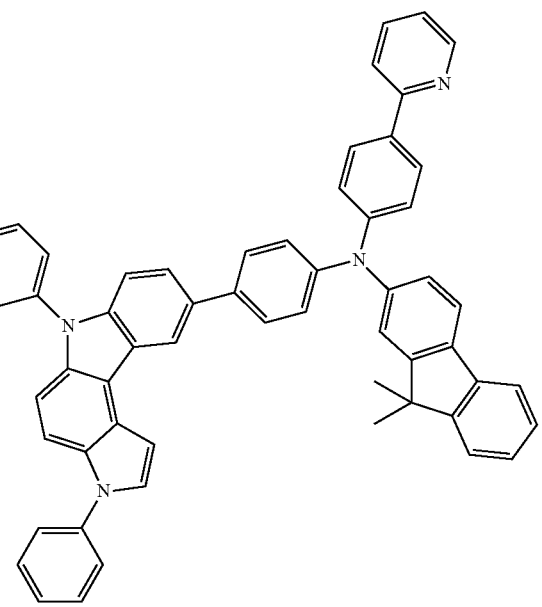

133
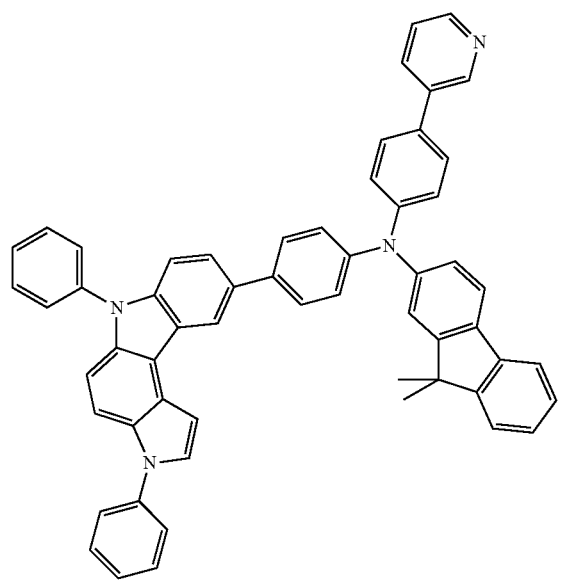
134
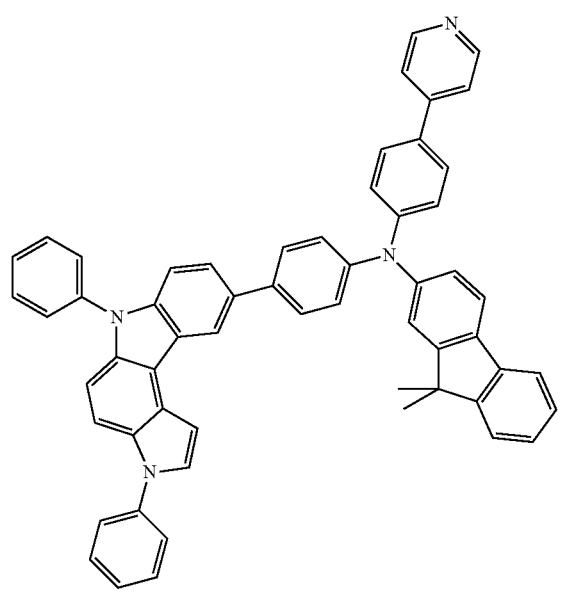
135
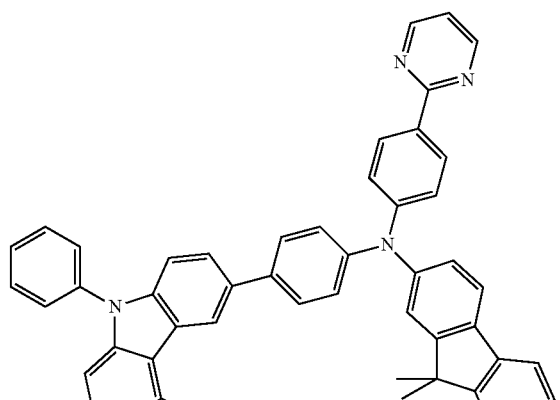
136
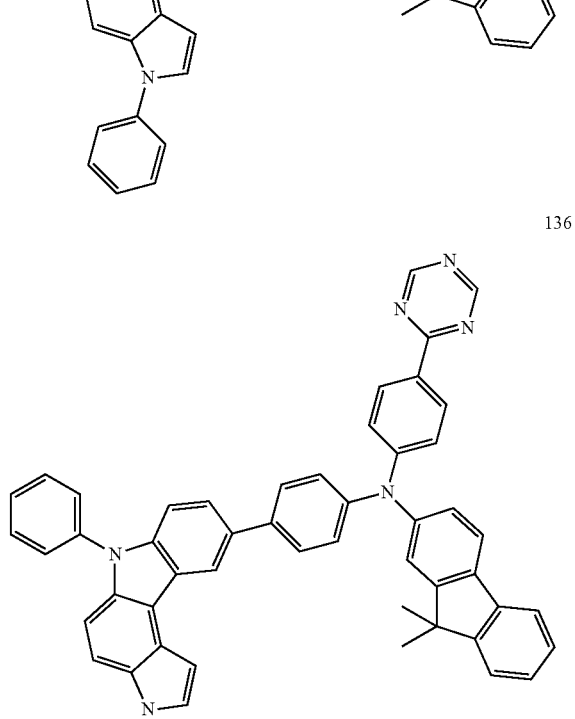
137

-continued
138
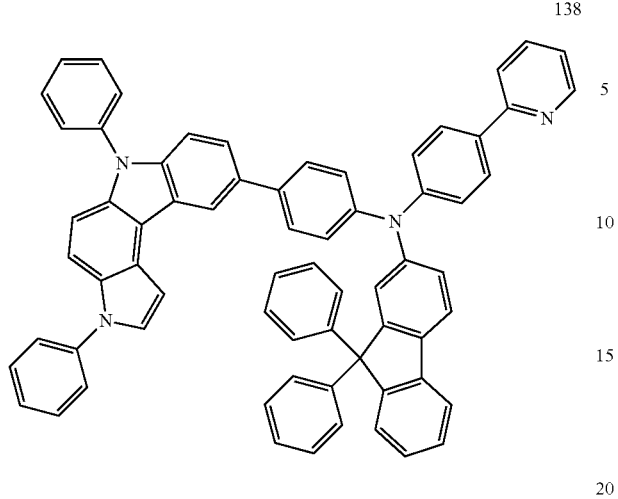
139
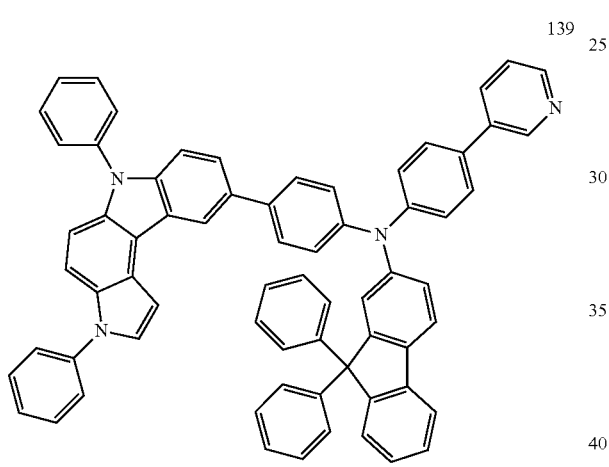
140
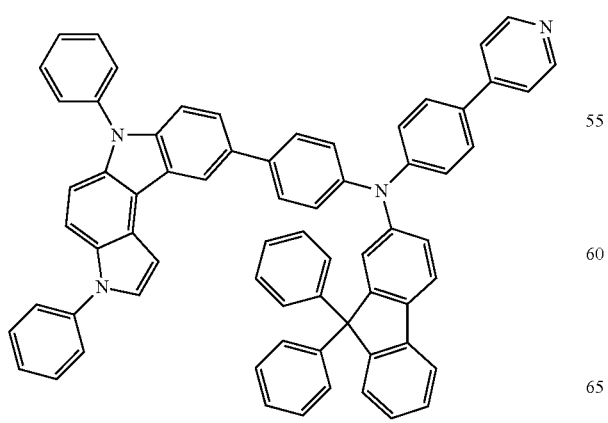
-continued
141
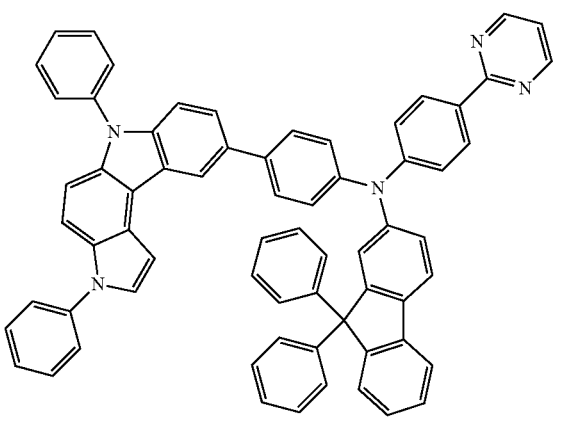
142
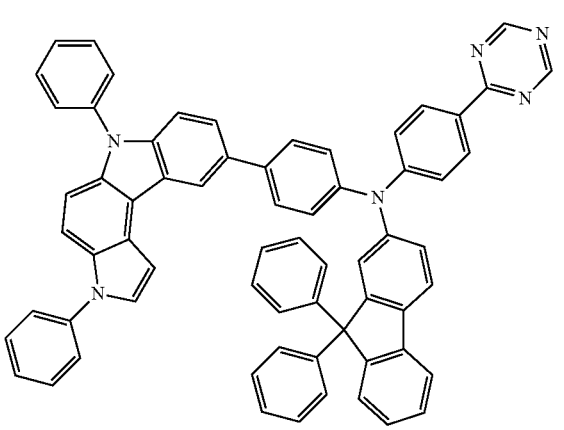
143
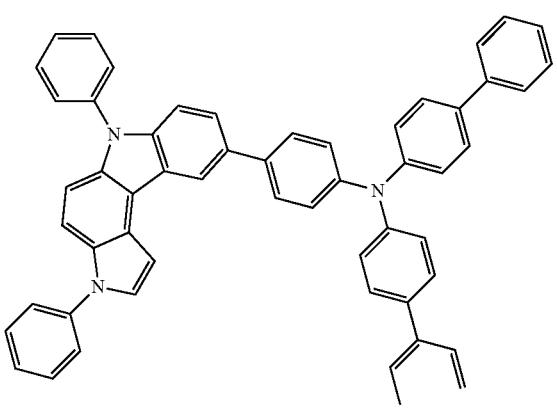

-continued
144
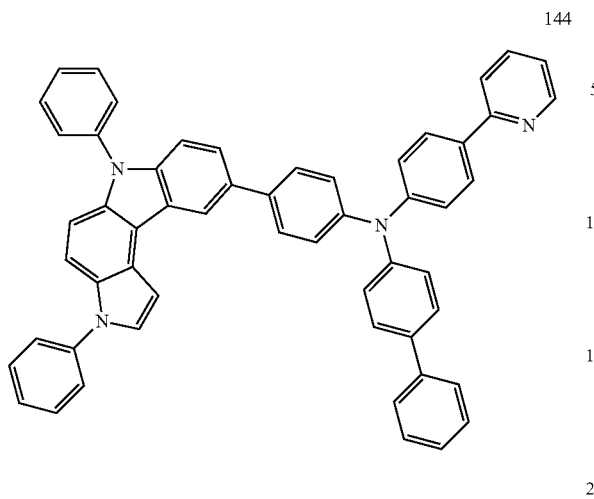
145
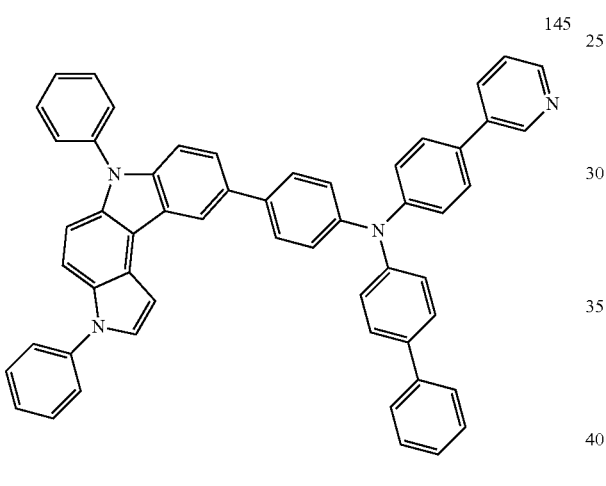
146
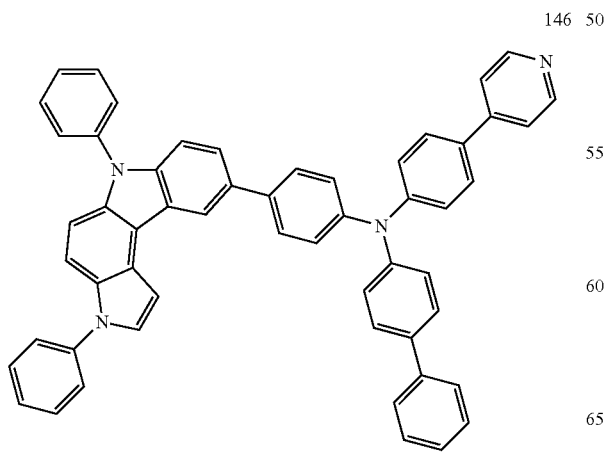
-continued
147
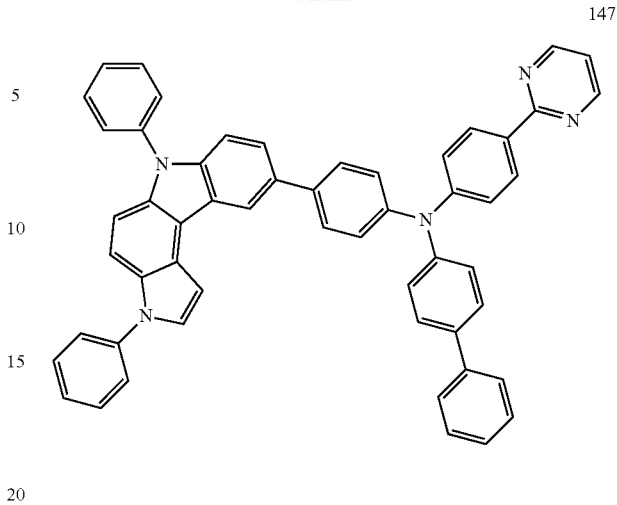
148
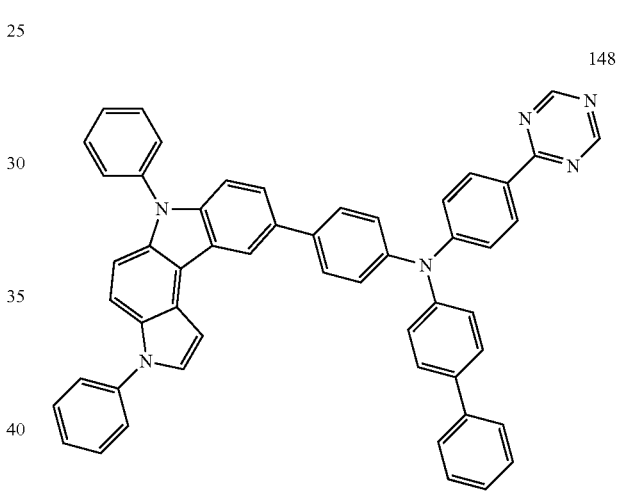
149
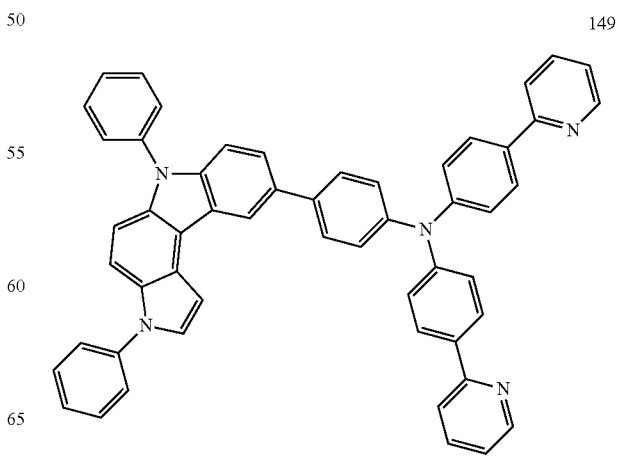

150
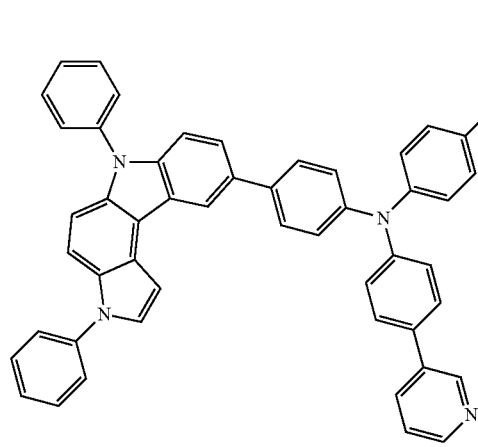
151
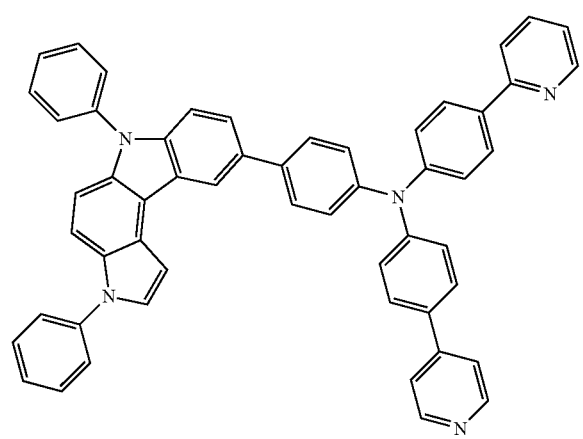
152
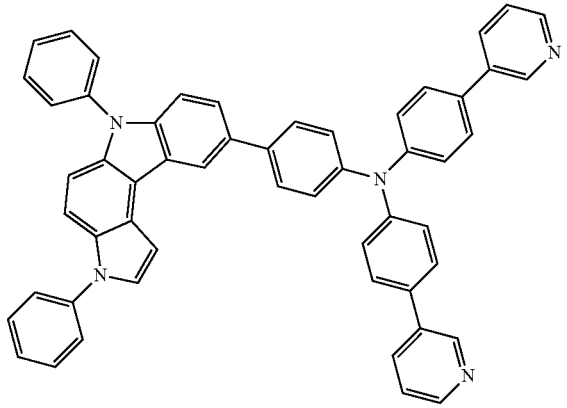
153
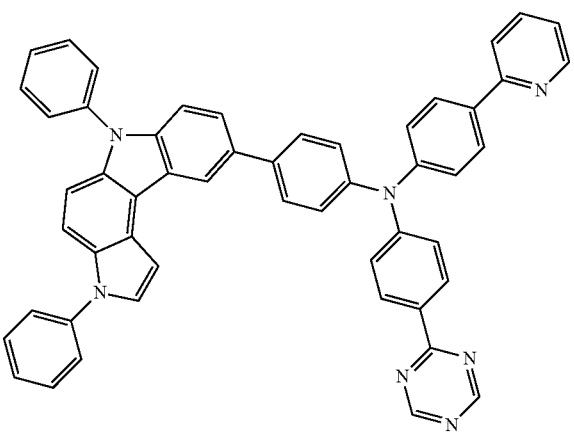
154
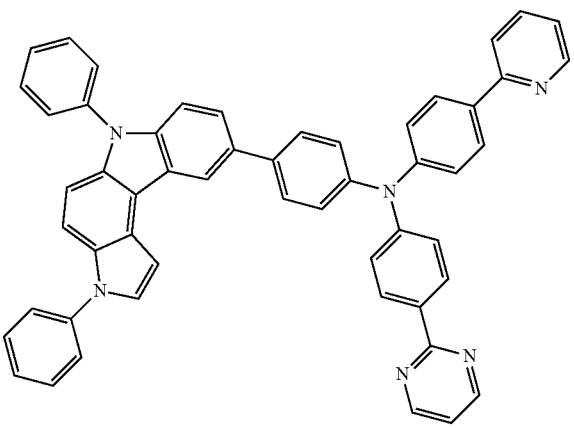
155
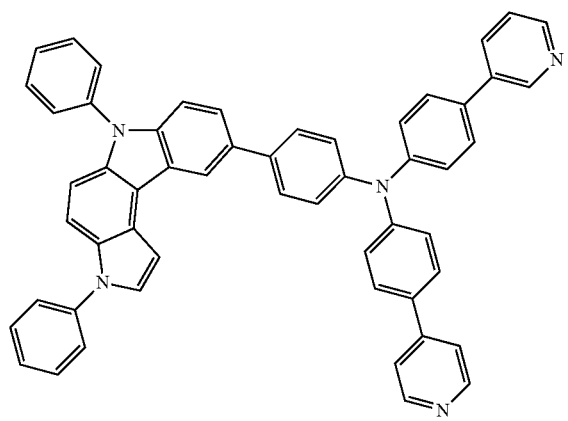

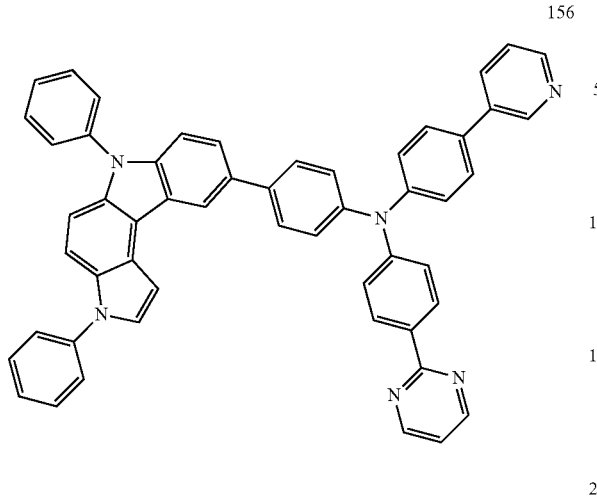
156
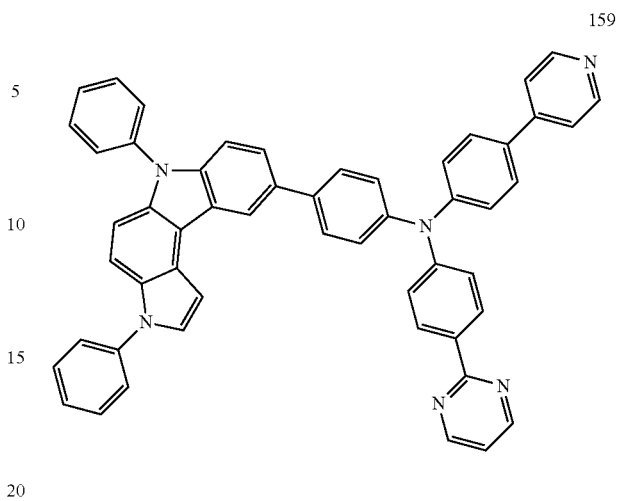
159
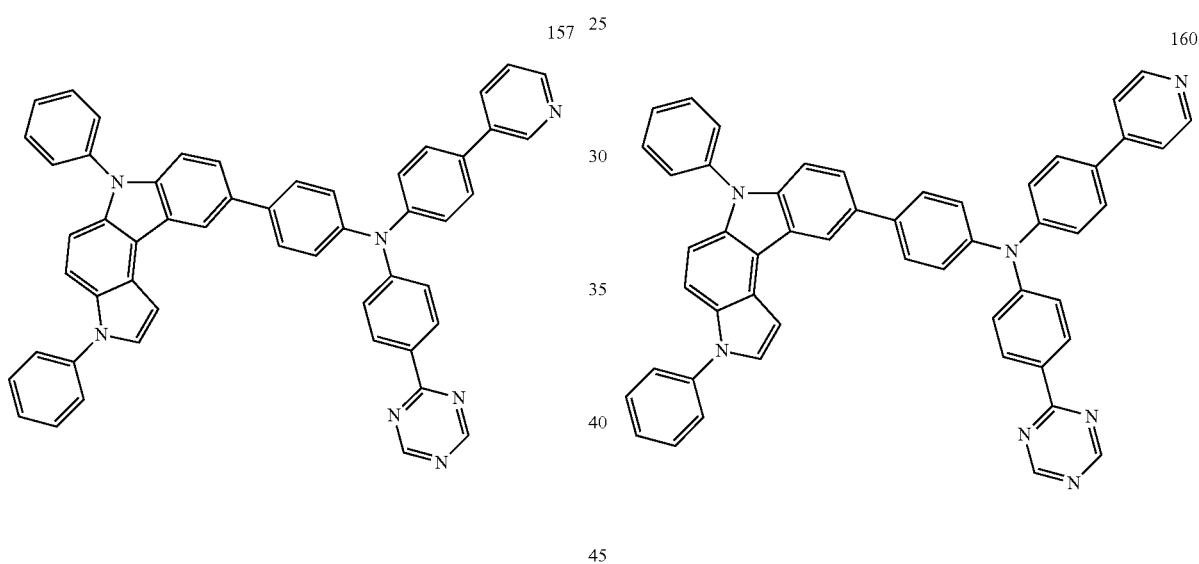
157
160
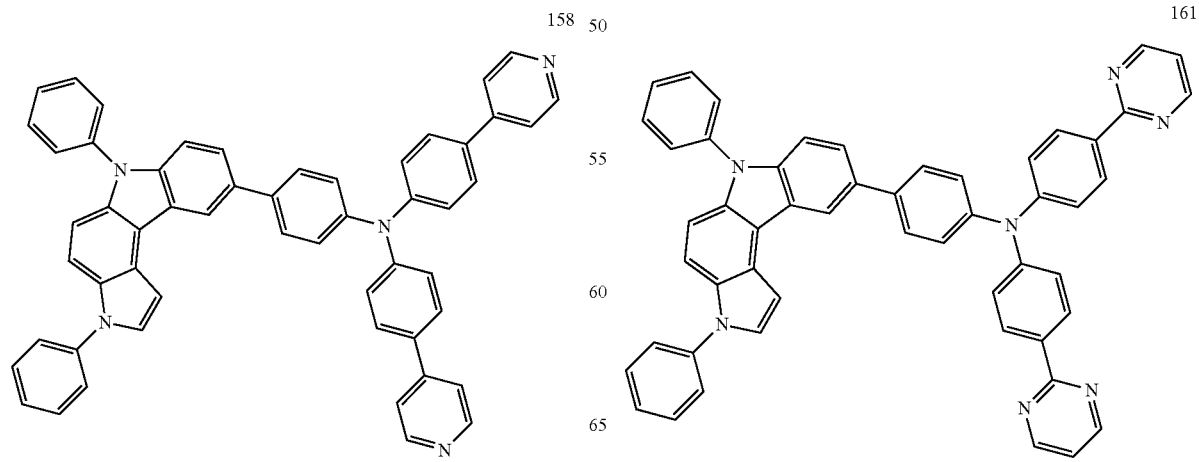
158
161

162
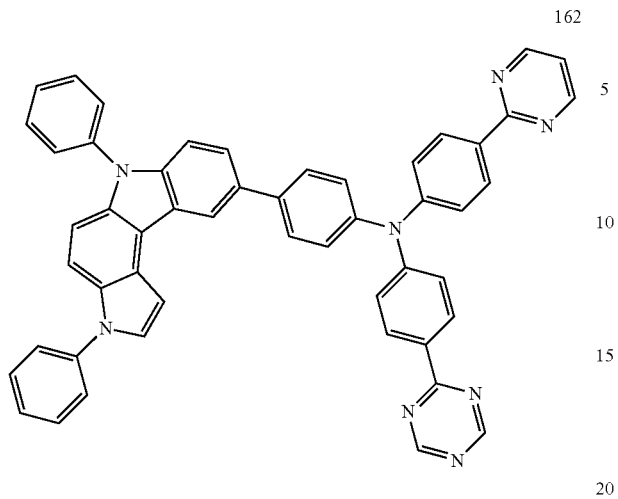
165
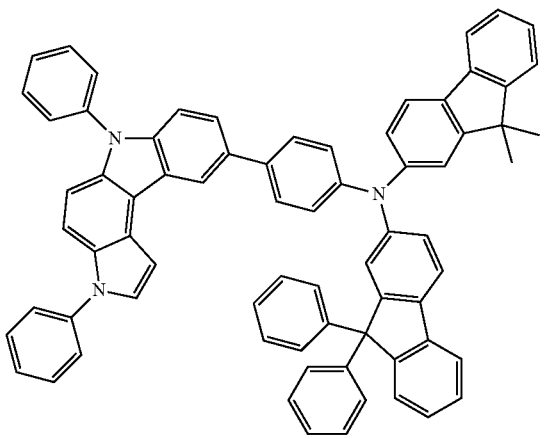
163
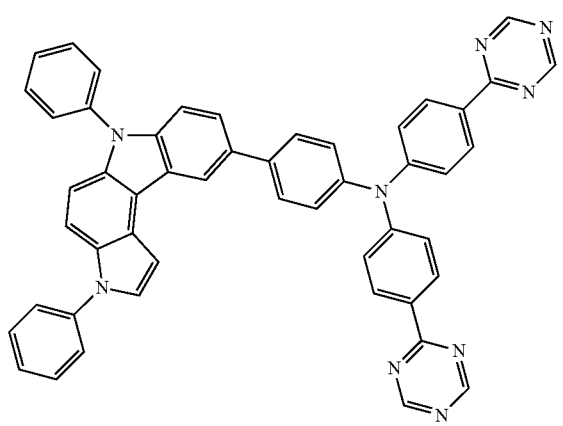
166
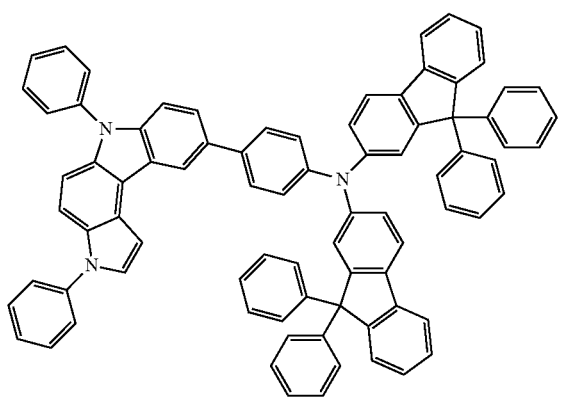
164
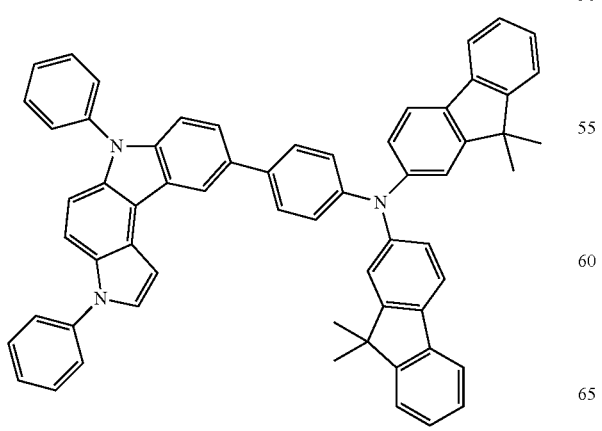
167
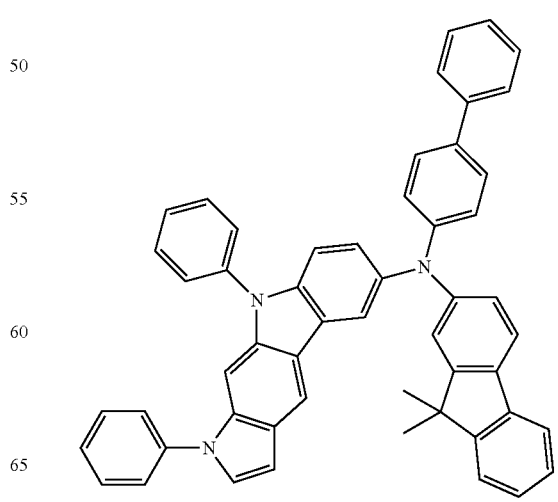

-continued
168
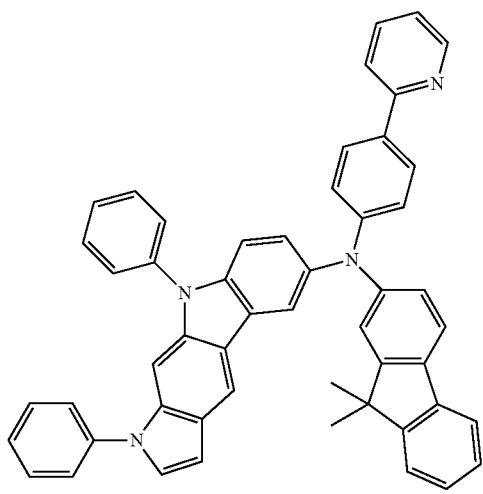
169
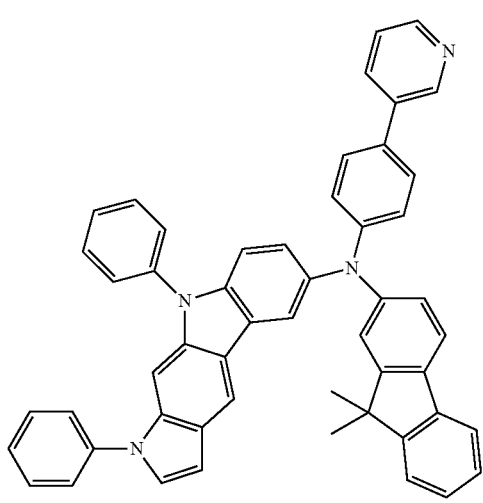
170
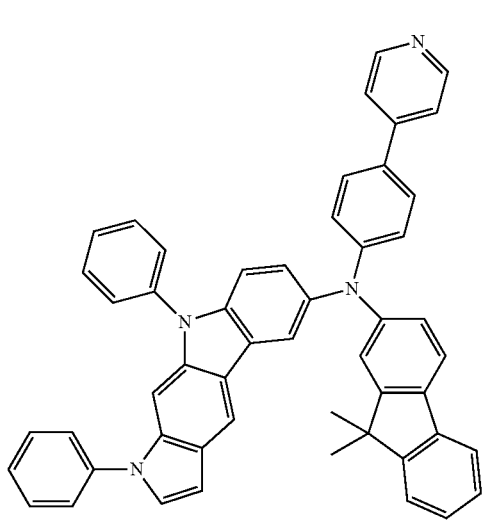
-continued
171
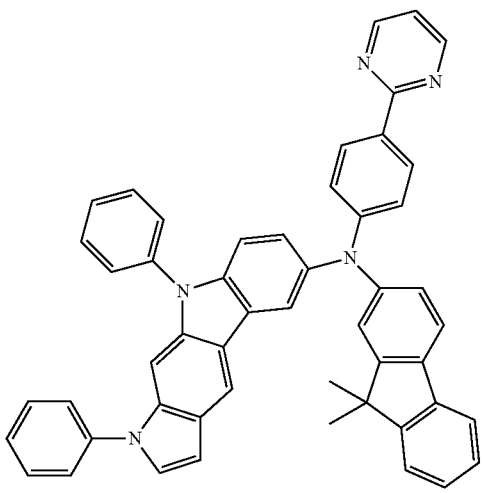
172
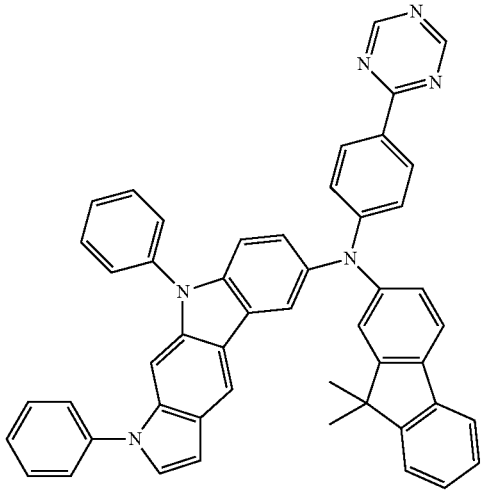
173
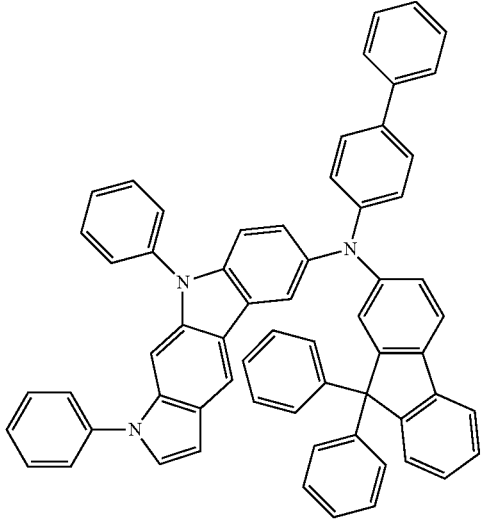

-continued
174
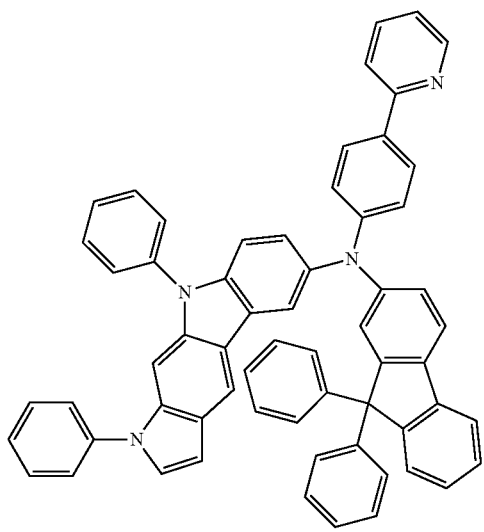
175
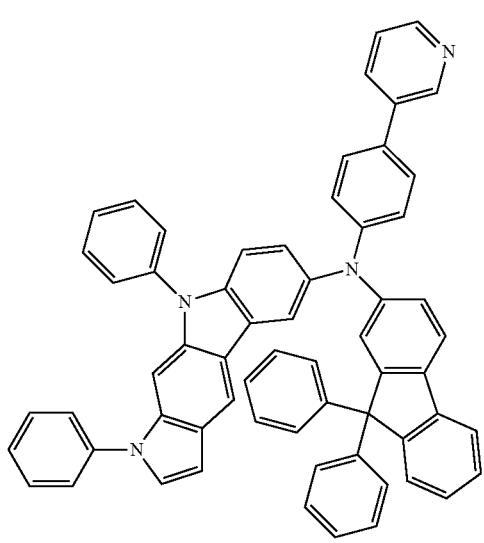
176
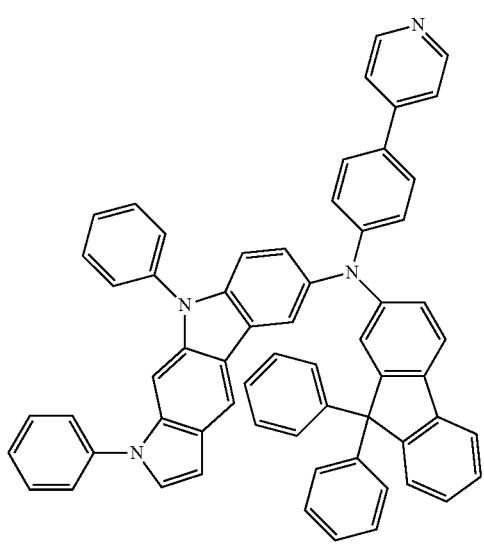
-continued
177
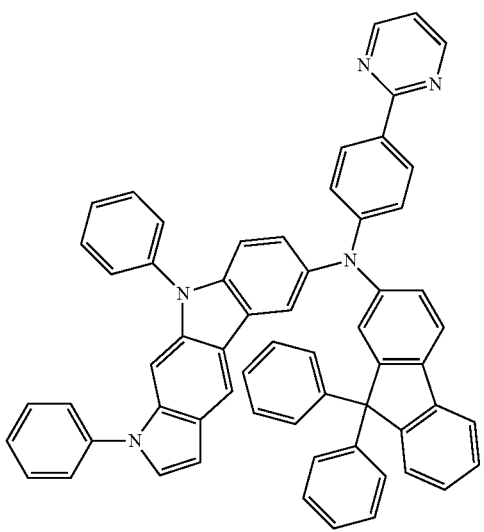
178
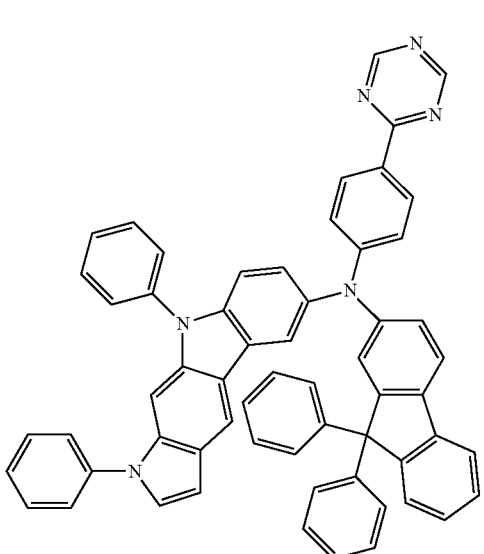
179
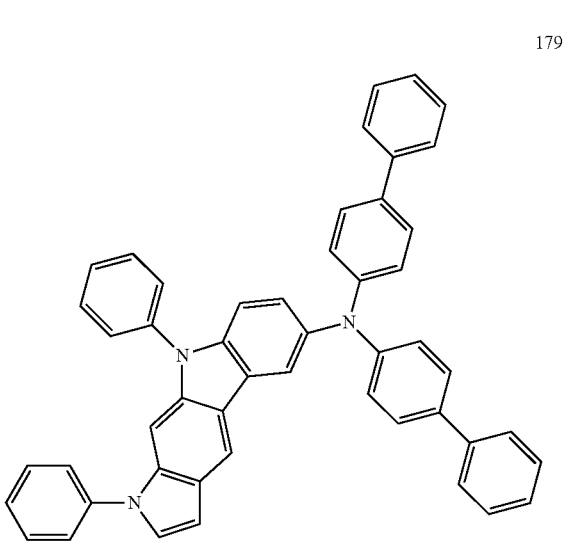

180
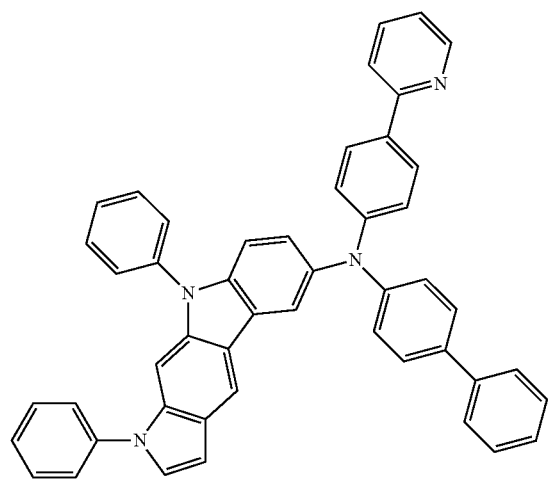
183
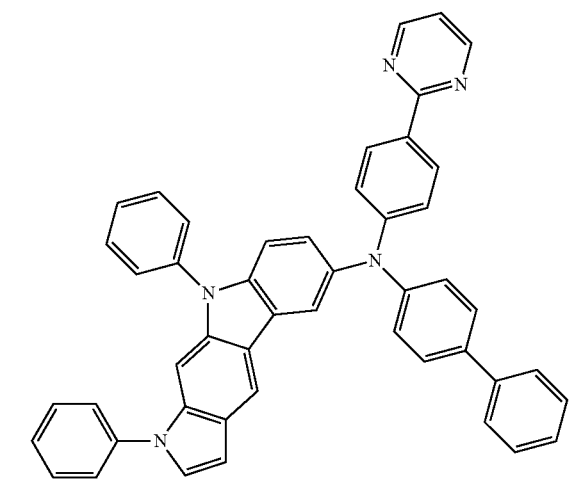
181
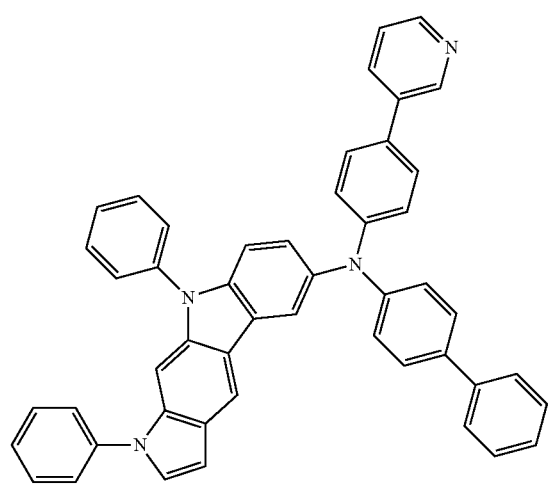
184
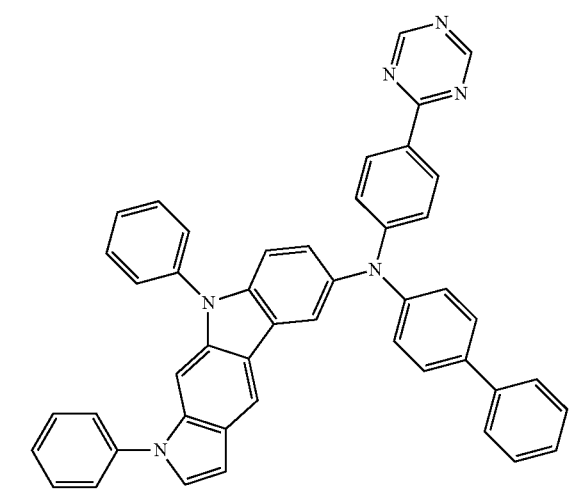
182
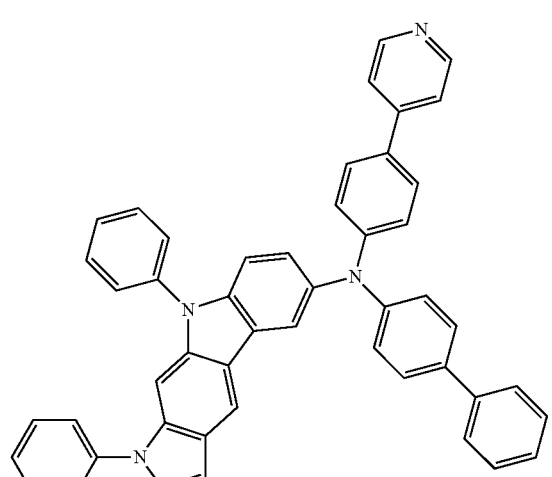
185
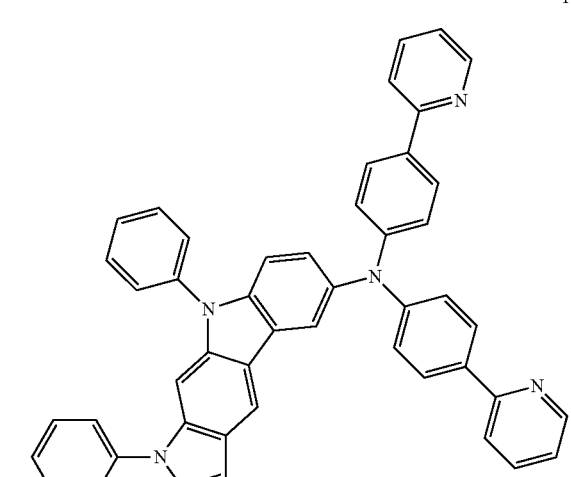

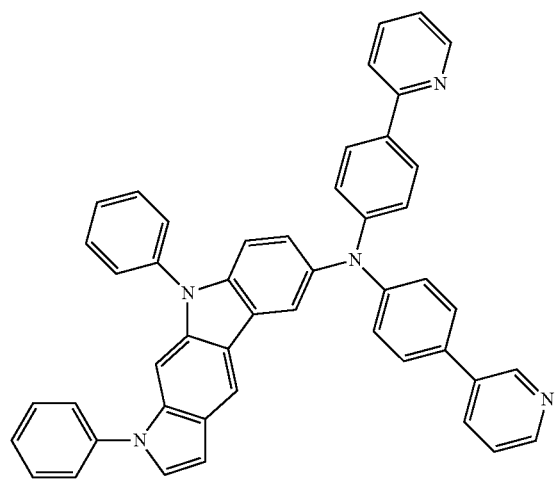
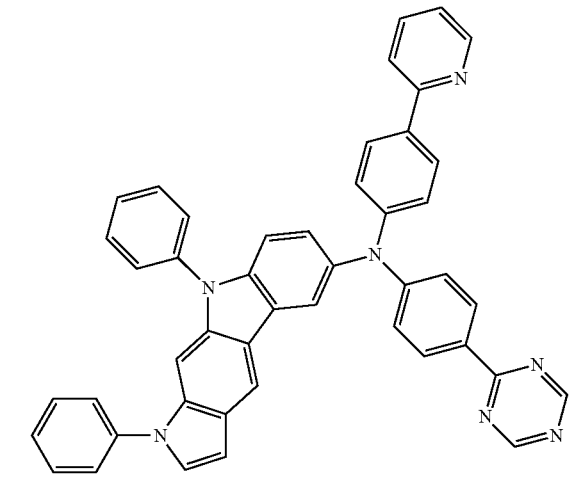
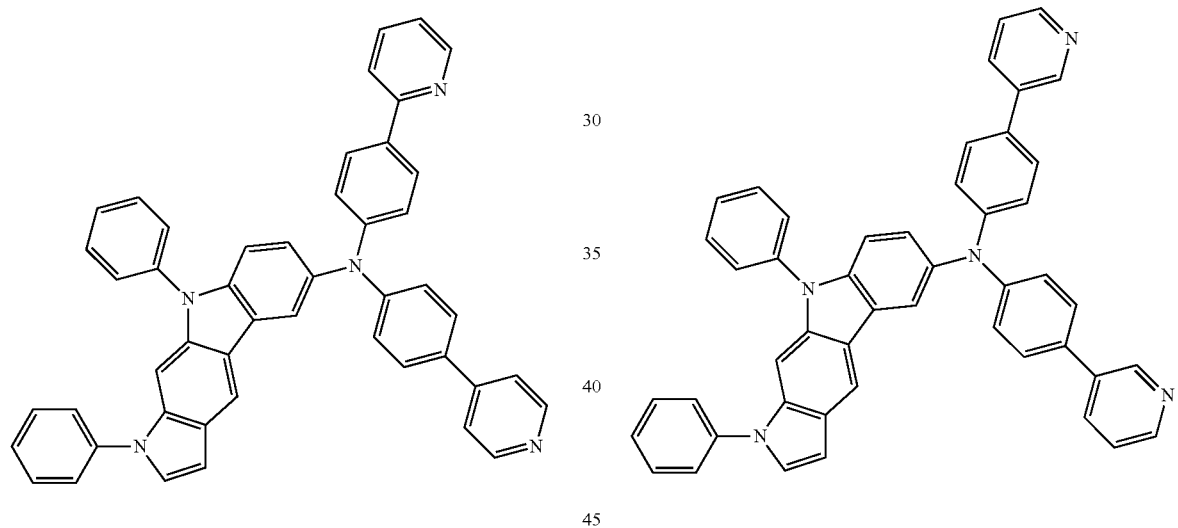
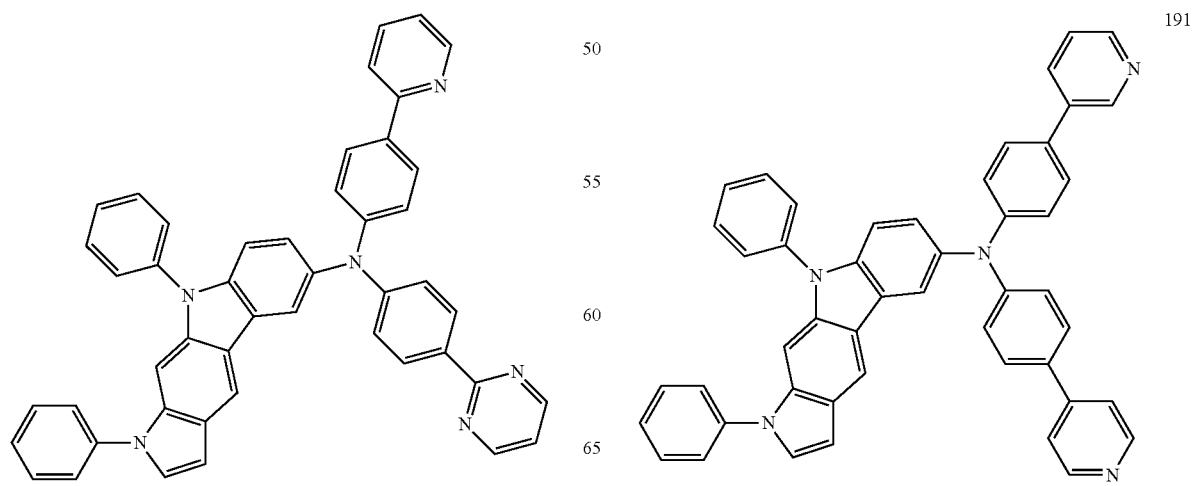

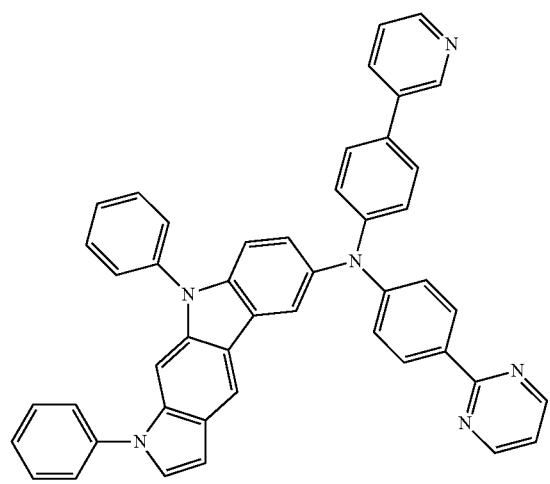
192
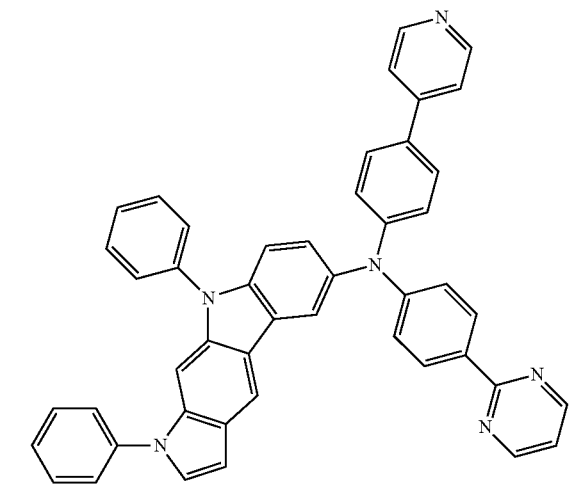
195
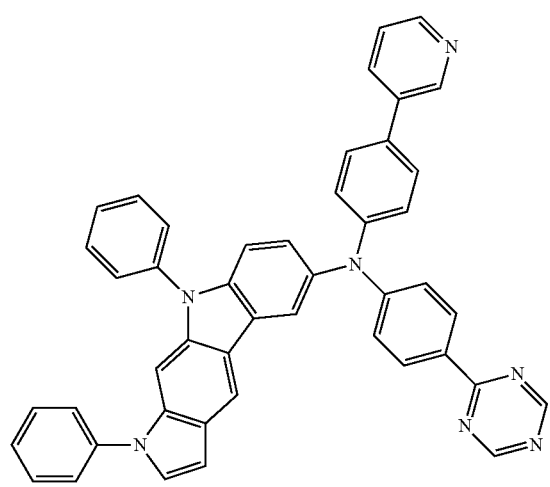
193
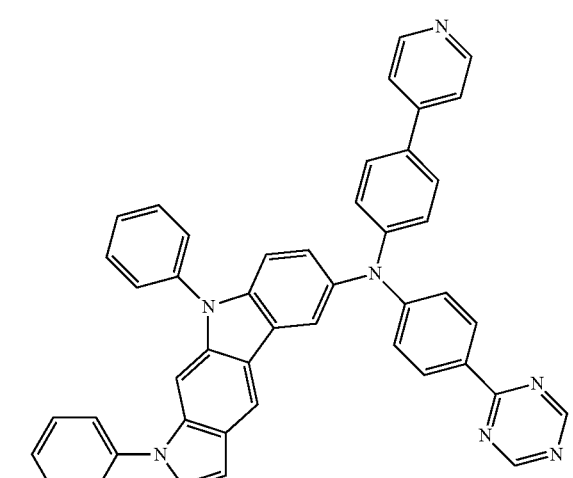
196
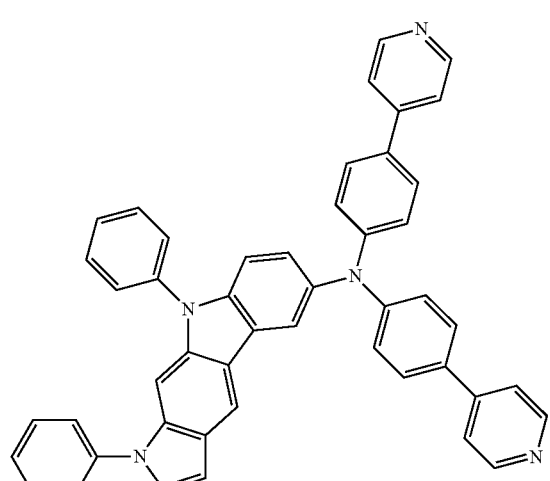
194
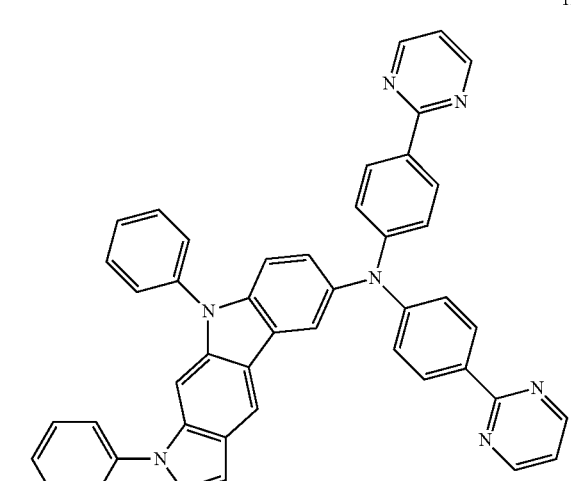
197

198
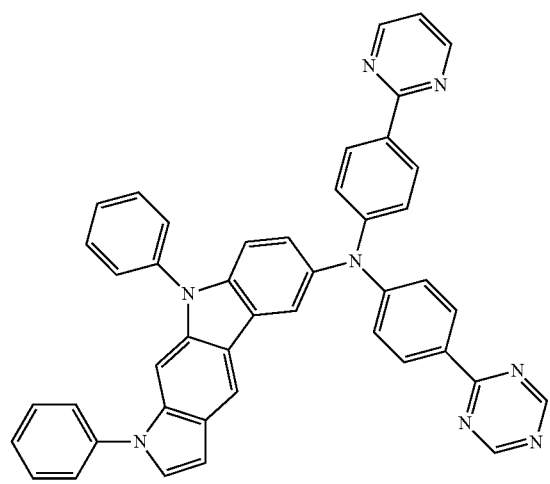
201
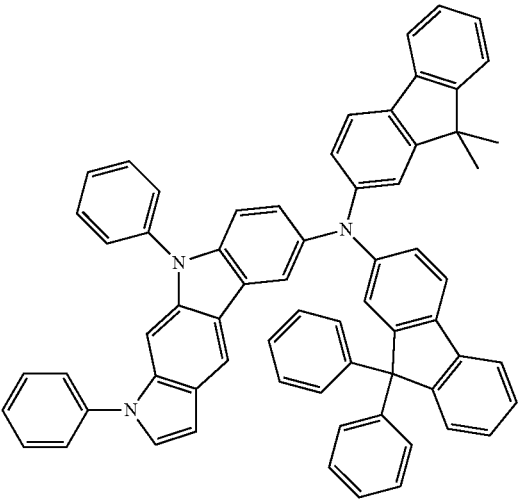
199
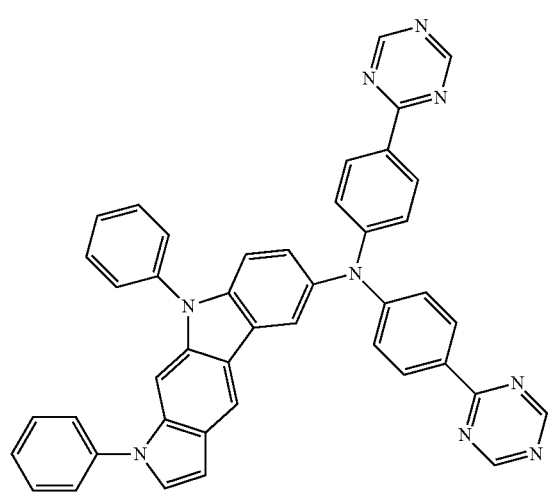
202
200
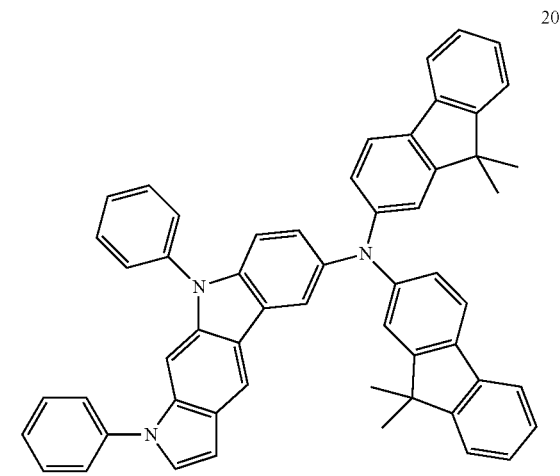
203
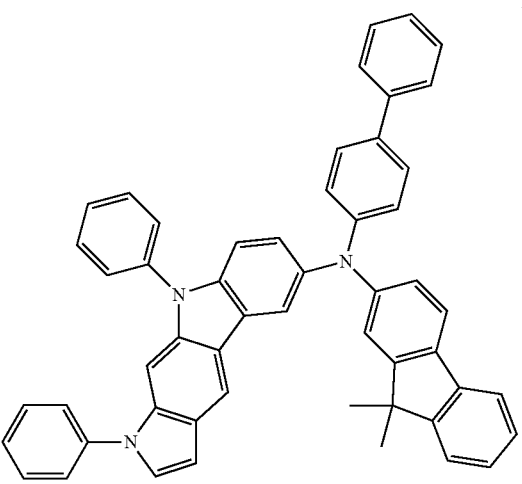

141
-continued
204
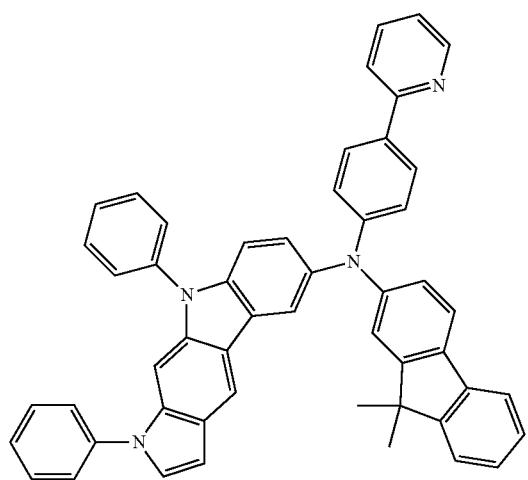
205
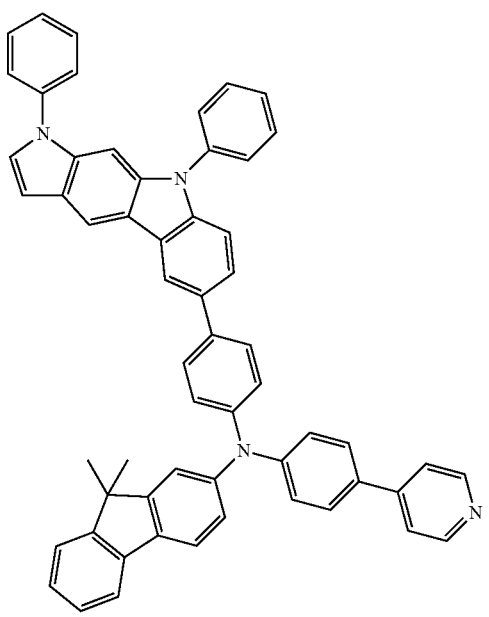
142
-continued
206
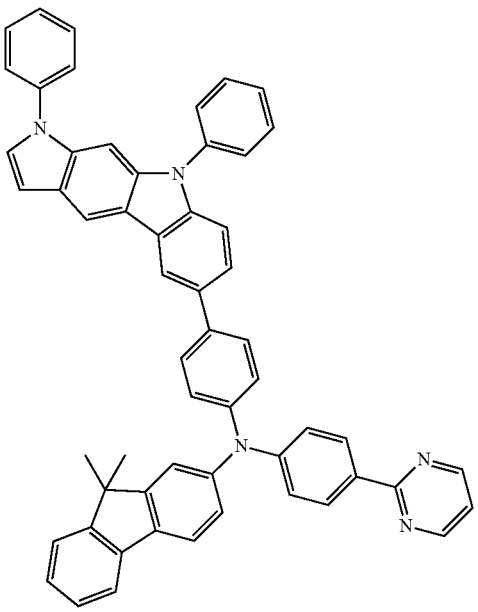
207

208
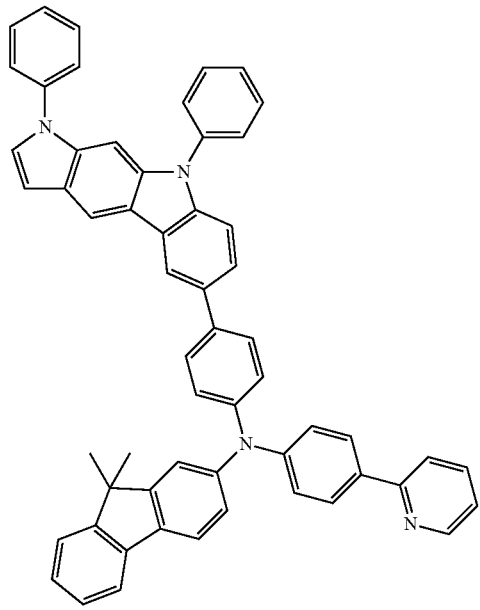
209
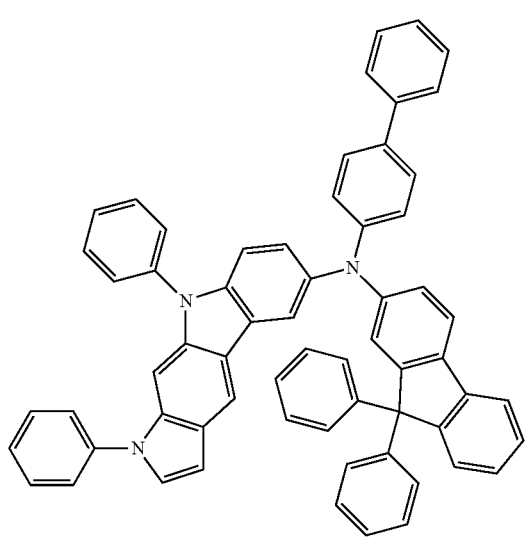
210
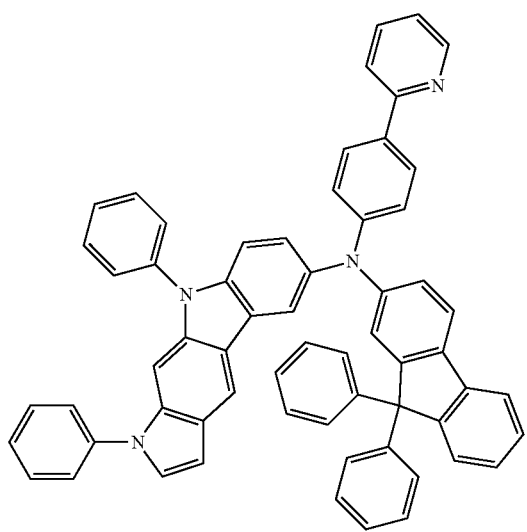
211
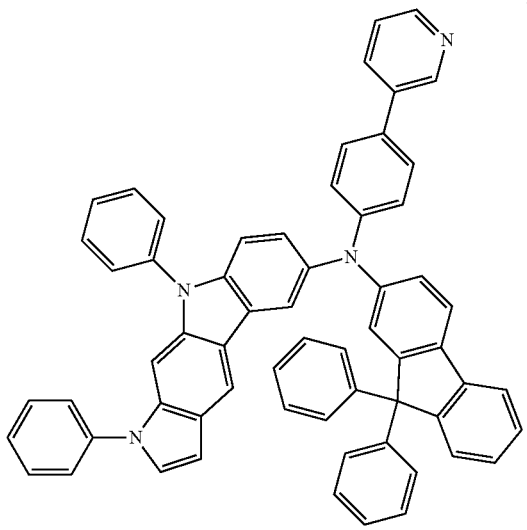
212
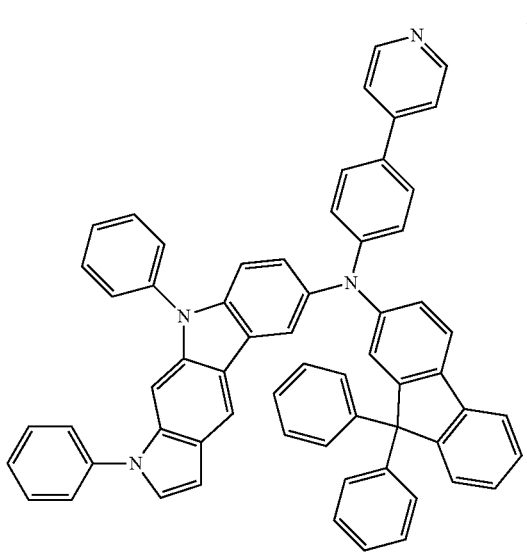
213
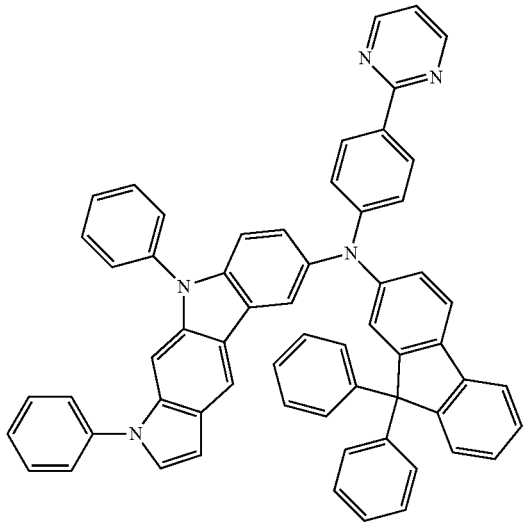

214
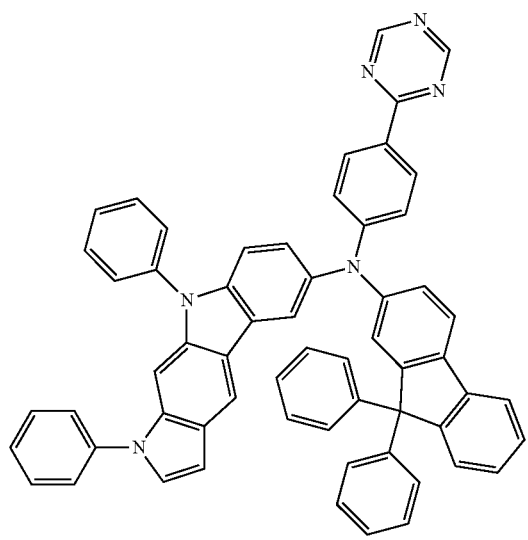
215
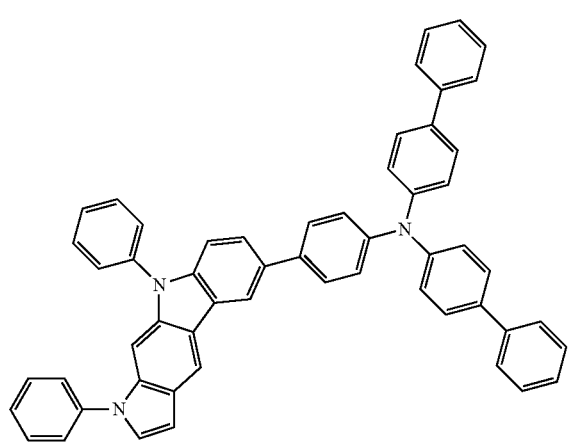
216
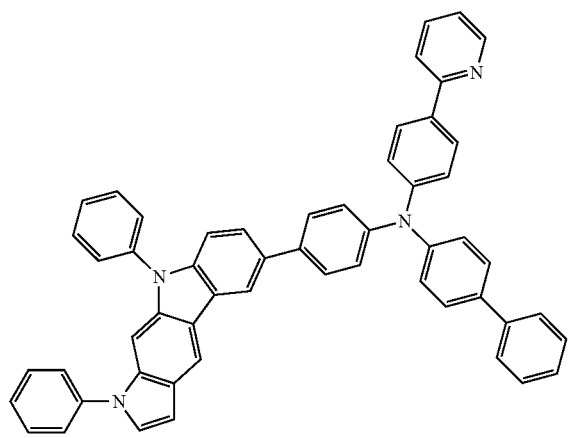
217
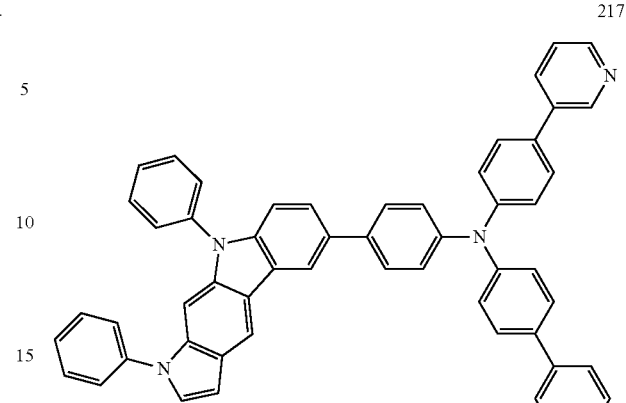
218
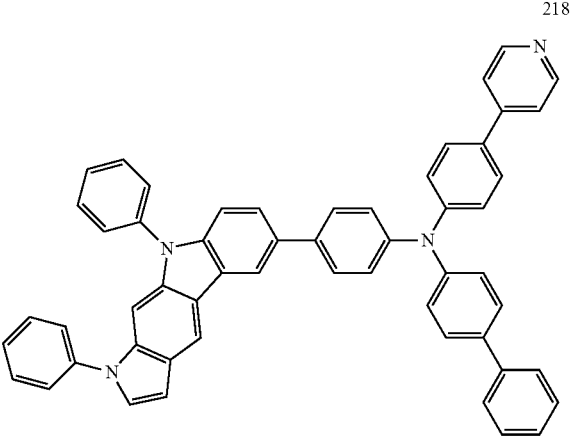
219
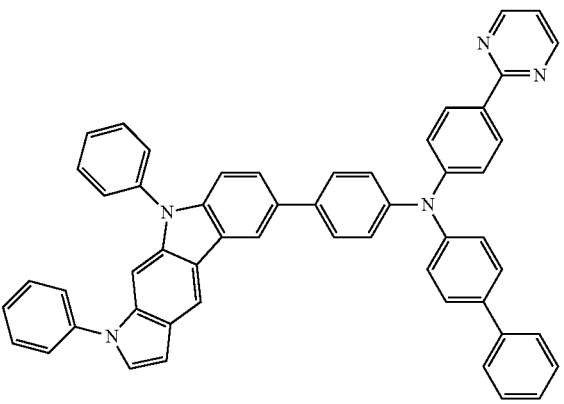

147
-continued
220
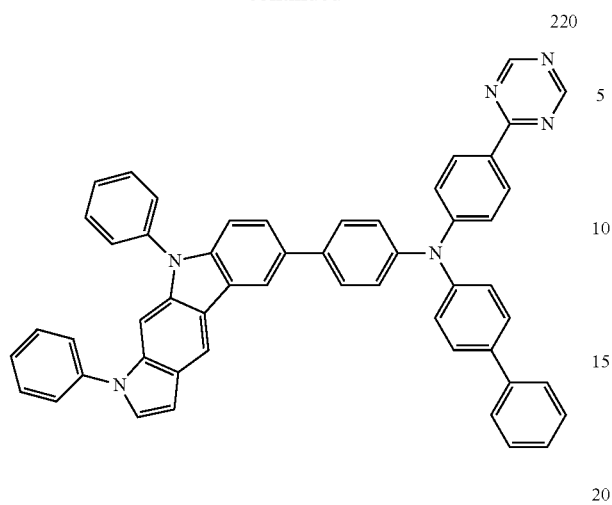
221
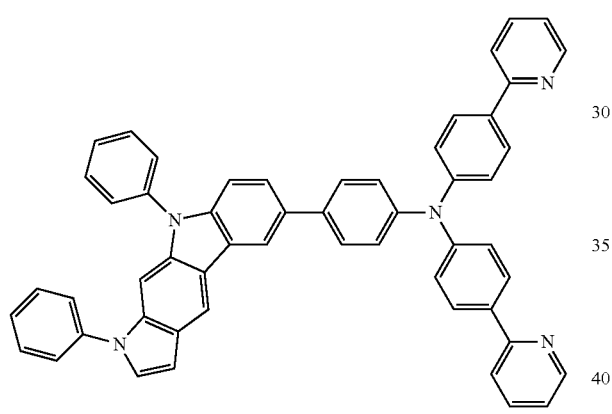
222
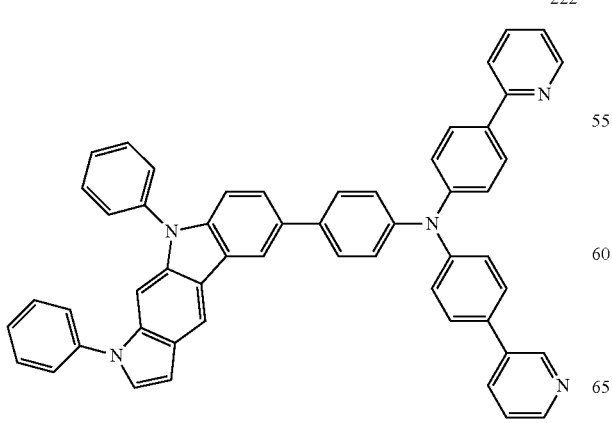
148
-continued
223
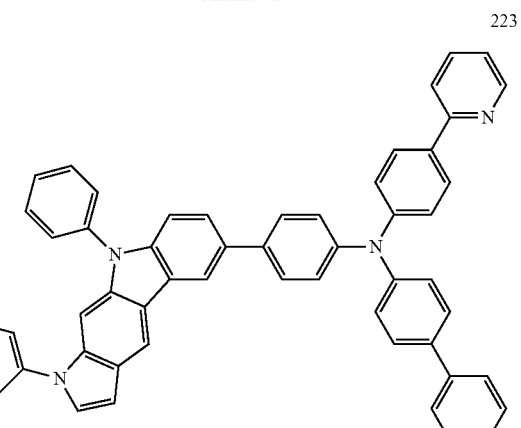
224
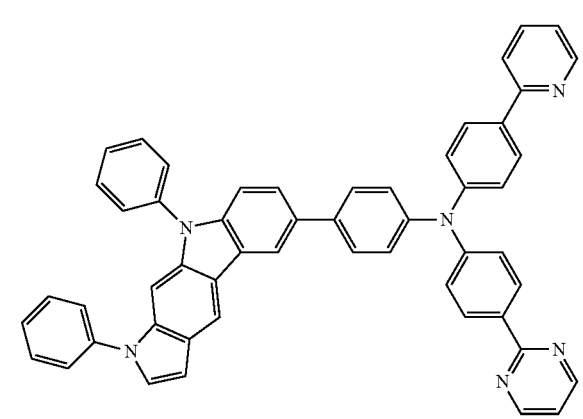
225
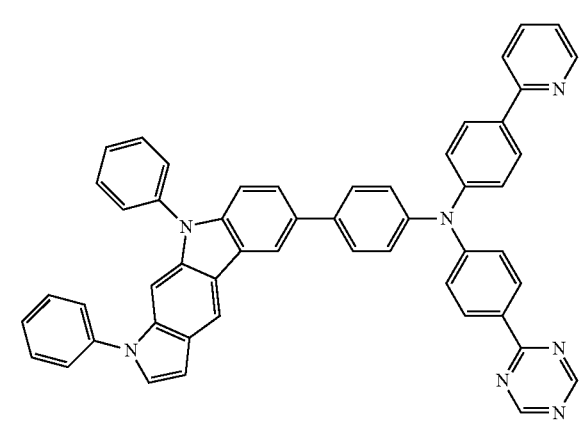

226
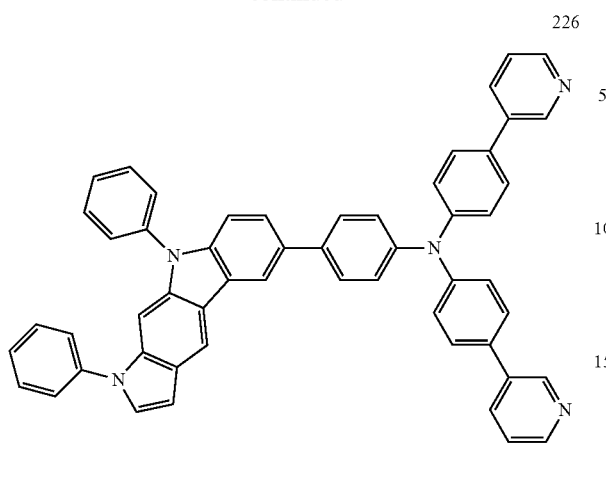
229
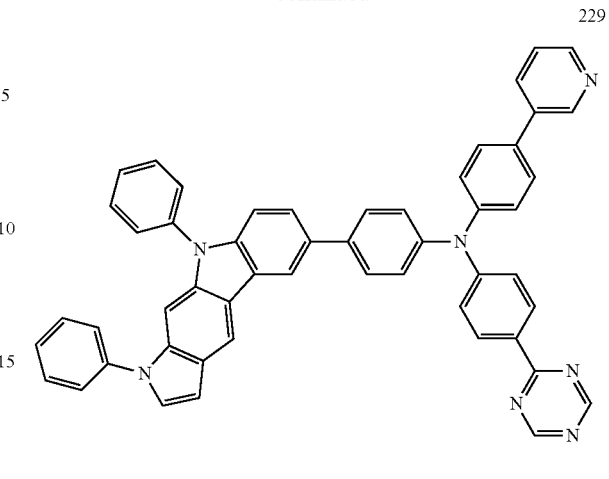
227
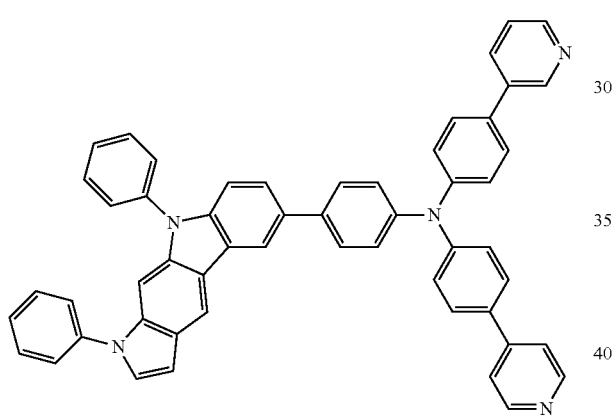
230
228
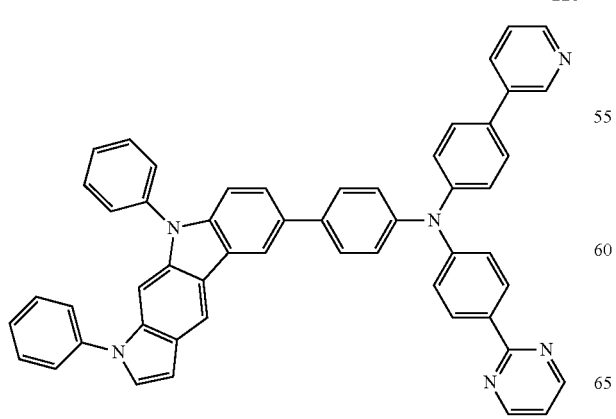
231
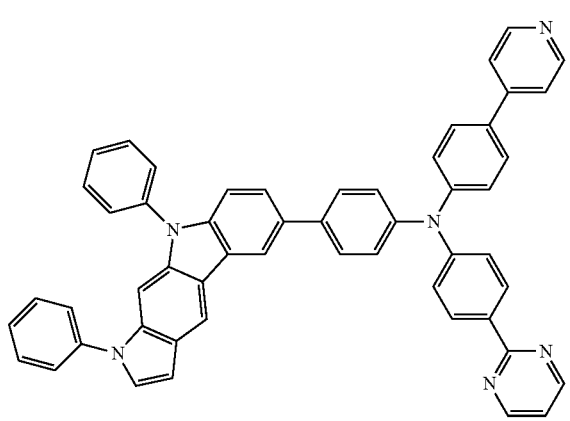

232
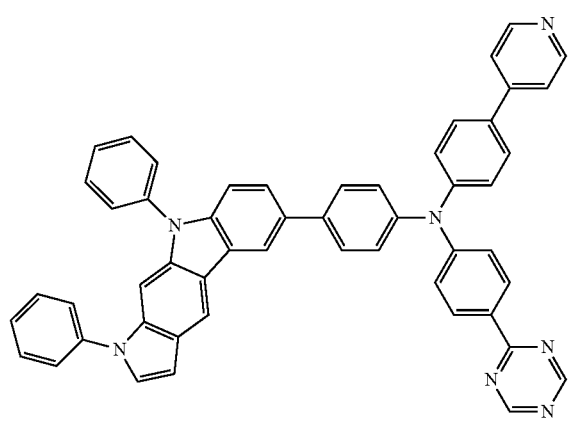
233
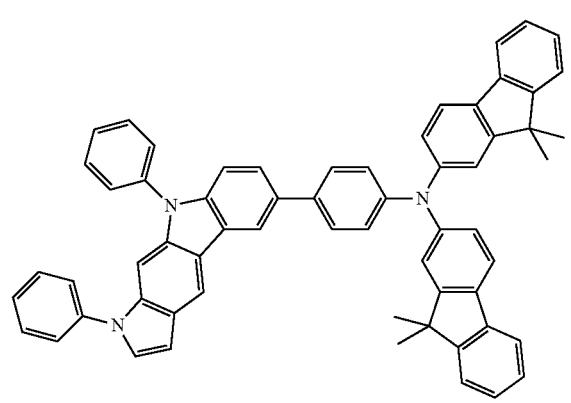
234
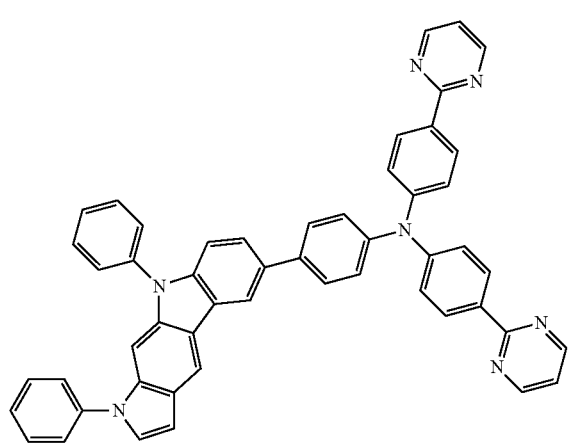
235
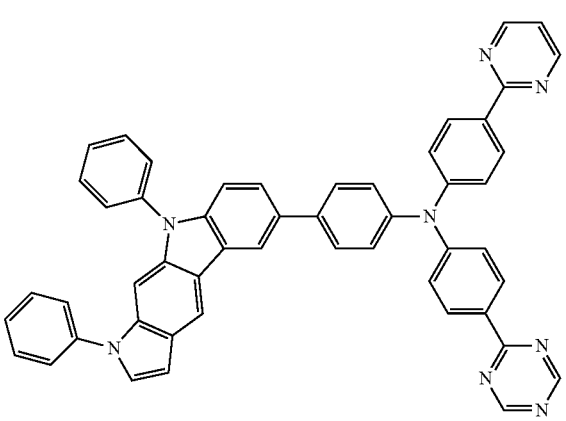
236
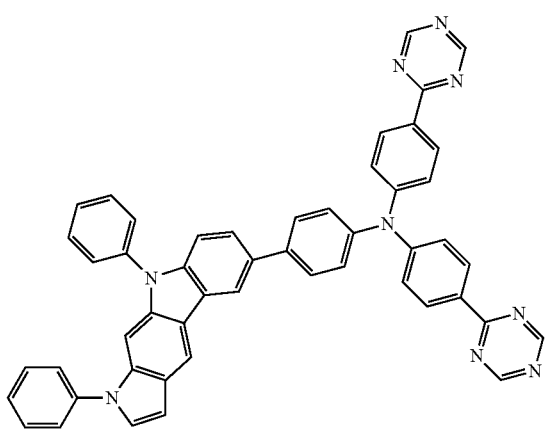
237
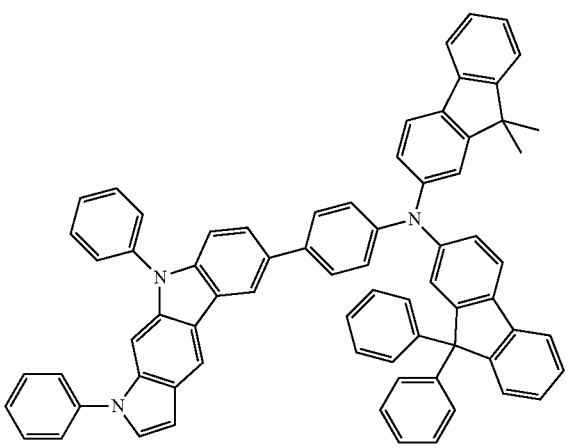

238
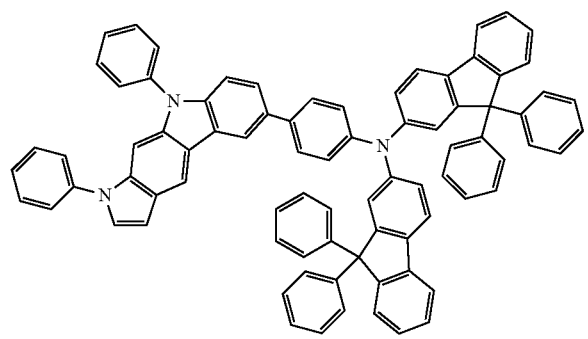
239
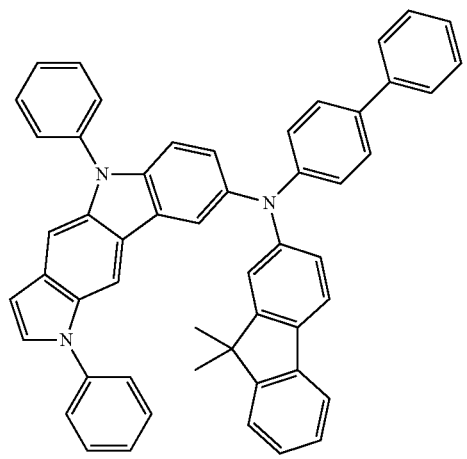
240
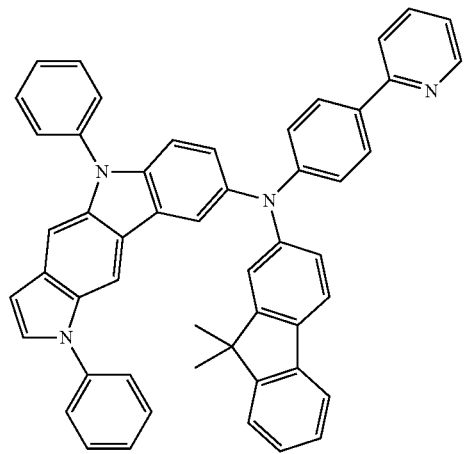
241
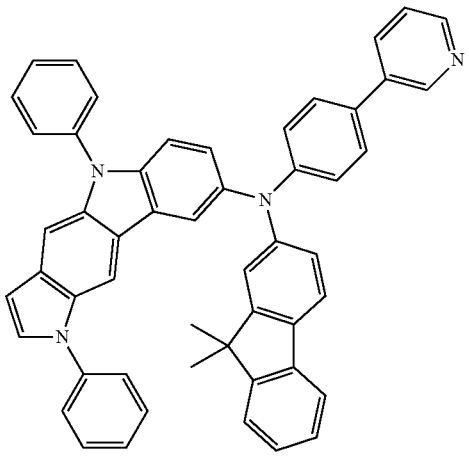
242
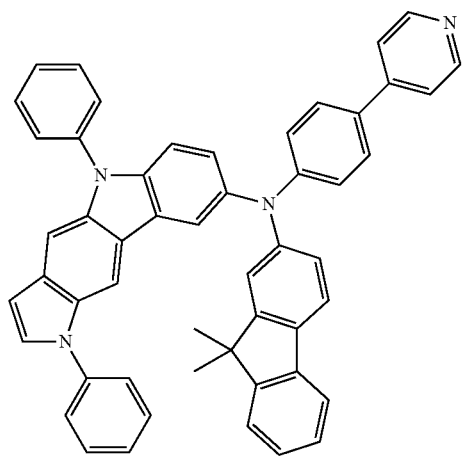
243
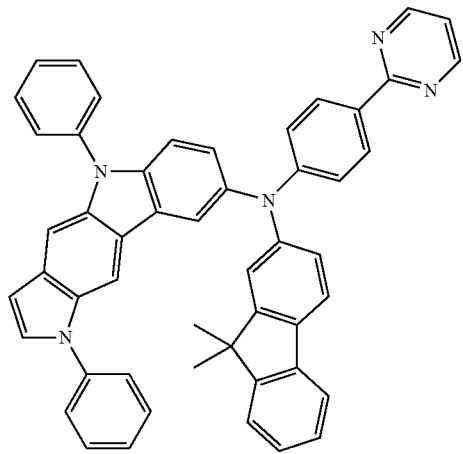

244
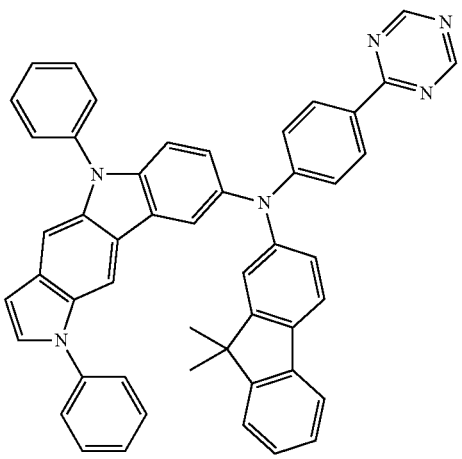
245
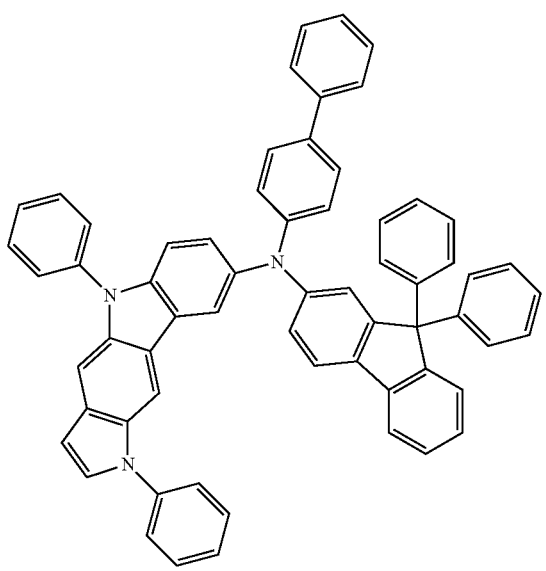
246
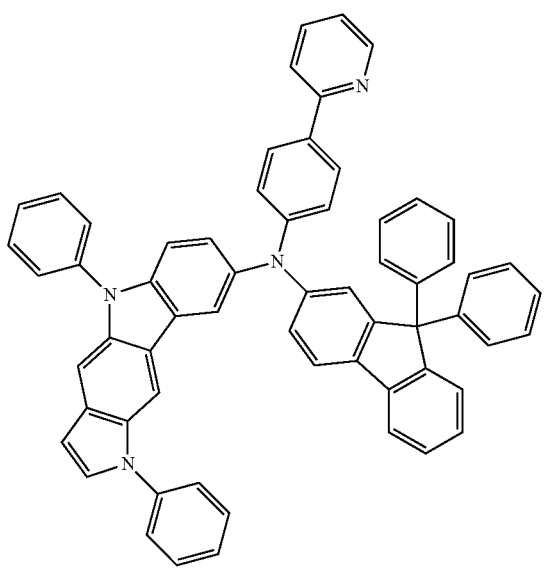
247
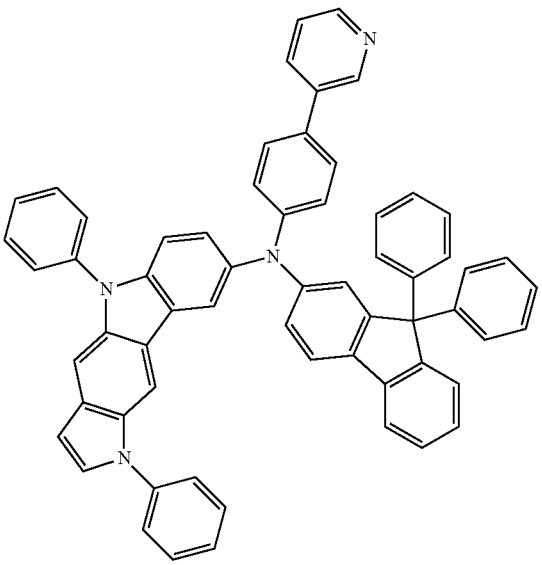
248
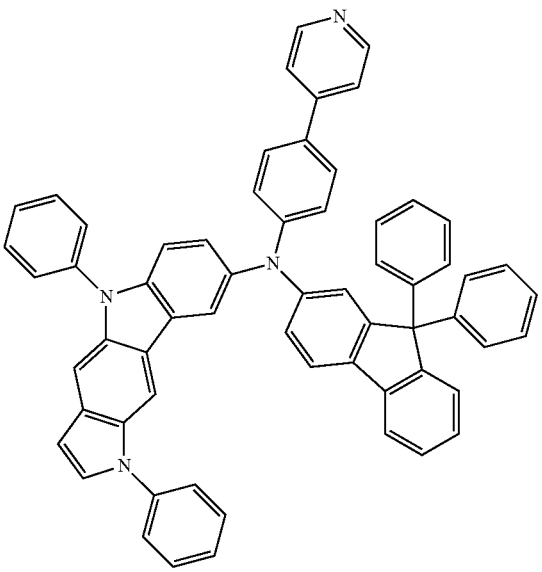

-continued
249
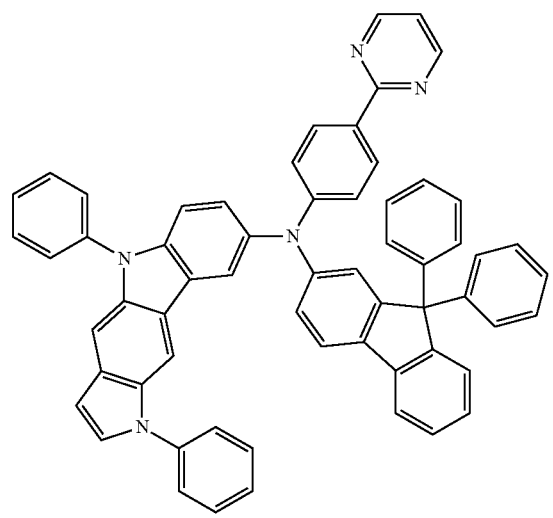
252
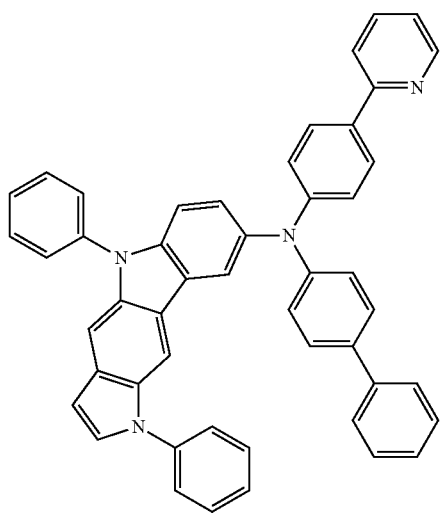
250
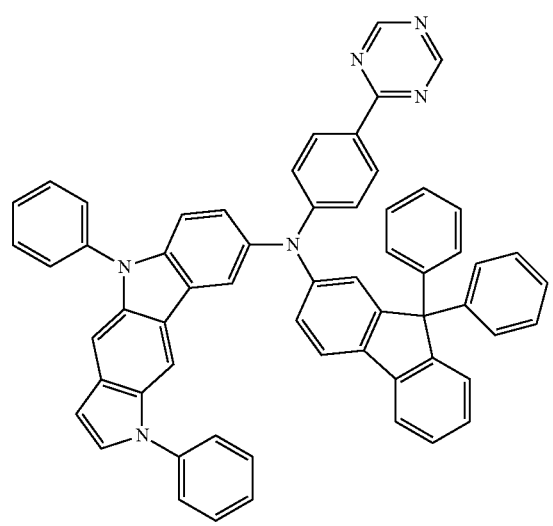
253
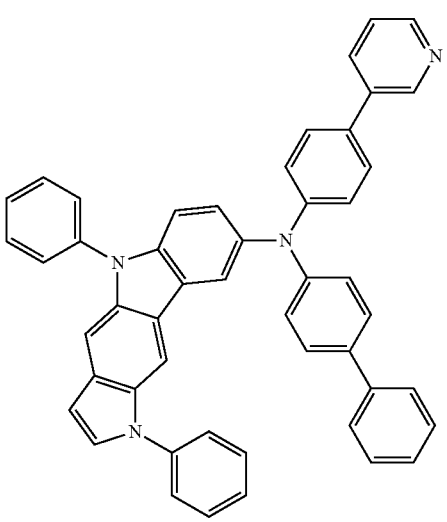
251
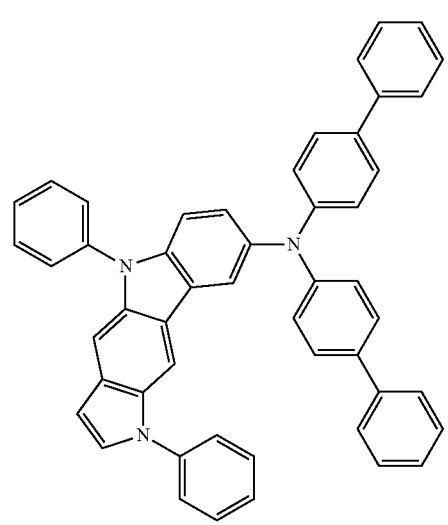
254
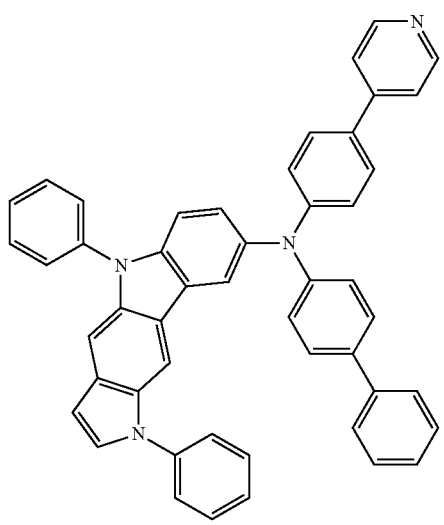

255 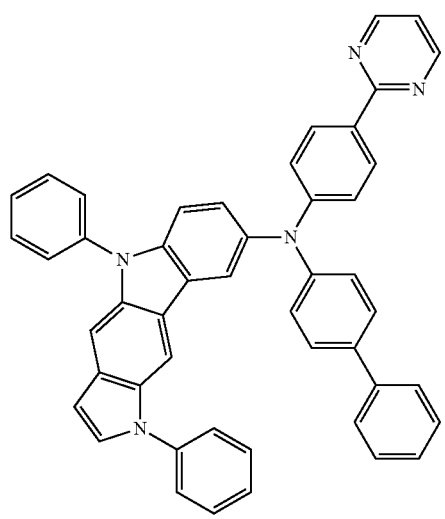
258 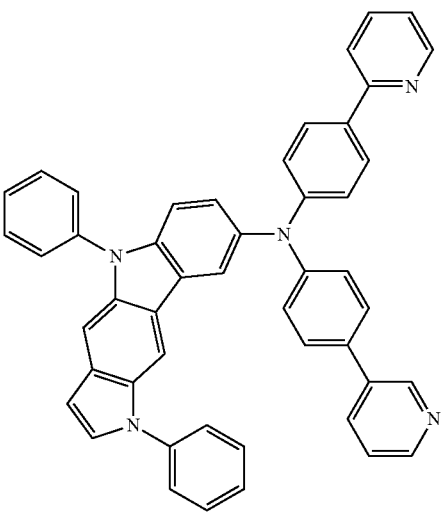
256 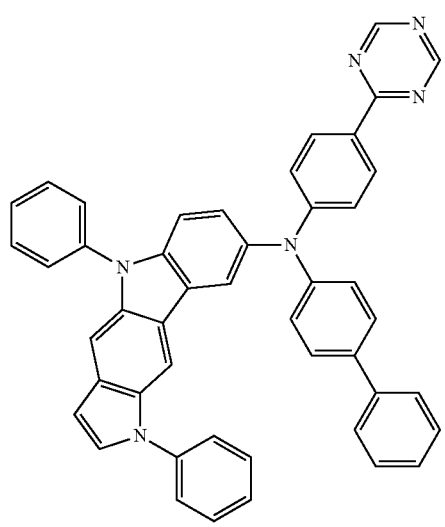
259 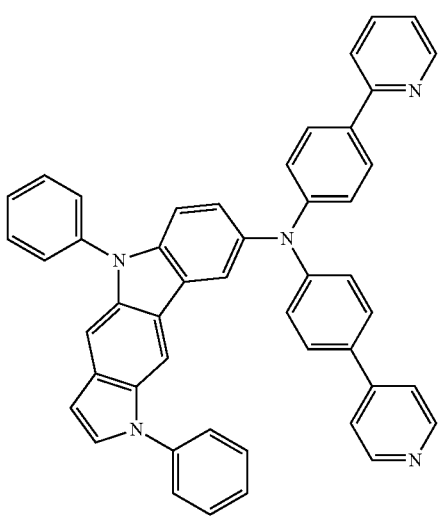
257 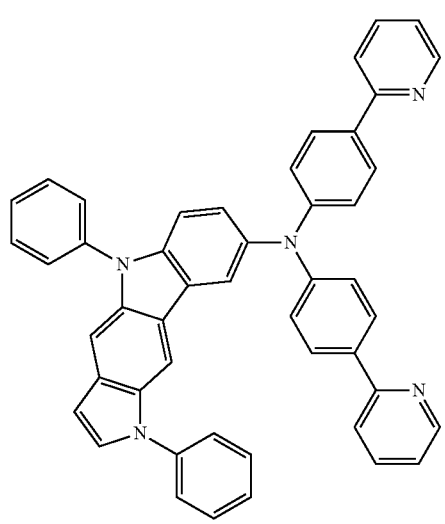
260

261
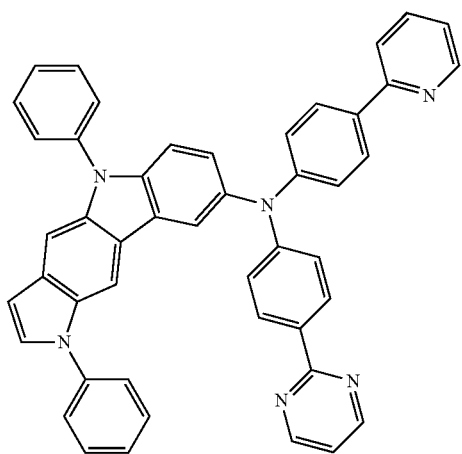
262
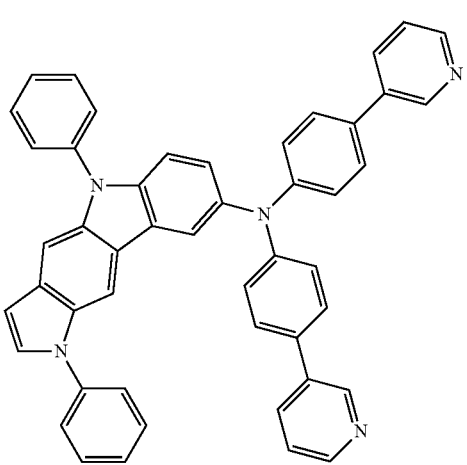
264
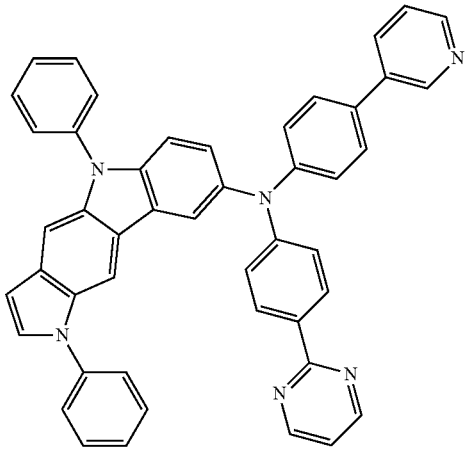
265
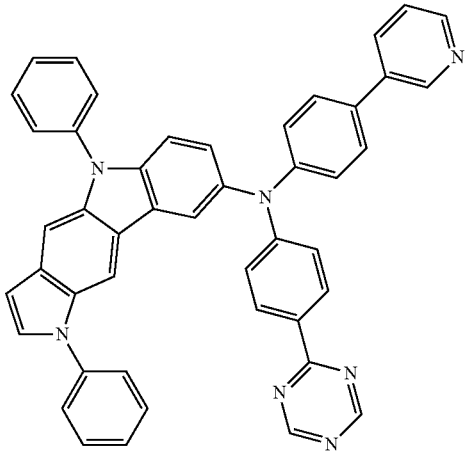
263
266
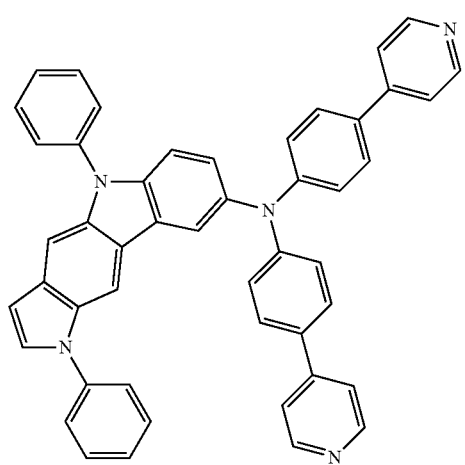

-continued
267
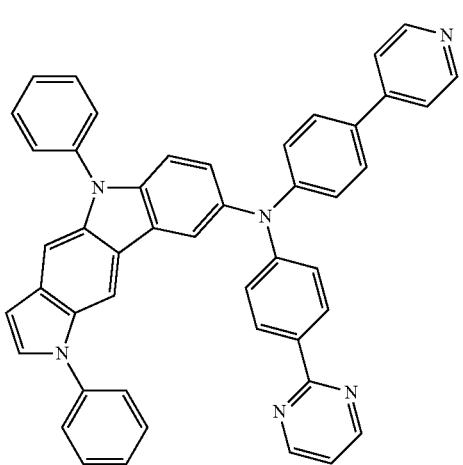
268
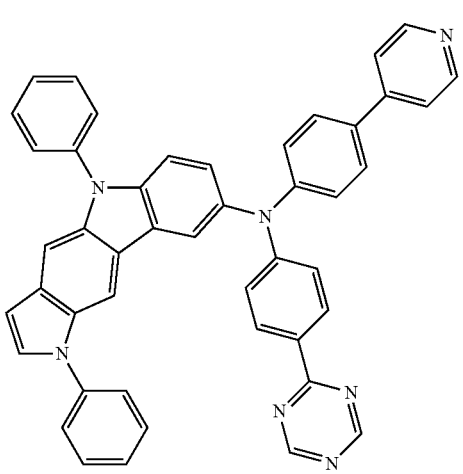
269
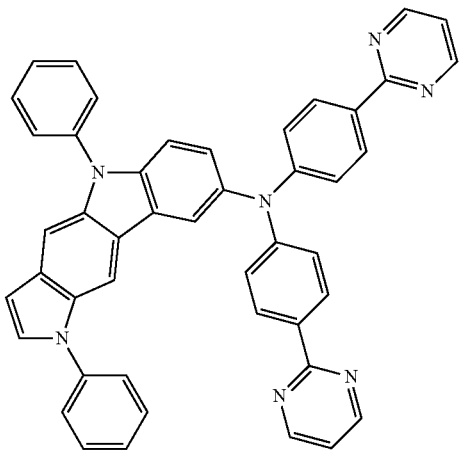
-continued
270
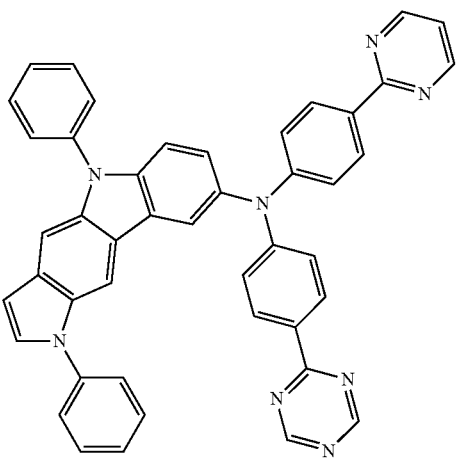
271
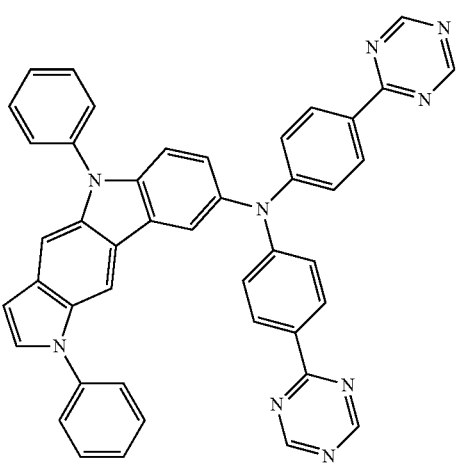
272
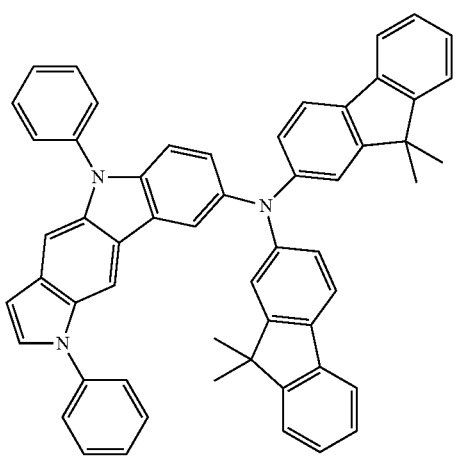

-continued
273
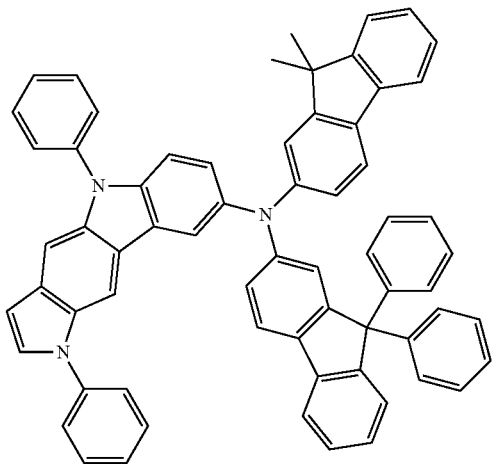
274
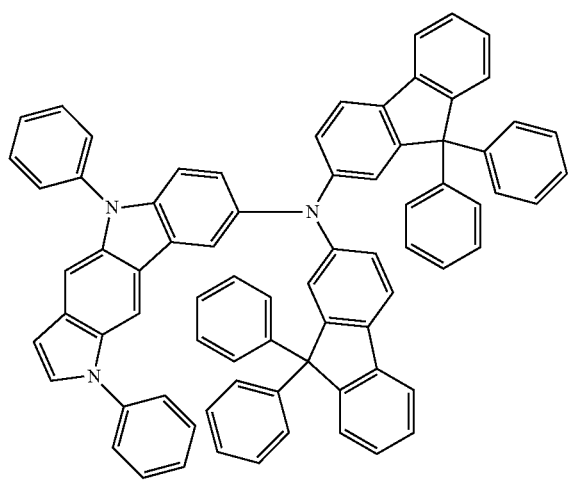
275
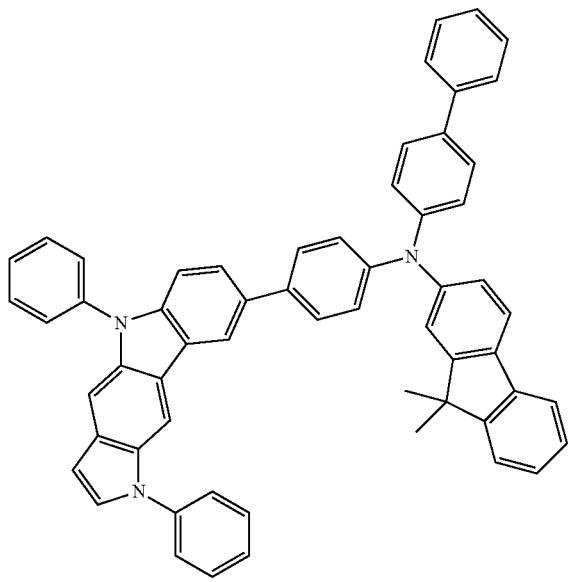
-continued
276
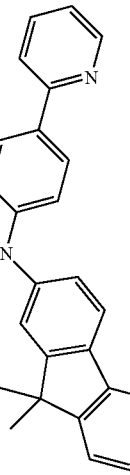
277
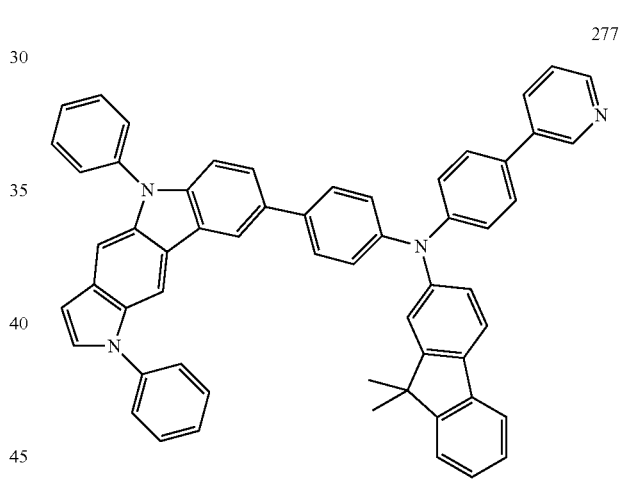
278
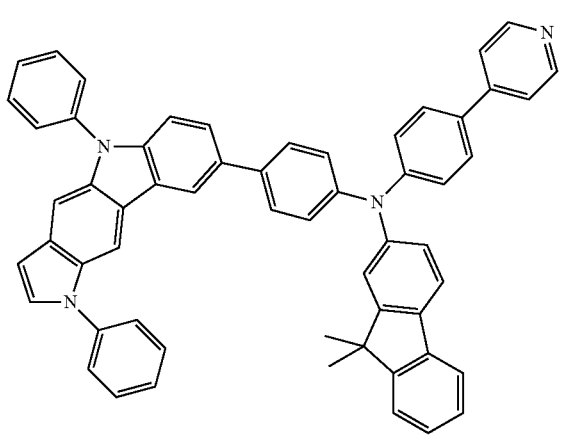

279
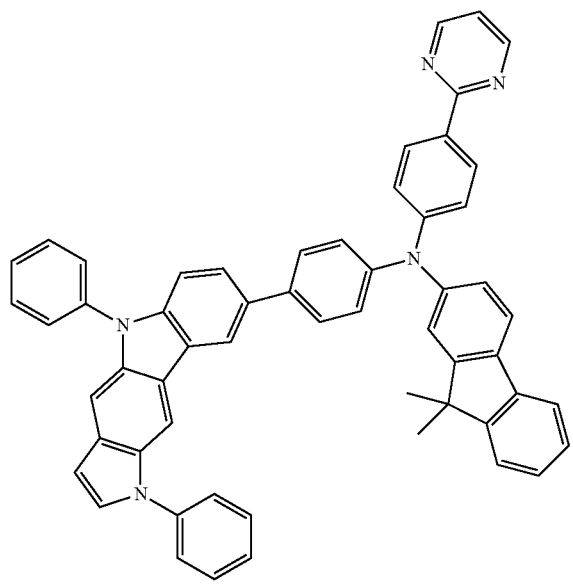
281
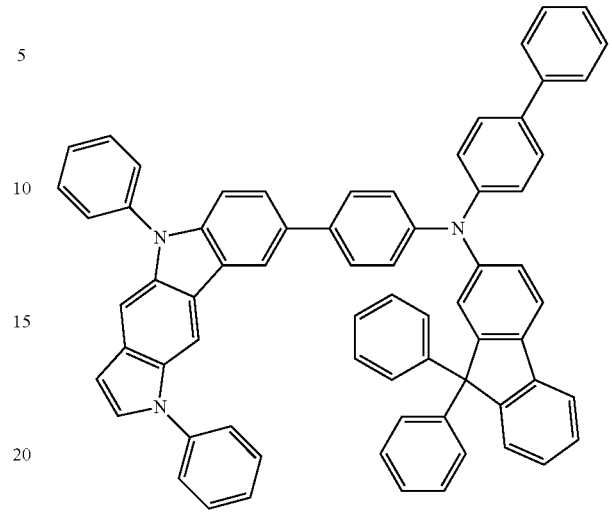
282
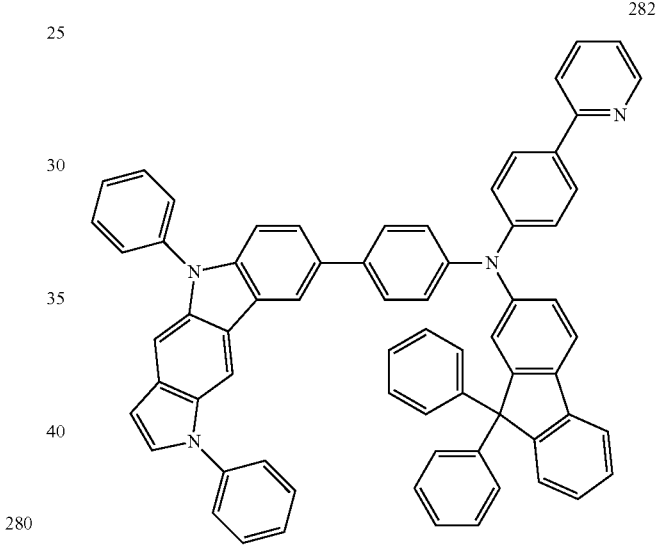
280
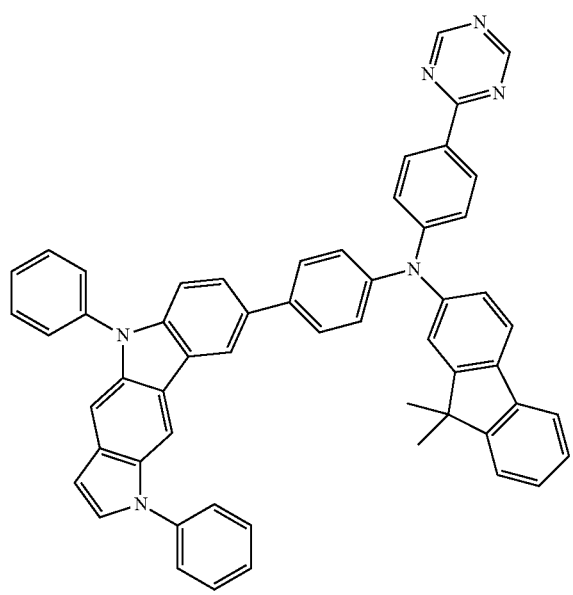
283
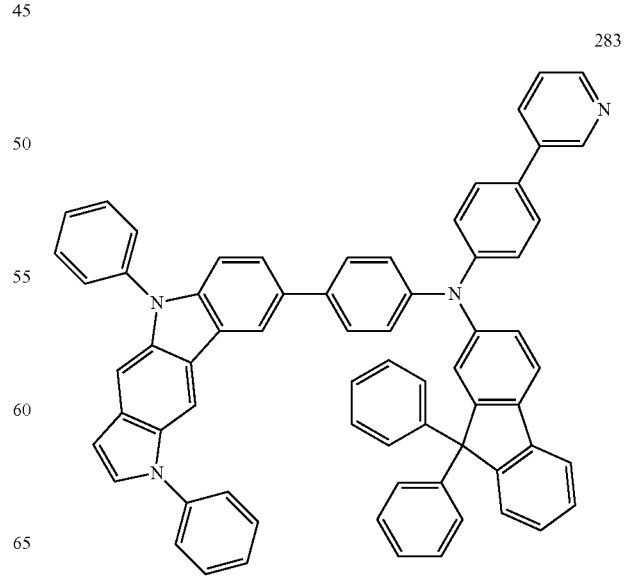

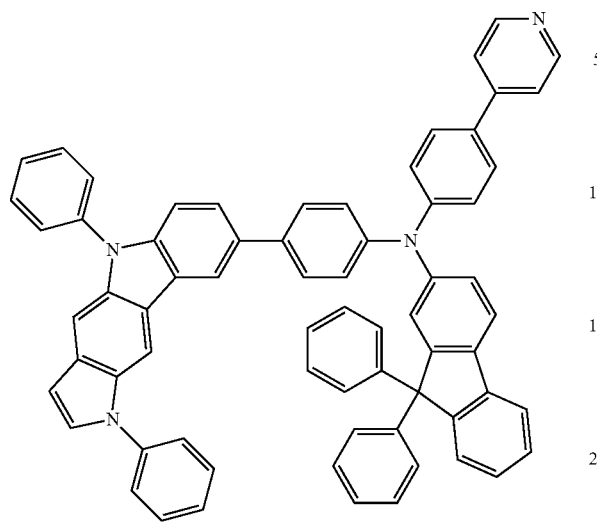
284
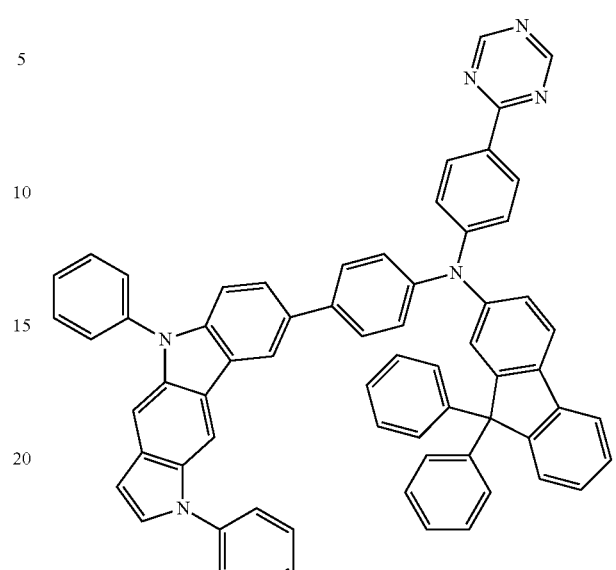
286
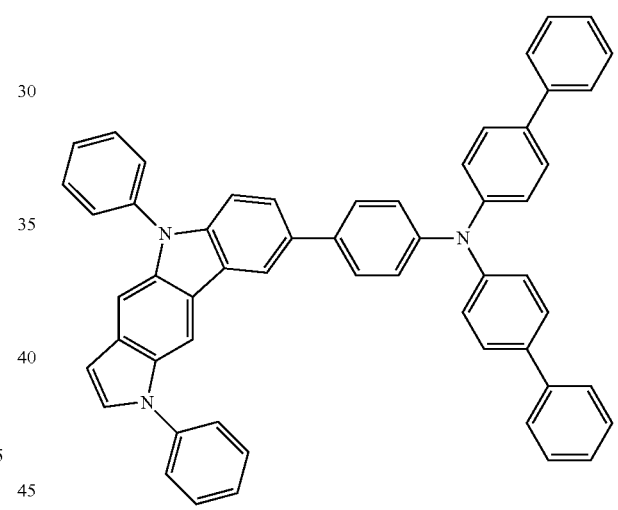
287
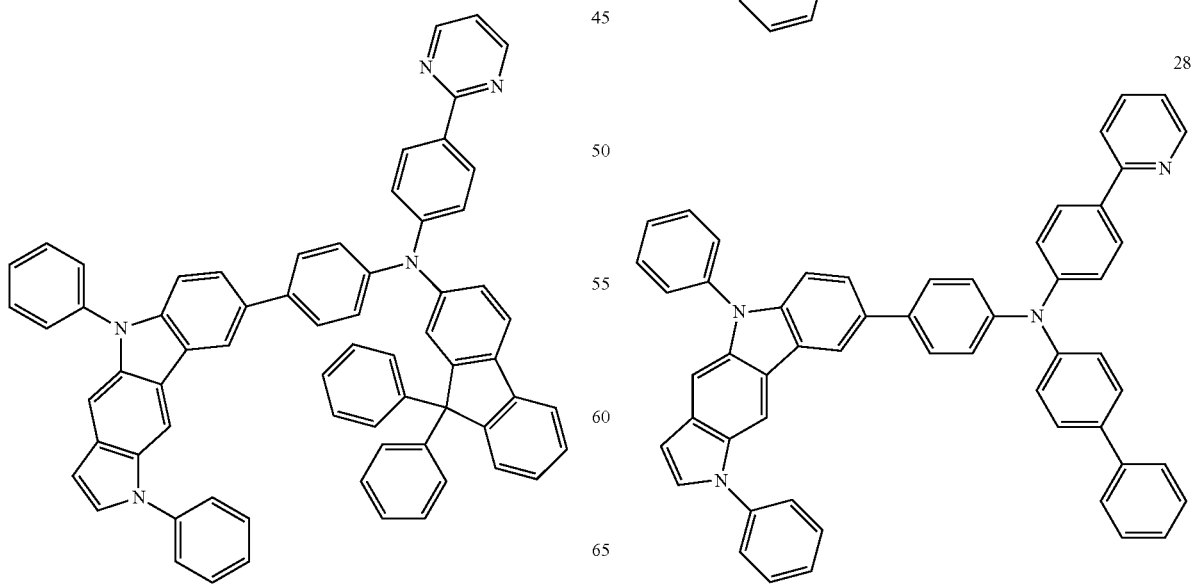

171
-continued
289
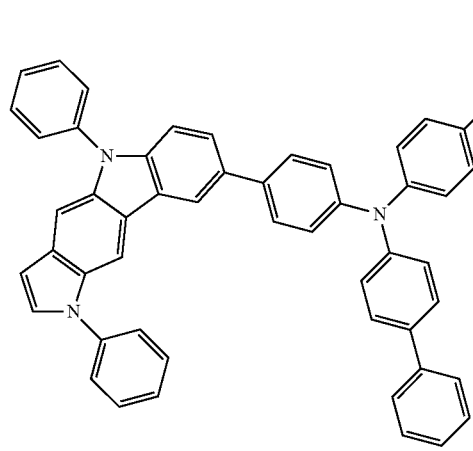
290
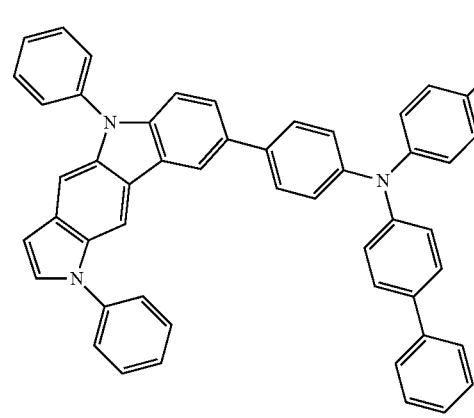
291
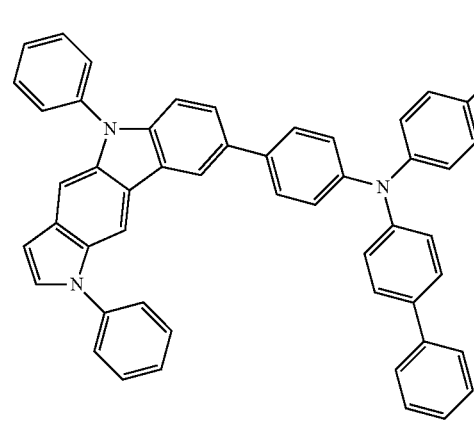
172
-continued
292
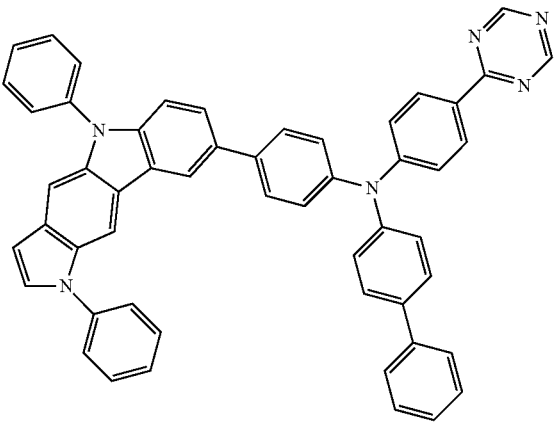
293
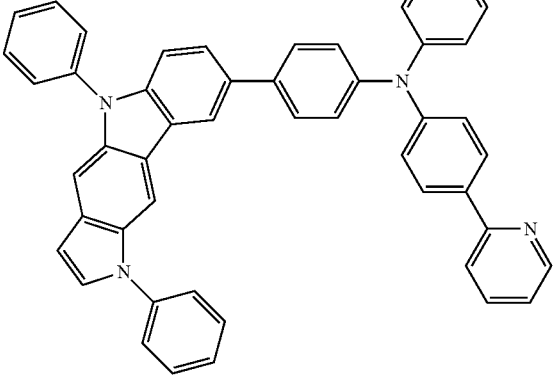
294
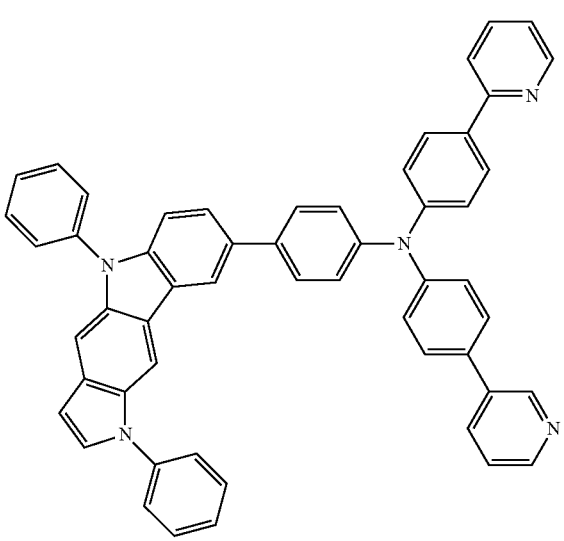

-continued
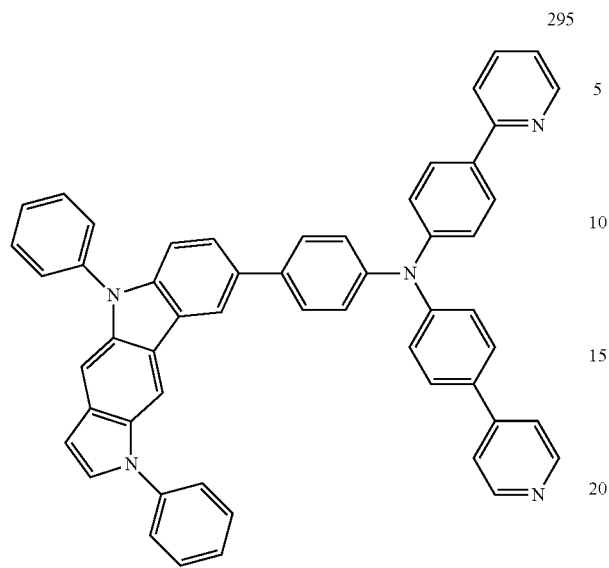
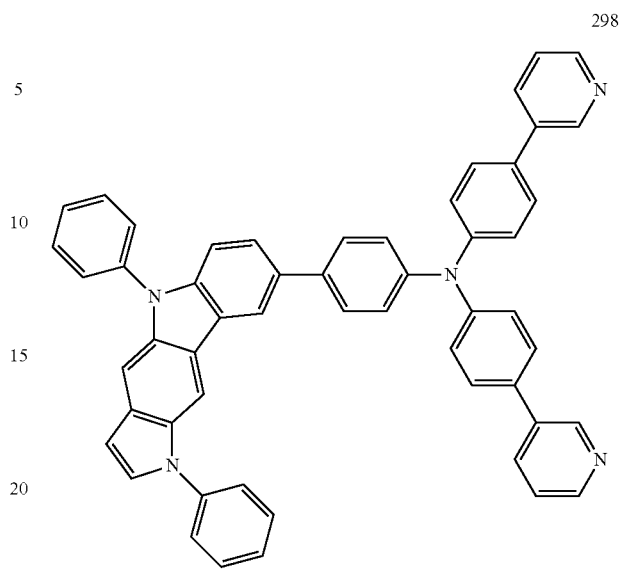
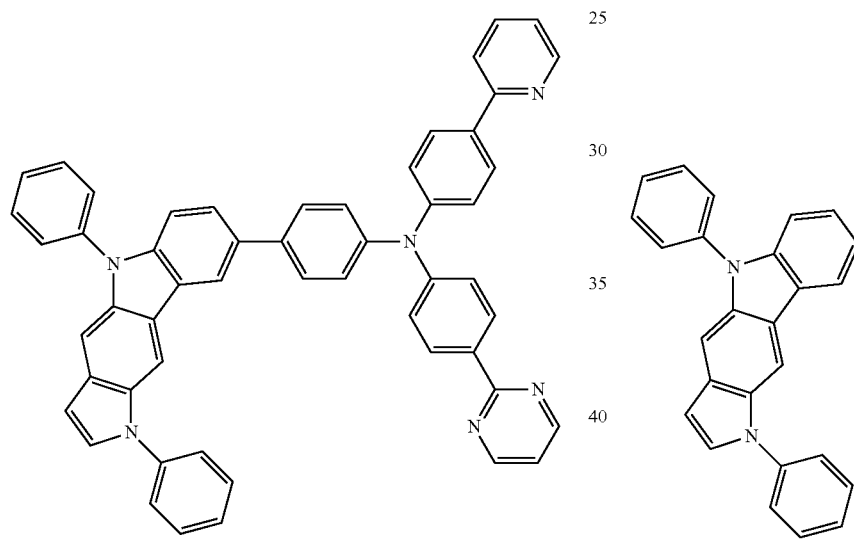
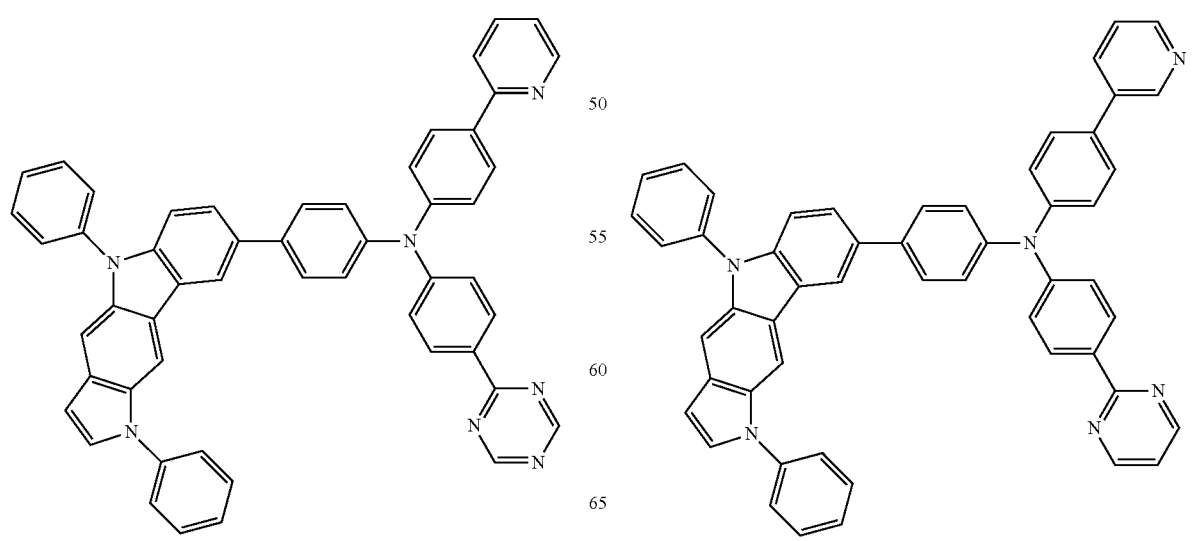

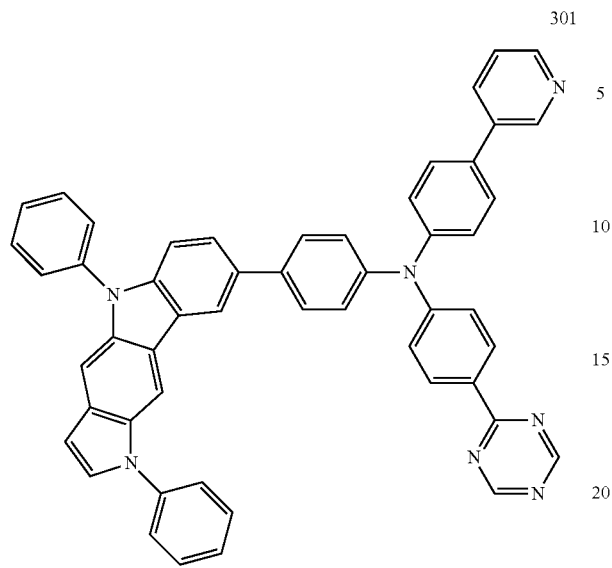
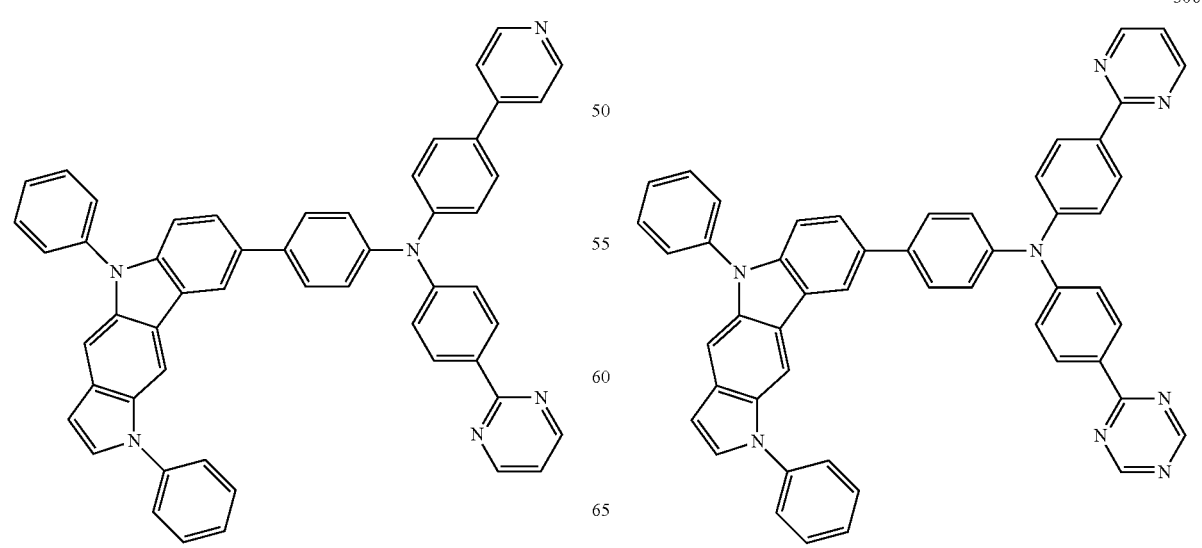
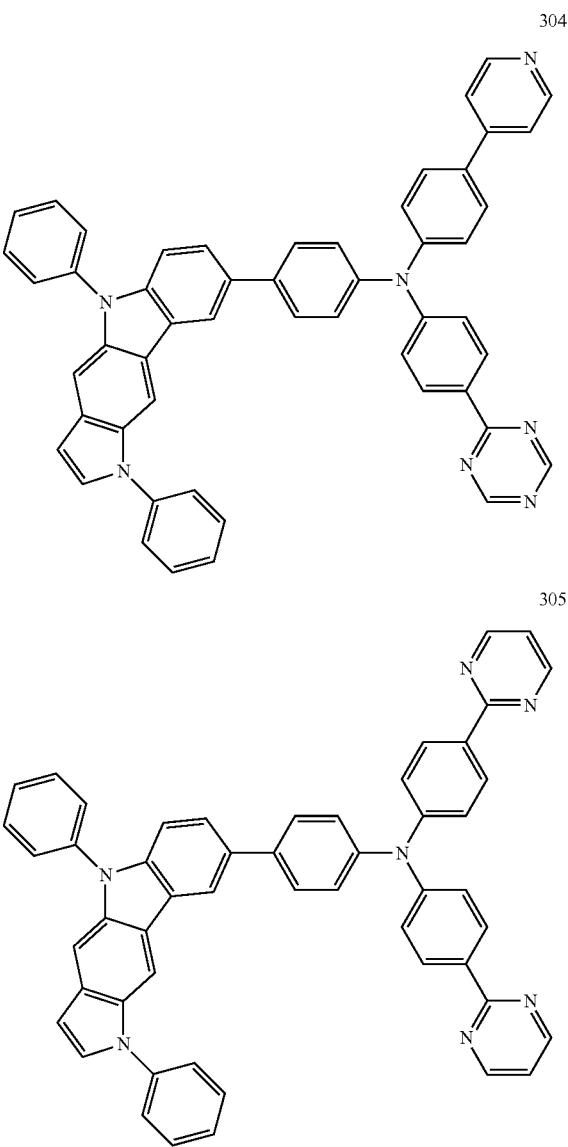

307
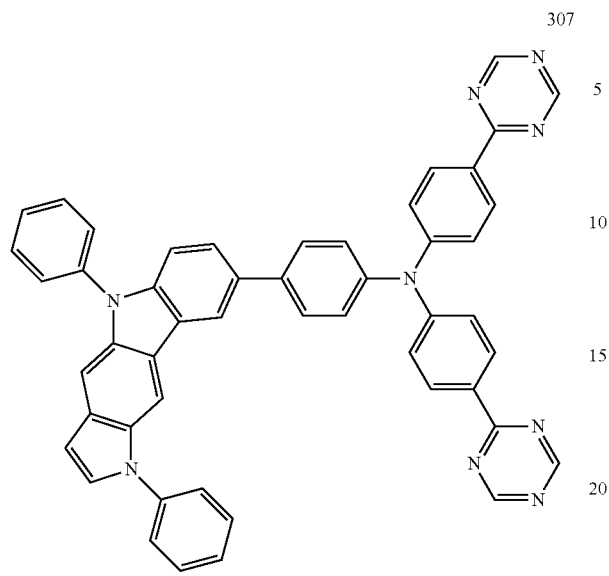
310
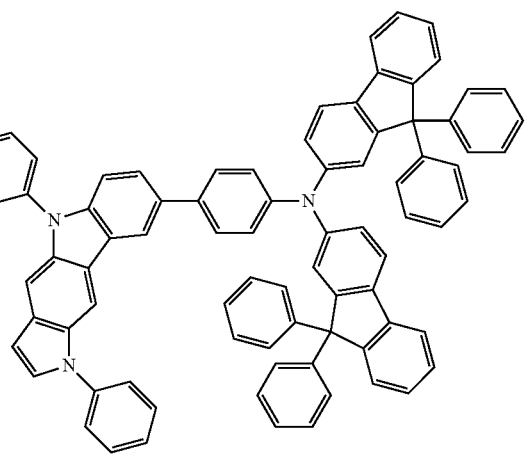
308
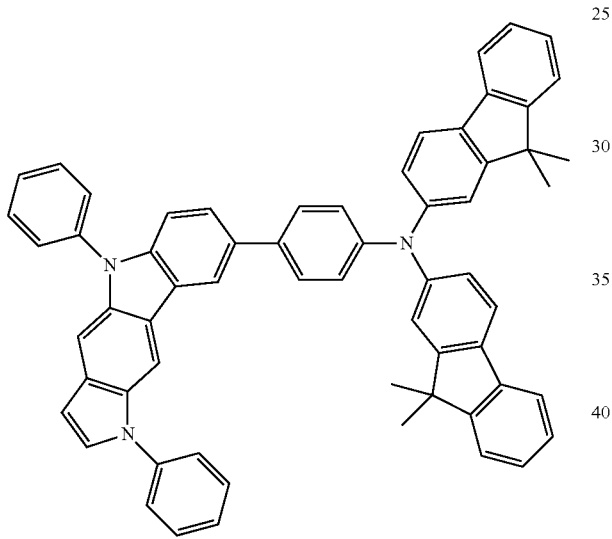
311
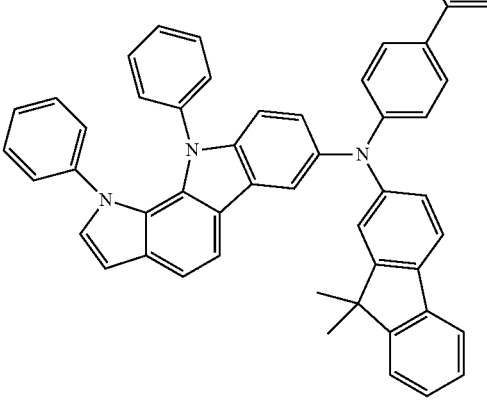
309
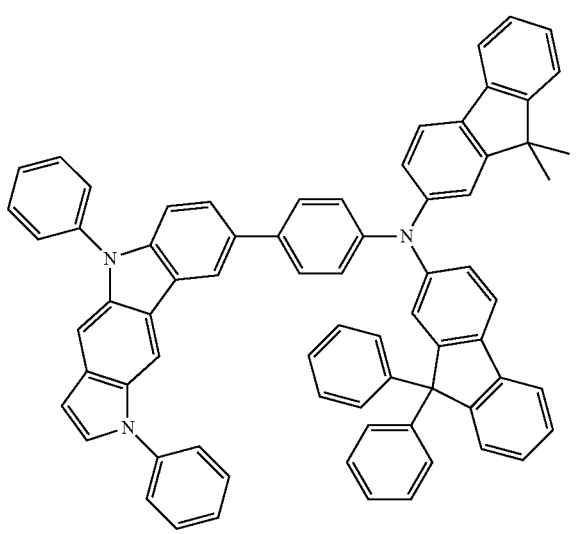
312
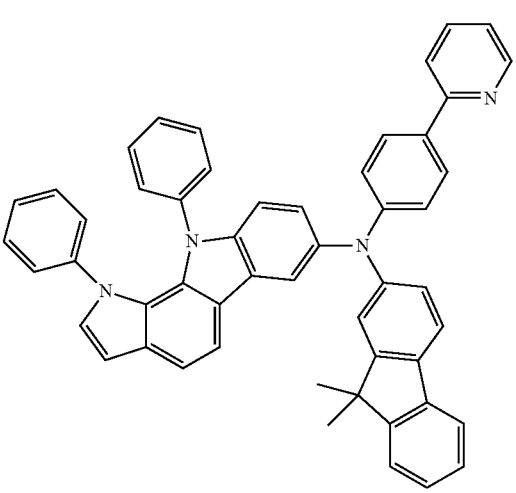

313
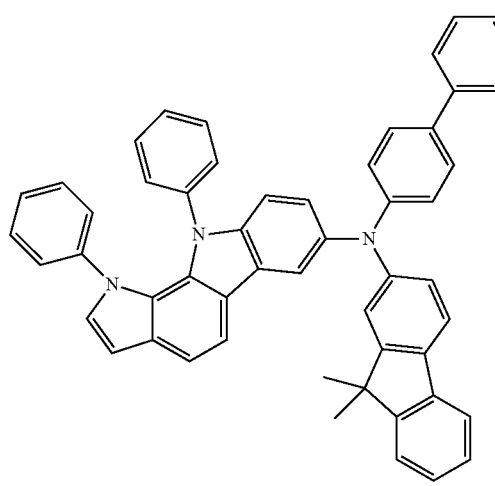
314
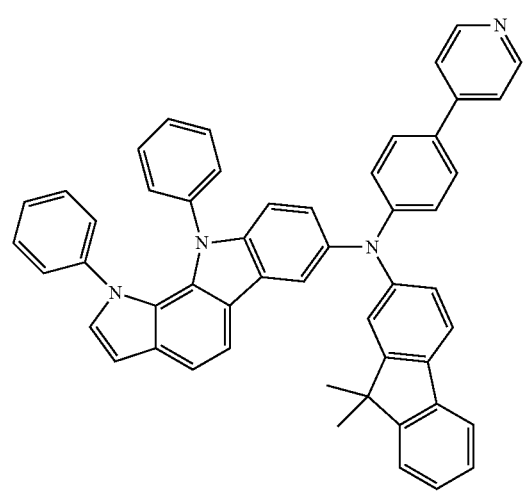
315
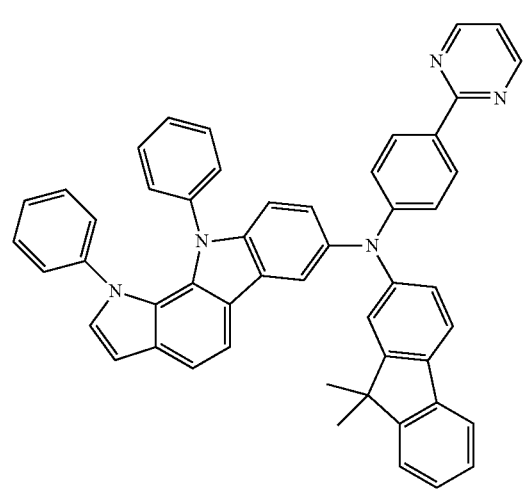
316
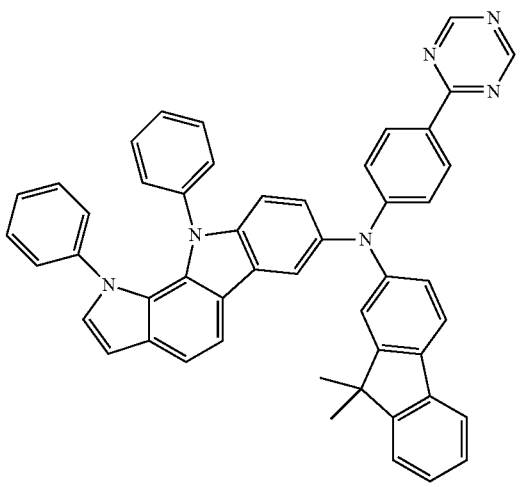
317
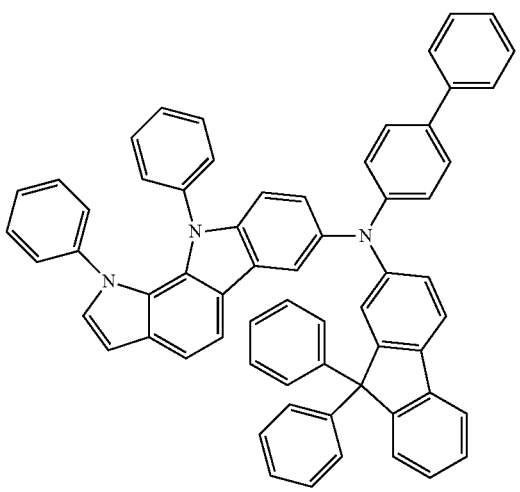
318
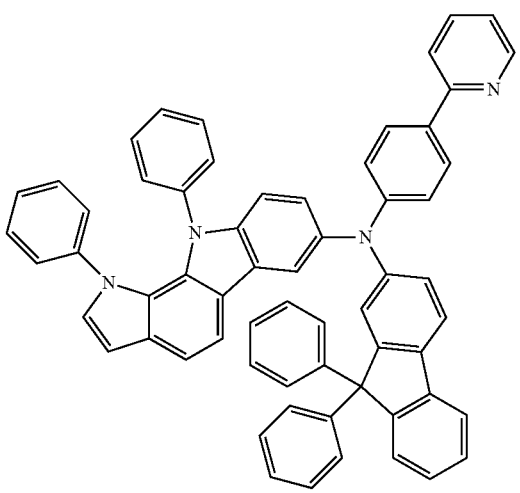

319
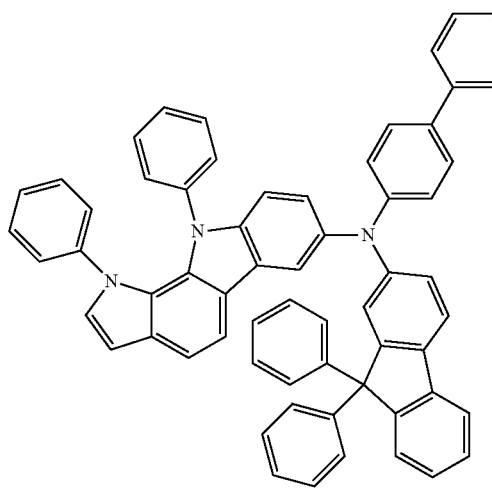
320
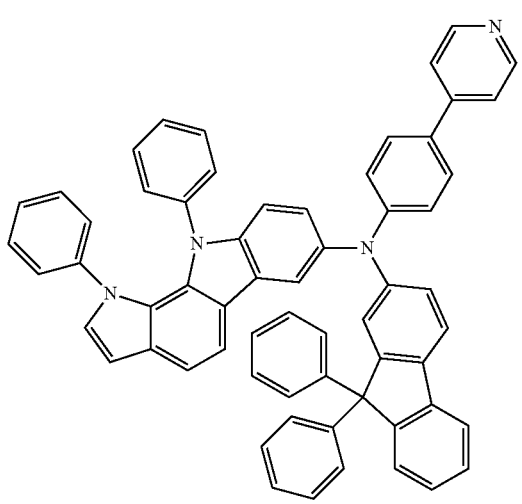
321
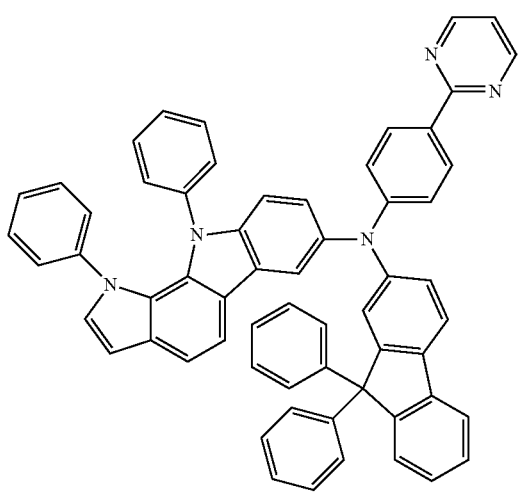
322
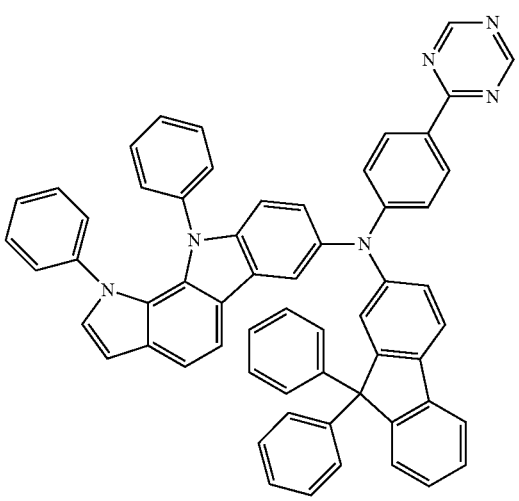
323
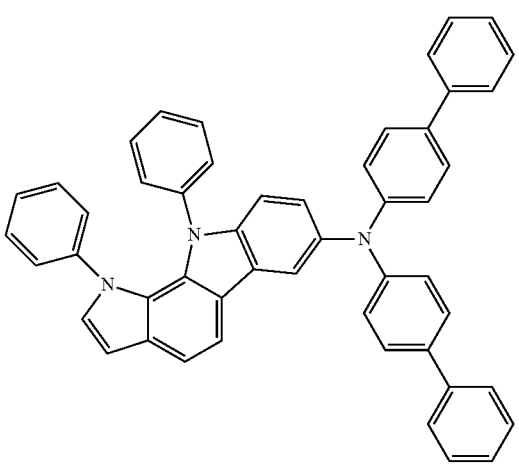
324
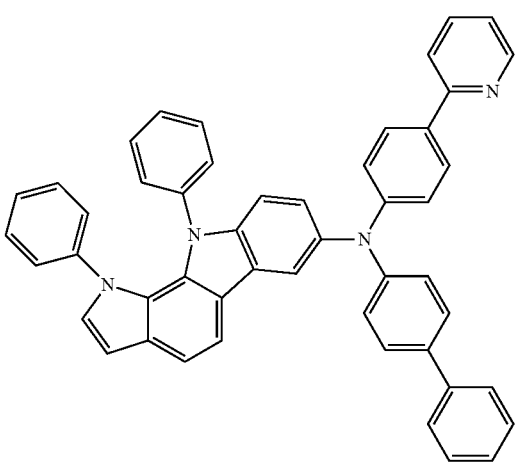

-continued
325
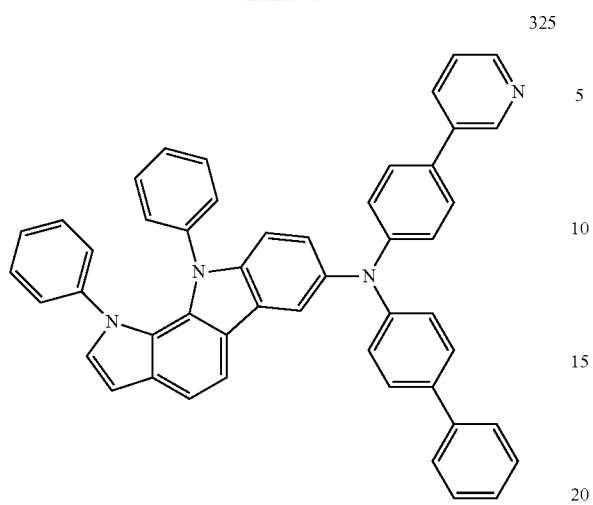
326
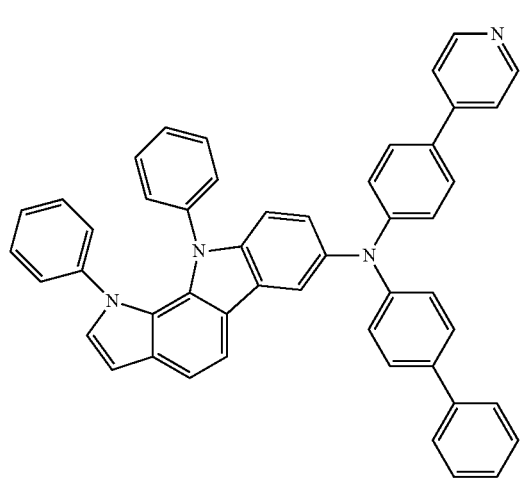
327
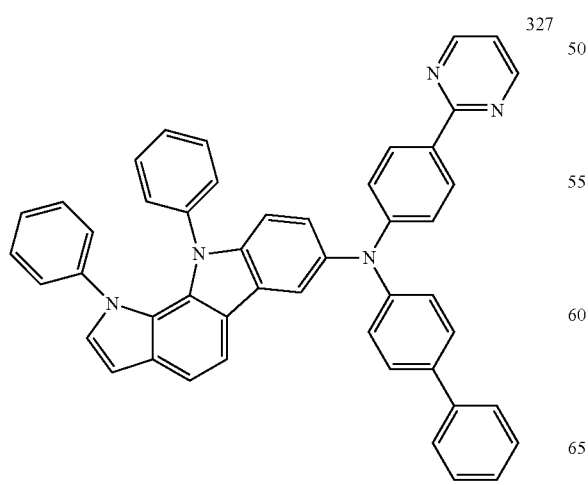
-continued
328
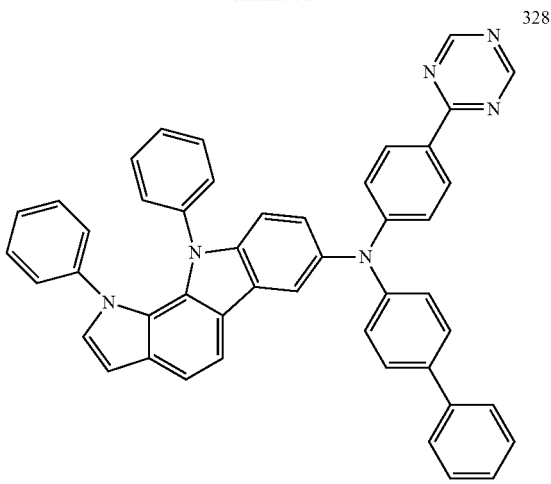
329
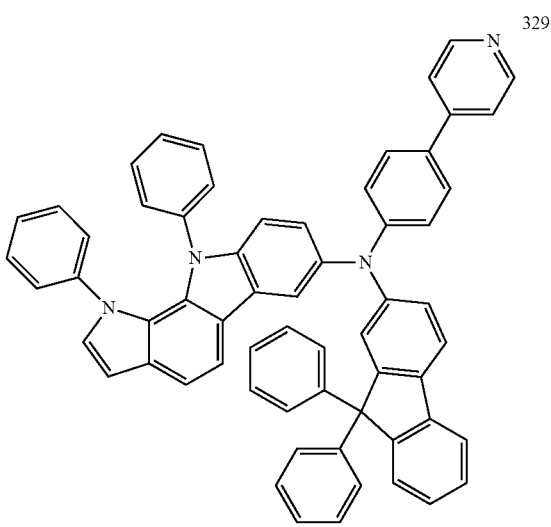
330
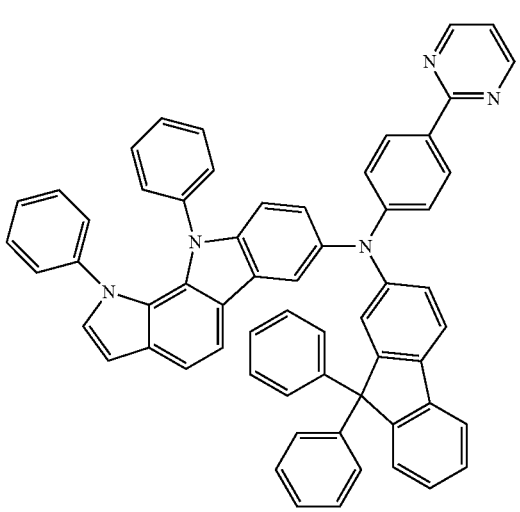

331
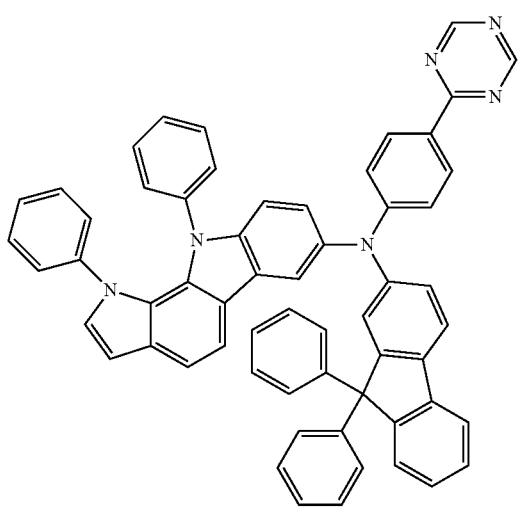
332
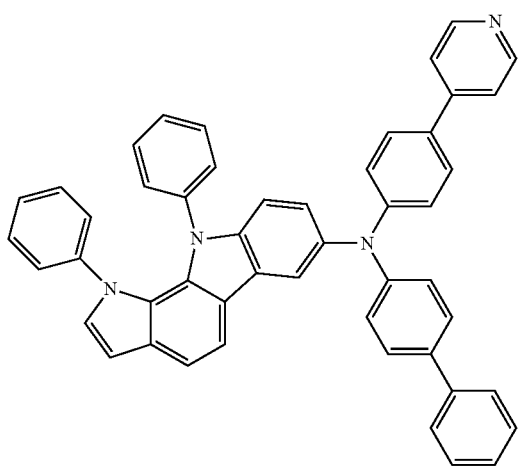
333
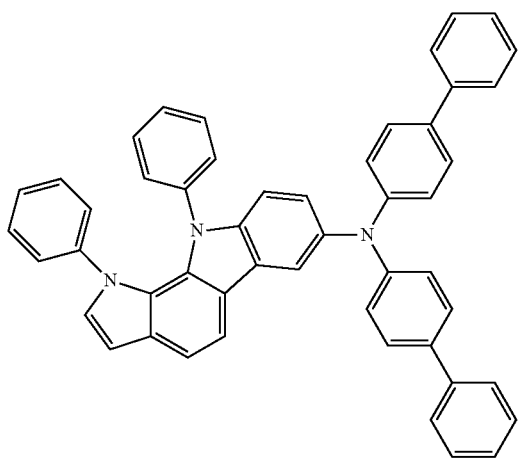
334
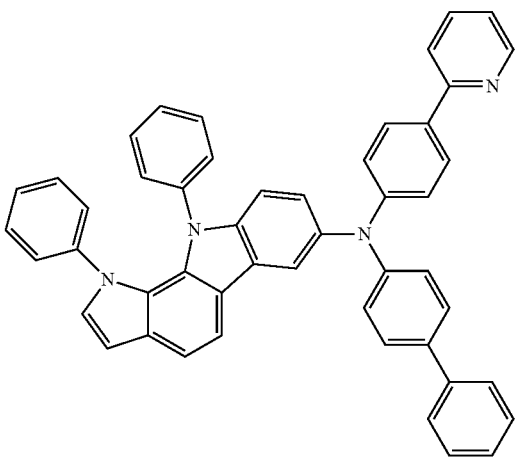
335
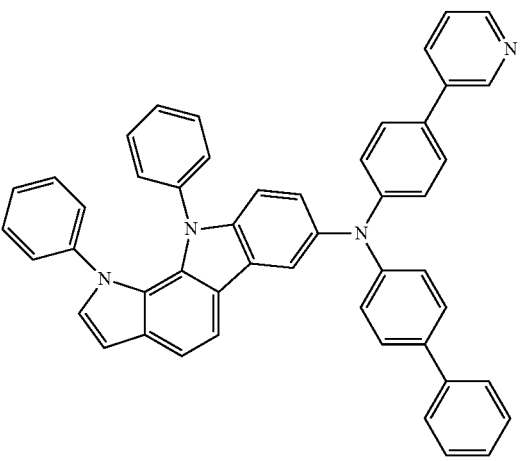
336
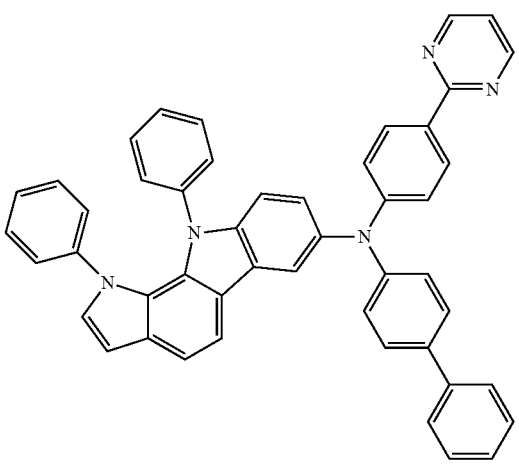

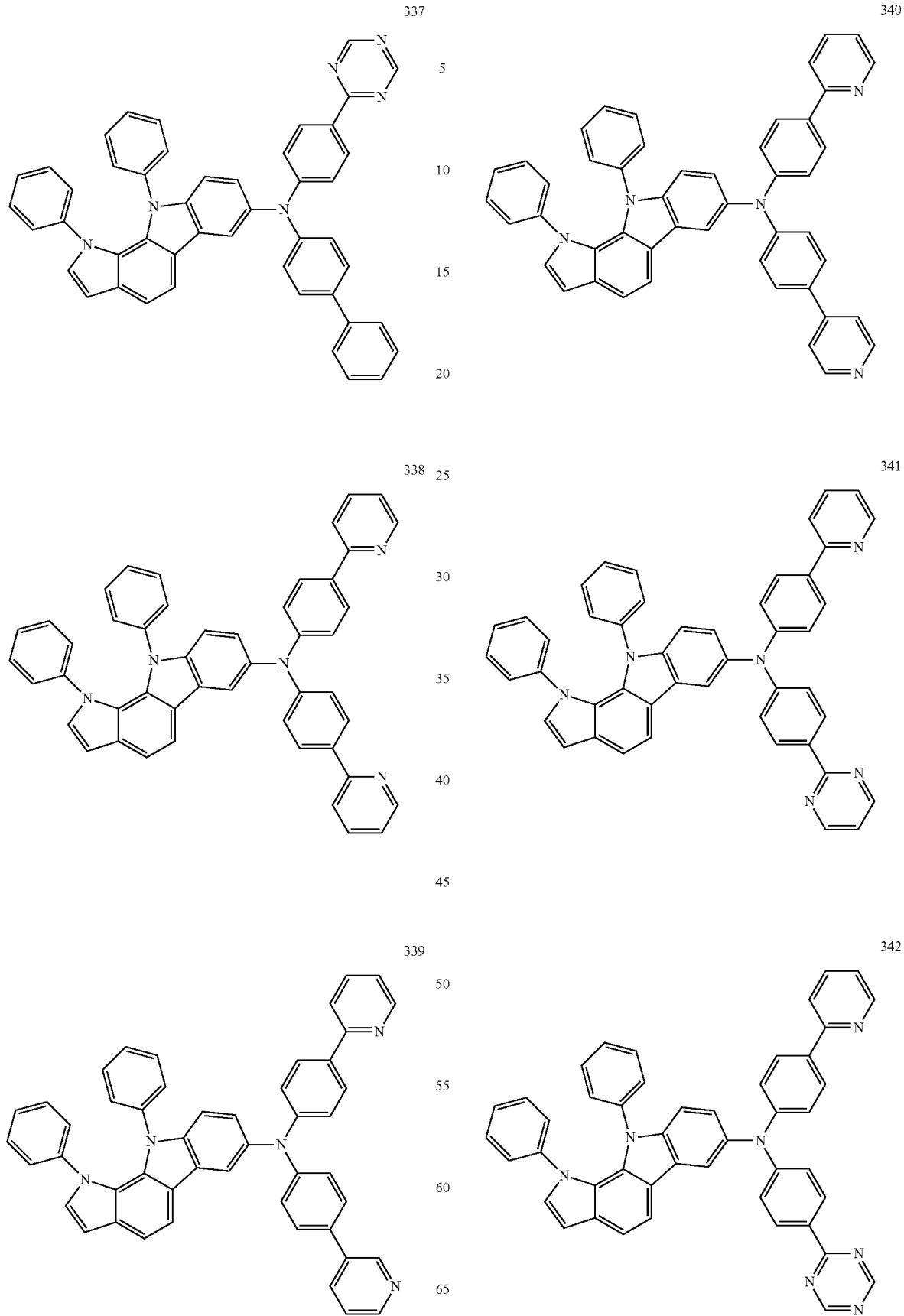

343
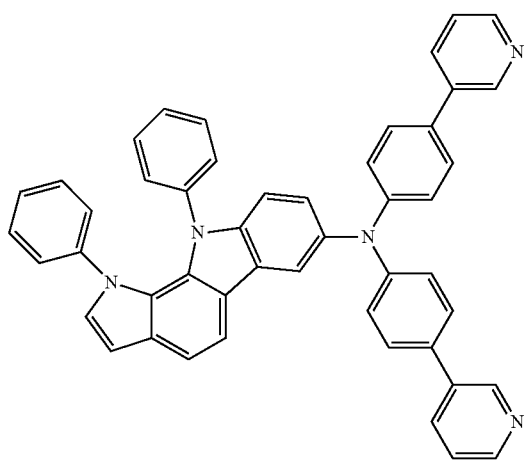
344
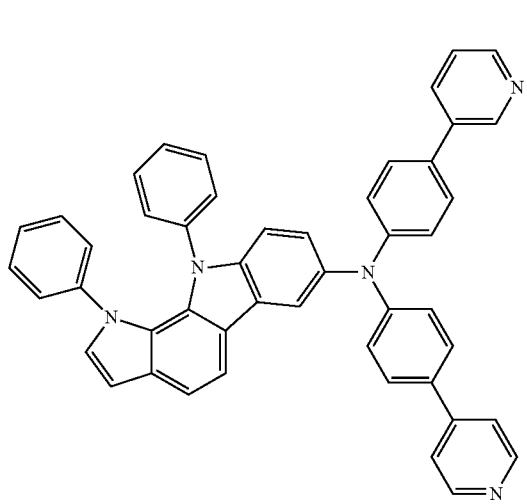
345
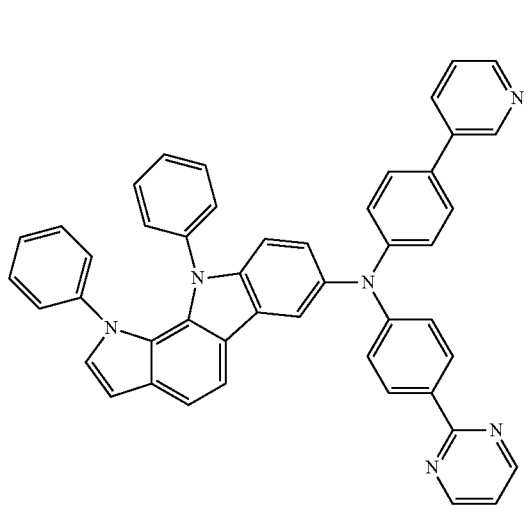
346
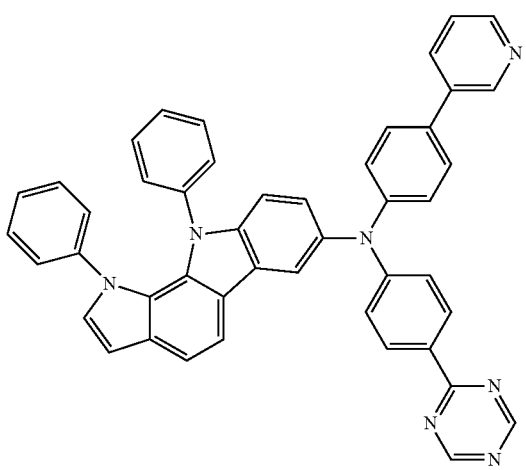
347
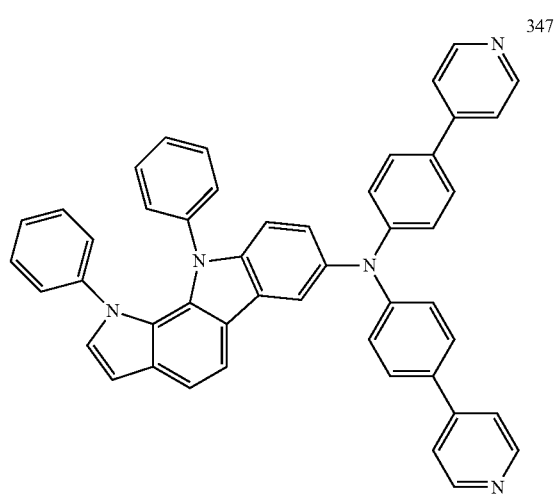
348
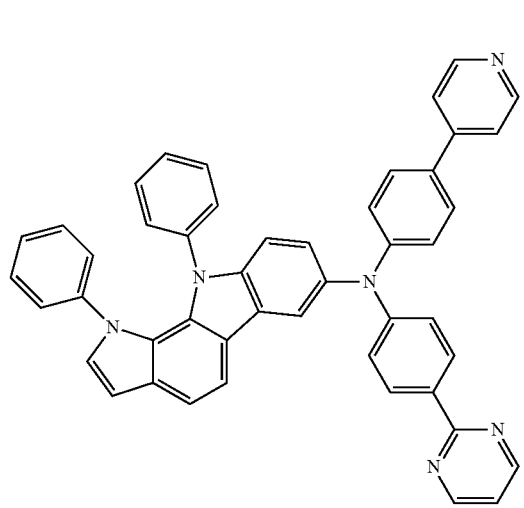

349
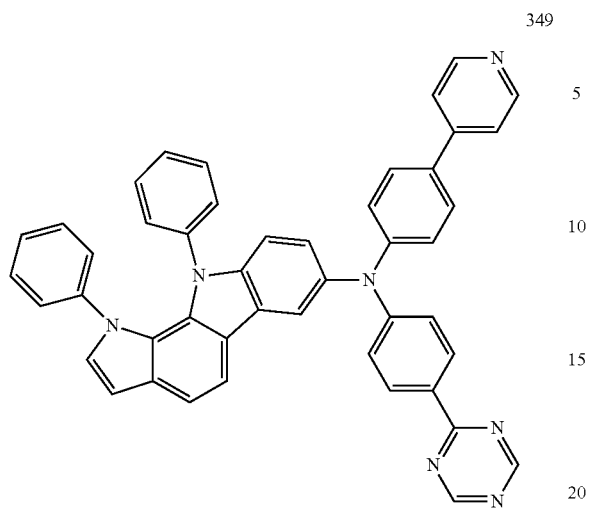
352
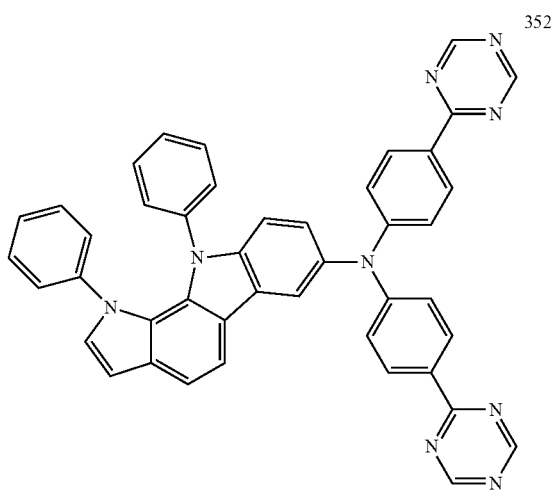
350
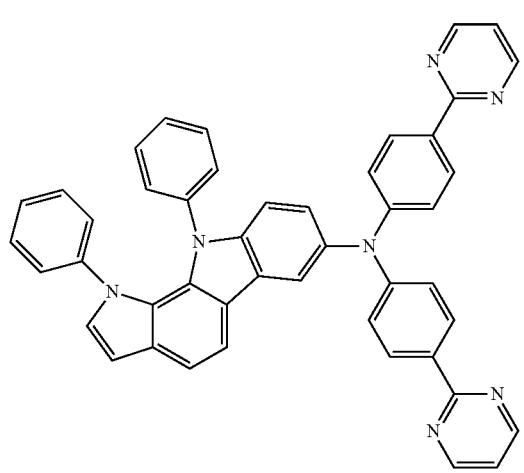
363
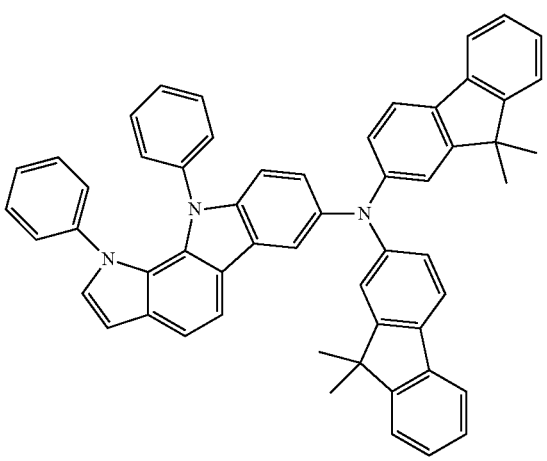
351
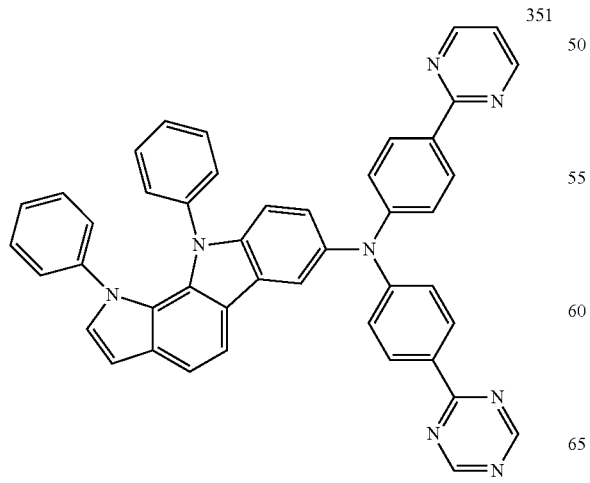
364
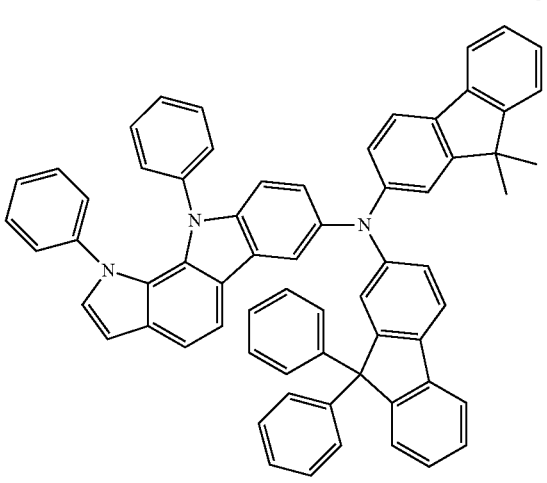

193
-continued
365
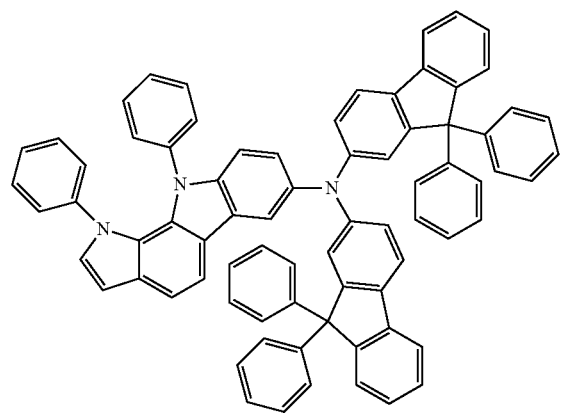
366
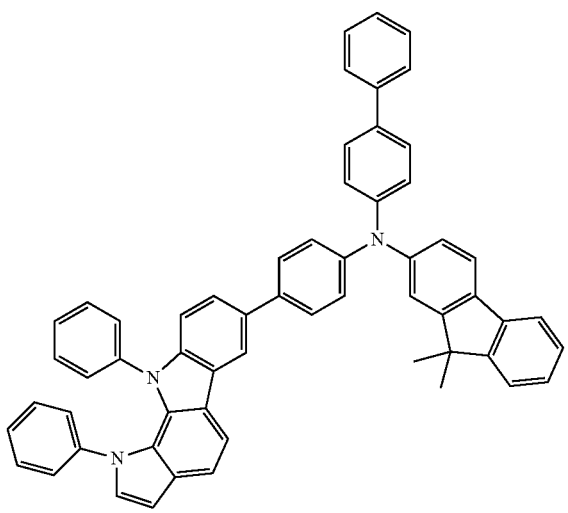
368
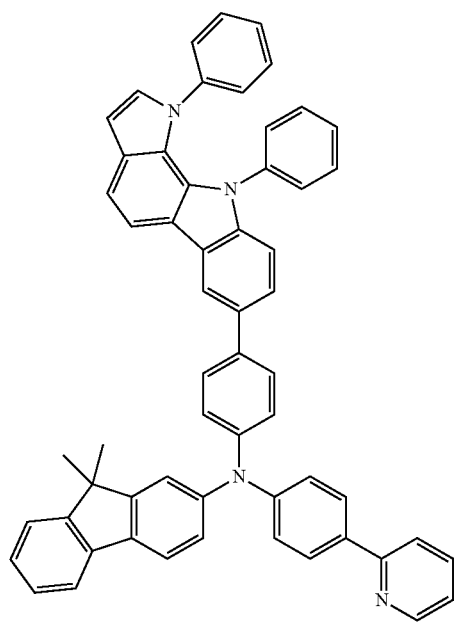
194
-continued
367
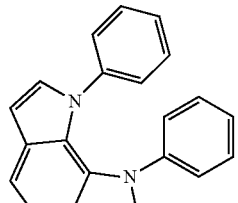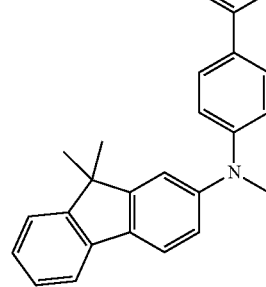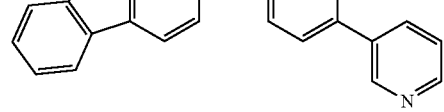
369
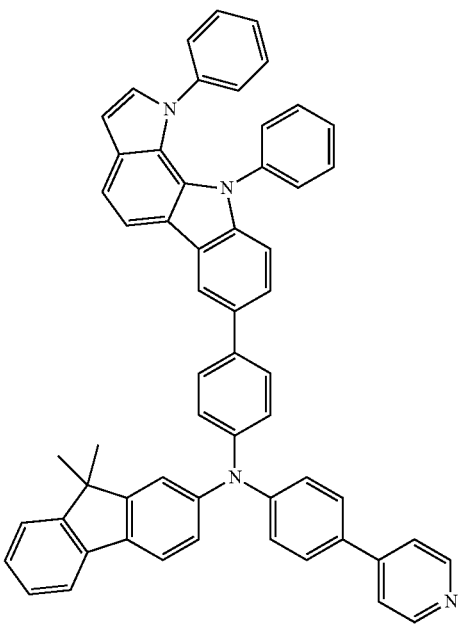

370
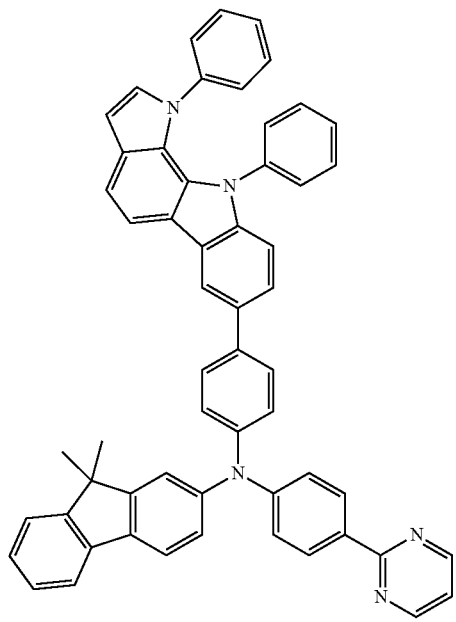
371
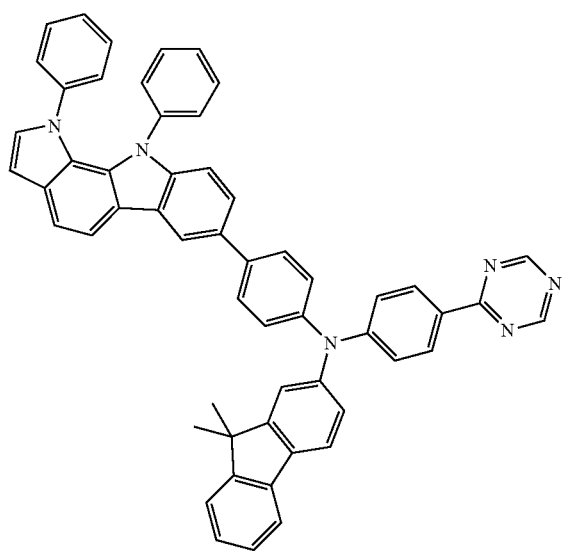
372
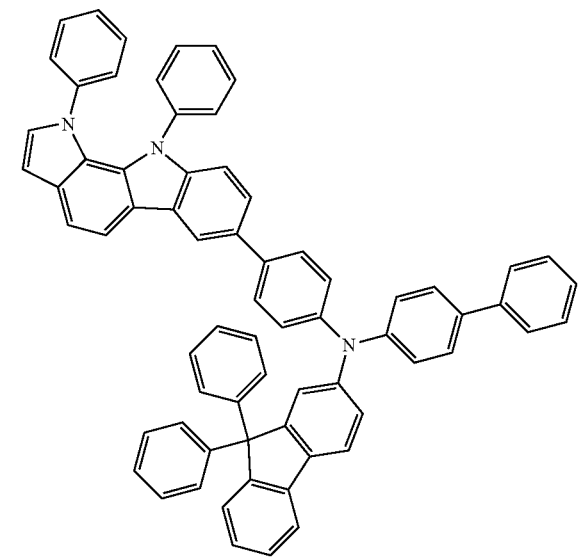
373
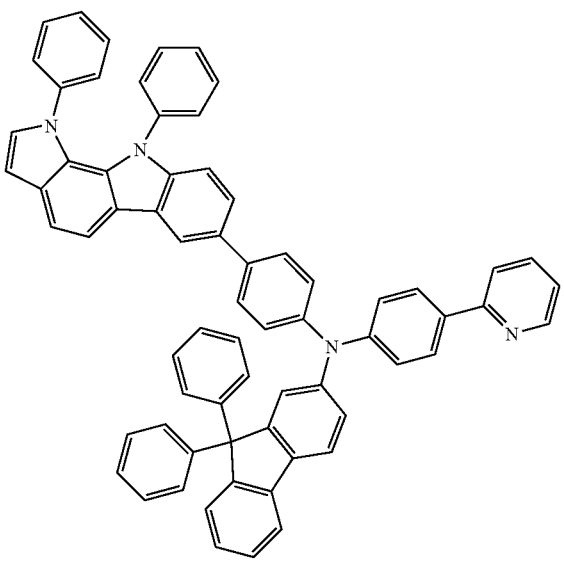

374
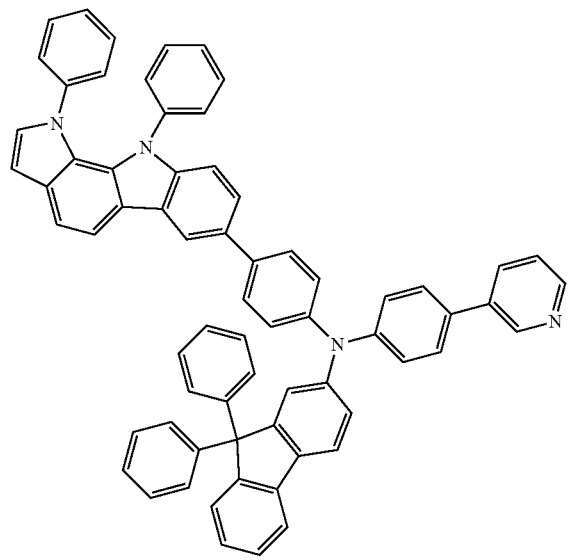
376
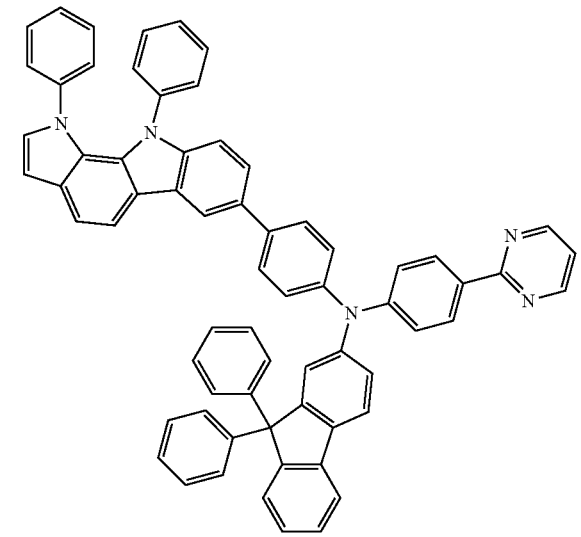
375
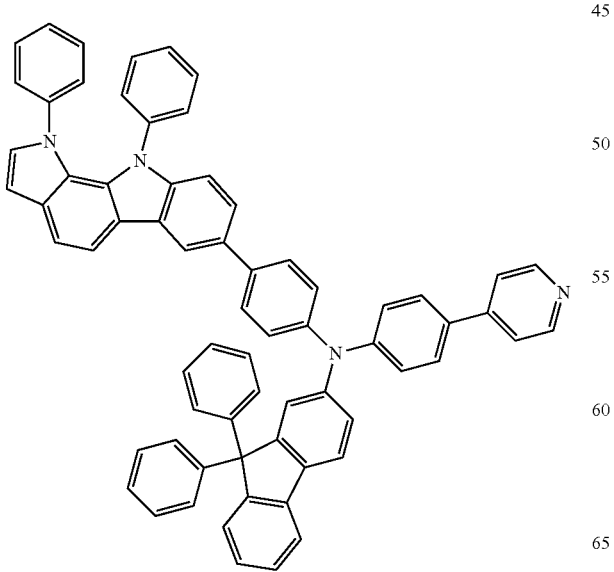
377
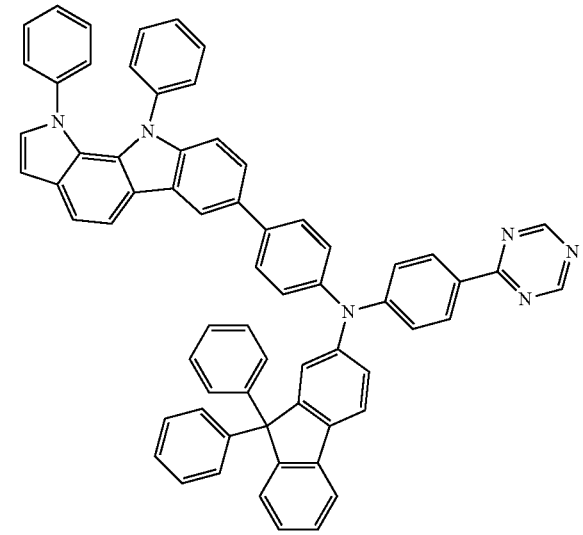

378
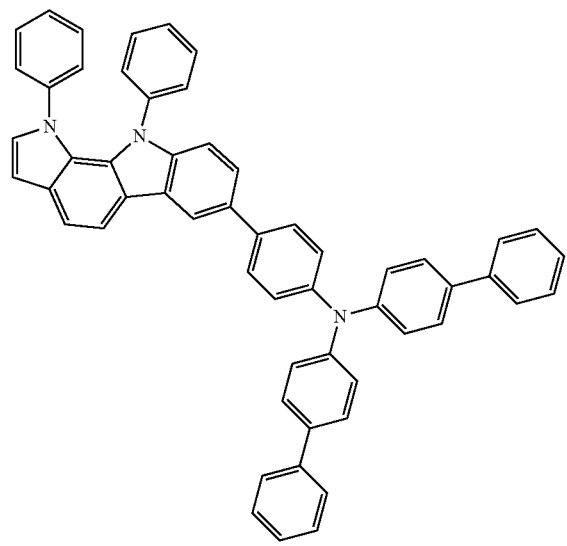
379
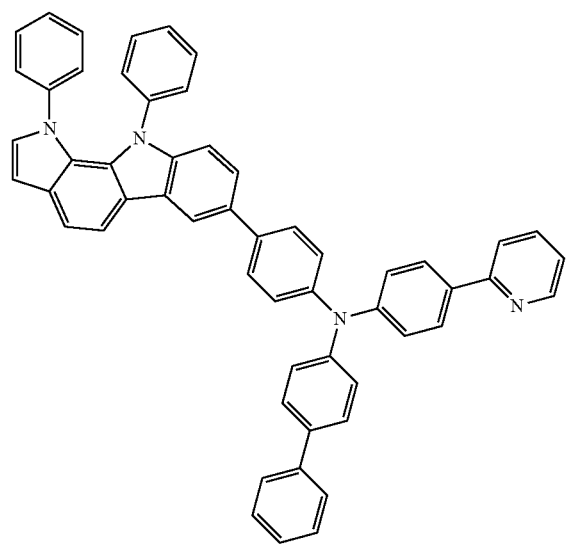
380
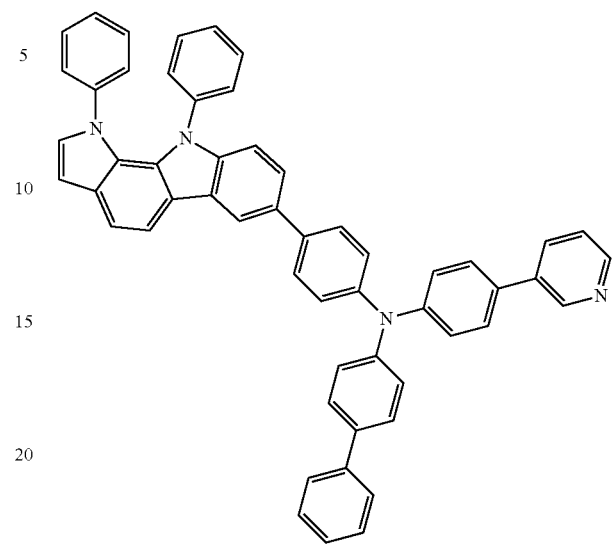
381
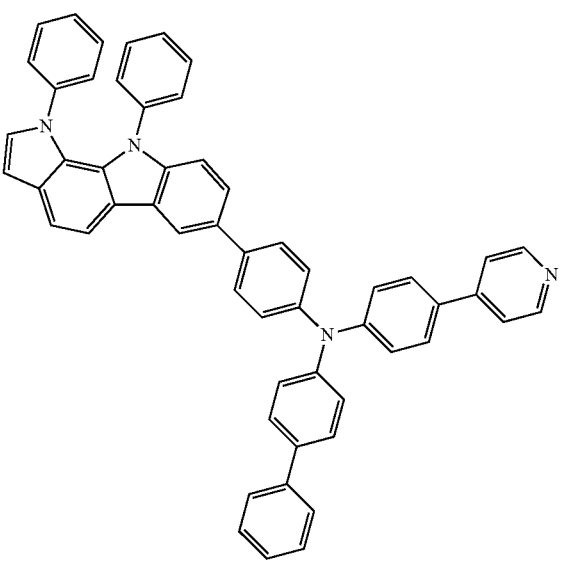

201
-continued
382
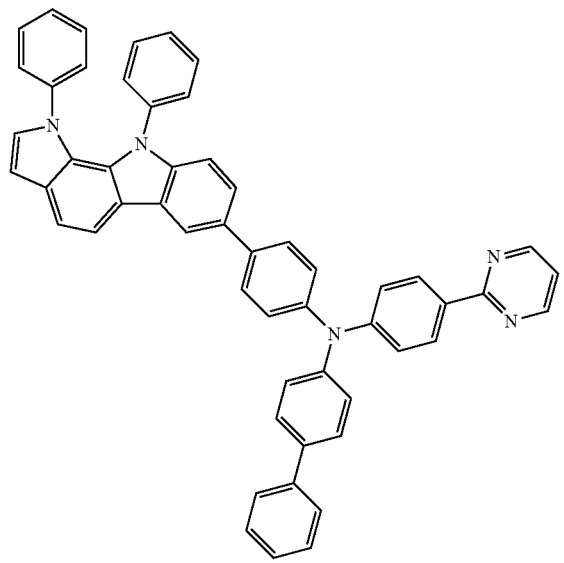
202
-continued
384
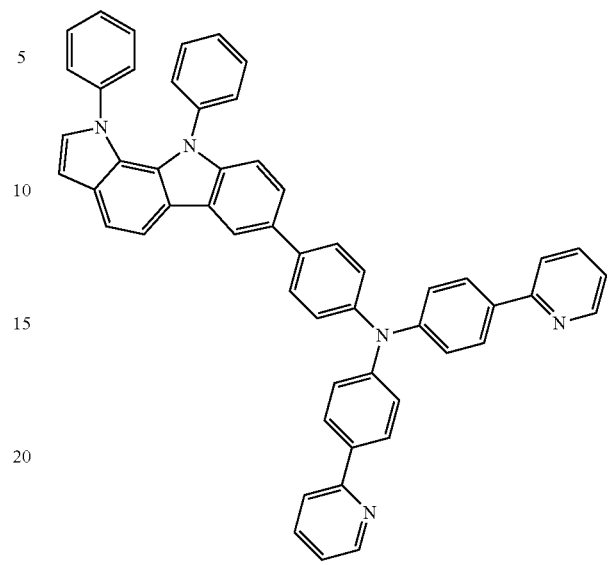
383
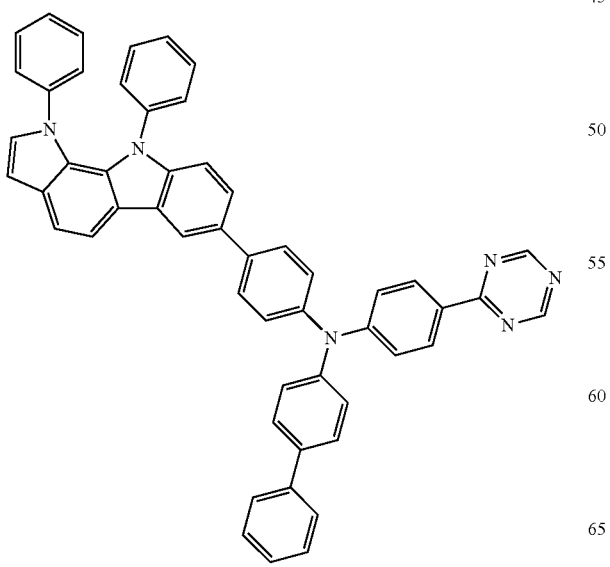
385
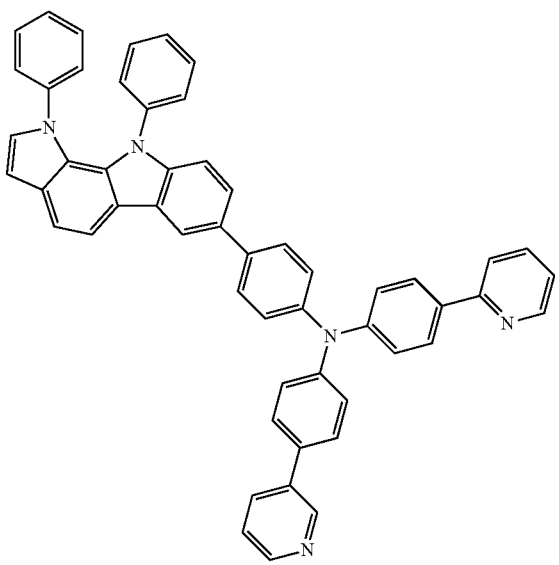

203
-continued
386
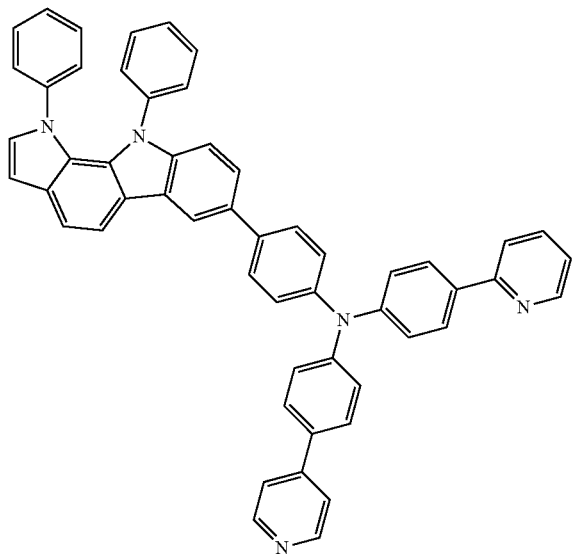
387
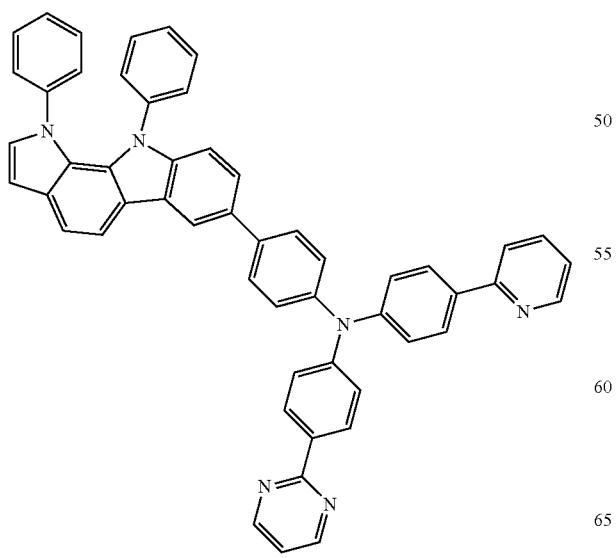
204
-continued
388
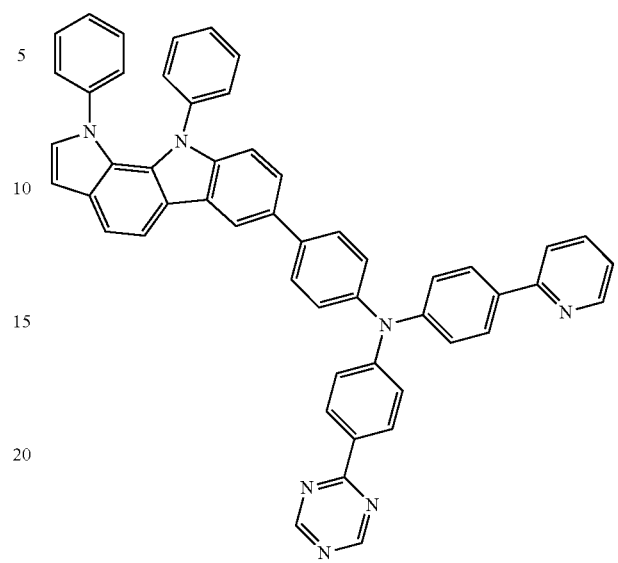
389
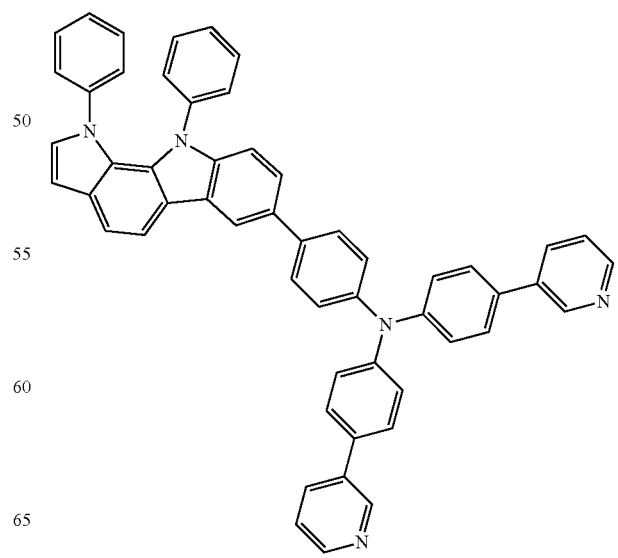

205
-continued
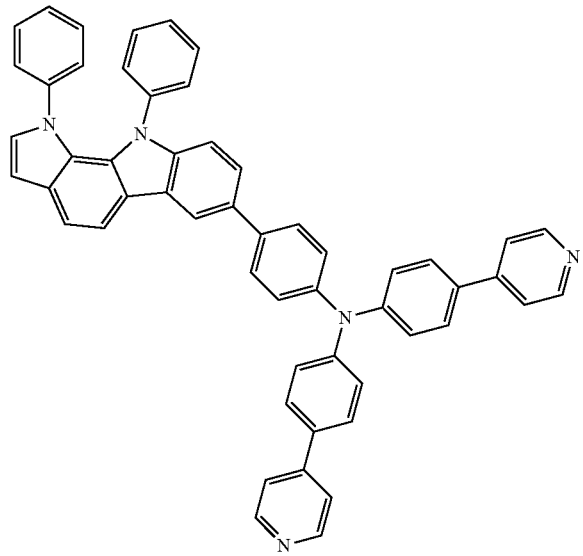
390
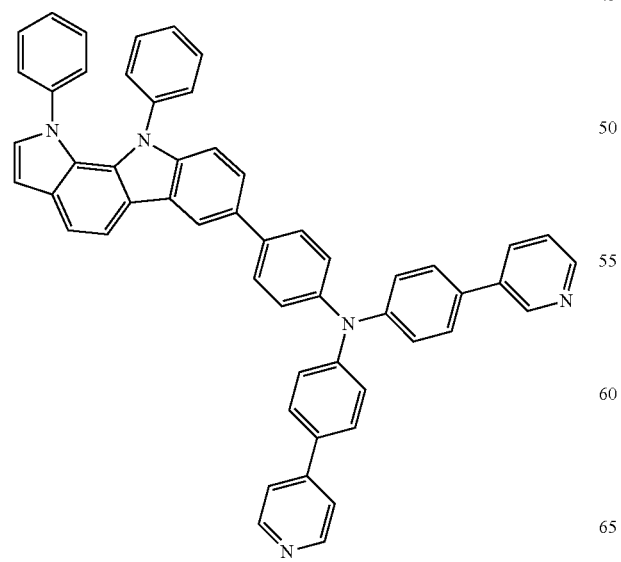
391
206
-continued
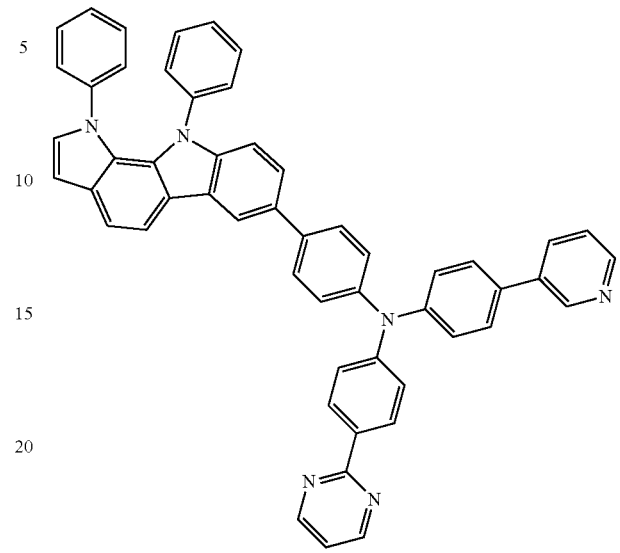
392
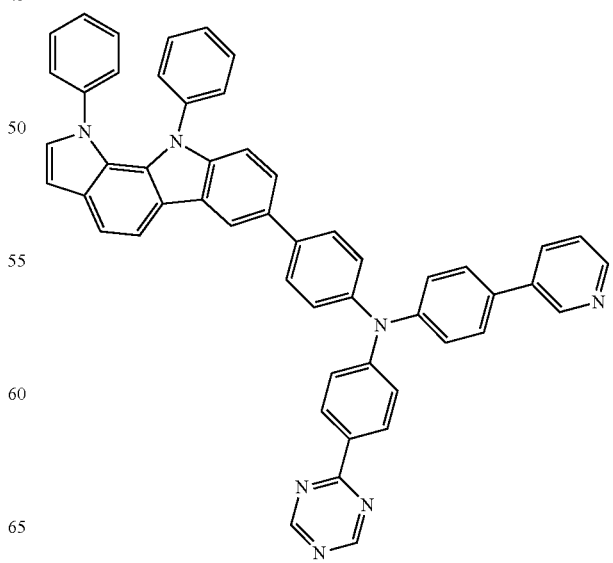
393

207
-continued
208
-continued
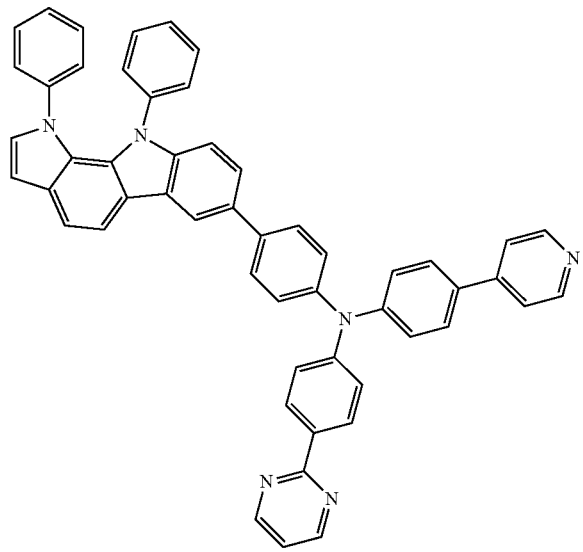
394
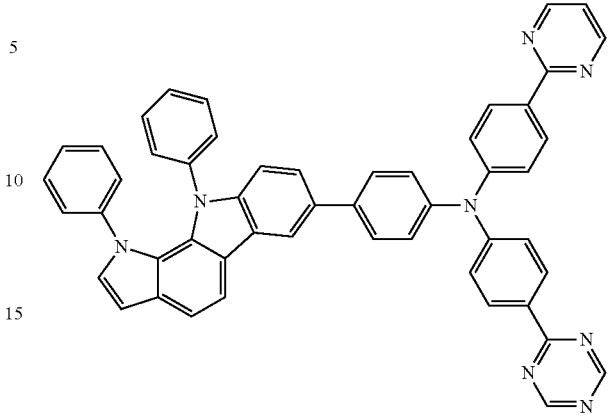
397
395
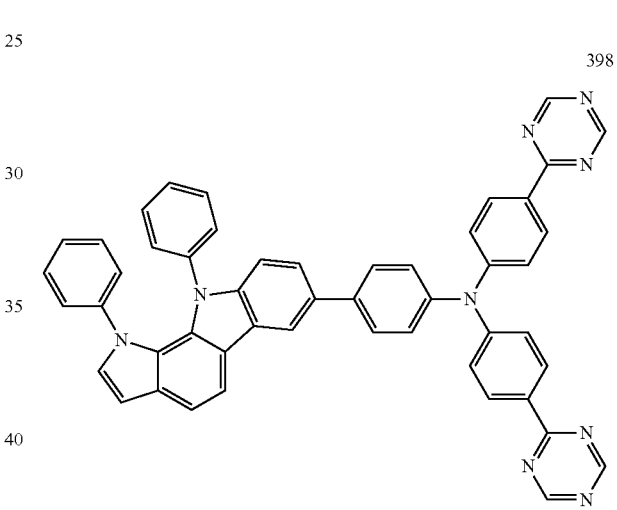
398
396
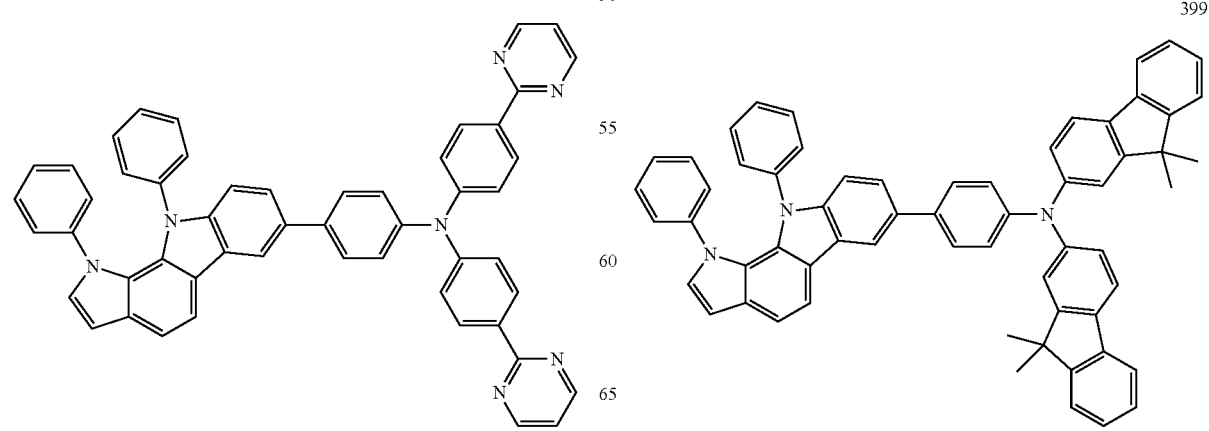
399

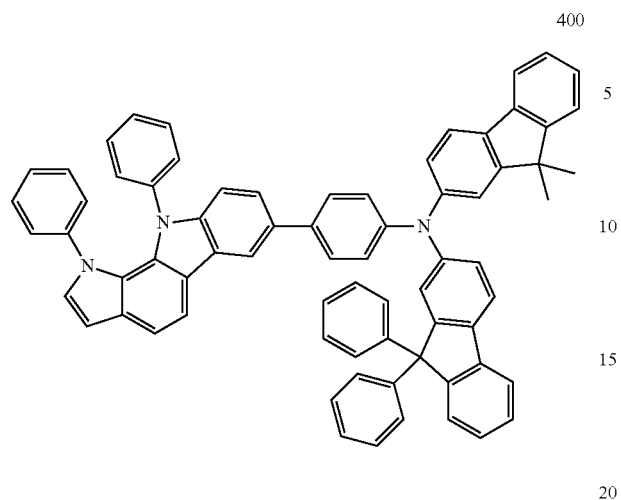
400
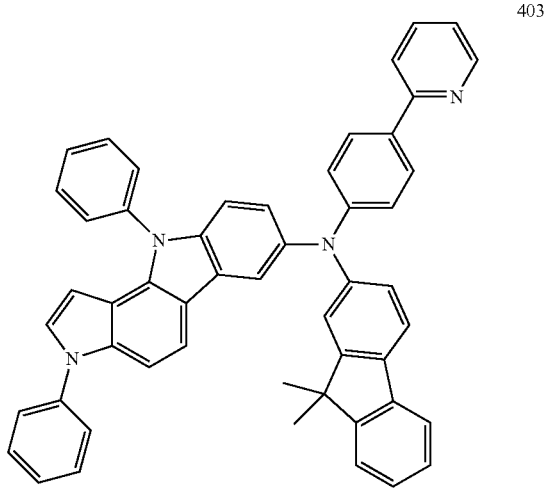
403
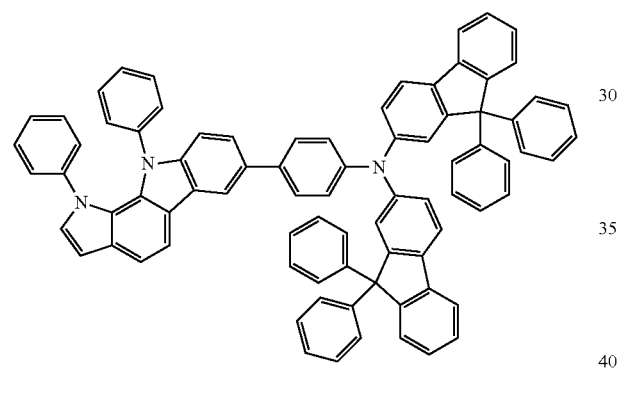
401
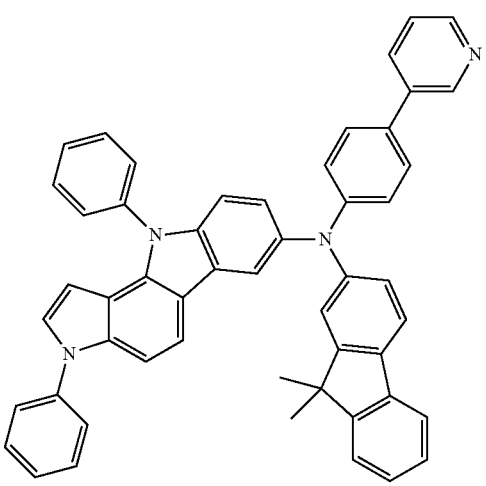
404
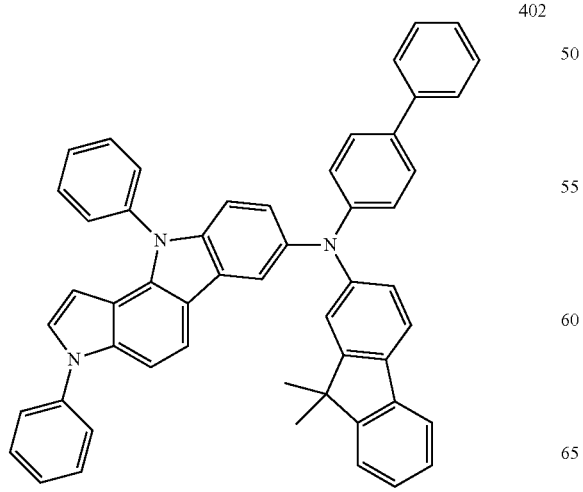
402
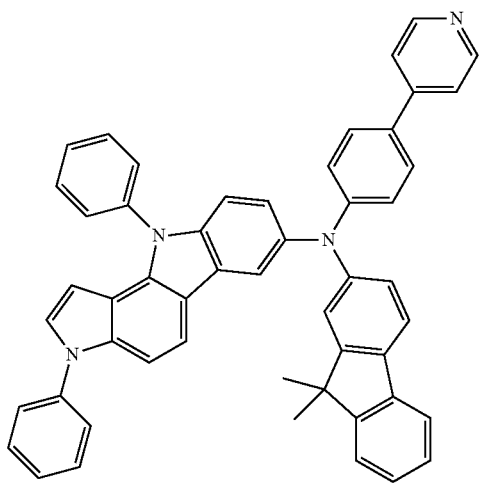
405

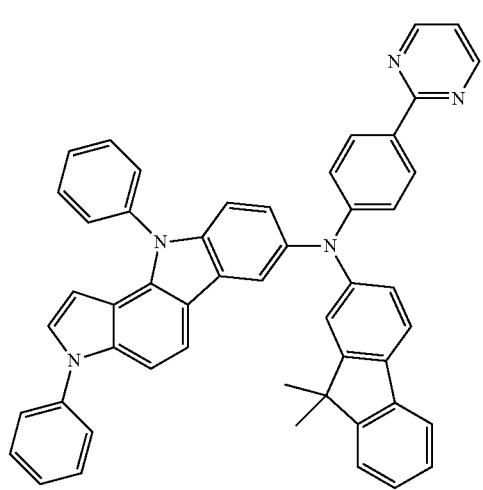
406
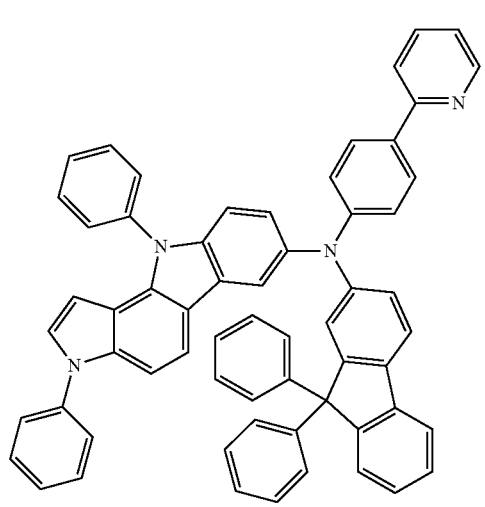
409
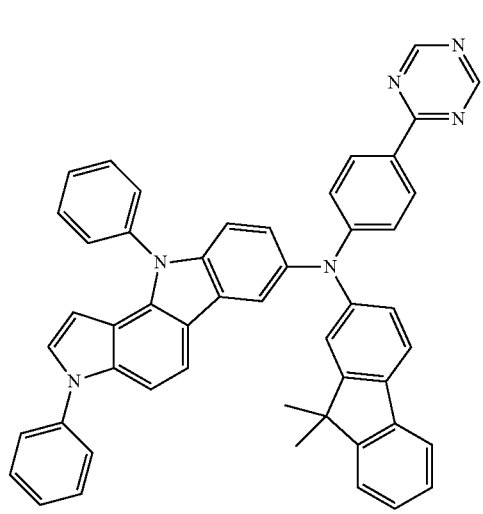
407
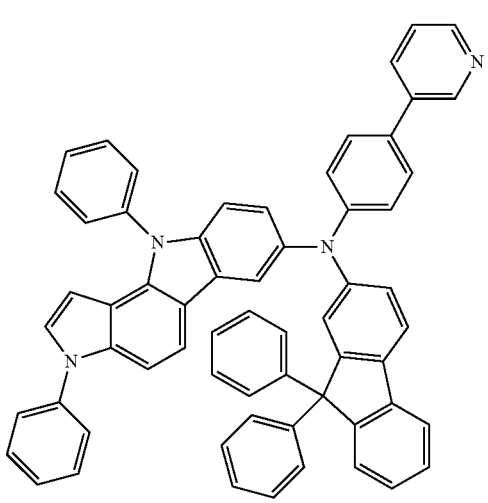
410
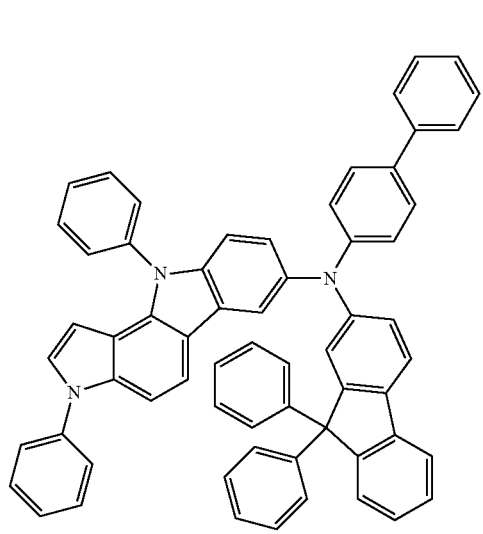
408
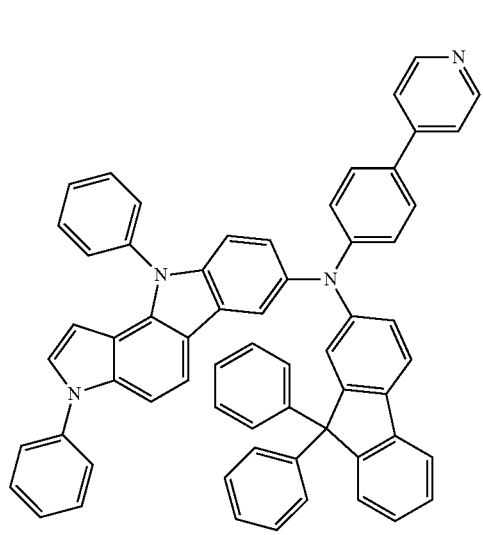
411

213
-continued
412
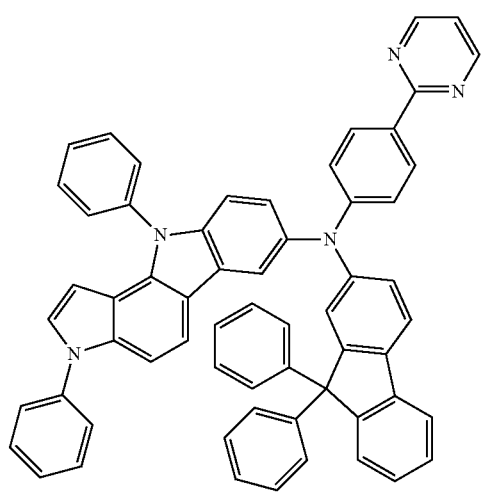
413
414
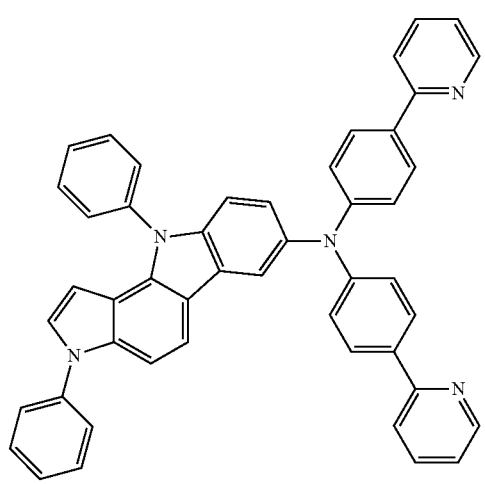
214
-continued
415
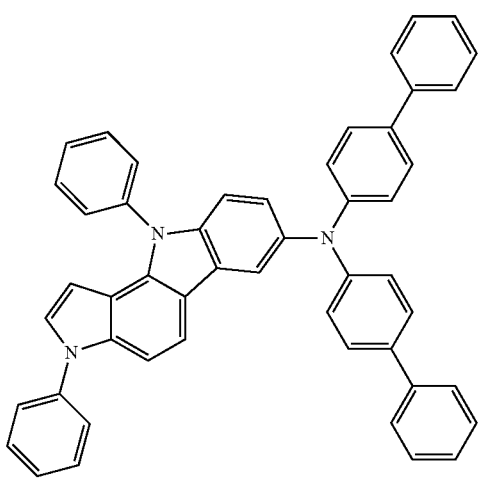
416
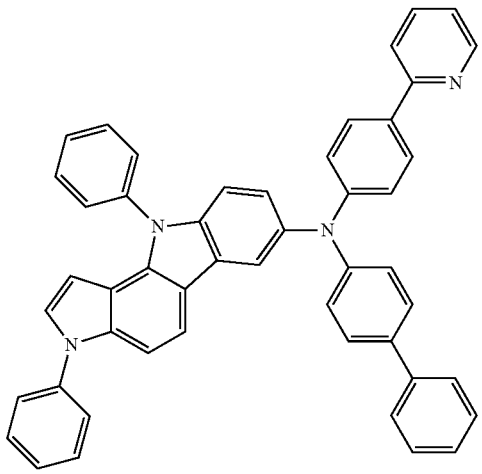
417
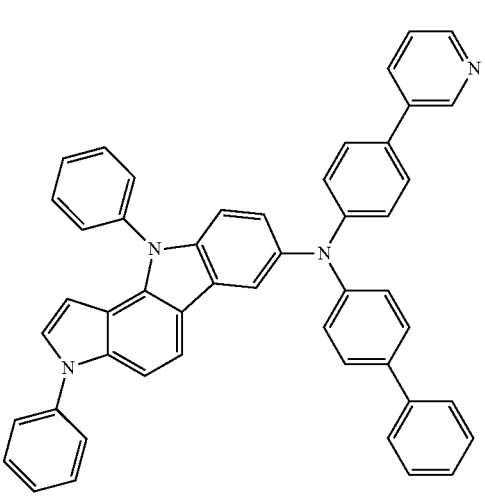

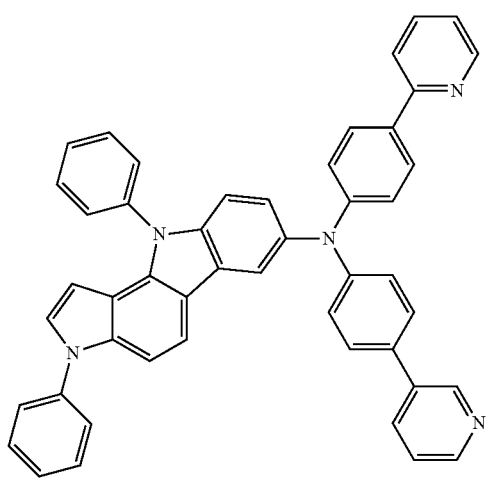
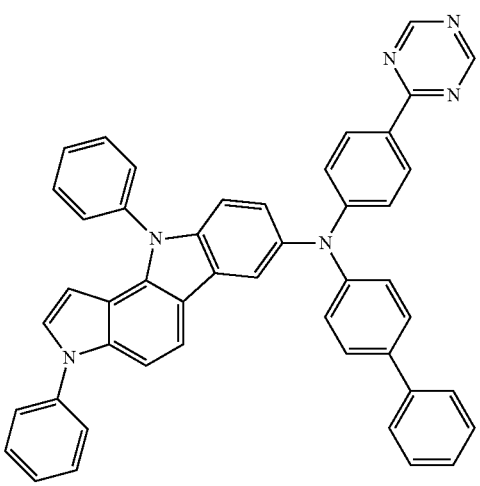

| 424 | 427 |
|---|---|
| 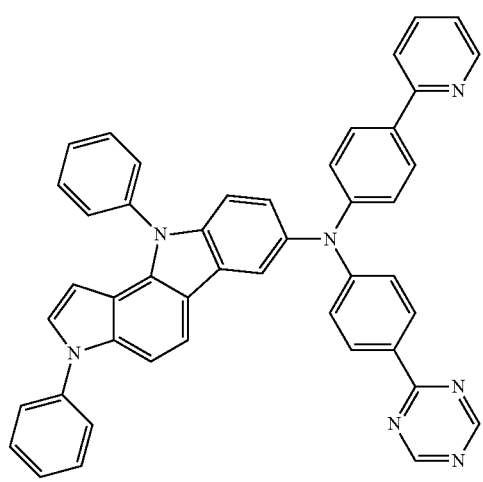 | 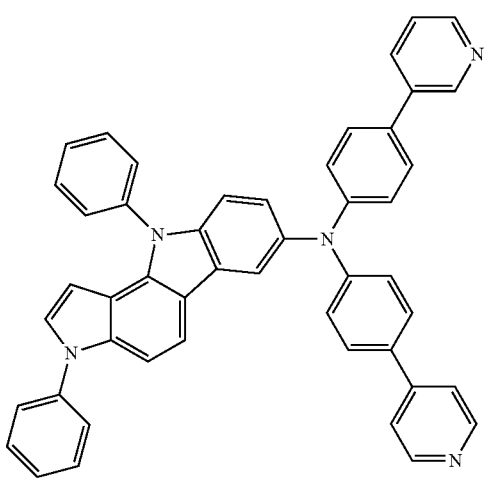 |
| 425 | 428 |
| 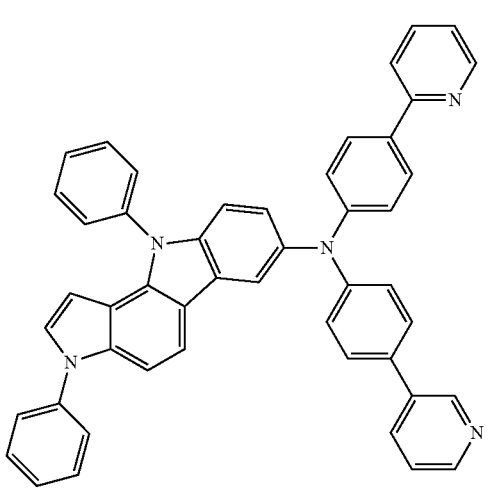 | 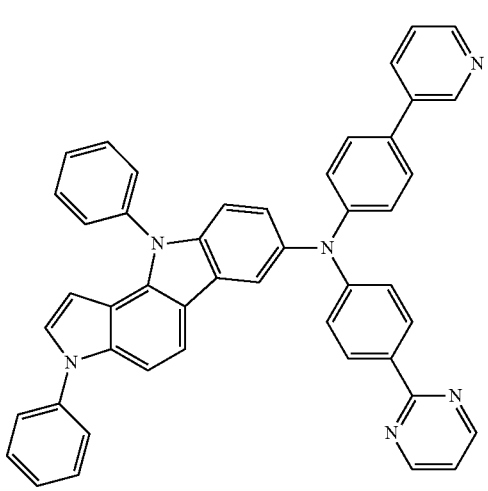 |
| 426 | 429 |
| 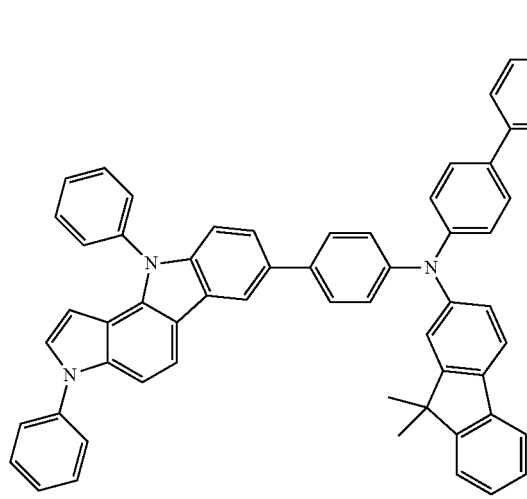 | 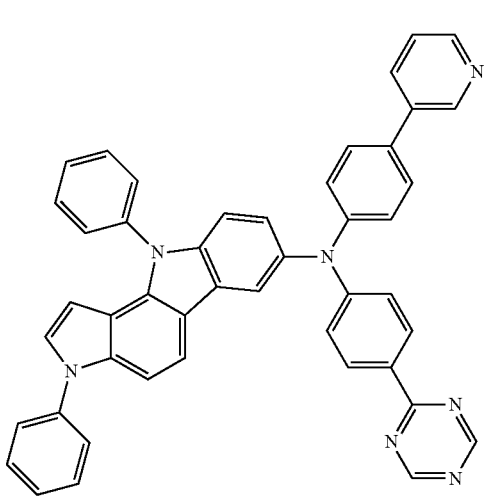 |

219
-continued
430
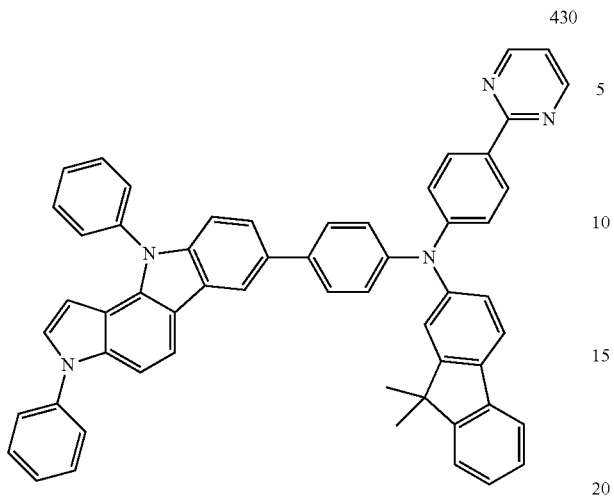
431
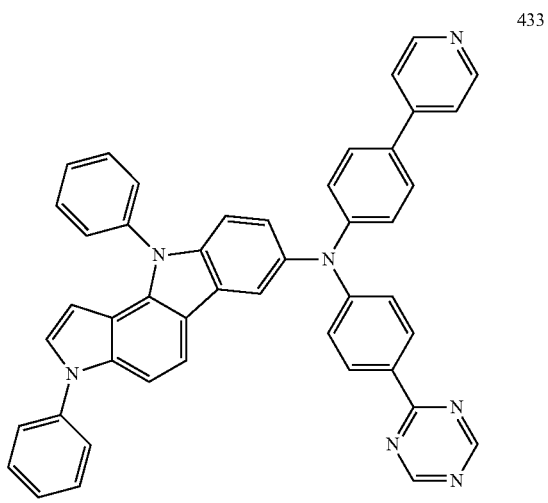
432
220
-continued
433
434
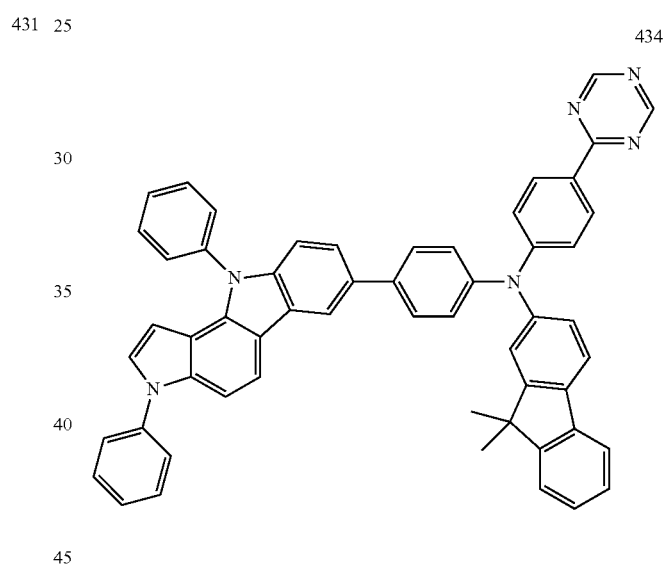
435
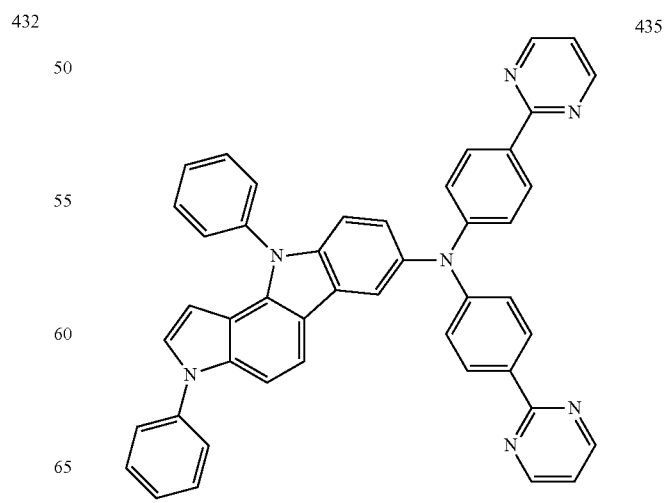

221
-continued
436
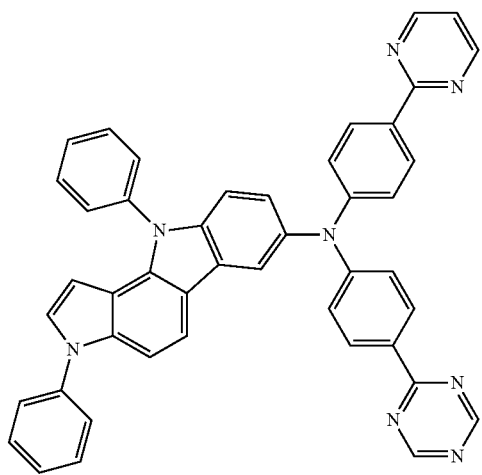
437
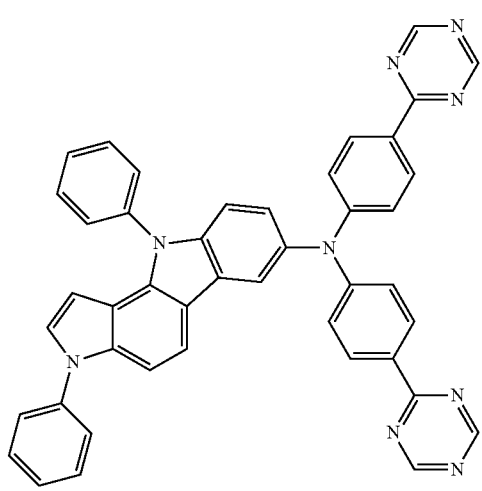
438
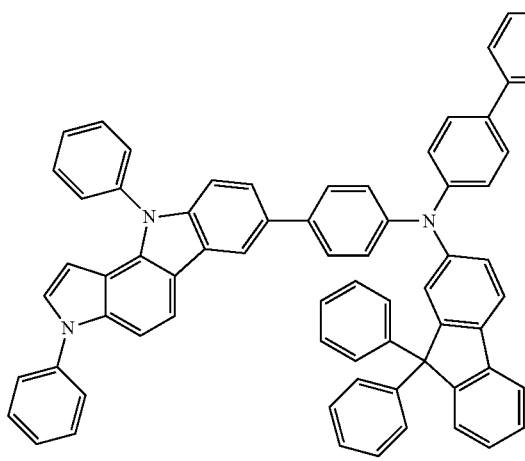
222
-continued
439
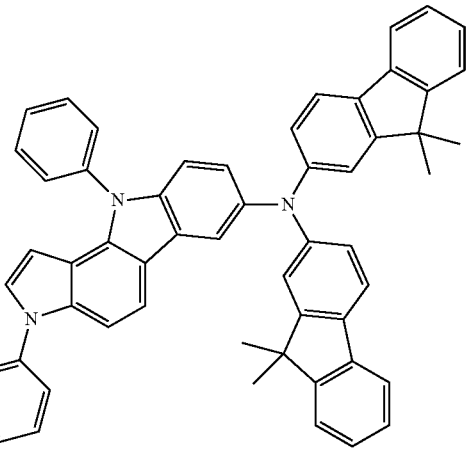
440
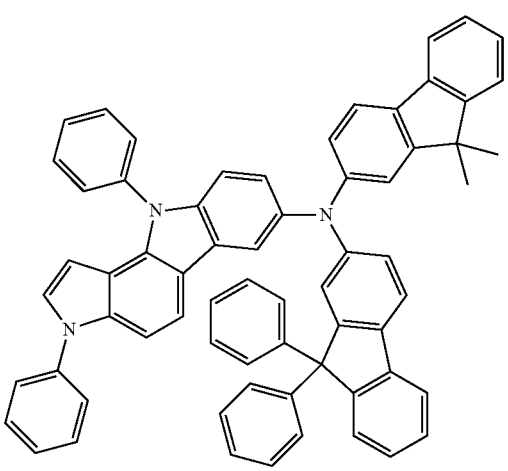
441
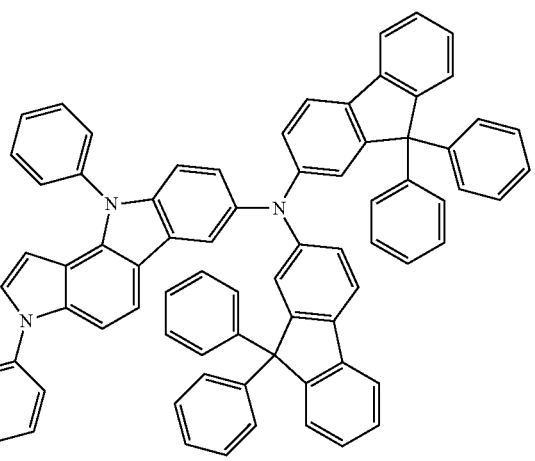

442
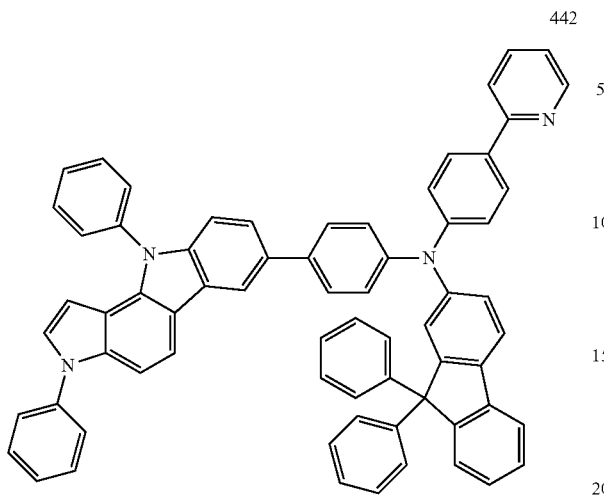
445
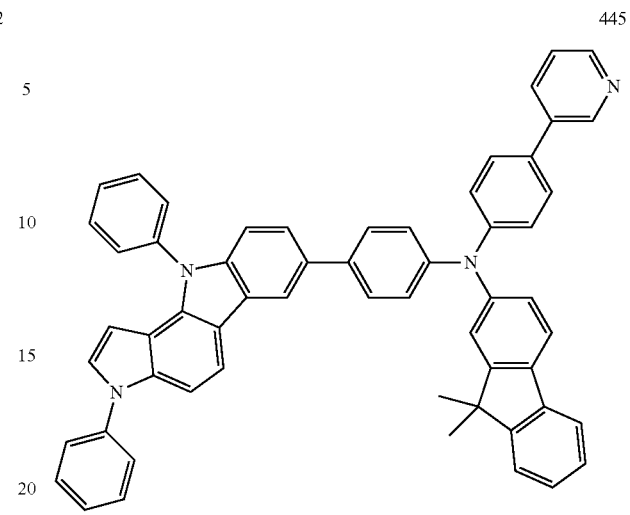
443
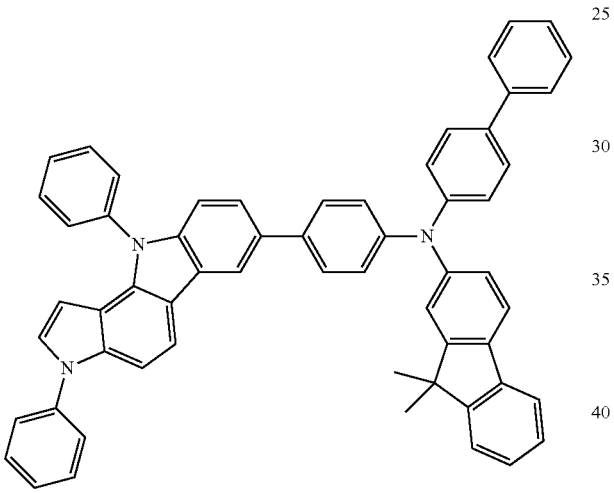
446
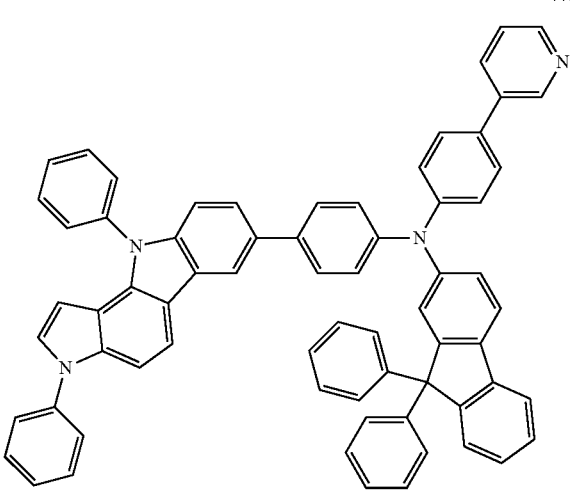
444
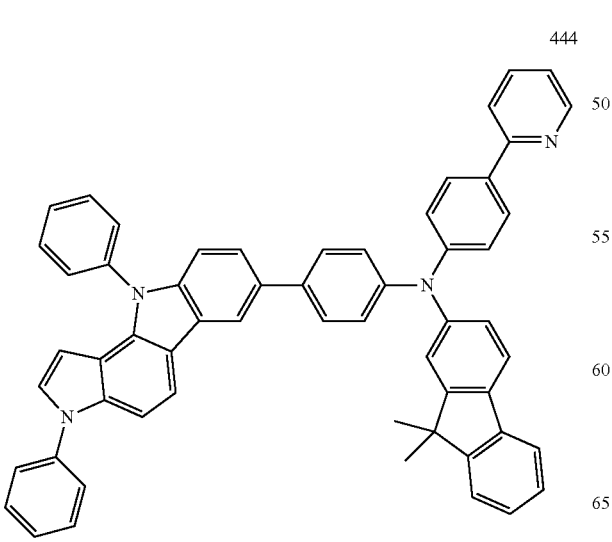
447
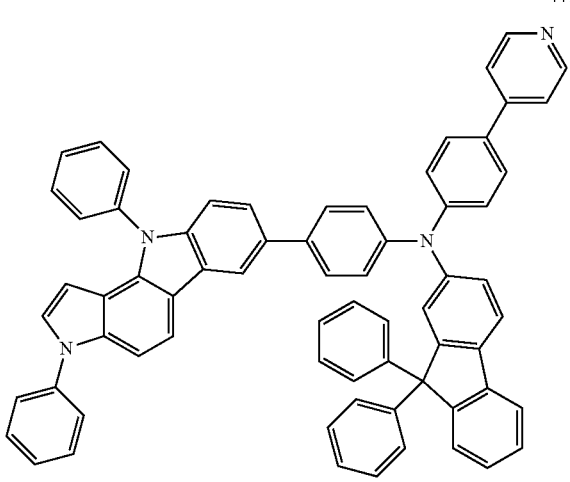

225
-continued
448
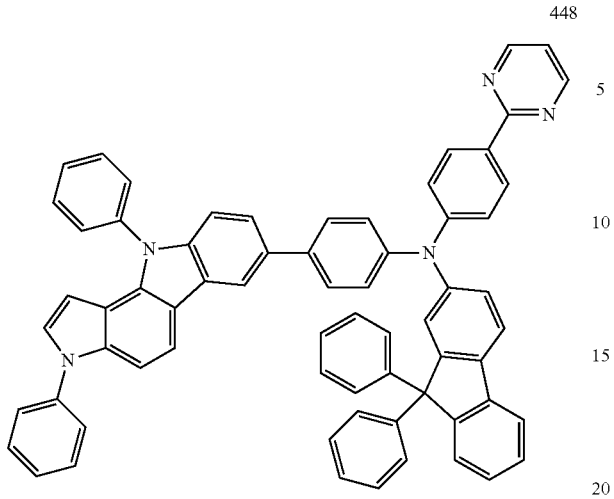
449
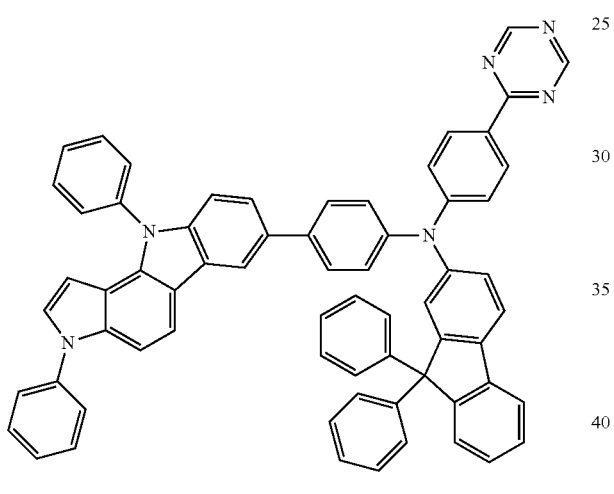
450
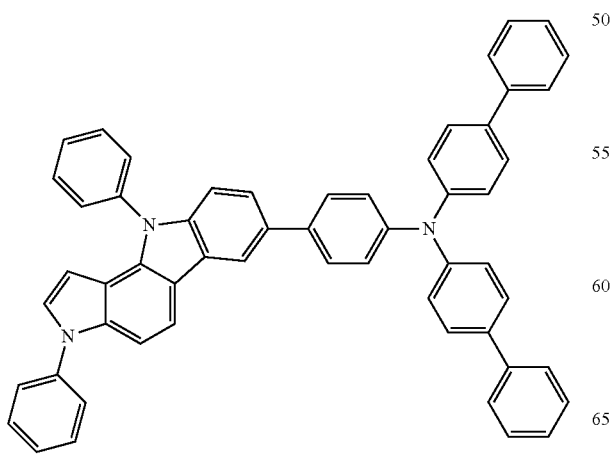
226
-continued
451
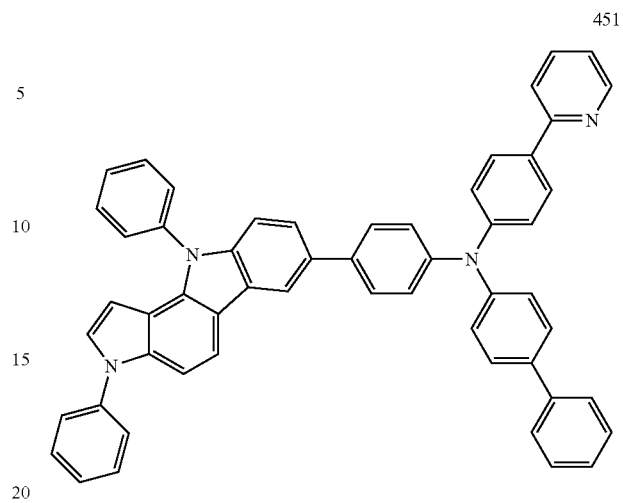
452
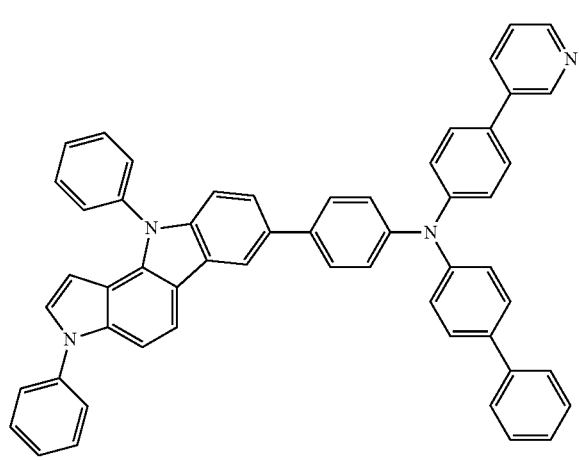
453
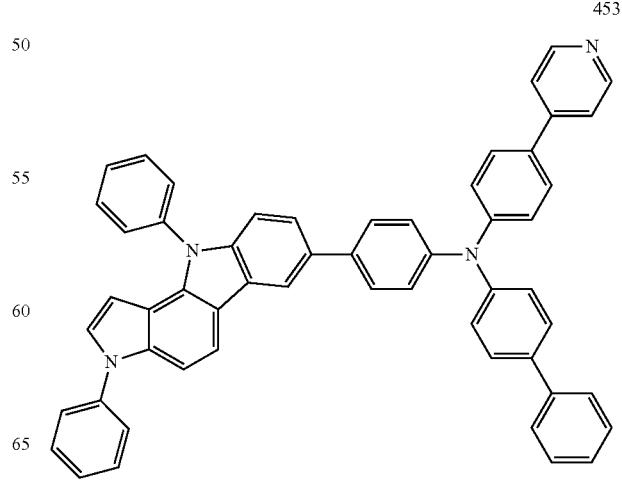

| 454 | 457 |
|---|---|
| 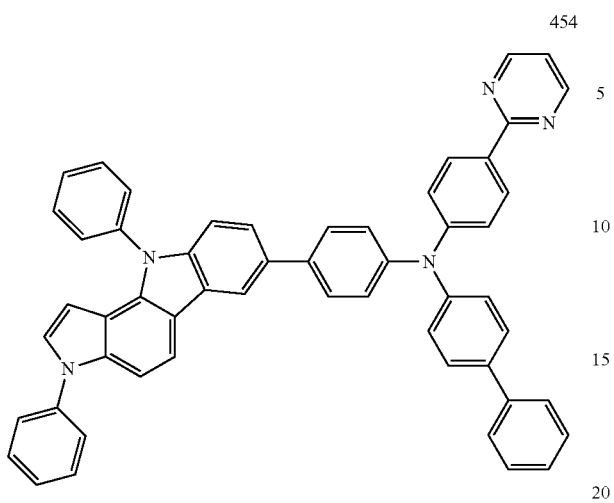 | 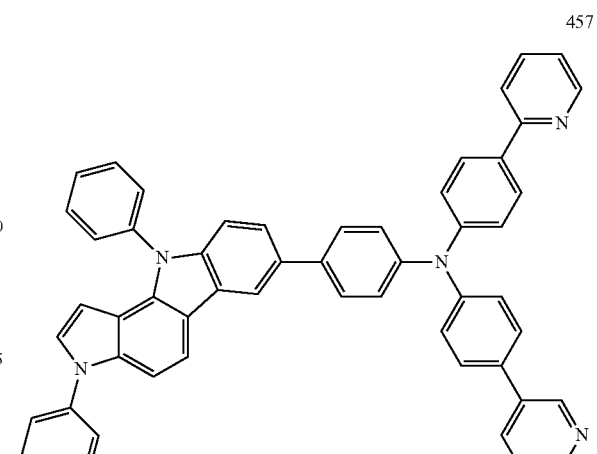 |
| 455 | 458 |
|---|---|
| 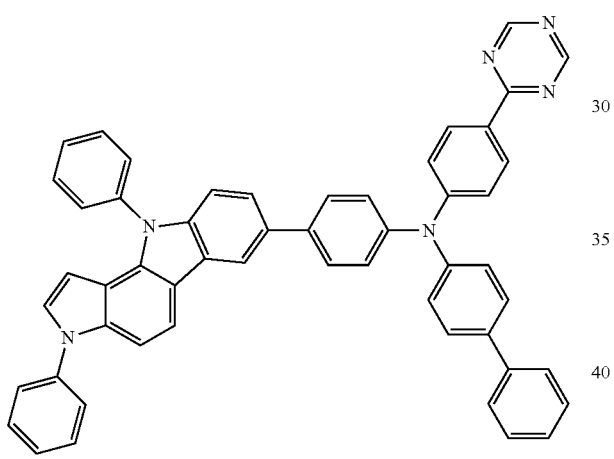 | 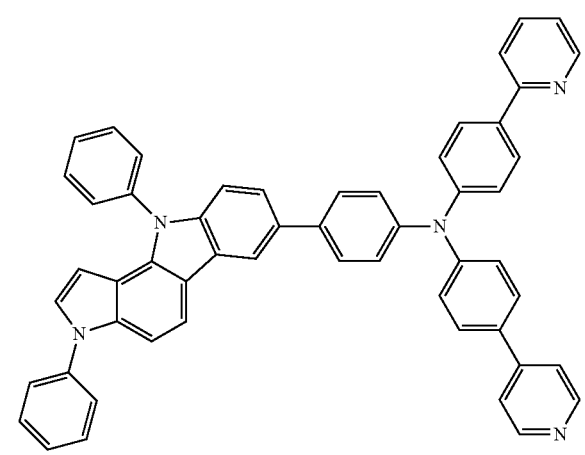 |
| 456 | 459 |
|---|---|
| 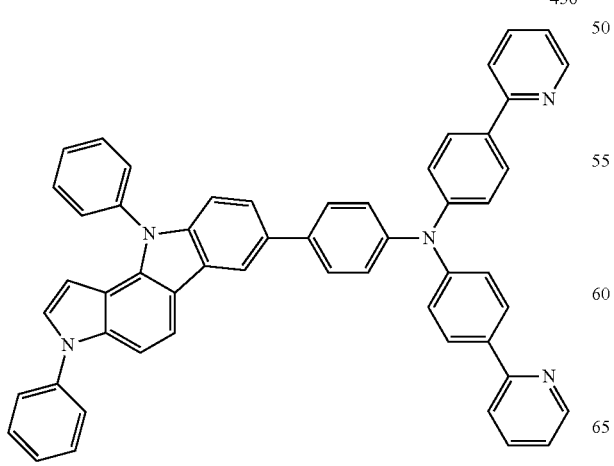 | 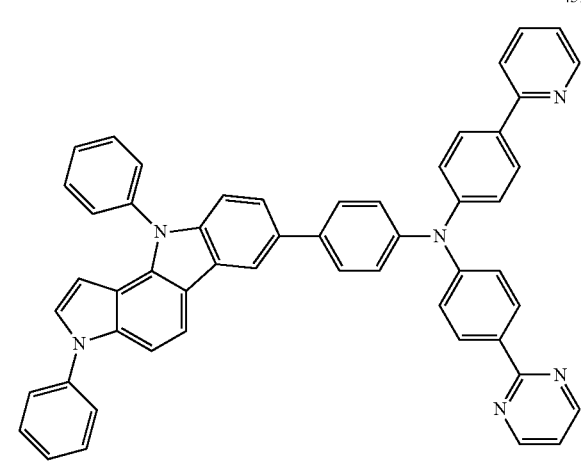 |

-continued
460
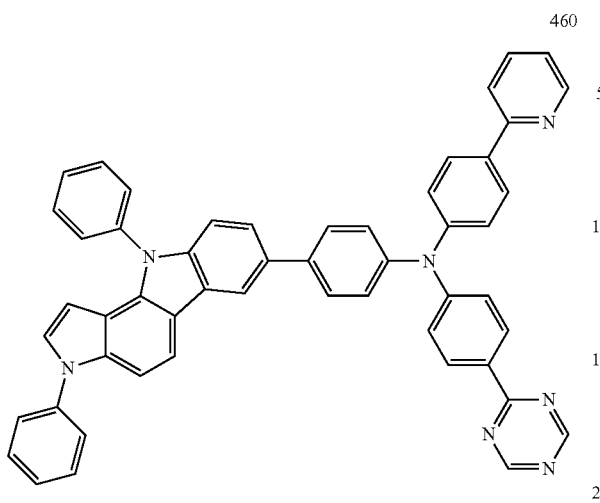
461
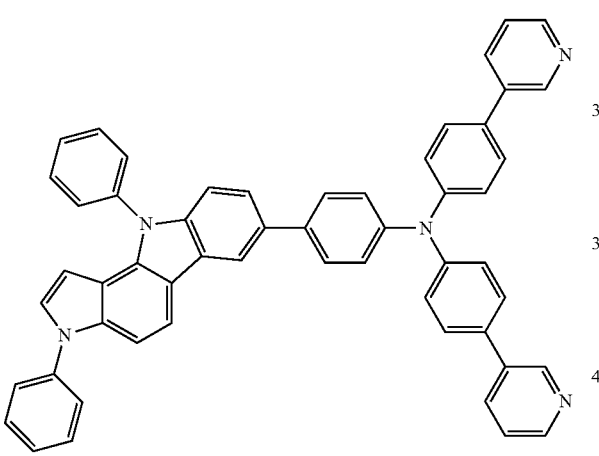
462
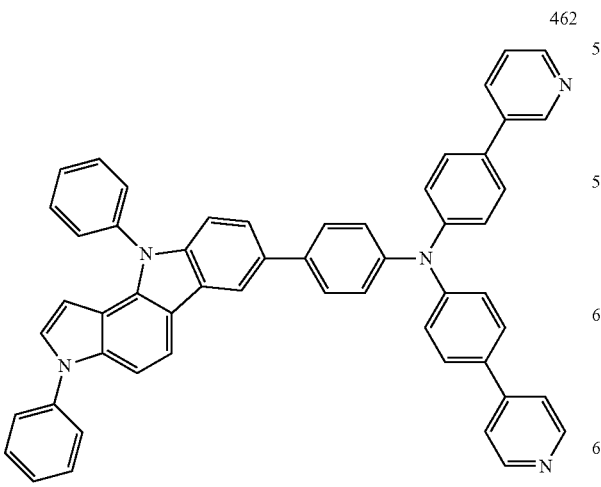
-continued
463
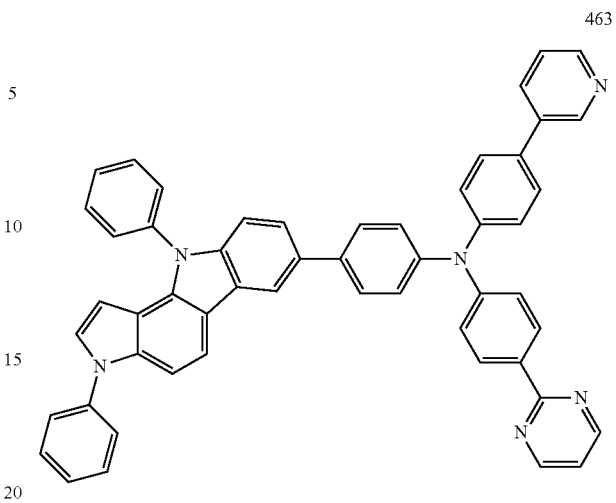
464
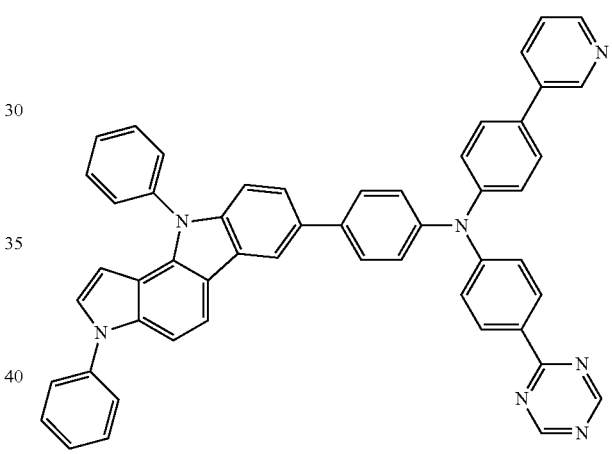
465
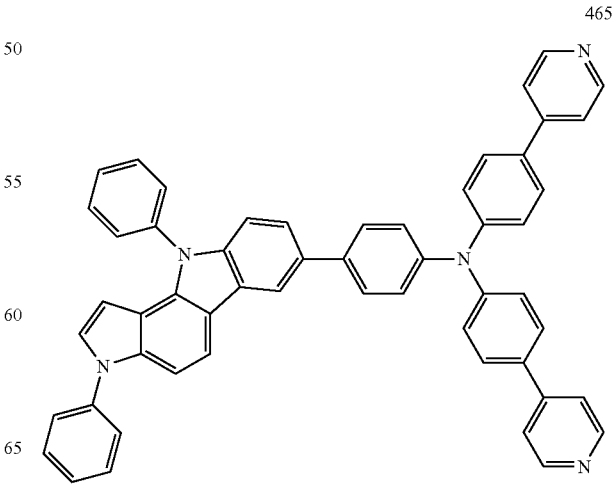

231
-continued
466
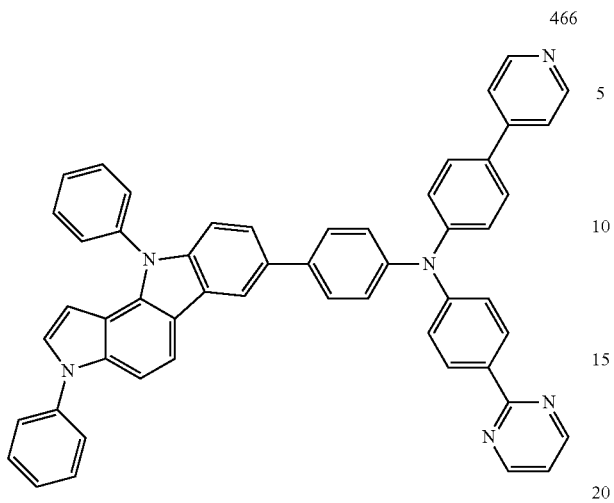
467
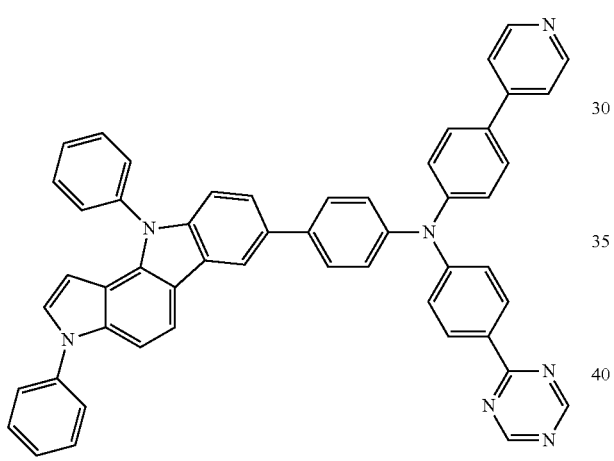
468
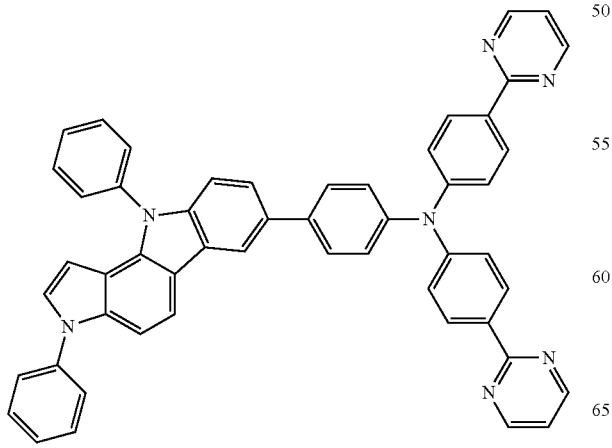
232
-continued
469
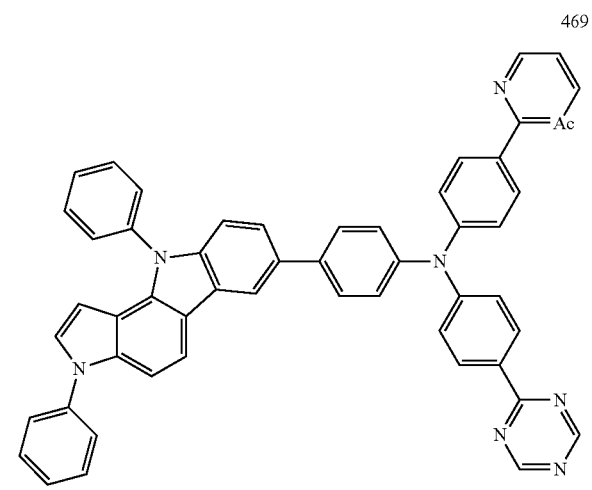
470
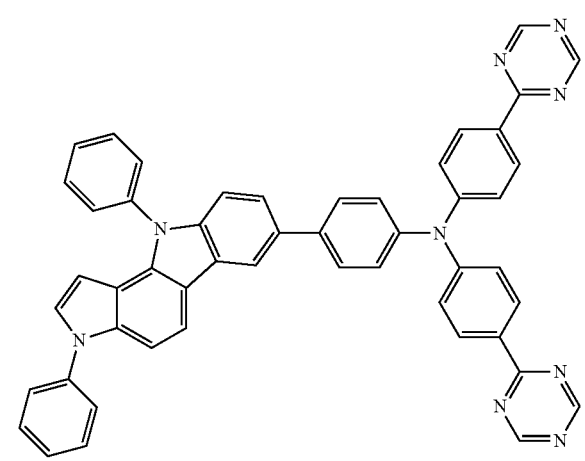
471
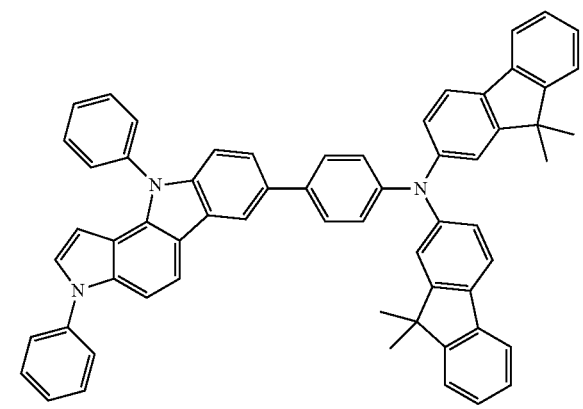

-continued
472
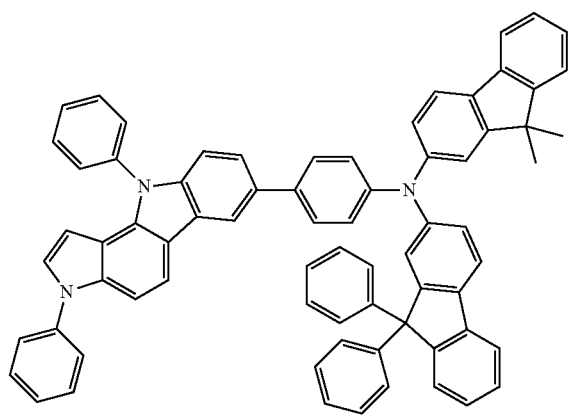
473
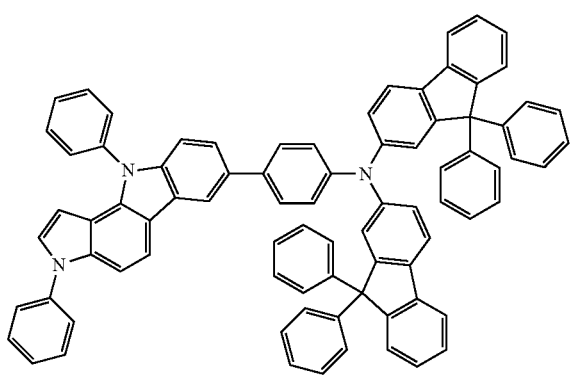
474
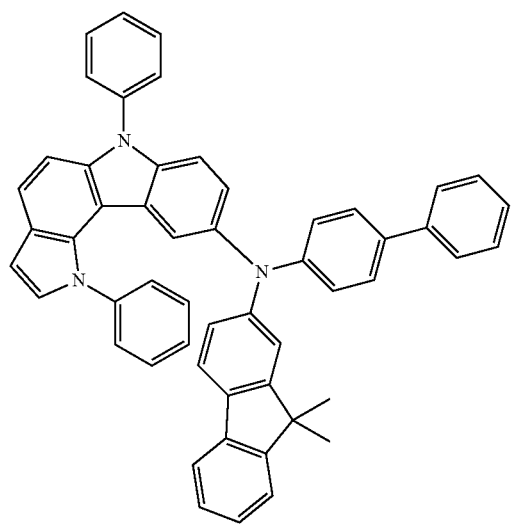
-continued
475
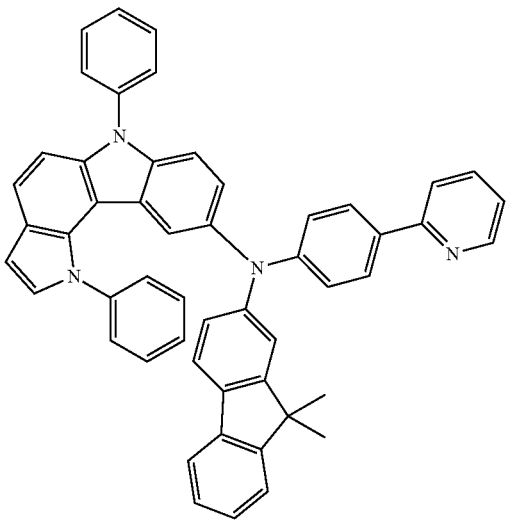
476
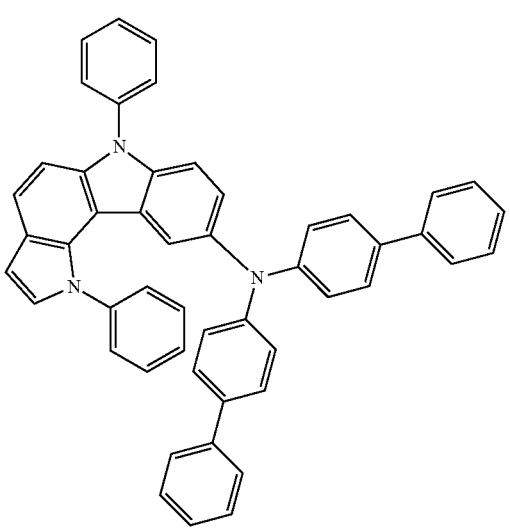
477
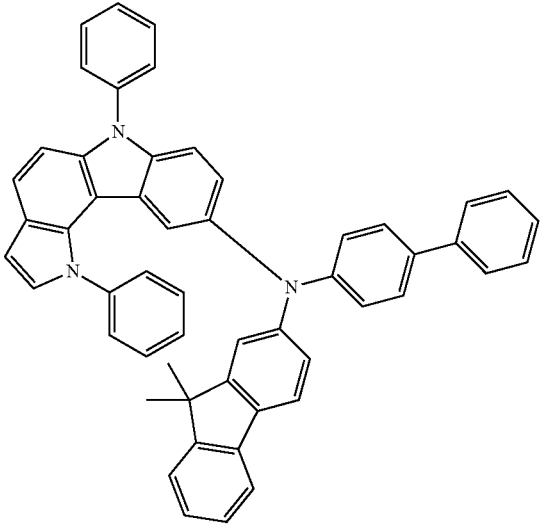

478
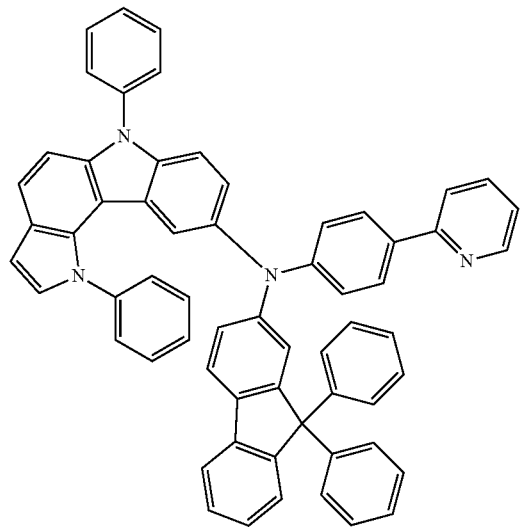
479
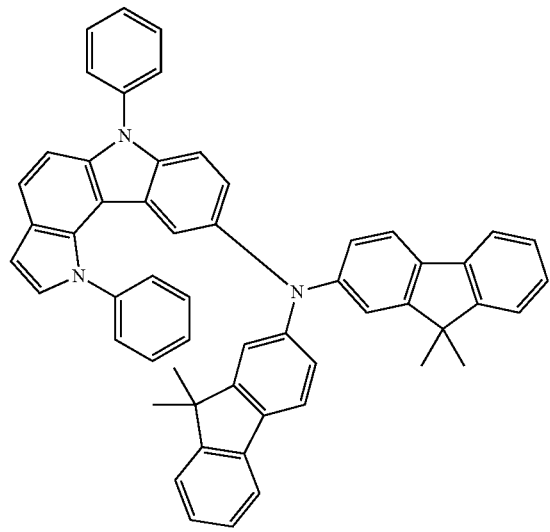
480
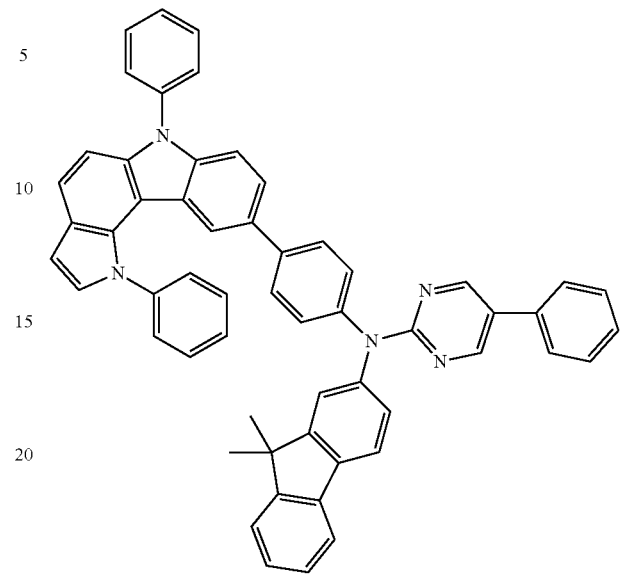
481
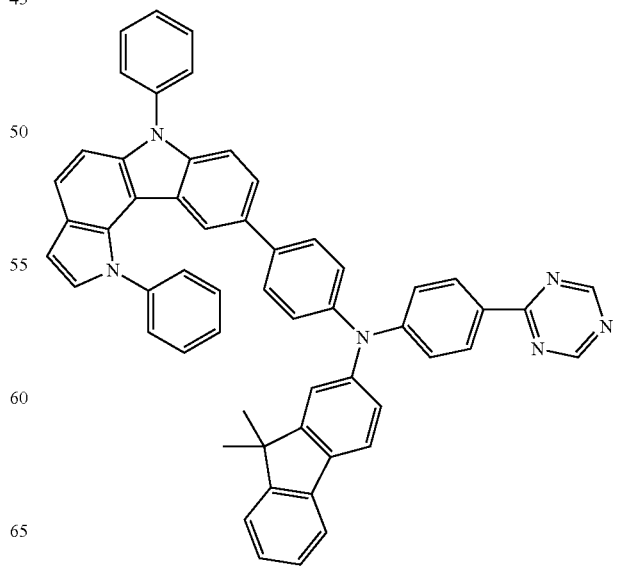

482
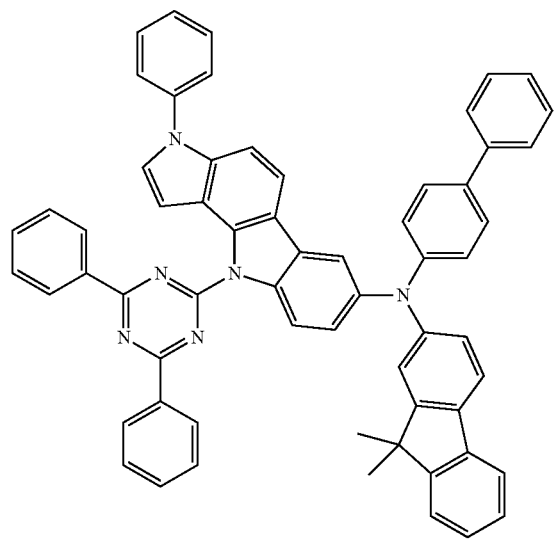
483
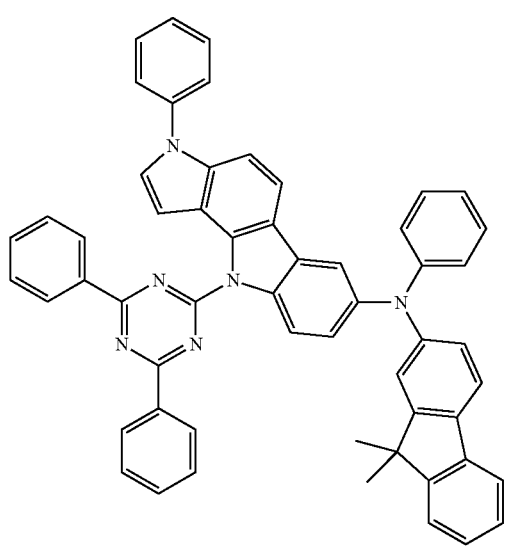
484
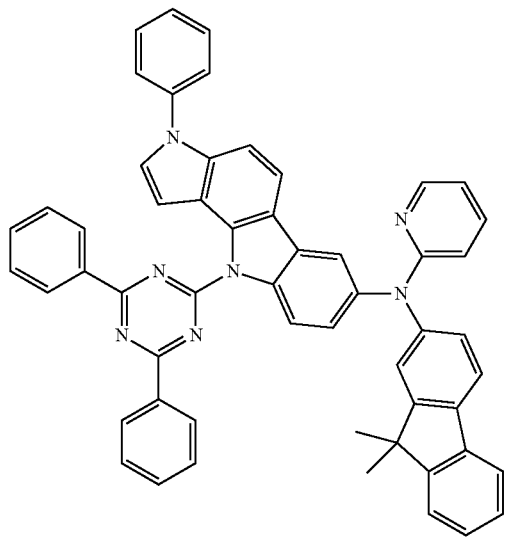
485
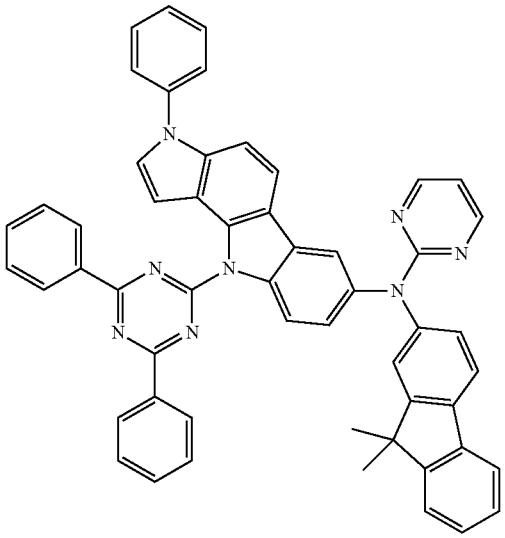
486
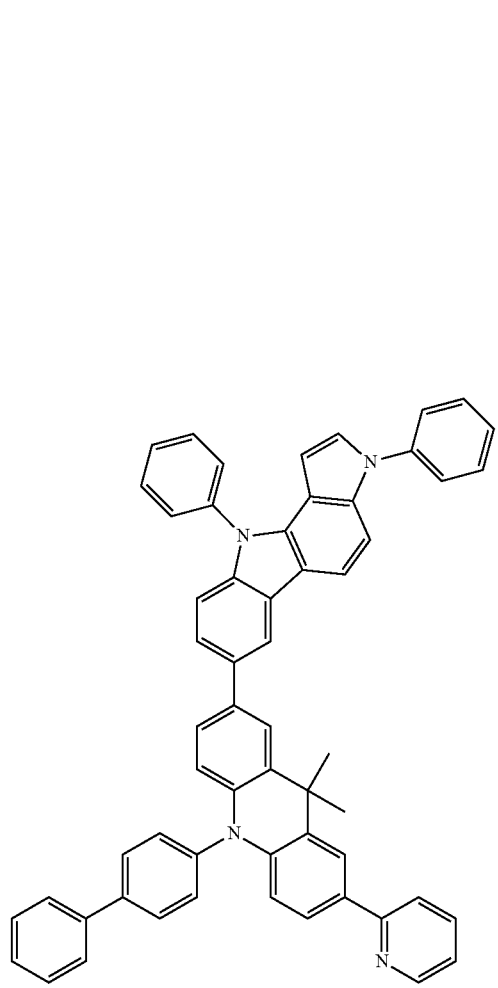

487

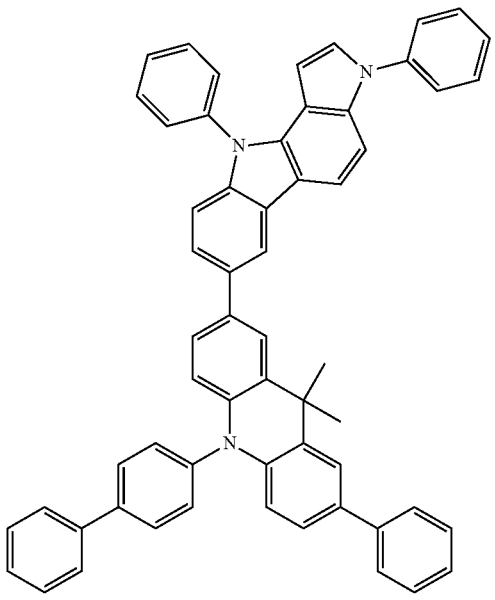

488

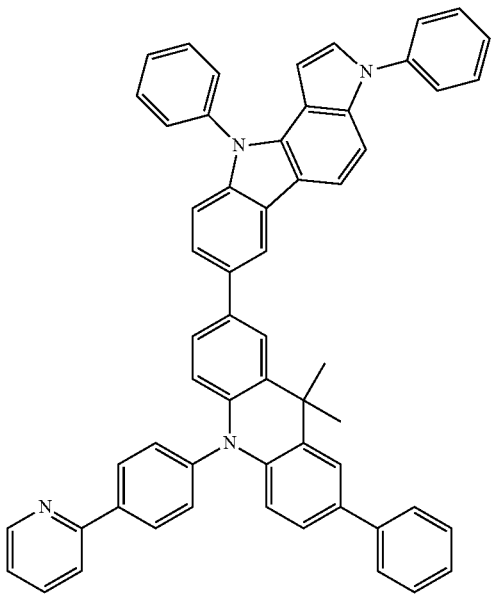

489

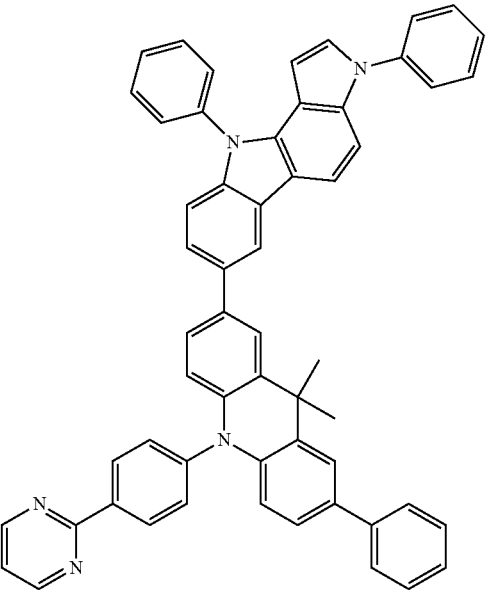

The "unsubstituted alkyl" used in the present disclosure means a monovalent functional group obtained by removing a hydrogen atom from a linear or branched, saturated hydrocarbon having 1 to 40 carbon atoms, and non-limiting examples thereof include methyl, ethyl, propyl, isobutyl, sec-butyl, pentyl, iso-amyl, hexyl, and the like.

Furthermore, the "unsaturated cycloalkyl" in the present disclosure means a monovalent functional group obtained by removing a hydrogen atom from a monocyclic or polycyclic non-aromatic hydrocarbon (saturated cyclic hydrocarbon) having 3 to 40 carbon atoms. Examples of the cycloalkyl include cyclopropyl, cyclopentyl, cyclohexyl, norbornyl, adamantine, and the like, but are not limited thereto.

Further, the "unsubstituted heterocycloalkyl" in the present disclosure means a monovalent functional group obtained by removing a hydrogen atom from a non-aromatic hydrocarbon (saturated cyclic hydrocarbon) having 3 to 40 nuclear atoms, and in this case, one or more carbons in the ring, preferably 1 to 3 carbons, are substituted with a heteroatom such as N, O, or S. Non-limiting examples thereof include morpholine, piperazine, and the like.

In addition, the "unsubstituted aryl" in the present disclosure means a monovalent functional group obtained by removing a hydrogen atom from an aromatic hydrocarbon having 6 to 60 carbon atoms of a single ring or a combination of two or more rings. In this case, two or more rings may be simply pendant to each other or pendant to each other in a fused form. Non-limiting examples thereof include phenyl, biphenyl, terphenyl, naphthyl, phenanthryl, anthryl, and the like.

Furthermore, the "unsubstituted heteroaryl" in the present disclosure is a monovalent functional group obtained by removing a hydrogen atom from a monoheterocyclic or polyheterocyclic aromatic hydrocarbon having 5 to 60 nuclear atoms, and one or more carbons in the ring, preferably 1 to 3 carbons, are substituted with a heteroatom such as nitrogen (N), oxygen (O), sulfur (S), or selenium (Se). In this case, in the heteroaryl, two or more rings may be simply pendant to each other or pendant to each other in a fused form, and furthermore, a form that is fused with an aryl group is also included. Non-limiting examples of the heteroaryl include: a six-membered monocyclic ring, such as pyridyl, pyrazinyl, pyrimidinyl, pyridazinyl, and triazinyl; and a polycyclic ring such as phenoxathienyl, indolizinyl, indolyl, purinyl, quinolyl, benzothiazole, and carbazolyl, and it is interpreted that 2-furanyl, N-imidazolyl, 2-isoxazolyl, 2-pyridinyl, 2-pyrimidinyl, and the like are also included.

Further, the "unsubstituted alkyloxy" in the present disclosure means a monovalent functional group represented by RO—, and in this case, it is interpreted that R is an alkyl having 1 to 40 carbon atoms, and includes a linear, branched, or cyclic structure. Non-limiting examples of the alkyloxy include methoxy, ethoxy, n-propoxy, 1-propoxy, t-butoxy, n-butoxy, pentoxy, and the like, and are not limited thereto.

In addition, the "unsubstituted aryloxy" in the present disclosure means a monovalent functional group represented by R'O—, and in this case, R' is an aryl having 6 to 60 carbon atoms. Non-limiting examples of the aryloxy include phenyloxy, naphthyloxy, diphenyloxy, and the like.

Furthermore, the "unsubstituted arylamine" in the present disclosure means an amine substituted with an aryl having 6 to 60 carbon atoms.

Further, the "fused ring" in the present disclosure means a fused aliphatic ring, a fused aromatic ring, a fused heteroaliphatic ring, a fused heteroaromatic ring, or a combined form thereof.

The compound represented by Formula 1 according to the present disclosure may be synthesized according to a general synthesis method [see Chem. Rev., 60:313 (1960); J. Chem. SOC. 4482 (1955); Chem. Rev. 95: 2457 (1995), and the like]. The detailed synthesis process on the compound of the present disclosure will be specifically described in the Synthesis Examples to be described below.

Meanwhile, the present disclosure provides an organic electroluminescent device including the aforementioned compound represented by Formula 1 (preferably the compound represented by any one of Formulae 4 to 9, and more preferably the compound represented by any one of Formulae 10 to 15).

Specifically, the organic electroluminescent device according to the present disclosure includes an anode, a cathode, and an organic material layer including one or more layers interposed between the anode and the cathode, in which at least one of the organic material layers including one or more layers includes one or more of the compounds represented by Formula 1 (preferably the compound represented by any one of Formulae 4 to 9, and more preferably the compound represented by any one of Formulae 10 to 15).

Examples of the organic material layer including one or more layers include a hole injection layer, a hole transporting layer, a light-emitting layer, an electron transporting layer, an electron injection layer, and the like, and among them, at least one organic material layer may include the compound represented by Formula 1. Preferably, the organic material layer including one or more layers, which includes the compound of Formula 1, may be a hole transporting layer, a hole injection layer, or a light-emitting layer, more preferably a light-emitting layer or a hole transporting layer, and even more preferably a hole transporting layer. In this case, the light-emitting efficiency, brightness, power efficiency, thermal stability, and service life of the device may be enhanced due to the compound.

The structure of the organic electroluminescent device according to the present disclosure is not particularly limited, but non-limiting examples thereof include a structure in which a substrate, an anode, a hole injection layer, a hole transporting layer, a light-emitting layer, an electron transporting layer, and a cathode are sequentially stacked. Optionally, an electron injection layer may also be additionally stacked on the electron transporting layer. Furthermore, the organic electroluminescent device according to the present disclosure may have a structure in which an anode, an organic material layer including one or more layers, and a cathode are sequentially laminated and may also have a structure in which an insulating layer or an adhesive layer may be inserted into the interface between the electrode and the organic material layer.

The organic electroluminescent device according to the present disclosure may be manufactured by forming another organic material layer and another electrode using materials and methods known in the art, except that one or more layers (for example, a light-emitting layer, a hole transporting layer and/or an electron transporting layer) of the organic material layer are formed so as to include the compound represented by Formula 1.

The organic material layer may be formed by a vacuum deposition method or a solution application method. Examples of the solution application method include spin coating, dip coating, doctor blading, inkjet printing, or a thermal transfer method, but are not limited thereto.

As a substrate which may be used in the present disclosure, a silicon wafer, a quartz or glass plate, a metal plate, a plastic film or sheet, and the like may be used, and examples of the substrate are not limited thereto.

Further, examples of an anode material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; a conductive polymer, such as polythiophene, poly(3-methylthiophene), poly[3,4-(ethylene-1,2-dioxy)thiophene] (PEDT), polypyrrole, and polyaniline; or carbon black, and the like, but are not limited thereto.

In addition, examples of a cathode material include: a metal, such as magnesium, calcium, sodium, potassium, titanium, indium, yttrium, lithium, gadolinium, aluminum, silver, tin, or lead, or alloys thereof; a multi-layer structured material, such as LiF/Al or $LiO_2$/Al, and the like, but are not limited thereto.

Furthermore, the hole injection layer, the hole transporting layer, the electron injection layer, and the electron transporting layer are not particularly limited, and typical materials known in the art may be used.

Hereinafter, the present disclosure will be described in detail as follows through the Examples. However, the following Examples are only for exemplifying the present disclosure, and the present disclosure is not limited by the following Examples.

PREPARATION EXAMPLE 1

Synthesis of Compound IC-1

<Step 1> Synthesis of 5-(4,4,5,5-tetramethyl-1,3,2-dioxaborolan-2-yl)-1H-indole

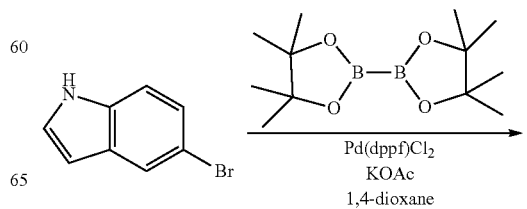

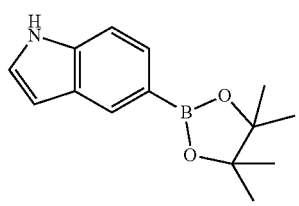

5-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl$_2$ (5.2 g, 5 mol), KOAc (37.55 g, 0.383 mol), and 1,4-dioxane (500 ml) were mixed under nitrogen flow, and then the resulting mixture was stirred at 130° C. for 12 hours.

After the reaction was terminated, 5-(4,4,5,5-tetramethyl-1,3,2-dioxaborolan-2-yl)-1H-indole (22.32 g, yield 72%) was obtained by performing extraction with ethyl acetate, removing moisture over MgSO$_4$, and purifying the residue with column chromatography [Hexane:ethyl acetate (EA)=10:1 (v/v)].

$^1$H-NMR: δ 1.24 (s, 12H), 6.45 (d, 1H), 7.27 (d, 1H), 7.42 (d, 1H), 7.52 (d, 1H), 7.95 (s, 1H), 8.21 (s, 1H)

<Step 2> Synthesis of
5-(5-bromo-2-nitrophenyl)-1H-indole

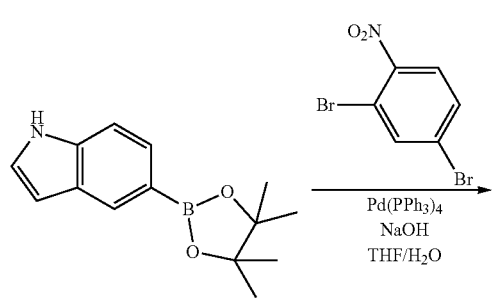

The 5-(4,4,5,5-tetramethyl-1,3,2-dioxaborolan-2-yl)-1H-indole (22 g, 90.49 mmol) synthesized in <Step 1> of Preparation Example 1 was mixed with 2,4-dibromo-1-nitrobenzene (21.18 g, 75.41 mmol), NaOH (9.05 g, 226.24 mmol), and THF/H$_2$O (400 ml/200 ml) under nitrogen flow, Pd(PPh$_3$)$_4$ (4.36 g, 5 mol) was added thereto at 40° C., and then the resulting mixture was stirred at 80° C. for 12 hours.

After the reaction was terminated, an organic layer was obtained by performing extraction with methylene chloride, adding MgSO$_4$ thereto, and filtering the product. 5-(5-bromo-2-nitrophenyl)-1H-indole (9.6 g, yield 40%) was obtained by removing the solvent from the obtained organic layer, and then purifying the residue with column chromatography [Hexane:EA=3:1 (v/v)].

<Step 3> Synthesis of
5-(5-bromo-2-nitrophenyl)-1-phenyl-1H-indole

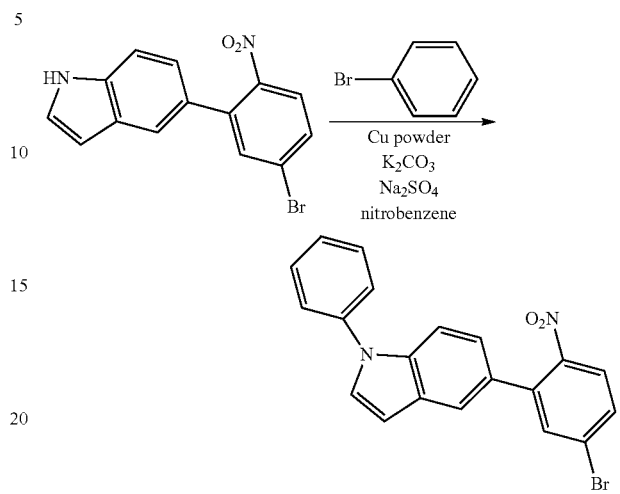

The 5-(5-bromo-2-nitrophenyl)-1H-indole (14.64 g, 46.17 mmol) obtained in <Step 2> of Preparation Example 1, iodobenzene (14.13 g, 69.26 mmol), Cu powder (0.29 g, 4.62 mmol), K$_2$CO$_3$ (6.38 g, 46.17 mmol), Na$_2$SO$_4$ (6.56 g, 46.17 mmol), and nitrobenzene (200 ml) were mixed under nitrogen flow, and then the resulting mixture was stirred at 190° C. for 12 hours.

After the reaction was terminated, nitrobenzene was removed, the organic layer was separated by methylene chloride, and water was removed from the separated organic layer by using MgSO$_4$. 5-(5-bromo-2-nitrophenyl)-1-phenyl-1H-indole (12.89 g, yield 71%) was obtained by removing the solvent from the organic layer from which water had been removed, and then purifying the residue with column chromatography [Hexane:methylene chloride (MC)=3:1 (v/v)].

<Step 4> Synthesis of 7-bromo-3-phenyl-3,10-dihydropyrrolo[3,2-a]carbazole

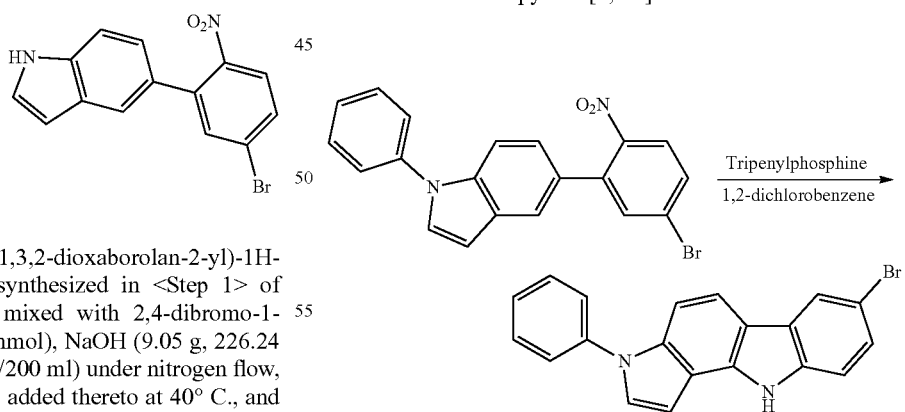

The 5-(5-bromo-2-nitrophenyl)-1-phenyl-1H-indole (6.25 g, 15.91 mmol) obtained in <Step 3> of Preparation Example 1, triphenylphosphine (10.43 g, 39.77 mmol), and 1,2-dichlorobenzene (50 ml) were mixed under nitrogen flow, and the resulting mixture was stirred for 12 hours.

After the reaction was terminated, an organic layer was obtained by removing 1,2-dichlorobenzene, and then performing extraction with dichloromethane. 7-bromo-3-phenyl-3,10-dihydropyrrolo[3,2-a]carbazole (3.04 g, yield 53%) was obtained by removing water from the obtained organic layer using MgSO$_4$, and then purifying the residue with column chromatography [Hexane:MC=3:1 (v/v)].

<Step 5> Synthesis of Compound IC-1

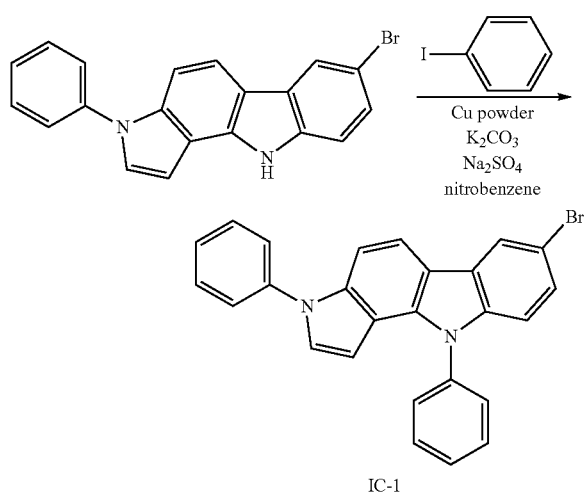

IC-1

The 7-bromo-3-phenyl-3,10-dihydropyrrolo[3,2-a]carbazole (5 g, 13.84 mmol) obtained in <Step 4> of Preparation Example 1, iodobenzene (4.24 g, 20.76 mmol), Cu powder (0.09 g, 1.38 mmol), K$_2$CO$_3$ (1.91 g, 13.84 mmol), Na$_2$SO$_4$ (1.97 g, 13.84 mmol), and nitrobenzene (70 ml) were mixed under nitrogen flow, and then the resulting mixture was stirred at 190° C. for 12 hours.

After the reaction was terminated, nitrobenzene was removed, the organic layer was separated by methylene chloride, and water was removed from the separated organic layer by using MgSO$_4$. Compound IC-1 (3.63 g, yield 60%) was obtained by removing the solvent from the organic layer from which water had been removed, and then purifying the residue with column chromatography [Hexane:MC=3:1 (v:v)].

PREPARATION EXAMPLE 2

Synthesis of Compound IC-2

<Step 1> Synthesis of 4-(4,4,5,5-tetramethyl-1,3,2-dioxaborolan-2-yl)-1H-indole

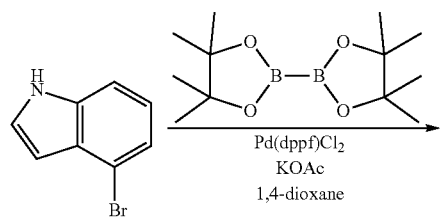

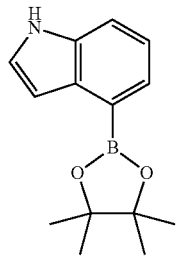

4-(4,4,5,5-tetramethyl-1,3,2-dioxaborolan-2-yl)-1H-indole was obtained by performing the same procedure as in <Step 1> of Preparation Example 1, except that 4-bromo-1H-indole (25 g, 0.128 mol) was used instead of the 5-bromo-1H-indole used in <Step 1> of Preparation Example 1.

<Step 2> Synthesis of 4-(5-bromo-2-nitrophenyl)-1H-indole

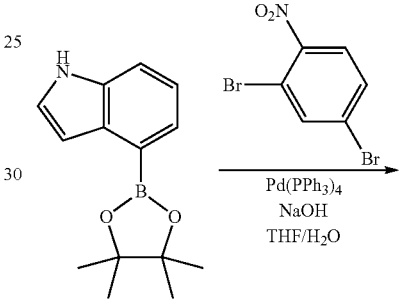

4-(2-nitrophenyl)-1H-indole was obtained by performing the same procedure as in <Step 2> of Preparation Example 1, except that the 4-(4,4,5,5-tetramethyl-1,3,2-dioxaborolan-2-yl)-1H-indole (22 g, 90.49 mmol) synthesized in <Step 1> of Preparation Example 2 was used instead of the 5-(4,4,5,5-tetramethyl-1,3,2-dioxaborolan-2-yl)-1H-indole used in <Step 2> of Preparation Example 1.

<Step 3> Synthesis of 4-(5-bromo-2-nitrophenyl)-1-phenyl-1H-indole

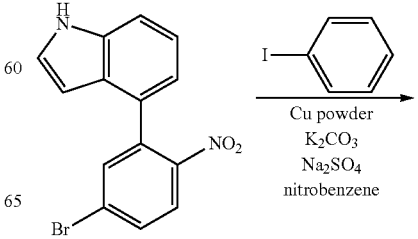

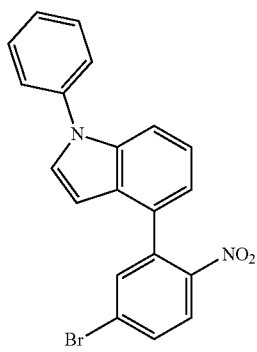

4-(2-nitrophenyl)-1-phenyl-1H-indole was obtained by performing the same procedure as in <Step 3> of Preparation Example 1, except that the 4-(2-nitrophenyl)-1H-indole (14.64 g, 46.17 mmol) synthesized in <Step 2> of Preparation Example 2 was used instead of the 5-(5-bromo-2-nitrophenyl)-1H-indole used in <Step 3> of Preparation Example 1.

<Step 4> Synthesis of 9-bromo-3-phenyl-3,6-dihydropyrrolo[2,3-c]carbazole

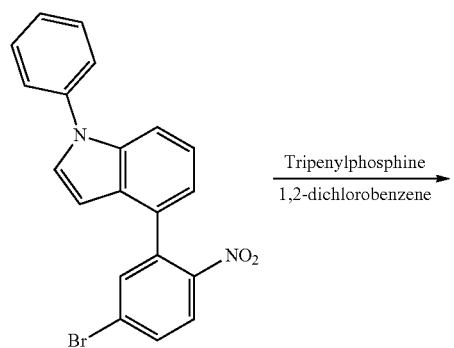

9-bromo-3-phenyl-3,6-dihydropyrrolo[2,3-c]carbazole was obtained by performing the same procedure as in <Step 4> of Preparation Example 1, except that the 4-(2-nitrophenyl)-1-phenyl-1H-indole (6.25 g, 15.91 mmol) synthesized in <Step 3> of Preparation Example 2 was used instead of the 5-(2-nitrophenyl)-1-phenyl-1H-indole used in <Step 4> of Preparation Example 1.

<Step 5> Synthesis of Compound IC-2

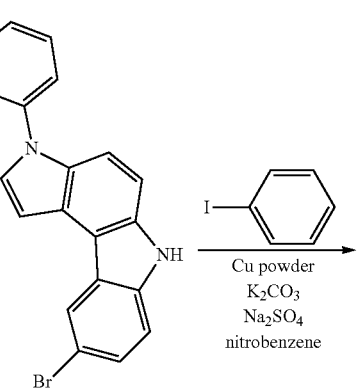

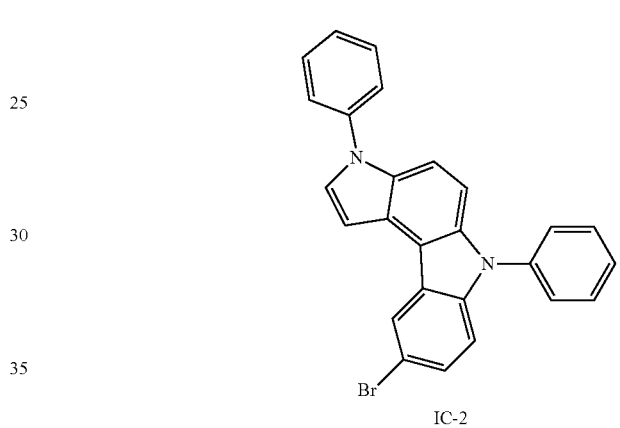

Compound IC-2 was obtained by performing the same procedure as in <Step 5> of Preparation Example 1, except that the 9-bromo-3-phenyl-3,6-dihydropyrrolo[2,3-c]carbazole (5 g, 13.84 mmol) synthesized in <Step 4> of Preparation Example 2 was used instead of the 7-bromo-3-phenyl-3,10-dihydropyrrolo[3,2-a]carbazole used in <Step 5> of Preparation Example 1.

PREPARATION EXAMPLE 3

Synthesis of Compound IC-3

<Step 1> Synthesis of 5-(4,4,5,5-tetramethyl-1,3,2-dioxaborolan-2-yl)-1H-indole

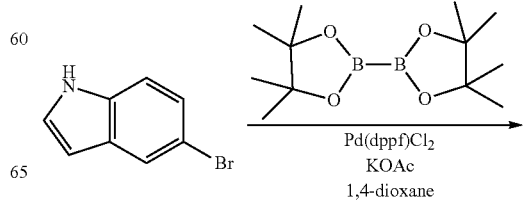

-continued

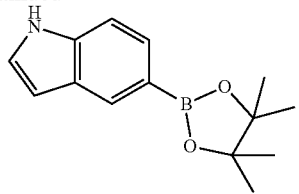

5-(4,4,5,5-tetramethyl-1,3,2-dioxaborolan-2-yl)-1H-indole was obtained by performing the same procedure as in <Step 1> of Preparation Example 1.

<Step 2> Synthesis of 5-(5-bromo-2-nitrophenyl)-1H-indole

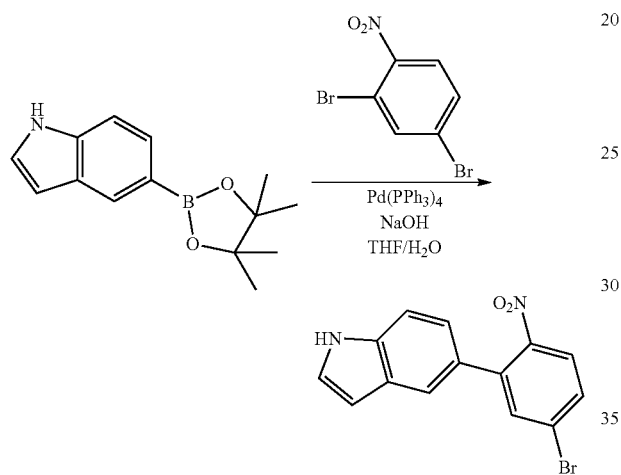

5-(5-bromo-2-nitrophenyl)-1H-indole was obtained by performing the same procedure as in <Step 2> of Preparation Example 1.

<Step 3> Synthesis of 5-(5-bromo-2-nitrophenyl)-1-phenyl-1H-indole

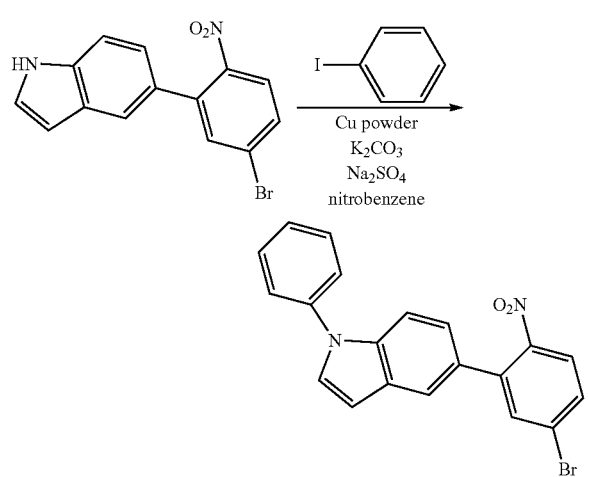

5-(5-bromo-2-nitrophenyl)-1-phenyl-1H-indole was obtained by performing the same procedure as in <Step 3> of Preparation Example 1.

<Step 4> Synthesis of 6-bromo-1-phenyl-1,9-dihydropyrrolo[2,3-b]carbazole

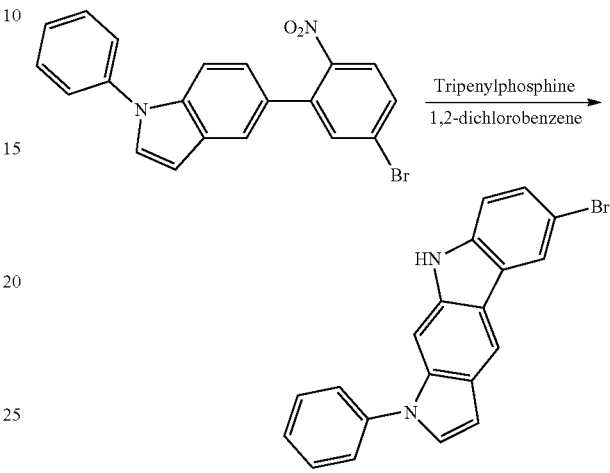

6-bromo-1-phenyl-1,9-dihydropyrrolo[2,3-b]carbazole was obtained by performing the same procedure as in <Step 4> of Preparation Example 1.

<Step 5> Synthesis of Compound IC-3

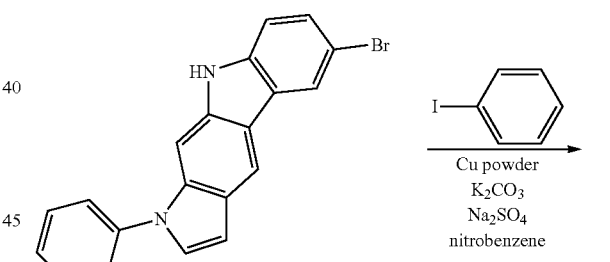

Compound IC-3 was obtained by performing the same procedure as in <Step 5> of Preparation Example 1, except that 6-bromo-1-phenyl-1,9-dihydropyrrolo[2,3-b]carbazole (5 g, 13.84 mmol) was used instead of the 7-bromo-3-phenyl-3,10-dihydropyrrolo[3,2-a]carbazole used in <Step 5> of Preparation Example 1.

PREPARATION EXAMPLE 4

Synthesis of Compound IC-4

<Step 1> Synthesis of 6-(4,4,5,5-tetramethyl-1,3,2-dioxaborolan-2-yl)-1H-indole

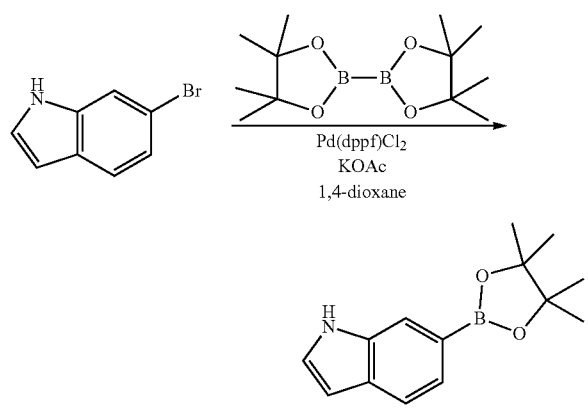

6-(4,4,5,5-tetramethyl-1,3,2-dioxaborolan-2-yl)-1H-indole was obtained by performing the same procedure as in <Step 1> of Preparation Example 1, except that 6-bromo-1H-indole (25 g, 0.128 mol) was used instead of the 5-bromo-1H-indole used in <Step 1> of Preparation Example 1.

<Step 2> Synthesis of 6-(5-bromo-2-nitrophenyl)-1H-indole

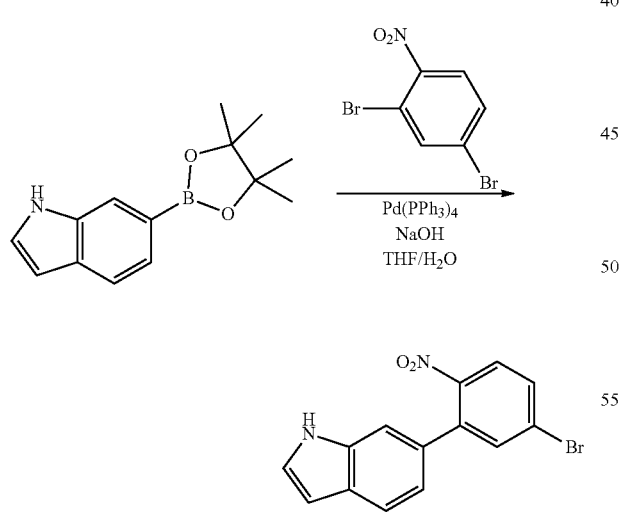

6-(5-bromo-2-nitrophenyl)-1H-indole was obtained by performing the same procedure as in <Step 2> of Preparation Example 1, except that 6-(4,4,5,5-tetramethyl-1,3,2-dioxaborolan-2-yl)-1H-indole (22 g, 90.49 mmol) was used instead of the 5-(4,4,5,5-tetramethyl-1,3,2-dioxaborolan-2-yl)-1H-indole used in <Step 2> of Preparation Example 1.

<Step 3> Synthesis of 6-(5-bromo-2-nitrophenyl)-1-phenyl-1H-indole

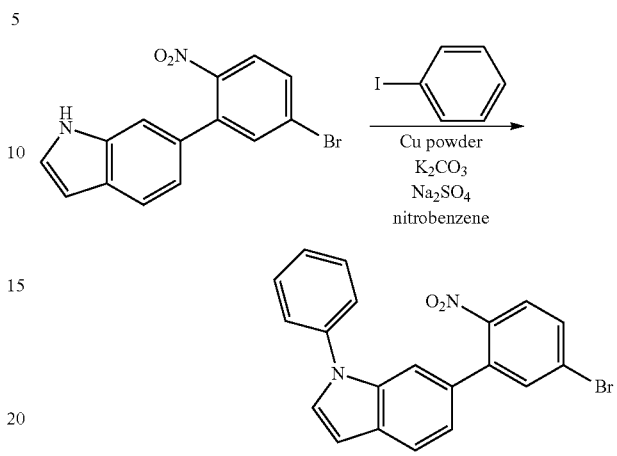

6-(5-bromo-2-nitrophenyl)-1-phenyl-1H-indole was obtained by performing the same procedure as in <Step 3> of Preparation Example 1, except that 6-(5-bromo-2-nitrophenyl)-1H-indole (14.64 g, 46.17 mmol) was used instead of the 5-(5-bromo-2-nitrophenyl)-1H-indole used in <Step 3> of Preparation Example 1.

<Step 4> Synthesis of 8-bromo-1-phenyl-1,5-dihydropyrrolo[3,2-b]carbazole

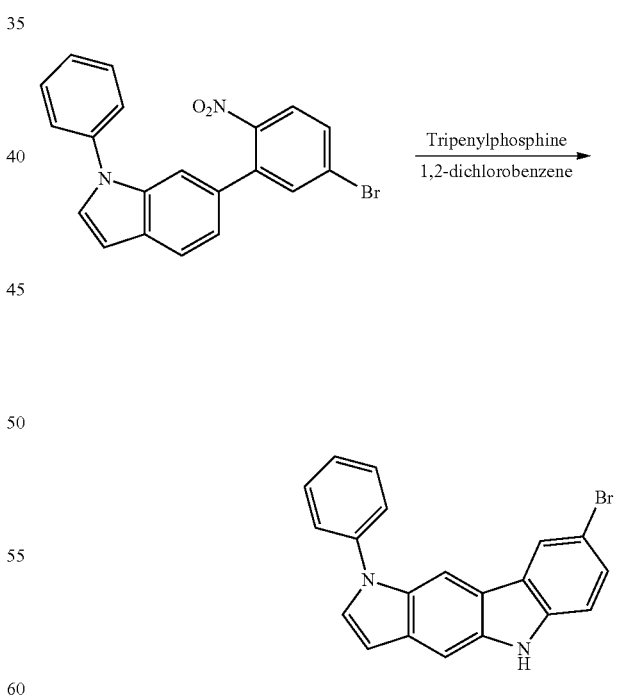

8-bromo-1-phenyl-1,5-dihydropyrrolo[3,2-b]carbazole was obtained by performing the same procedure as in <Step 4> of Preparation Example 1, except that 6-(5-bromo-2-nitrophenyl)-1-phenyl-1H-indole (6.25 g, 15.91 mmol) was used instead of the 5-(5-bromo-2-nitrophenyl)-1-phenyl-1H-indole used in <Step 4> of Preparation Example 1.

\<Step 5\> Synthesis of Compound IC-4

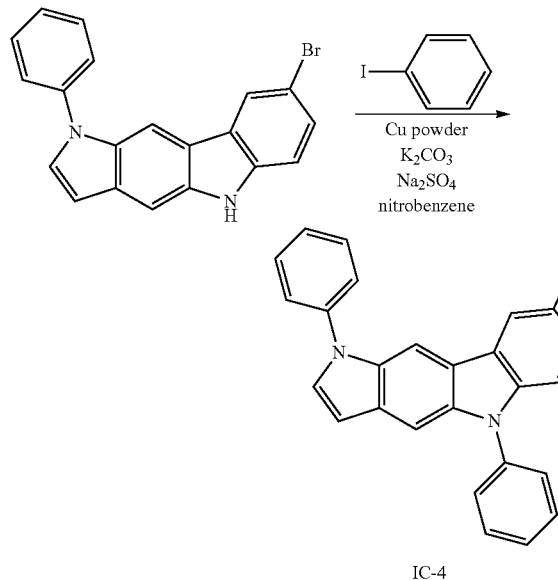

IC-4

Compound IC-4 was obtained by performing the same procedure as in \<Step 5\> of Preparation Example 1, except that the 8-bromo-1-phenyl-1,5-dihydropyrrolo[3,2-b]carbazole (5 g, 13.84 mmol) synthesized in \<Step 4\> of Preparation Example 4 was used instead of the 7-bromo-3-phenyl-3,10-dihydropyrrolo[3,2-a]carbazole used in \<Step 5\> of Preparation Example 1.

PREPARATION EXAMPLE 5

Synthesis of Compound IC-5

\<Step 1\> Synthesis of 6-(4,4,5,5-tetramethyl-1,3,2-dioxaborolan-2-yl)-1H-indole

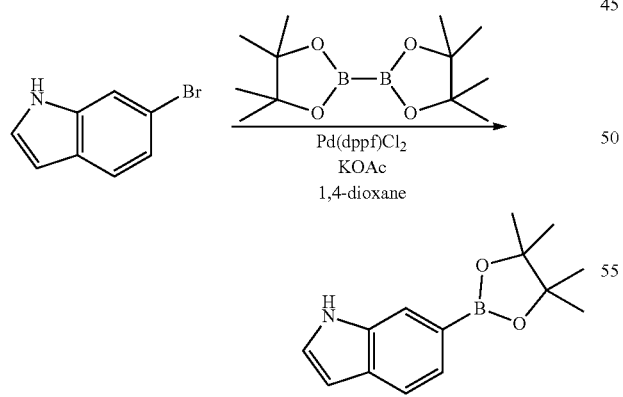

6-(4,4,5,5-tetramethyl-1,3,2-dioxaborolan-2-yl)-1H-indole was obtained by performing the same procedure as in \<Step 1\> of Preparation Example 1, except that 6-bromo-1H-indole (25 g, 0.128 mol) was used instead of the 5-bromo-1H-indole used in \<Step 1\> of Preparation Example 1.

\<Step 2\> Synthesis of 6-(5-bromo-2-nitrophenyl)-1H-indole

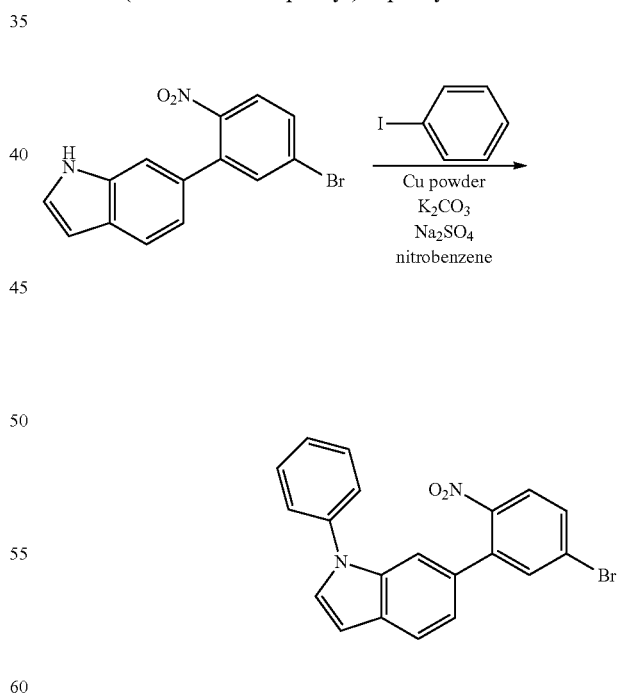

6-(5-bromo-2-nitrophenyl)-1H-indole was obtained by performing the same procedure as in \<Step 2\> of Preparation Example 1, except that the 6-(4,4,5,5-tetramethyl-1,3,2-dioxaborolan-2-yl)-1H-indole (22 g, 90.49 mmol) synthesized in \<Step 1\> of Preparation Example 5 was used instead of the 5-(4,4,5,5-tetramethyl-1,3,2-dioxaborolan-2-yl)-1H-indole used in \<Step 2\> of Preparation Example 1.

\<Step 3\> Synthesis of 6-(5-bromo-2-nitrophenyl)-1-phenyl-1H-indole 6-(5-bromo-2-nitrophenyl)-1-phenyl-1H-indole was obtained by performing the same procedure as in \<Step 3\> of Preparation Example 1, except that the 6-(5-bromo-2-nitrophenyl)-1H-indole (14.64 g, 46.17 mmol) synthesized in \<Step 2\> of Preparation Example 5 was used instead of the 5-(5-bromo-2-nitrophenyl)-1H-indole used in \<Step 3\> of Preparation Example 1.

\<Step 4\> Synthesis of 7-bromo-1-phenyl-1,10-dihydropyrrolo[2,3-a]carbazole

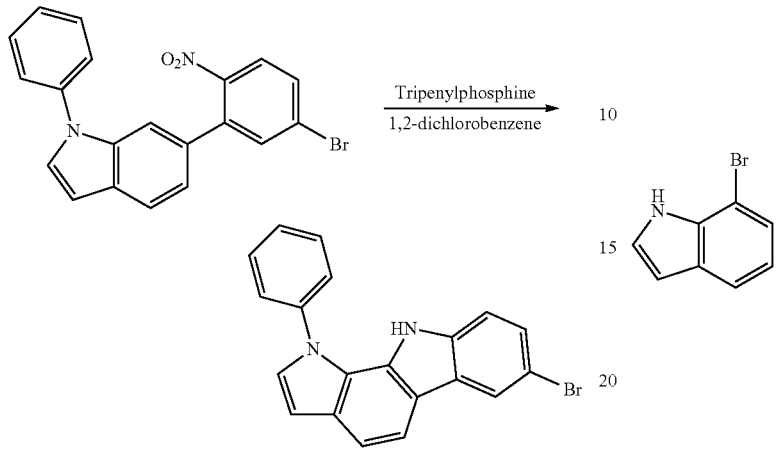

7-bromo-1-phenyl-1,10-dihydropyrrolo[2,3-a]carbazole was obtained by performing the same procedure as in \<Step 4\> of Preparation Example 1, except that the 6-(5-bromo-2-nitrophenyl)-1-phenyl-1H-indole (6.25 g, 15.91 mmol) synthesized in \<Step 3\> of Preparation Example 5 was used instead of the 5-(5-bromo-2-nitrophenyl)-1-phenyl-1H-indole used in \<Step 4\> of Preparation Example 1.

\<Step 5\> Synthesis of Compound IC-5

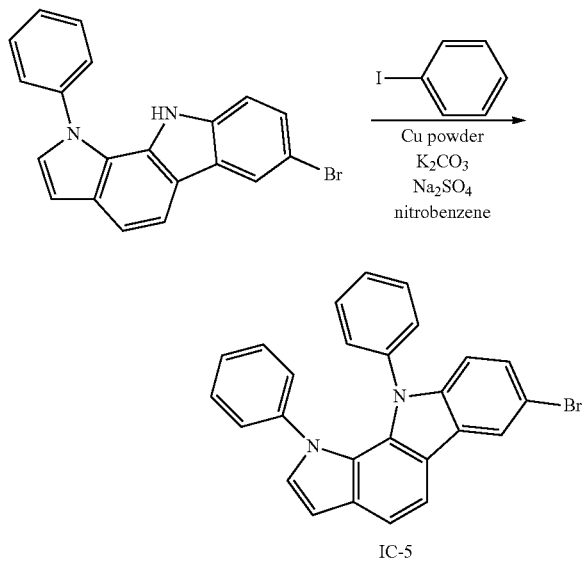

Compound IC-5 was obtained by performing the same procedure as in \<Step 5\> of Preparation Example 1, except that the 7-bromo-1-phenyl-1,10-dihydropyrrolo[2,3-a]carbazole (5 g, 13.84 mmol) synthesized in \<Step 4\> of Preparation Example 5 was used instead of the 7-bromo-3-phenyl-3,10-dihydropyrrolo[3,2-a]carbazole used in \<Step 5\> of Preparation Example 1.

PREPARATION EXAMPLE 6

Synthesis of Compound IC-6

\<Step 1\> Synthesis of 7-(4,4,5,5-tetramethyl-1,3,2-dioxaborolan-2-yl)-1H-indole

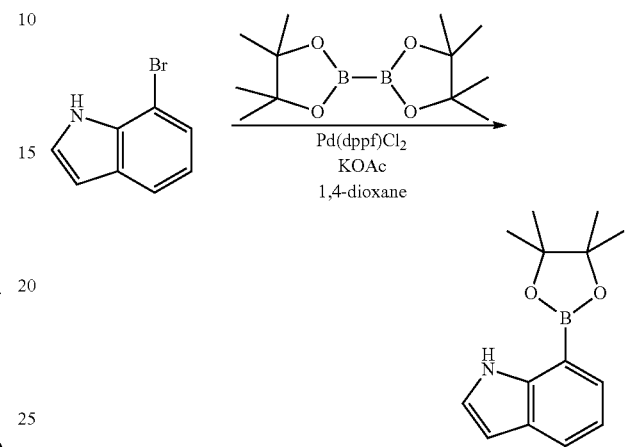

7-(4,4,5,5-tetramethyl-1,3,2-dioxaborolan-2-yl)-1H-indole was obtained by performing the same procedure as in \<Step 1\> of Preparation Example 1, except that 7-bromo-1H-indole (25 g, 0.128 mol) was used instead of the 5-bromo-1H-indole used in \<Step 1\> of Preparation Example 1.

\<Step 2\> Synthesis of 7-(5-bromo-2-nitrophenyl)-1H-indole

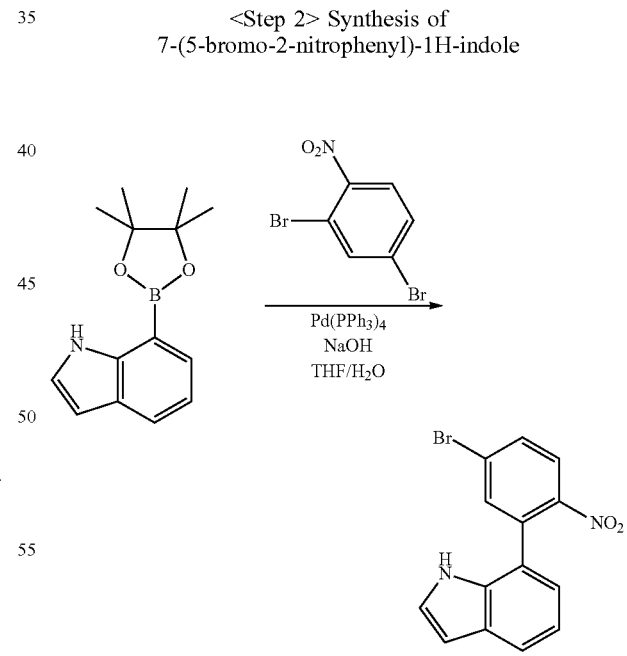

7-(5-bromo-2-nitrophenyl)-1H-indole was obtained by performing the same procedure as in \<Step 2\> of Preparation Example 1, except that the 7-(4,4,5,5-tetramethyl-1,3,2-dioxaborolan-2-yl)-1H-indole (22 g, 90.49 mmol) synthesized in \<Step 1\> of Preparation Example 6 was used instead of the 5-(4,4,5,5-tetramethyl-1,3,2-dioxaborolan-2-yl)-1H-indole used in \<Step 2\> of Preparation Example 1.

\<Step 3\> Synthesis of 7-(5-bromo-2-nitrophenyl)-1-phenyl-1H-indole

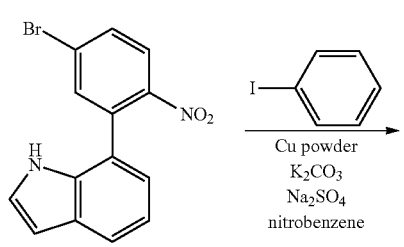

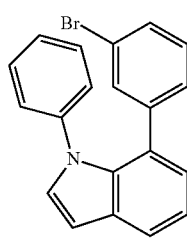

7-(5-bromo-2-nitrophenyl)-1-phenyl-1H-indole was obtained by performing the same procedure as in \<Step 3\> of Preparation Example 1, except that the 7-(5-bromo-2-nitrophenyl)-1H-indole (14.64 g, 46.17 mmol) synthesized in \<Step 2\> of Preparation Example 6 was used instead of the 5-(5-bromo-2-nitrophenyl)-1H-indole used in \<Step 3\> of Preparation Example 1.

\<Step 4\> Synthesis of 9-bromo-1-phenyl-1,6-dihydropyrrolo[3,2-c]carbazole

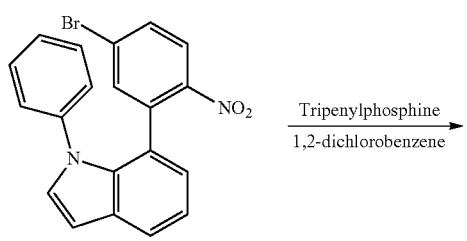

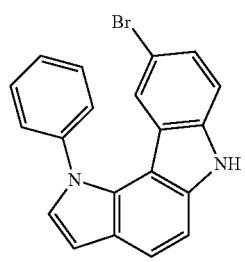

9-bromo-1-phenyl-1,6-dihydropyrrolo[3,2-c]carbazole was obtained by performing the same procedure as in \<Step 4\> of Preparation Example 1, except that the 7-(5-bromo-2-nitrophenyl)-1-phenyl-1H-indole (6.25 g, 15.91 mmol) synthesized in \<Step 4\> of Preparation Example 6 was used instead of the 5-(5-bromo-2-nitrophenyl)-1-phenyl-1H-indole used in \<Step 4\> of Preparation Example 1.

\<Step 5\> Synthesis of Compound IC-6

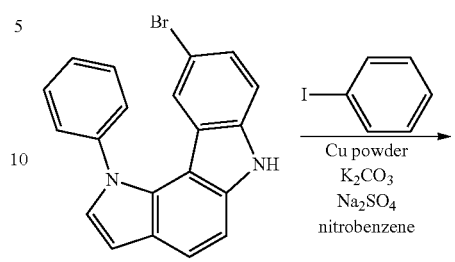

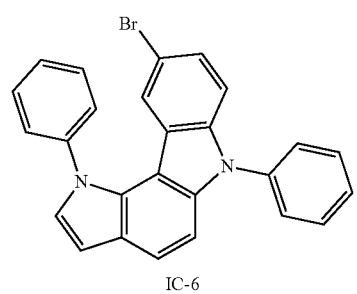

IC-6

Compound IC-6 was synthesized by performing the same procedure as in \<Step 5\> of Preparation Example 1, except that the 9-bromo-1-phenyl-1,6-dihydropyrrolo[3,2-c]carbazole (5 g, 13.84 mmol) synthesized in \<Step 4\> of Preparation Example 6 was used instead of the 7-bromo-3-phenyl-3,10-dihydropyrrolo[3,2-a]carbazole used in \<Step 5\> of Preparation Example 1.

PREPARATION EXAMPLE 7

Synthesis of IC-7

\<Step 1\> Synthesis of 5-(4,4,5,5-tetramethyl-1,3,2-dioxaborolan-2-yl)-1H-indole

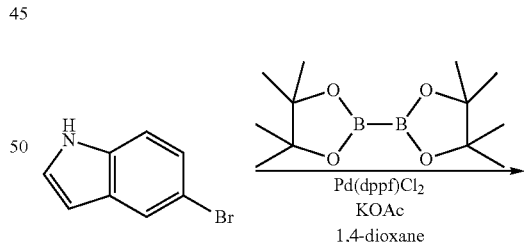

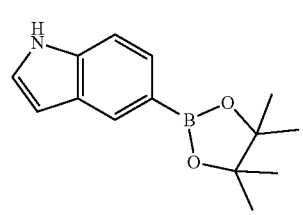

5-(4,4,5,5-tetramethyl-1,3,2-dioxaborolan-2-yl)-1H-indole was obtained by performing the same procedure as in \<Step 1\> of Preparation Example 1.

<Step 2> Synthesis of
5-(5-bromo-2-nitrophenyl)-1H-indole

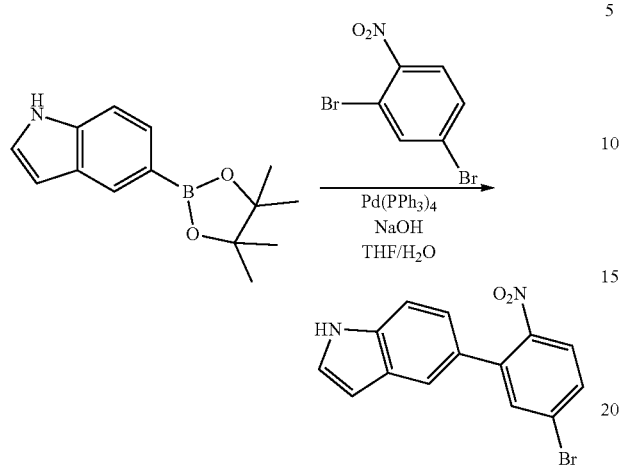

5-(5-bromo-2-nitrophenyl)-1H-indole was obtained by performing the same procedure as in <Step 2> of Preparation Example 1.

<Step 3> Synthesis of
5-(5-bromo-2-nitrophenyl)-1-phenyl-1H-indole

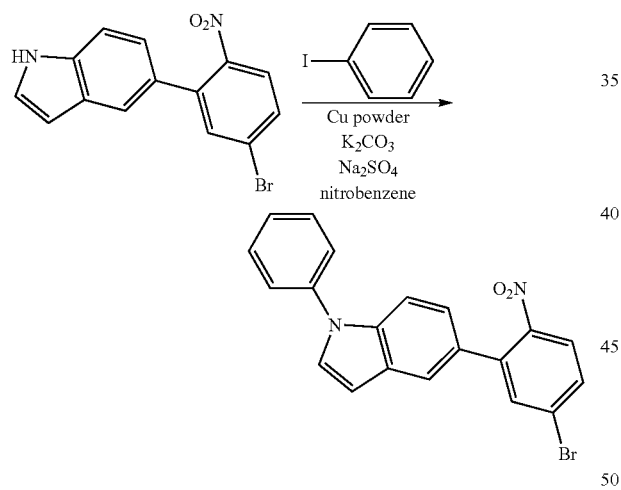

5-(5-bromo-2-nitrophenyl)-1-phenyl-1H-indole was obtained by performing the same procedure as in <Step 3> of Preparation Example 1.

<Step 4> Synthesis of 7-bromo-3-phenyl-3,10-dihydropyrrolo[3,2-a]carbazole

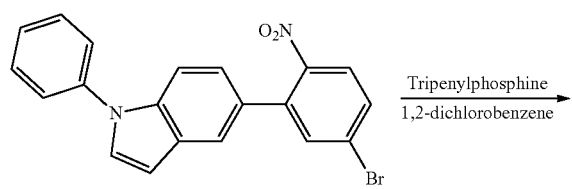

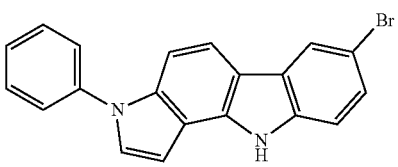

7-bromo-3-phenyl-3,10-dihydropyrrolo[3,2-a]carbazole was obtained by performing the same procedure as in <Step 4> of Preparation Example 1.

<Step 5> Synthesis of Compound IC-7

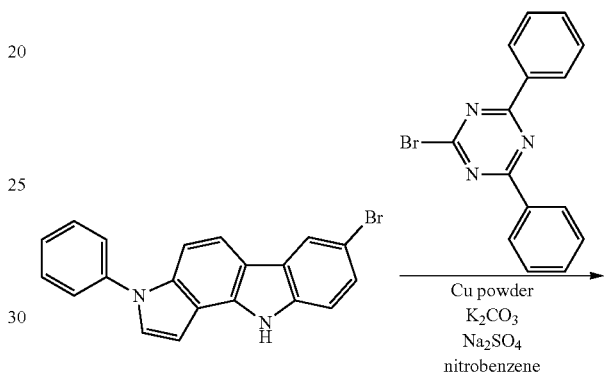

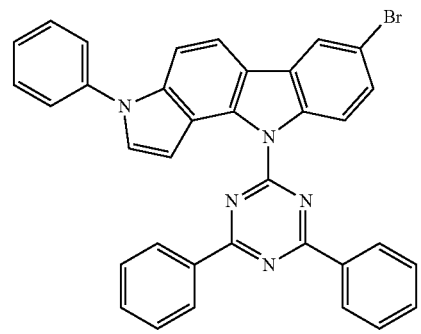

IC-7

Compound IC-7 was obtained by performing the same procedure as in <Step 5> of Preparation Example 1, except that 2-bromo-4,6-diphenyl-1,3,5-triazine (6.48 g, 20.76 mmol) was used instead of the iodobenzene used in <Step 5> of Preparation Example 1.

SYNTHESIS EXAMPLE 1

Synthesis of Compound Mat-1

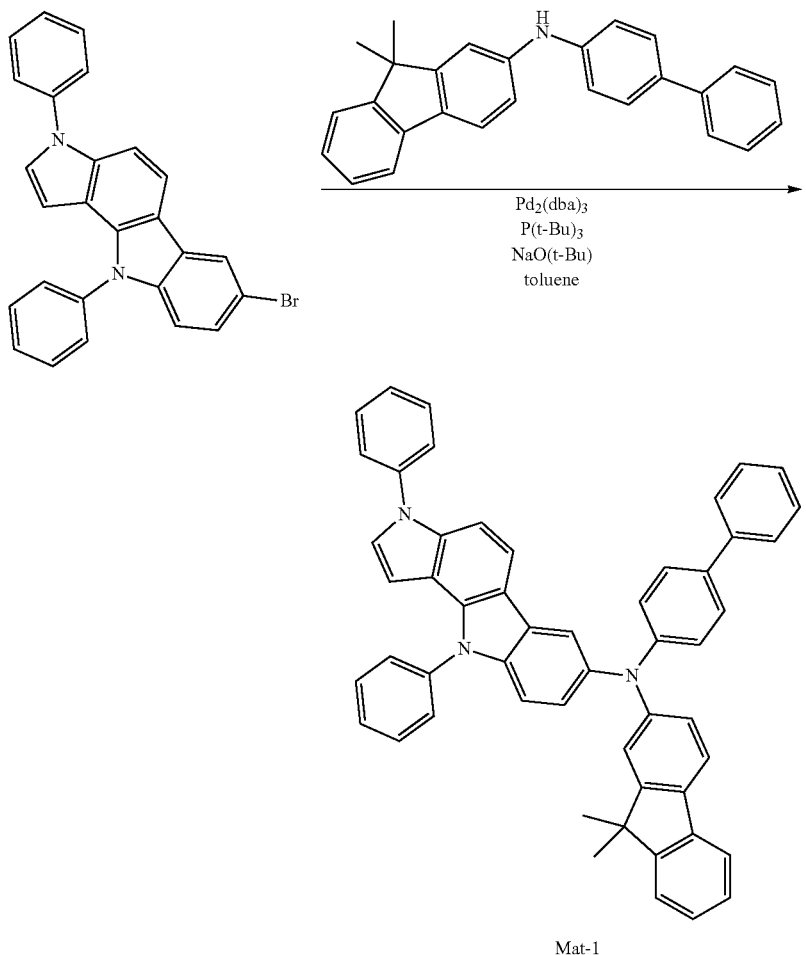

Mat-1

Compound IC-1 (10 g, 22.87 mmol) synthesized in Preparation Example 1, N-(biphenyl-4-yl)-9,9-dimethyl-9H-fluoren-2-amine (9.1 g, 25.16 mmol), sodium tert-butoxide (6.59 g, 68.61 mmol), tris(dibenzylideneacetone)dipalladium(0) (0.65 g, 0.6861 mmol), and tri-tert-butyl phosphine (0.14 g, 0.6861 mmol) were mixed under nitrogen flow, and then the resulting mixture was stirred under reflux in 220 ml of toluene overnight.

After the reaction was terminated, Mat-1 (9.85 g, yield 60%) was obtained by filtering the reaction solution through celite, removing the solvent, and then purifying the residue with column chromatography [Hexane:MC=4:1 (v:v)].

SYNTHESIS EXAMPLE 2

Synthesis of Compound Mat-2

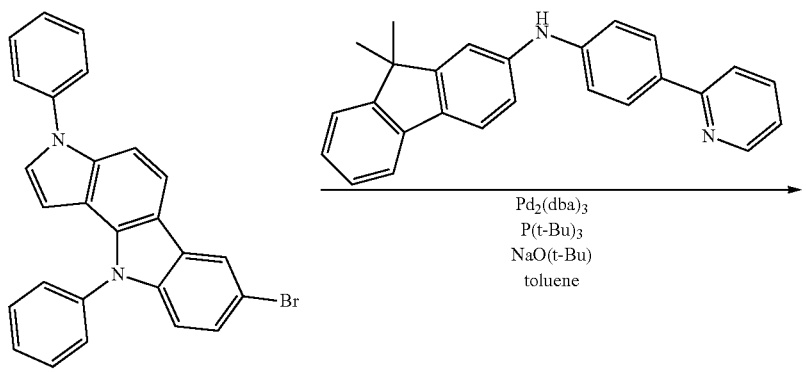

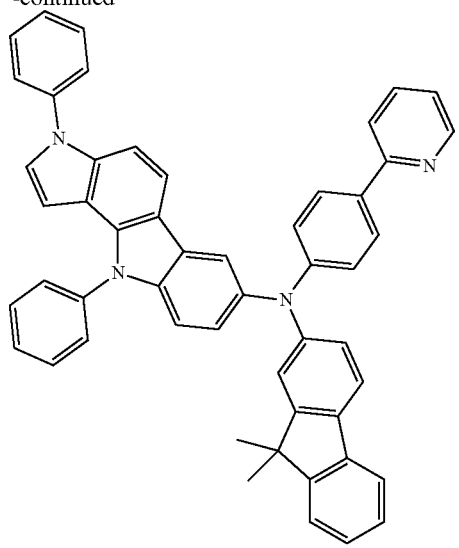
Mat-2
Compound Mat-2 was obtained by performing the same procedure as in Synthesis Example 1, except that 9,9-dimethyl-N-(4-(pyridin-2-yl)phenyl)-9H-fluoren-2-amine (9.1 g, 25.16 mmol) was used instead of the N-(biphenyl4-yl)-9,9-dimethyl-9H-fluoren-2-amine used in Synthesis Example 1.
SYNTHESIS EXAMPLE 3
Synthesis of Compound Mat-3
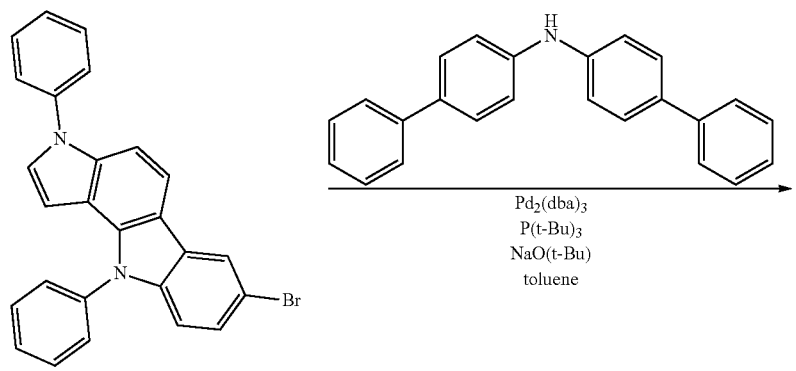

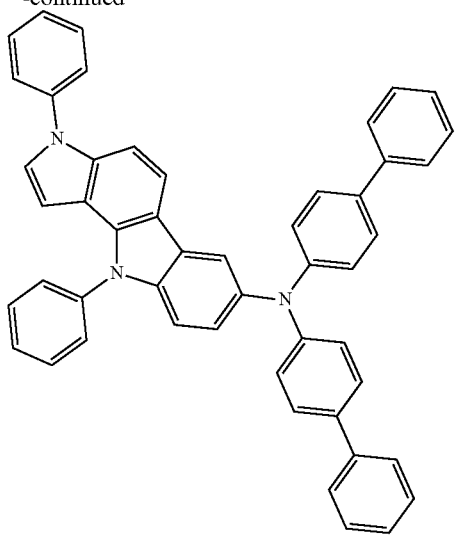

Mat-3

Compound Mat-3 was synthesized by performing the same procedure as in Synthesis Example 1, except that 9,9-dimethyl-N-(4-(pyridin-2-yl)phenyl)-9H-fluoren-2-amine (8.1 g, 25.16 mmol) was used instead of the N-(biphenyl-4-yl)-9,9-dimethyl-9H-fluoren-2-amine used in Synthesis Example 1.

SYNTHESIS EXAMPLE 4

Synthesis of Compound Mat-4

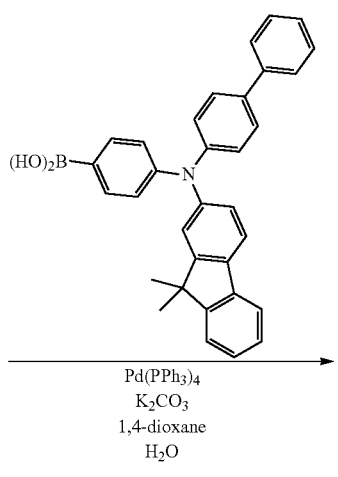

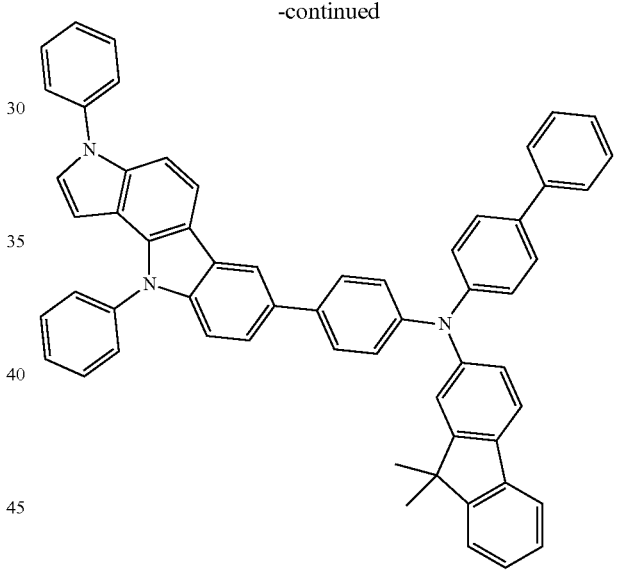

Mat-4

Compound IC-1 (10 g, 22.87 mmol) synthesized in Preparation Example 1, 4-(biphenyl-4-yl(9,9-dimethyl-9H-fluoren-2-yl)amino)phenylboronic acid (12.11 g, 25.16 mmol), tetrakis(triphenylphosphine)palladium(0) (0.79 g, 0.6861 mmol), and potassium carbonate (9.48 g, 68.61 mmol) were mixed under nitrogen flow, and then the resulting mixture was stirred under reflux in 220 ml of 1,4-dioxane and 35 ml of $H_2O$ overnight.

After the reaction was terminated, the organic layer was separated with methylene chloride and water was removed from the separated organic layer by using $MgSO_4$. Compound Mat-4 (12.71 g, yield 70%) was obtained by removing the solvent from the organic layer from which water had been removed, and then purifying the residue with column chromatography [Hexane:MC=3:1 (v:v)].

Elemental Analysis: C, 89.25; H, 5.46; N, 5.29/HRMS $[M]^+$: 793

SYNTHESIS EXAMPLE 5

Synthesis of Compound Mat-5

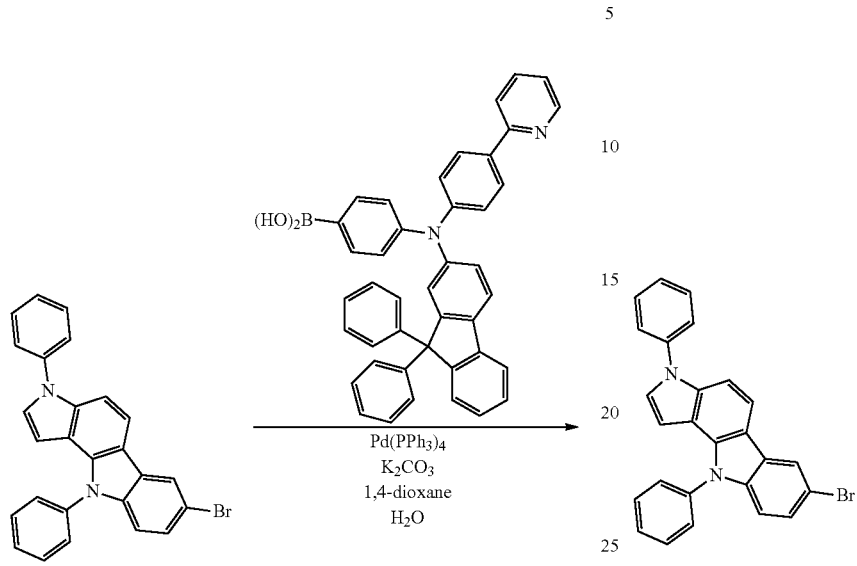

SYNTHESIS EXAMPLE 6

Synthesis of Compound Mat-6

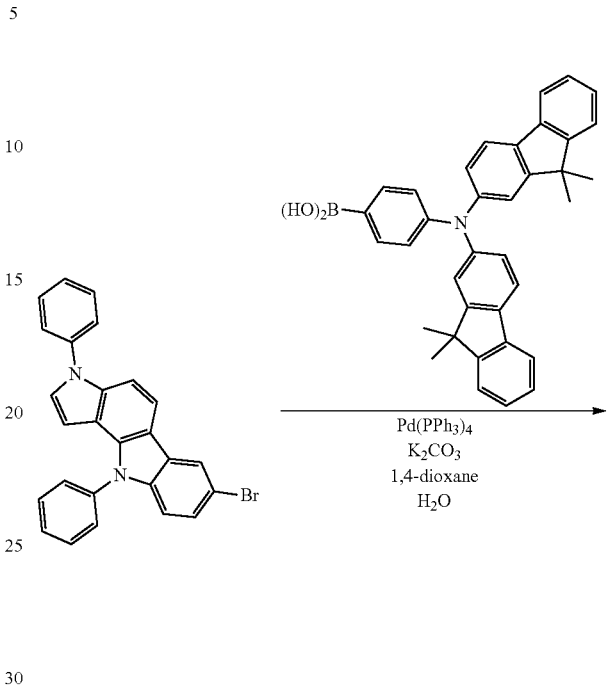

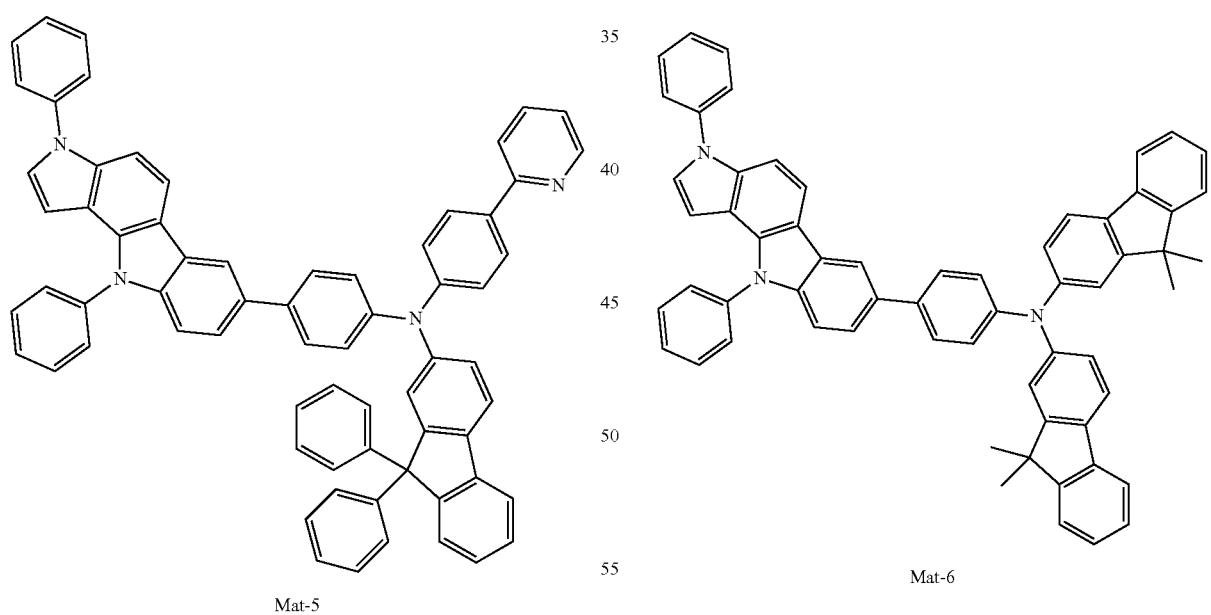

Compound Mat-5 was synthesized by performing the same procedure as in Synthesis Example 4, except that 4-((9,9-diphenyl-9H-fluoren-2-yl)(4-(pyridin-2-yl)phenyl)amino)phenylboronic acid (15.26 g, 25.16 mmol) was used instead of the 4-(biphenyl-4-yl(9,9-dimethyl-9H-fluoren-2yl)amino)phenylboronic acid used in Synthesis Example 4.

Elemental Analysis: C, 88.86; H, 5.04; N, 6.10/HRMS [M]+: 919

Compound Mat-6 was synthesized by performing the same procedure as in Synthesis Example 4, except that N-(4-bromophenyl)-N-(9,9-dimethyl-9H-fluoren-2-yl)-9,9-dimethyl-9H-fluoren-2-amine (13.1 g, 25.16 mmol) was used instead of the 4-(biphenyl-4-yl(9,9-dimethyl-9H-fluoren-2yl)amino)phenylboronic acid used in Synthesis Example 4.

Elemental Analysis: C, 89.28; H, 5.68; N, 5.04/HRMS [M]+: 834

SYNTHESIS EXAMPLE 7
Synthesis of Compound Mat-7
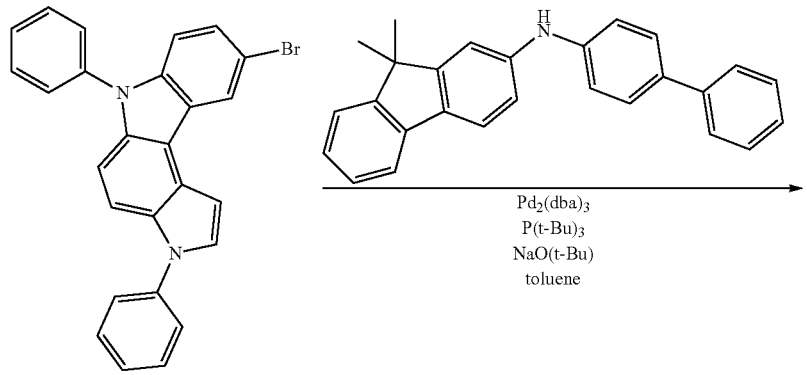
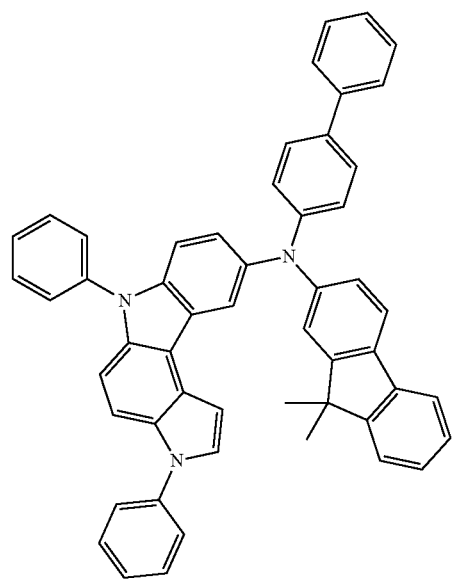
Mat-7

Compound Mat-7 was synthesized by performing the same procedure as in Synthesis Example 1, except that Compound IC-2 (10 g, 22.87 mmol) synthesized in Preparation Example 2 was used instead of Compound IC-1 used in Synthesis Example 1.
Elemental Analysis: C, 88.67; H, 5.48; N, 5.85/HRMS [M]+: 717
SYNTHESIS EXAMPLE 8
Synthesis of Compound Mat-8
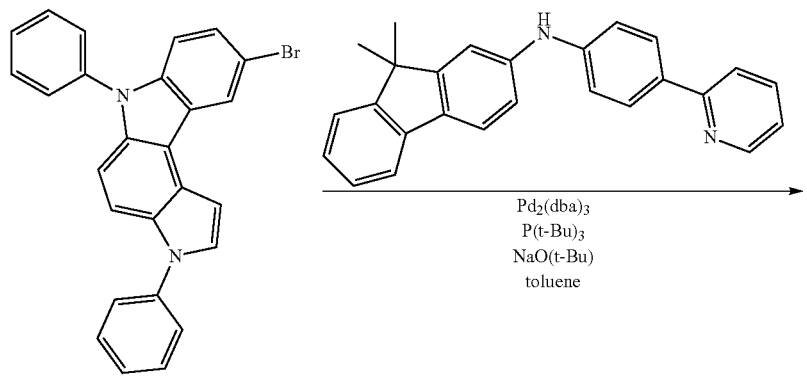
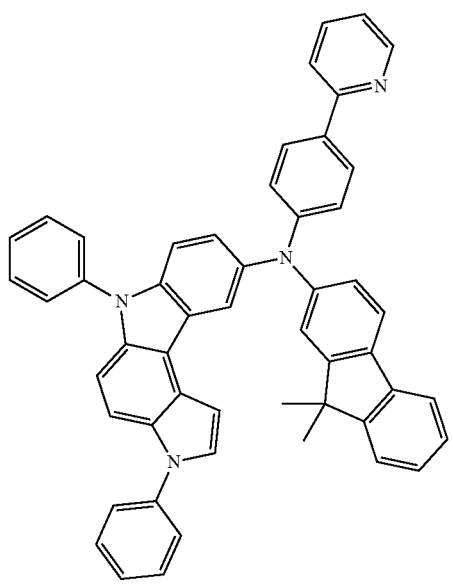
Mat-8

Compound Mat-8 was synthesized by performing the same procedure as in Synthesis Example 1, except that Compound IC-2 (10 g, 22.87 mmol) synthesized in Preparation Example 2 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

SYNTHESIS EXAMPLE 9

Synthesis of Compound Mat-9

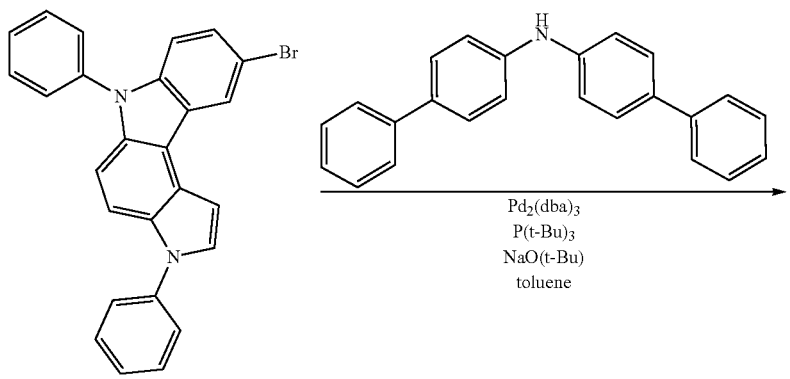

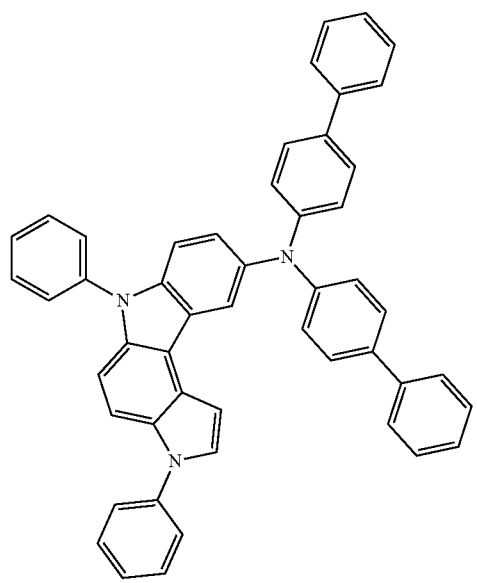

Mat-8

Compound Mat-9 was synthesized by performing the same procedure as in Synthesis Example 1, except that Compound IC-2 (10 g, 22.87 mmol) synthesized in Preparation Example 2 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

SYNTHESIS EXAMPLE 10

Synthesis of Compound Mat-10

SYNTHESIS EXAMPLE 11

Synthesis of Compound Mat-11

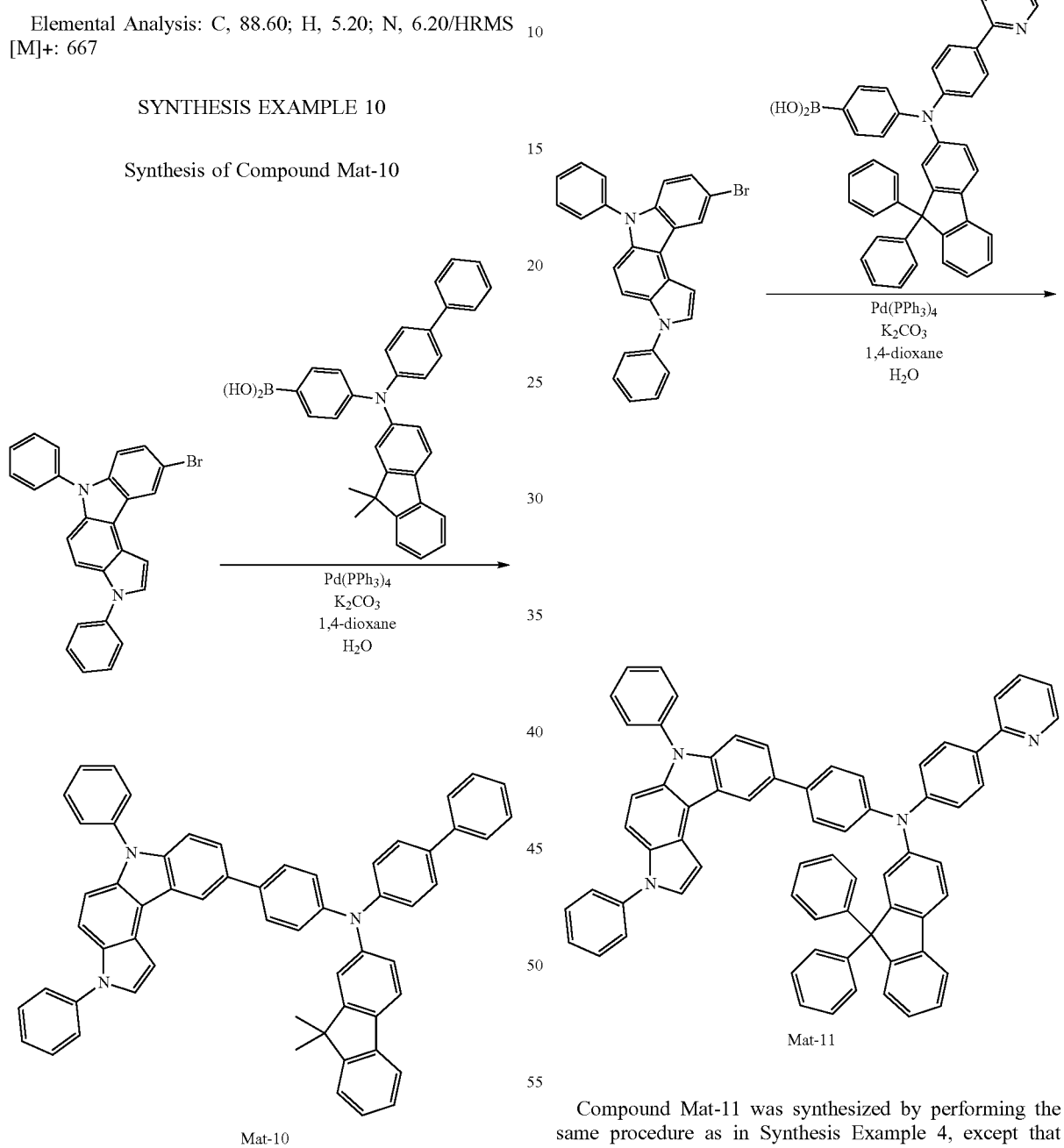

Mat-10

Mat-11

Compound Mat-10 was synthesized by performing the same procedure as in Synthesis Example 4, except that Compound IC-2 (10 g, 22.87 mmol) synthesized in Preparation Example 2 was used instead of Compound IC-1 used in Synthesis Example 4.

Elemental Analysis: C, 89.25; H, 5.46; N, 5.29/HRMS [M]+: 793

Compound Mat-11 was synthesized by performing the same procedure as in Synthesis Example 4, except that Compound IC-2 (10 g, 22.87 mmol) synthesized in Preparation Example 2 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

SYNTHESIS EXAMPLE 12
Synthesis of Compound Mat-12
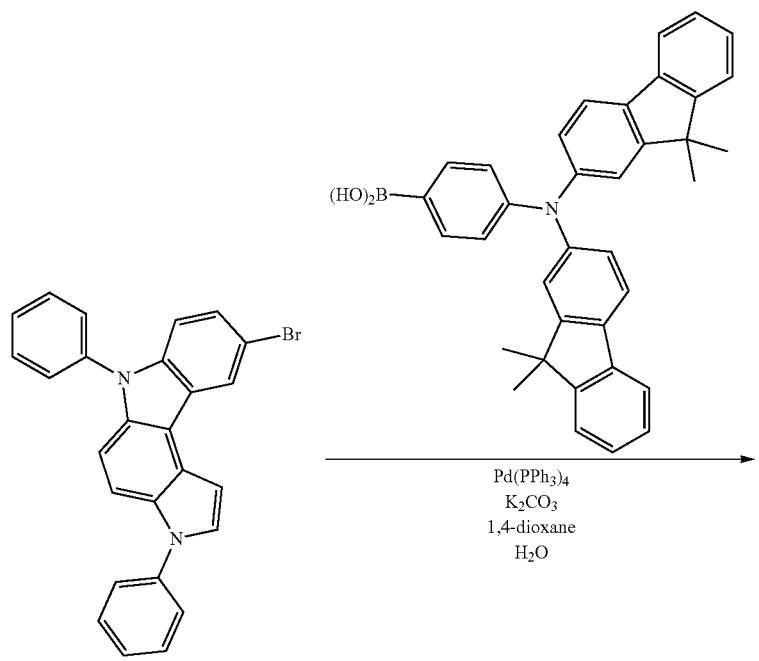
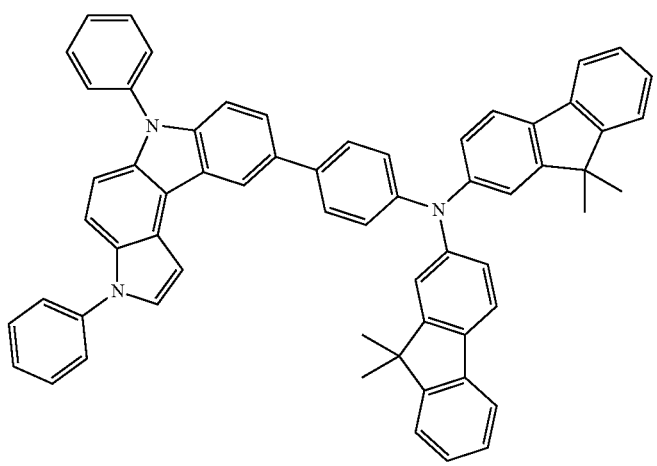
Mat-12

Compound Mat-12 was synthesized by performing the same procedure as in Synthesis Example 4, except that Compound IC-2 (10 g, 22.87 mmol) synthesized in Preparation Example 2 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

SYNTHESIS EXAMPLE 13

Synthesis of Compound Mat-13

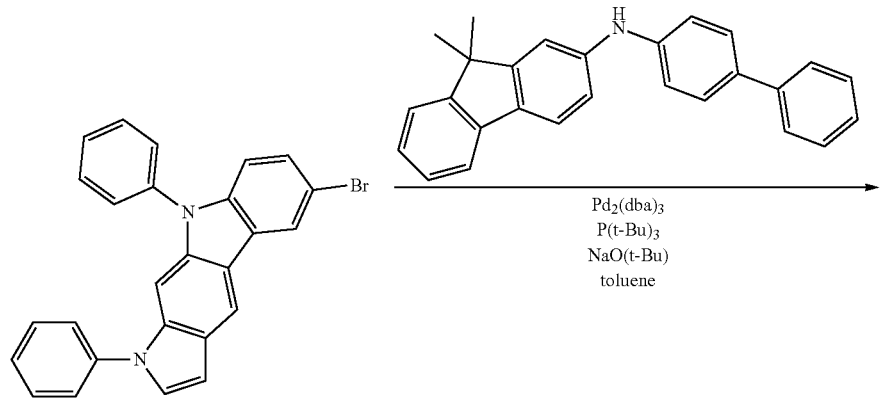

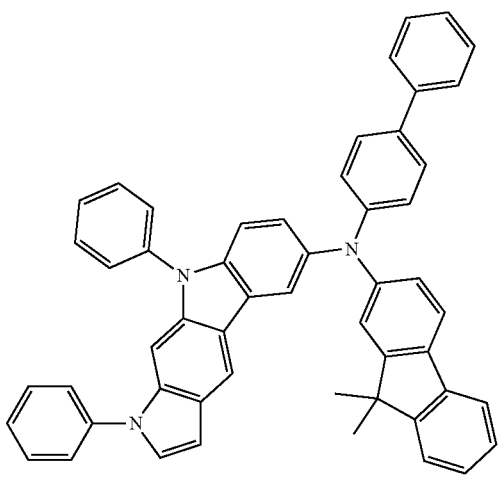

Mat-13

Compound Mat-13 was synthesized by performing the same procedure as in Synthesis Example 1, except that Compound IC-3 (10 g, 22.87 mmol) synthesized in Preparation Example 3 was used instead of Compound IC-1 used in Synthesis Example 1.
Elemental Analysis: C, 88.67; H, 5.48; N, 5.85/HRMS [M]+: 717
SYNTHESIS EXAMPLE 14
Synthesis of Compound Mat-14
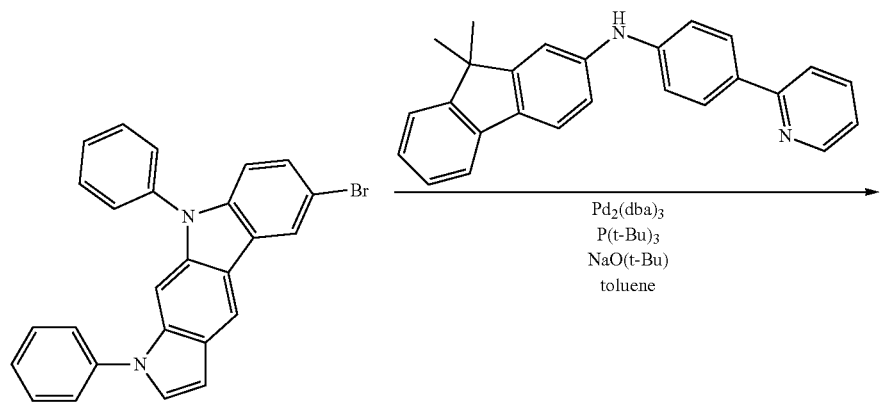
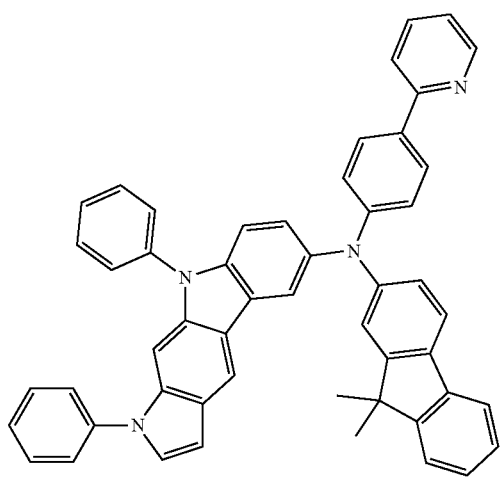
Mat-14

Compound Mat-14 was synthesized by performing the same procedure as in Synthesis Example 1, except that Compound IC-3 (10 g, 22.87 mmol) synthesized in Preparation Example 3 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

SYNTHESIS EXAMPLE 15

Synthesis of Compound Mat-15

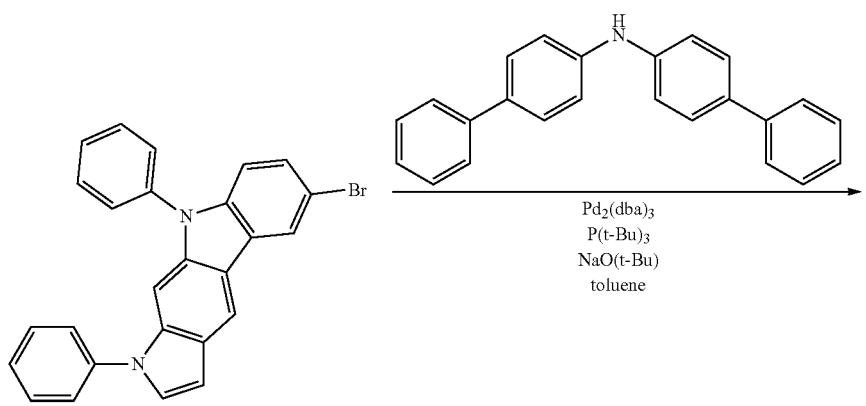

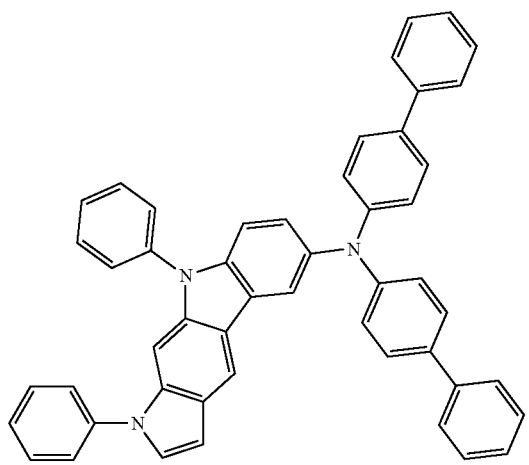

Mat-15

Compound Mat-15 was synthesized by performing the same procedure as in Synthesis Example 3, except that Compound IC-3 (10 g, 22.87 mmol) synthesized in Preparation Example 3 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

SYNTHESIS EXAMPLE 16

Synthesis of Mat-16

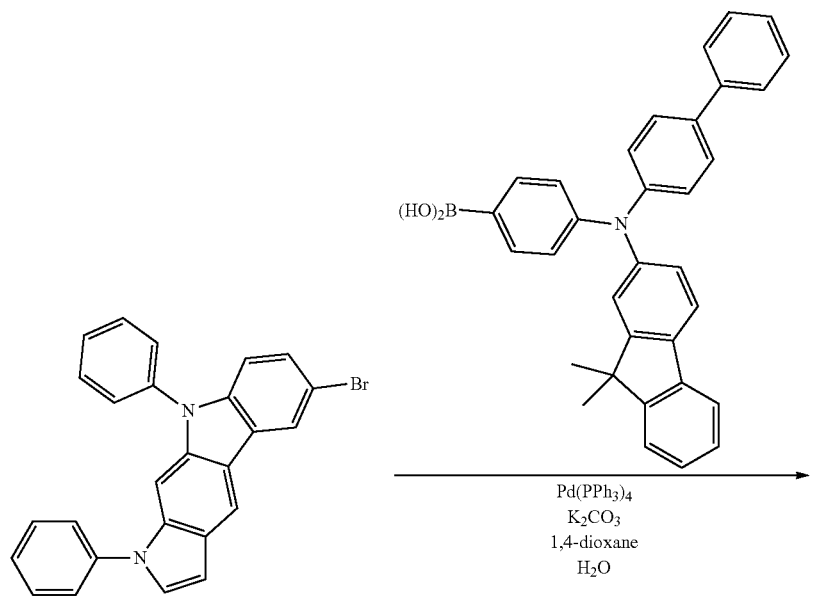

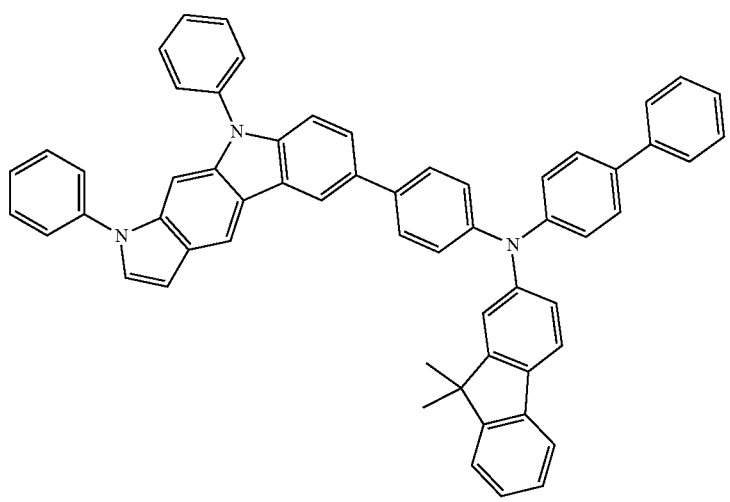

Mat-16

Compound Mat-16 was synthesized by performing the same procedure as in Synthesis Example 4, except that Compound IC-3 (10 g, 22.87 mmol) synthesized in Preparation Example 3 was used instead of Compound IC-1 used in Synthesis Example 1.
Elemental Analysis: C, 89.25; H, 5.46; N, 5.29/HRMS [M]+: 793
SYNTHESIS EXAMPLE 17
Synthesis of Compound Mat-17
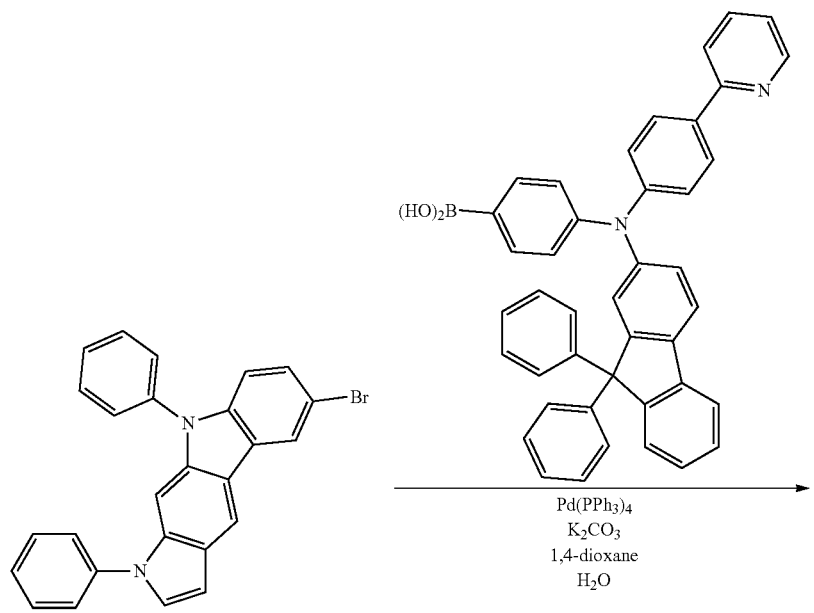
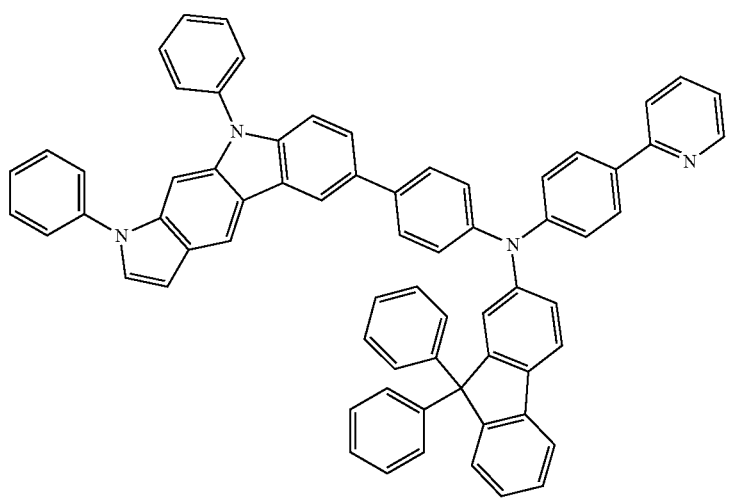
Mat-17

Compound Mat-17 was synthesized by performing the same procedure as in Synthesis Example 4, except that Compound IC-3 (10 g, 22.87 mmol) synthesized in Preparation Example 3 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

SYNTHESIS EXAMPLE 18

Synthesis of Compound Mat-18

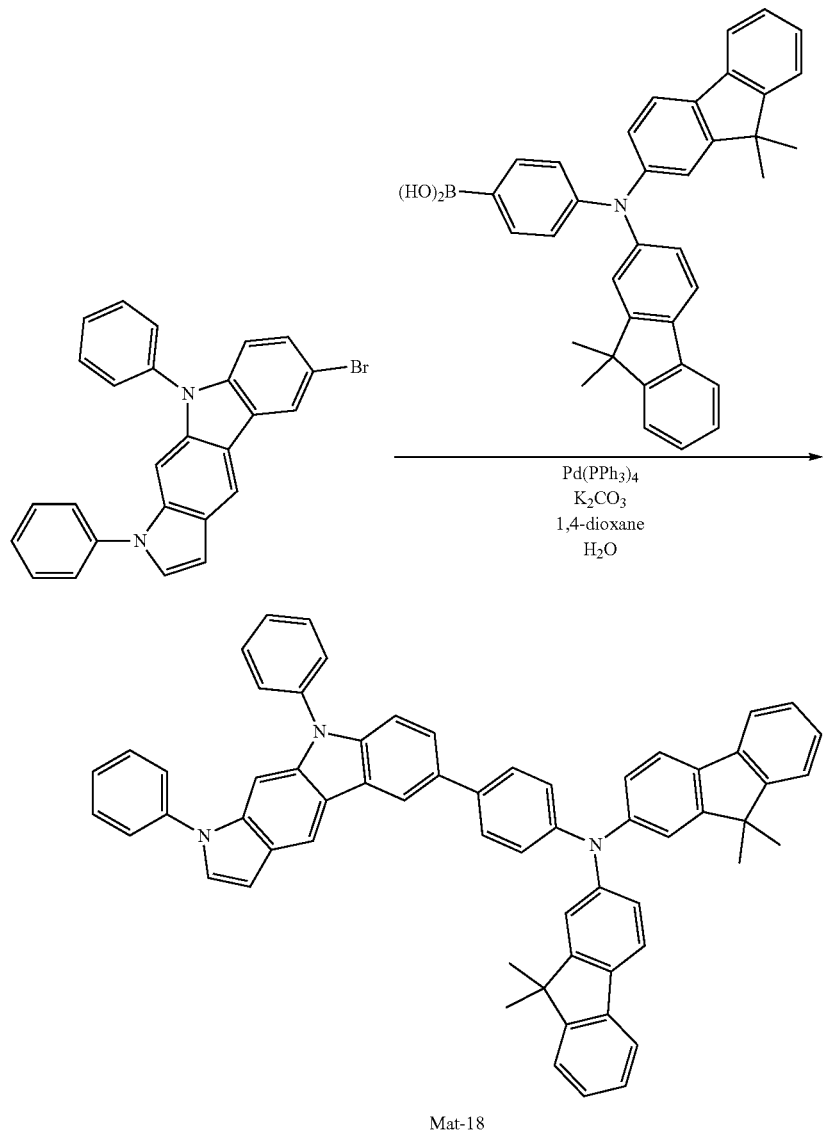 [SMILES: Brc1ccc2c(c1)c1cc3ccn(-c4ccccc4)c3cc1n2-c1ccccc1 ; CC1(C)c2ccccc2-c2ccc(N(c3ccc(B(O)O)cc3)c3ccc4c(c3)C(C)(C)c3ccccc3-4)cc21 ; CC1(C)c2ccccc2-c2ccc(N(c3ccc(-c4ccc5c(c4)c4cc6ccn(-c7ccccc7)c6cc4n5-c4ccccc4)cc3)c3ccc4c(c3)C(C)(C)c3ccccc3-4)cc21]

Mat-18

Compound Mat-18 was synthesized by performing the same procedure as in Synthesis Example 4, except that Compound IC-3 (10 g, 22.87 mmol) synthesized in Preparation Example 3 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

SYNTHESIS EXAMPLE 19
Synthesis of Compound Mat-19
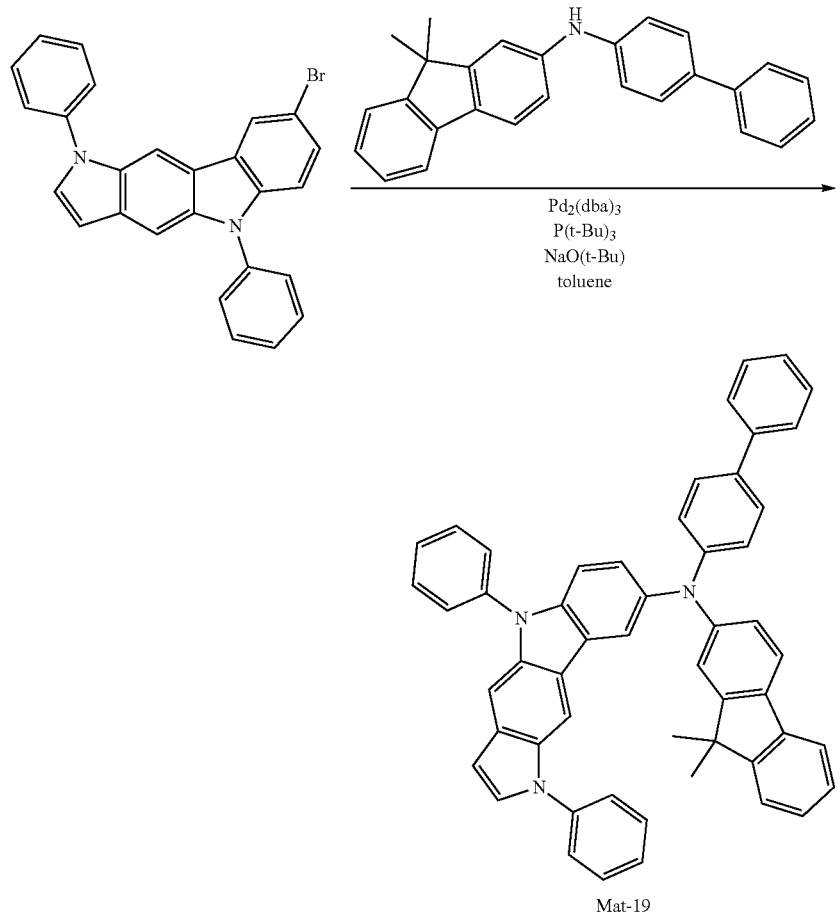
Mat-19
Compound Mat-19 was synthesized by performing the same procedure as in Synthesis Example 1, except that Compound IC-4 (10 g, 22.87 mmol) synthesized in Preparation Example 4 was used instead of Compound IC-1 used in Synthesis Example 1.
Elemental Analysis: C, 88.67; H, 5.48; N, 5.85/HRMS [M]+: 717
SYNTHESIS EXAMPLE 20
Synthesis of Compound Mat-20
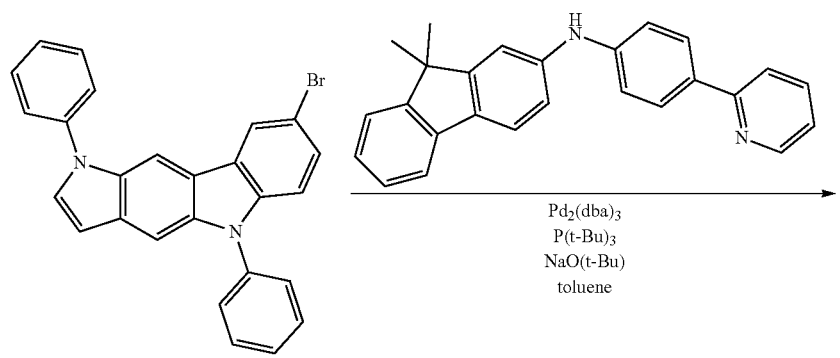

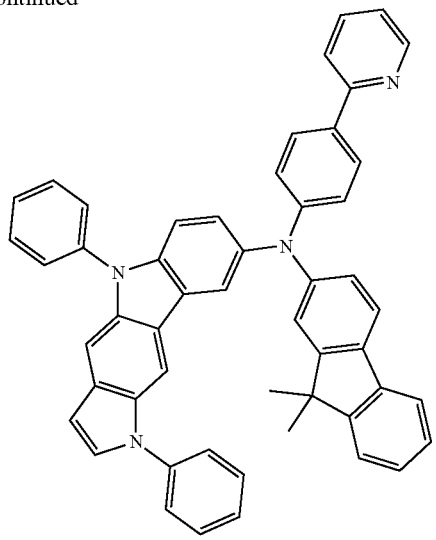

Mat-20

Compound Mat-20 was synthesized by performing the same procedure as in Synthesis Example 1, except that Compound IC-4 (10 g, 22.87 mmol) synthesized in Preparation Example 4 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

SYNTHESIS EXAMPLE 21

Synthesis of Compound Mat-21

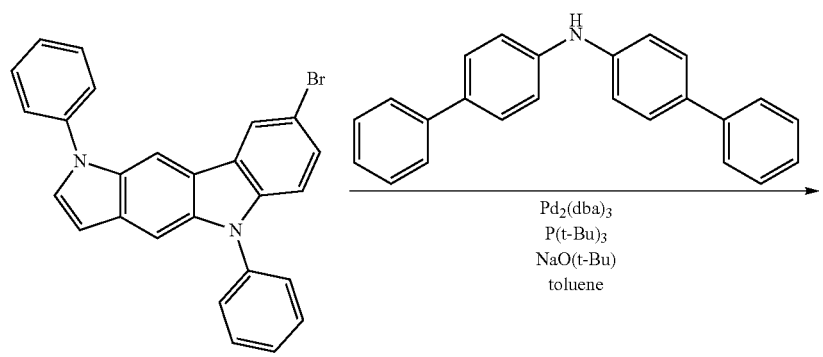

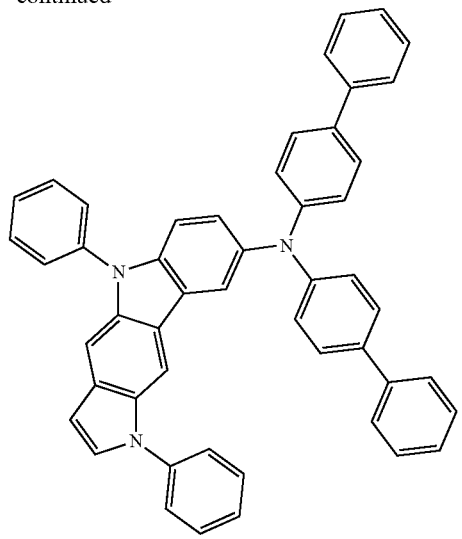

Mat-21

Compound Mat-21 was synthesized by performing the same procedure as in Synthesis Example 1, except that Compound IC-4 (10 g, 22.87 mmol) synthesized in Preparation Example 4 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

SYNTHESIS EXAMPLE 22

Synthesis of Compound Mat-22

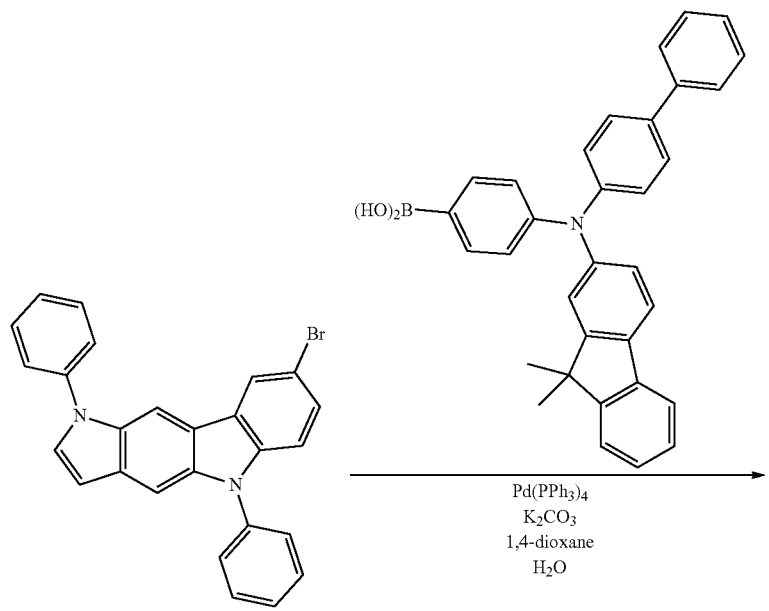

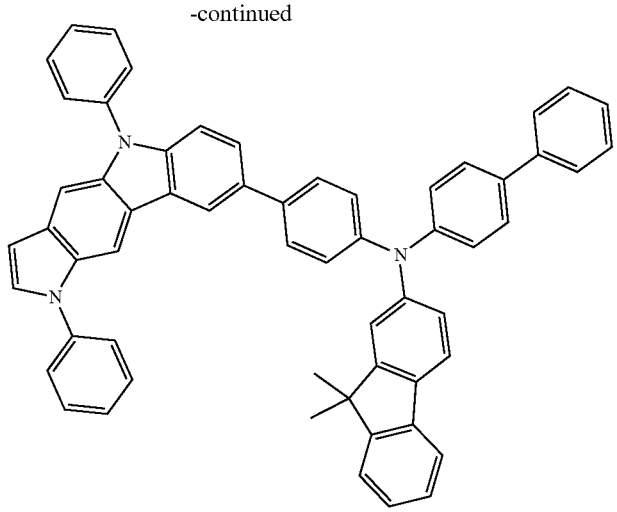
Mat-22
Compound Mat-22 was synthesized by performing the same procedure as in Synthesis Example 4, except that Compound IC-4 (10 g, 22.87 mmol) synthesized in Preparation Example 4 was used instead of Compound IC-1 used in Synthesis Example 4.
Elemental Analysis: C, 89.25; H, 5.46; N, 5.29/HRMS [M]+: 793
SYNTHESIS EXAMPLE 23
Synthesis of Compound Mat-23
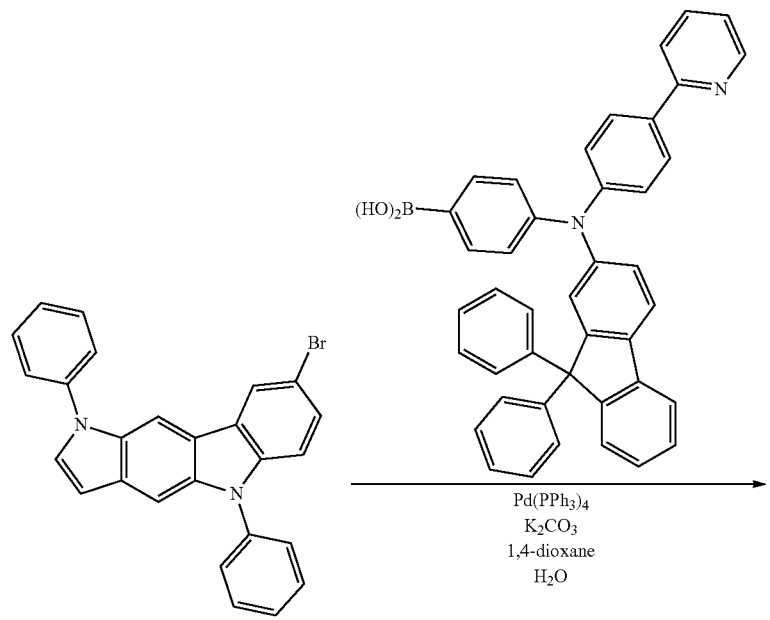

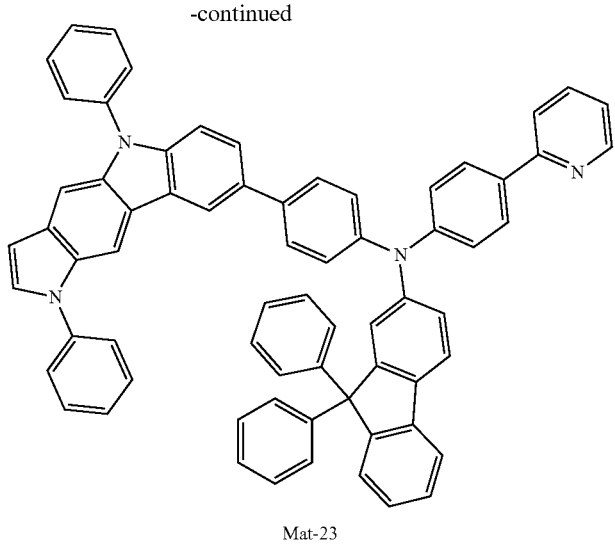

Mat-23

Compound Mat-23 was synthesized by performing the same procedure as in Synthesis Example 4, except that Compound IC-4 (10 g, 22.87 mmol) synthesized in Preparation Example 4 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

SYNTHESIS EXAMPLE 24

Synthesis of Compound Mat-24

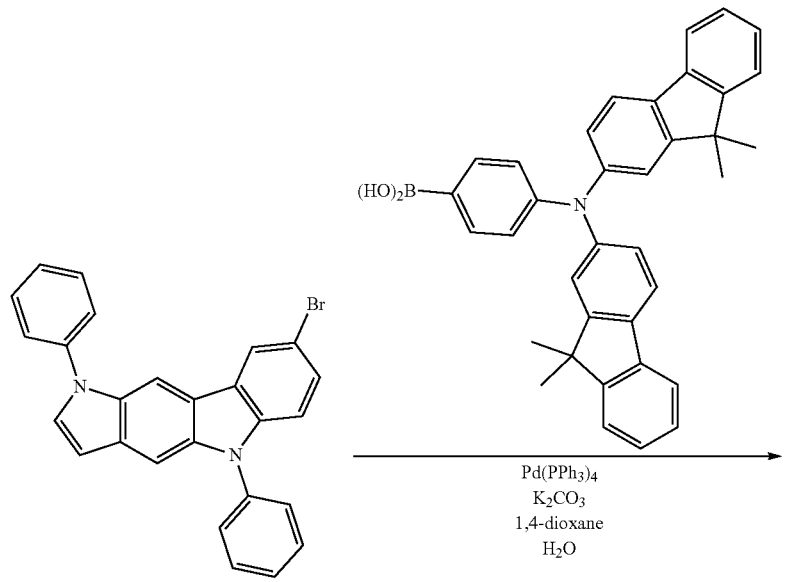

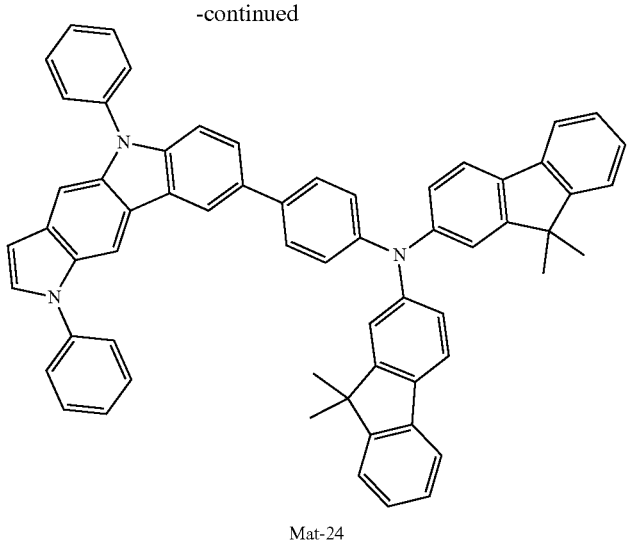

Mat-24

Compound Mat-24 was synthesized by performing the same procedure as in Synthesis Example 4, except that Compound IC-4 (10 g, 22.87 mmol) synthesized in Preparation Example 4 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

SYNTHESIS EXAMPLE 25

Synthesis of Compound Mat-25

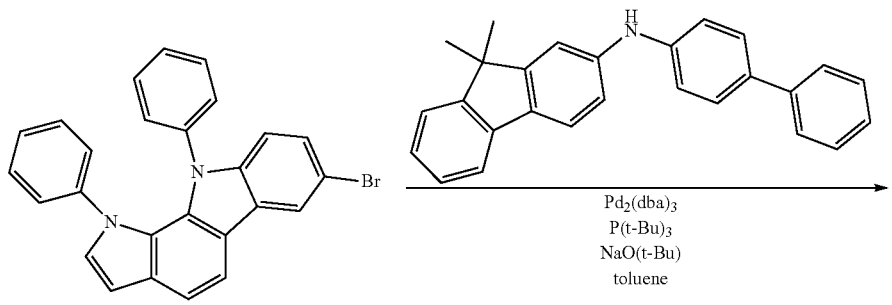

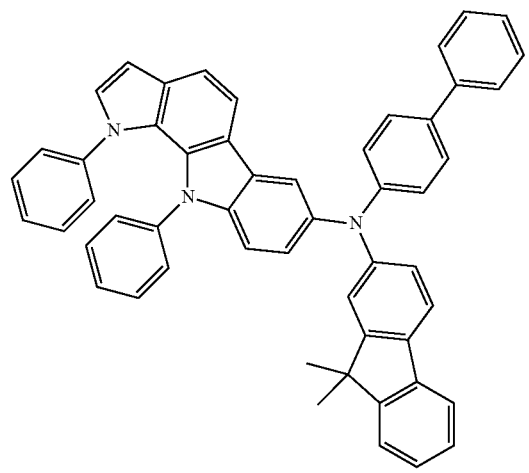

Mat-25

Compound Mat-25 was synthesized by performing the same procedure as in Synthesis Example 1, except that Compound IC-5 (10 g, 22.87 mmol) synthesized in Preparation Example 5 was used instead of Compound IC-1 used in Synthesis Example 1.

Elemental Analysis: C, 88.67; H, 5.48; N, 5.85/HRMS [M]+: 717

SYNTHESIS EXAMPLE 26

Synthesis of Compound Mat-26

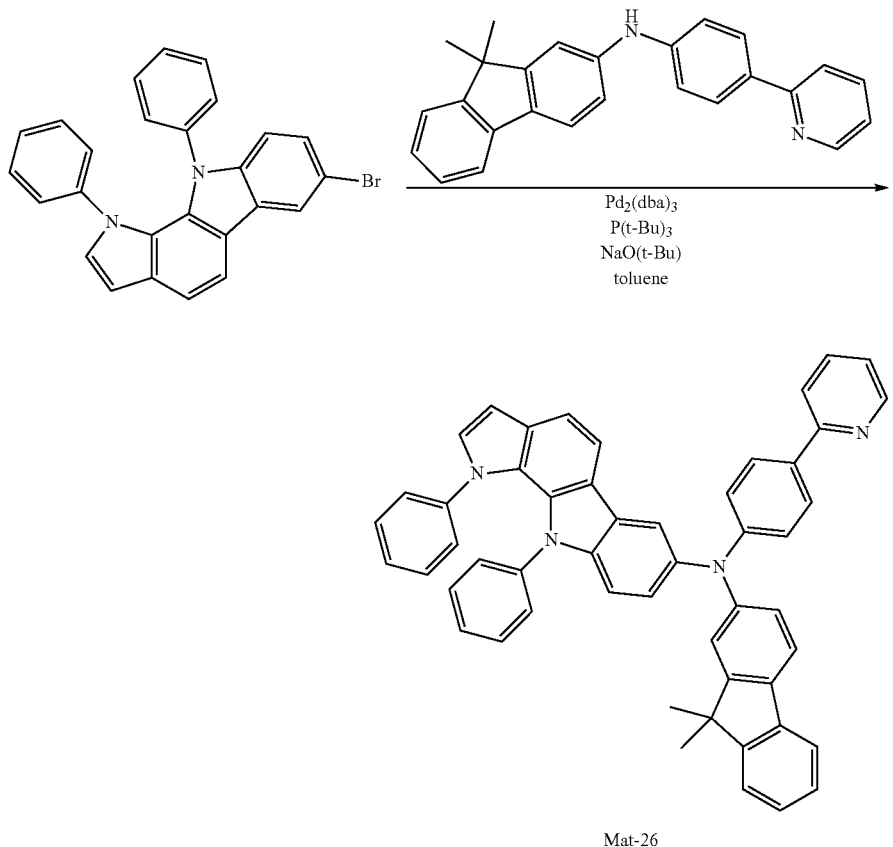

Mat-26

Compound Mat-26 was synthesized by performing the same procedure as in Synthesis Example 1, except that Compound IC-5 (10 g, 22.87 mmol) synthesized in Preparation Example 5 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

SYNTHESIS EXAMPLE 27

Synthesis of Compound Mat-27

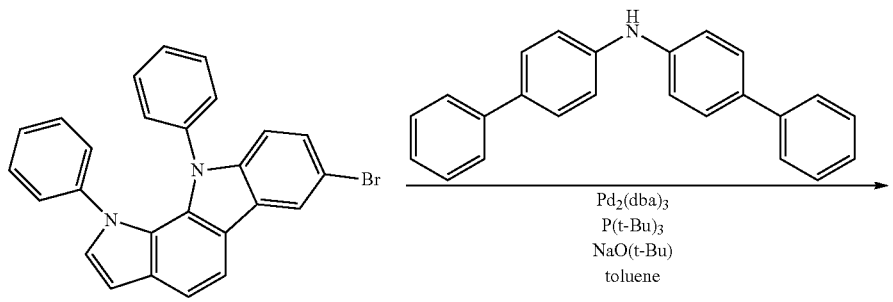

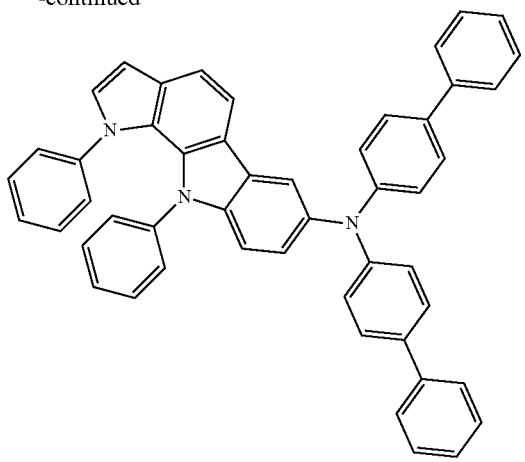

Mat-27

Compound Mat-27 was synthesized by performing the same procedure as in Synthesis Example 1, except that Compound IC-5 (10 g, 22.87 mmol) synthesized in Preparation Example 5 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

SYNTHESIS EXAMPLE 28

Synthesis of Compound Mat-28

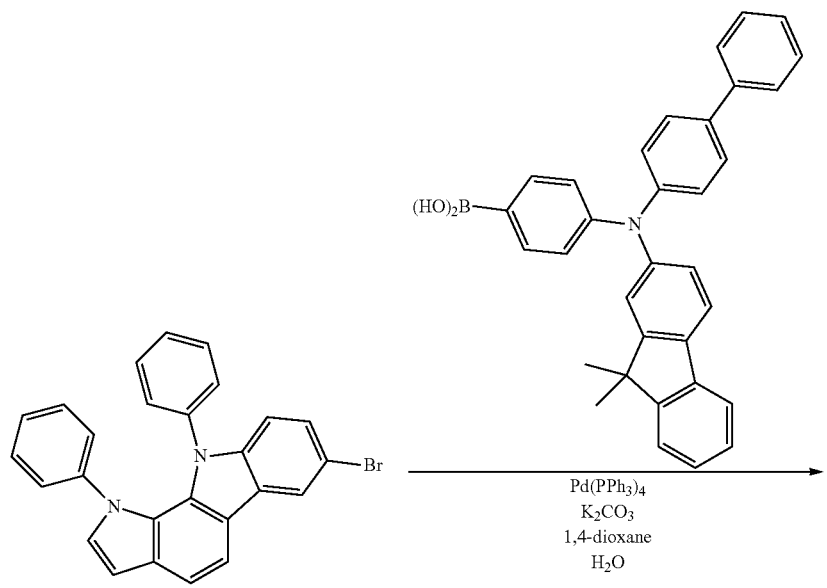

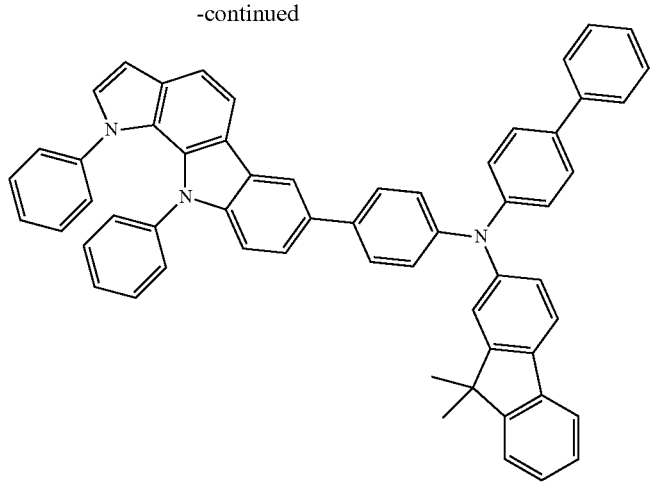
Mat-28
Compound Mat-28 was synthesized by performing the same procedure as in Synthesis Example 4, except that Compound IC-5 (10 g, 22.87 mmol) synthesized in Preparation Example 5 was used instead of Compound IC-1 used in Synthesis Example 4.
Elemental Analysis: C, 89.25; H, 5.46; N, 5.29/HRMS [M]+: 793
SYNTHESIS EXAMPLE 29
Synthesis of Compound Mat-29
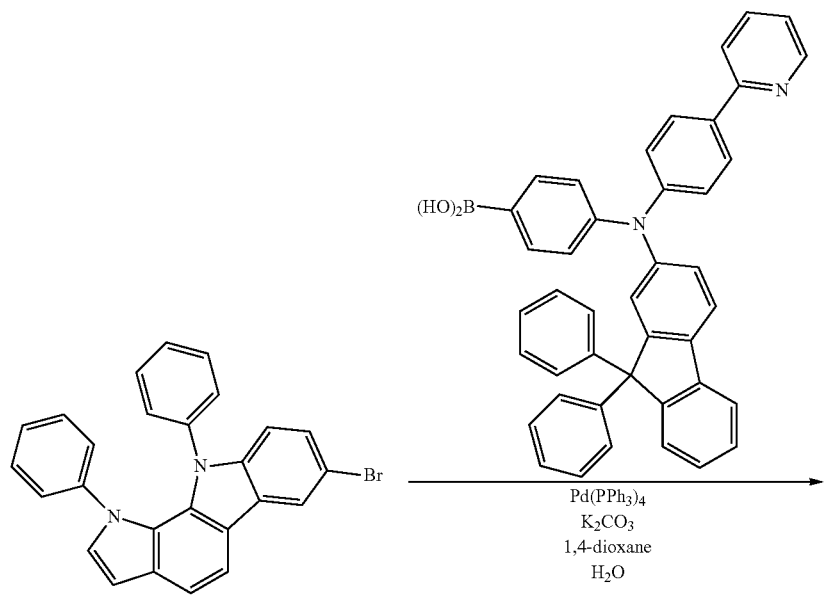

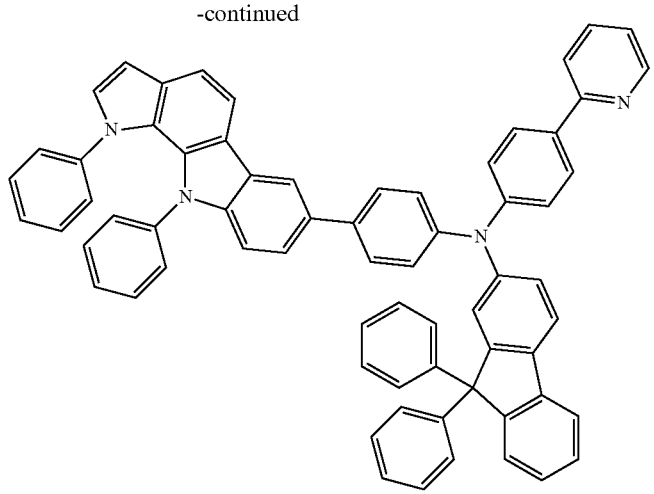

Mat-29

Compound Mat-29 was synthesized by performing the same procedure as in Synthesis Example 4, except that Compound IC-5 (10 g, 22.87 mmol) used in Preparation Example 5 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

SYNTHESIS EXAMPLE 30

Synthesis of Compound Mat-30

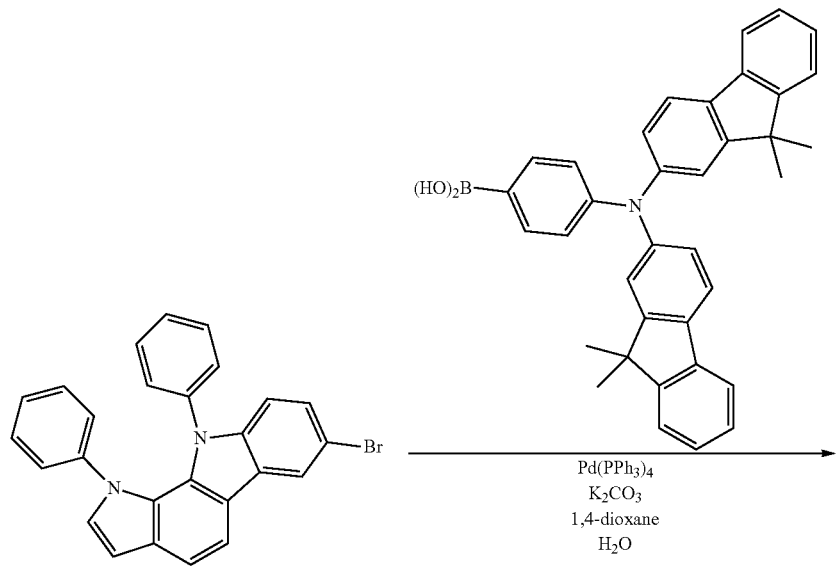

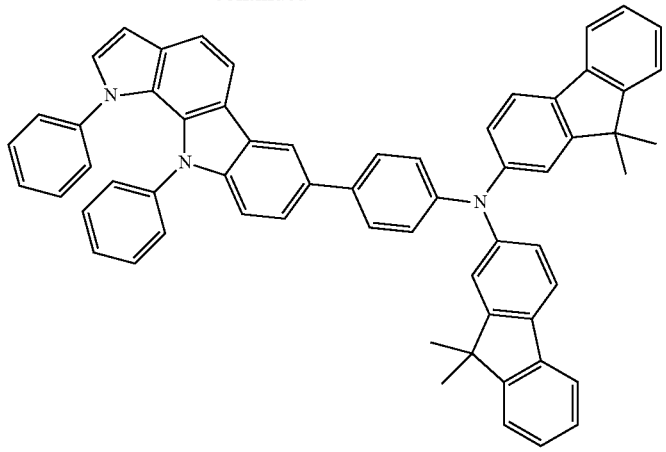

Mat-30

Compound Mat-30 was synthesized by performing the same procedure as in Synthesis Example 4, except that Compound IC-5 (10 g, 22.87 mmol) synthesized in Preparation Example 5 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

SYNTHESIS EXAMPLE 31

Synthesis of Compound Mat-31

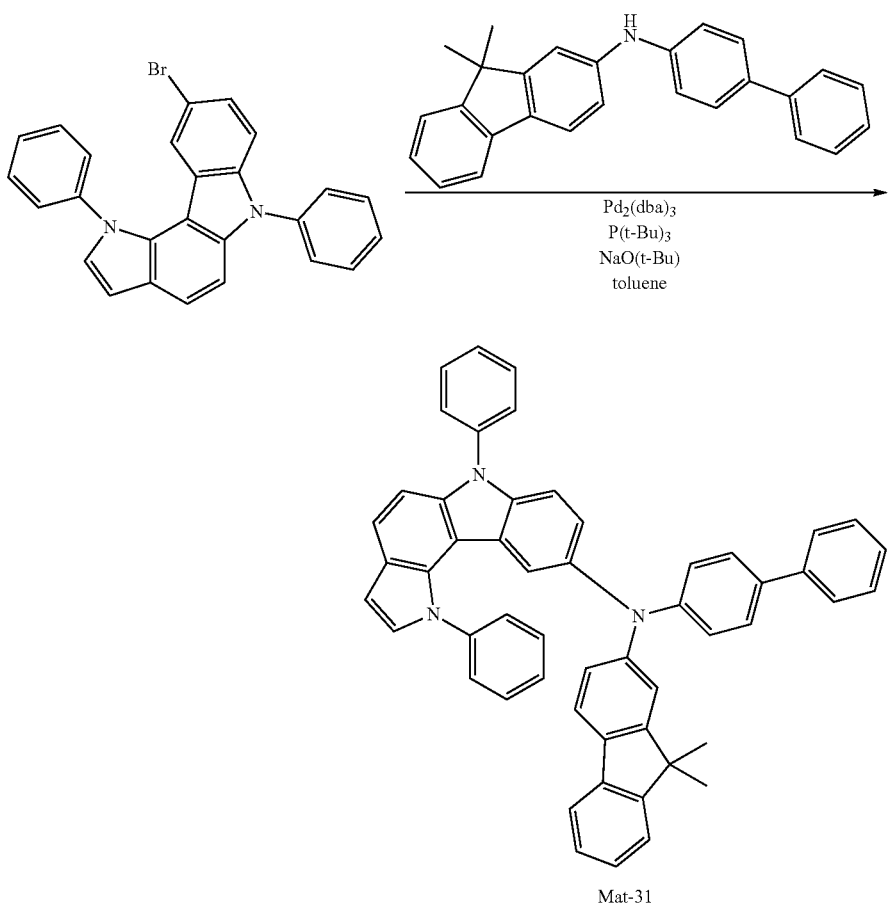

Mat-31

Compound Mat-31 was synthesized by performing the same procedure as in Synthesis Example 1, except that Compound IC-6 (10 g, 22.87 mmol) synthesized in Preparation Example 6 was used instead of Compound IC-1 used in Synthesis Example 1.
Elemental Analysis: C, 88.67; H, 5.48; N, 5.85/HRMS [M]+: 717
SYNTHESIS EXAMPLE 32
Synthesis of Compound Mat-32
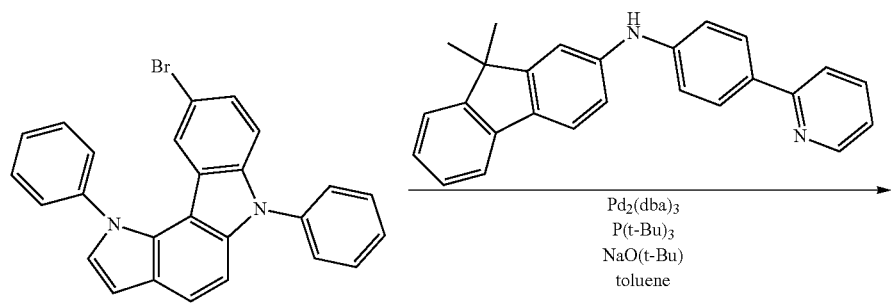
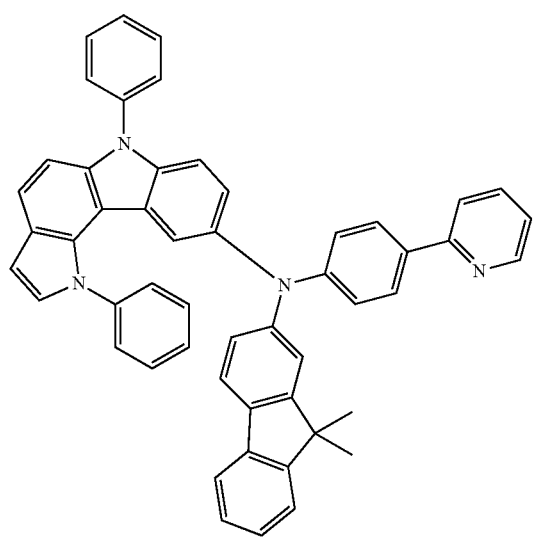
Mat-32

Compound Mat-32 was synthesized by performing the same procedure as in Synthesis Example 1, except that Compound IC-6 (10 g, 22.87 mmol) synthesized in Preparation Example 6 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

SYNTHESIS EXAMPLE 33

Synthesis of Compound Mat-33

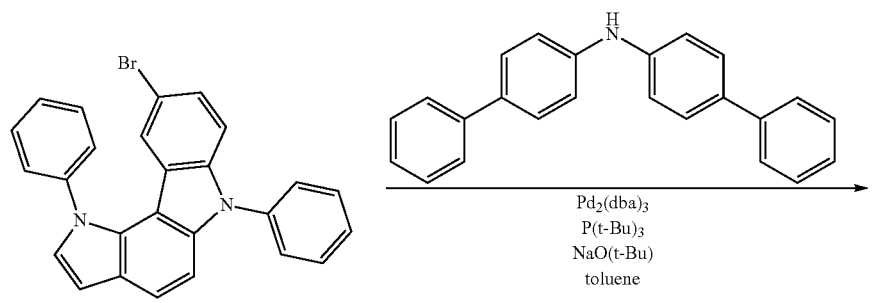

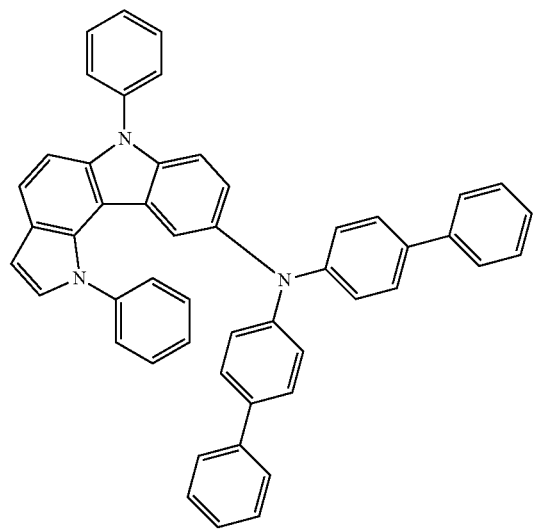

Mat-33

Compound Mat-33 was synthesized by performing the same procedure as in Synthesis Example 1, except that Compound IC-6 (10 g, 22.87 mmol) synthesized in Preparation Example 6 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

SYNTHESIS EXAMPLE 34

Synthesis of Compound Mat-34

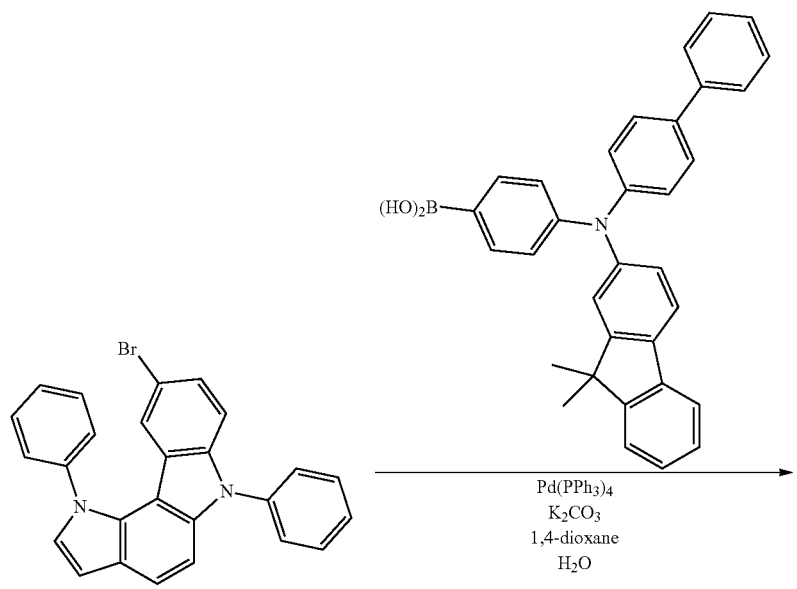

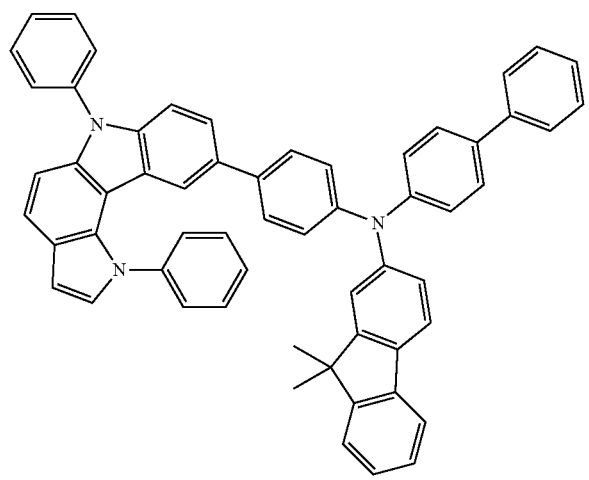

Mat-34

Compound Mat-34 was synthesized by performing the same procedure as in Synthesis Example 4, except that Compound IC-6 (10 g, 22.87 mmol) synthesized in Preparation Example 6 was used instead of Compound IC-1 used in Synthesis Example 4.
Elemental Analysis: C, 89.25; H, 5.46; N, 5.29/HRMS [M]+: 793
SYNTHESIS EXAMPLE 35
Synthesis of Compound Mat-35
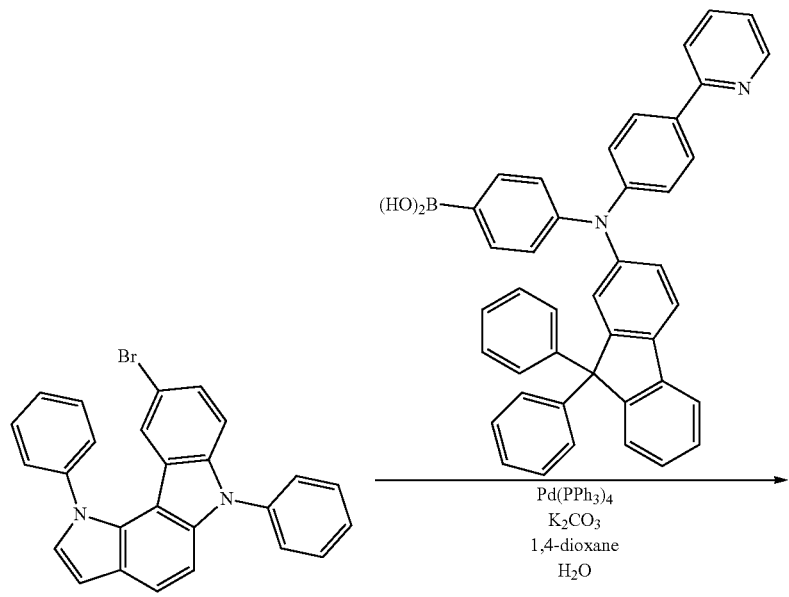
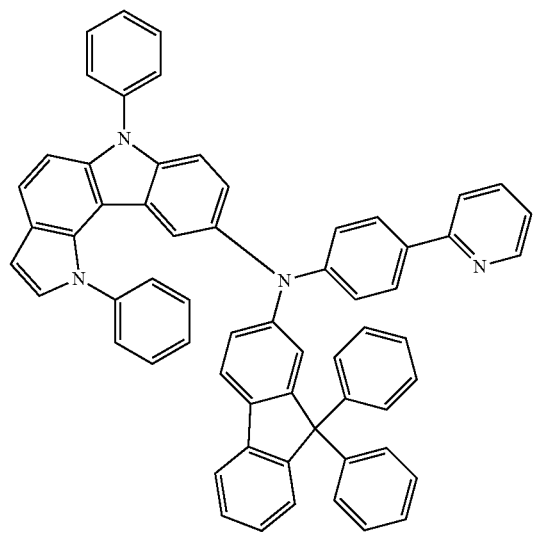
Mat-35

Compound Mat-35 was synthesized by performing the same procedure as in Synthesis Example 4, except that Compound IC-6 (10 g, 22.87 mmol) synthesized in Preparation Example 6 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

SYNTHESIS EXAMPLE 36

Synthesis of Compound Mat-36

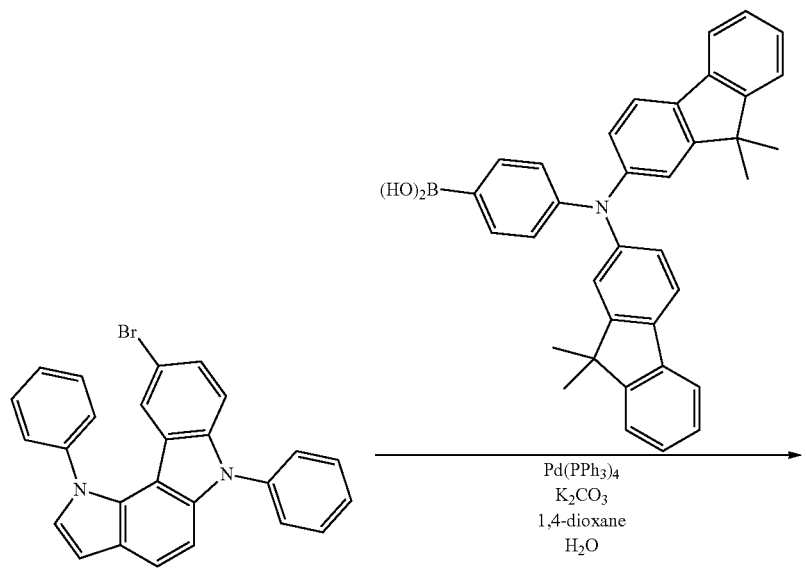

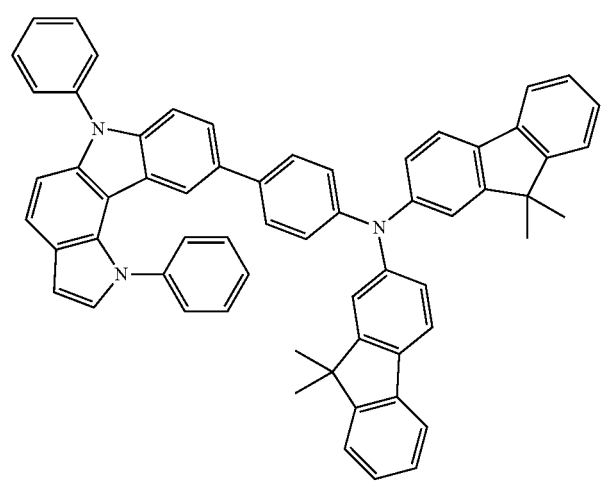

Mat-36

Compound Mat-36 was synthesized by performing the same procedure as in Synthesis Example 4, except that Compound IC-6 (10 g, 22.87 mmol) synthesized in Preparation Example 6 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

SYNTHESIS EXAMPLE 37

Synthesis of Compound Mat-37

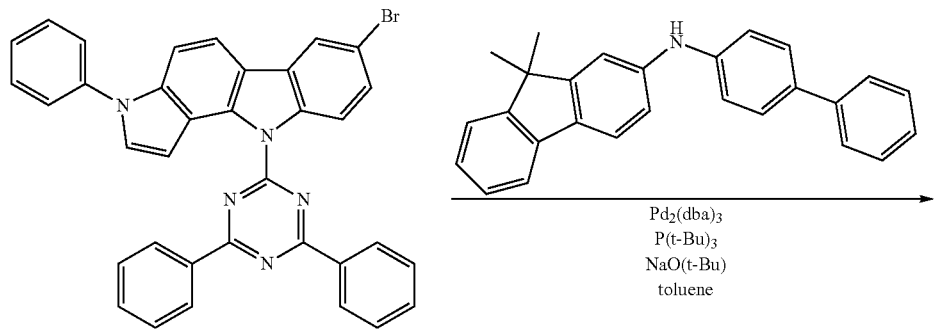

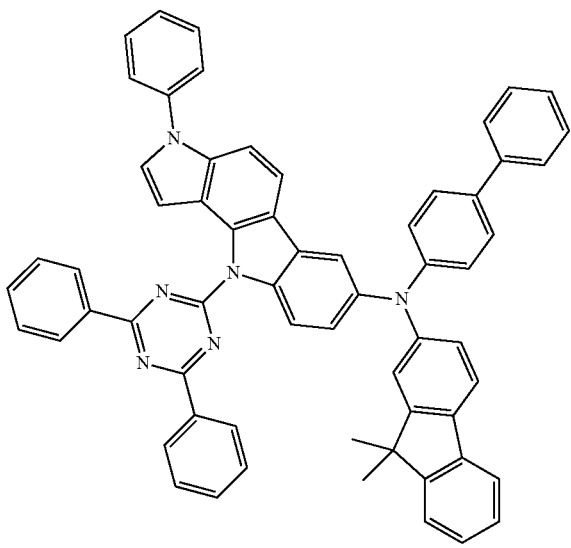

Mat-37

Compound Mat-37 was synthesized by performing the same procedure as in Synthesis Example 1, except that Compound IC-7 (13.55 g, 22.87 mmol) synthesized in Preparation Example 7 was used instead of Compound IC-1 used in Synthesis Example 1.
Elemental Analysis: C, 85.29; H, 5.08; N, 9.63/HRMS [M]+: 872
SYNTHESIS EXAMPLE 38
Synthesis of Compound Mat-38
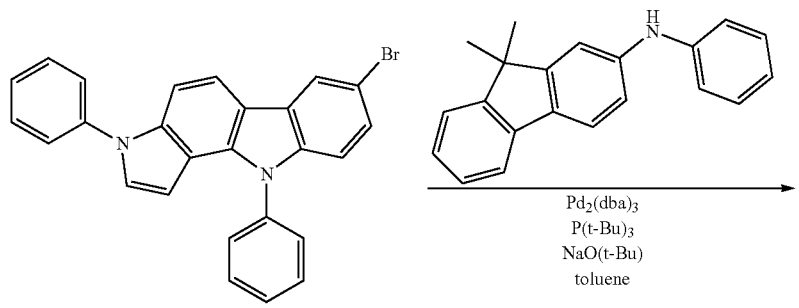
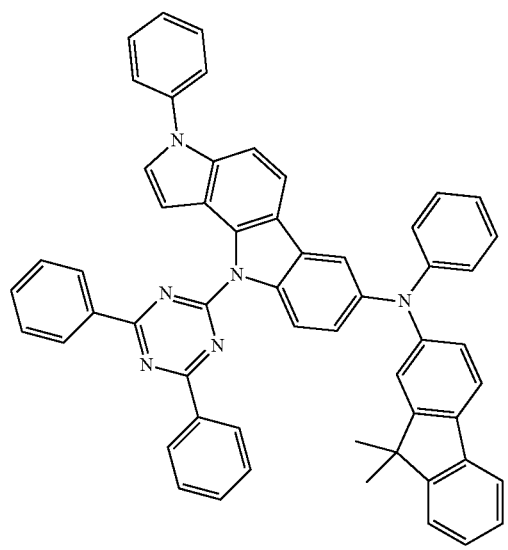
Mat-38

Compound Mat-38 was synthesized by performing the same procedure as in Synthesis Example 1, except that 9,9-dimethyl-N-phenyl-9H-fluoren-2-amine (7.18 g, 25.16 mmol) was used instead of the N-(biphenyl-4-yl)-9,9-dimethyl-9H-fluoren-2-amine used in Synthesis Example 1.
Elemental Analysis: C, 87.96; H, 5.50; N, 6.55/HRMS [M]+: 641
SYNTHESIS EXAMPLE 39
Synthesis of Compound Mat-39
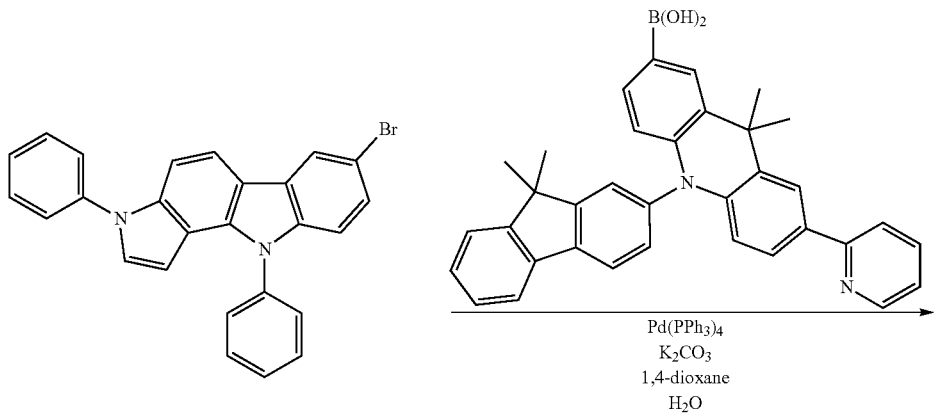
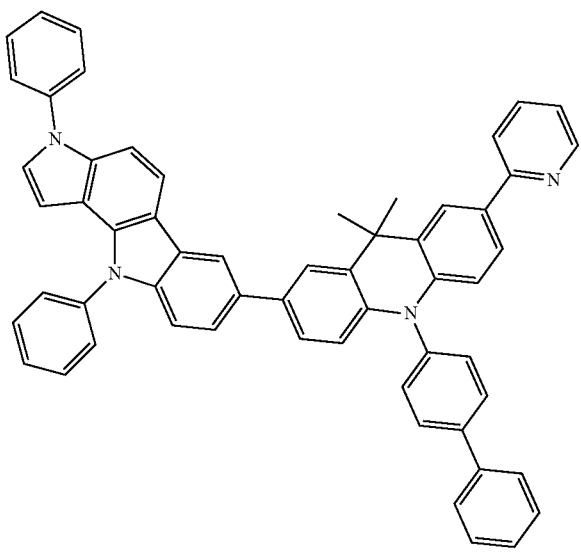
Mat-39

Compound Mat-39 was synthesized by performing the same procedure as in Synthesis Example 1, except that 10-(biphenyl-4-yl)-2-bromo-9,9-dimethyl-7-(pyridin-2-yl)-9,10-dihydroacridine (13.46 g, 25.16 mmol) was used instead of the N-(biphenyl-4-yl)-9,9-dimethyl-9H-fluoren-2-amine used in Synthesis Example 1.

Elemental Analysis: C, 87.63; H, 5.33; N, 7.05/HRMS [M]+: 794

EXAMPLE 1

Manufacture of Organic EL Device

A glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic EL device was manufactured by laminating m-MTDATA (60 nm)/Mat-1 (80 nm) which is a compound synthesized in Synthesis Example 1/DS-H522+5% DS-501 (300 nm)/BCP (10 nm)/Alq$_3$ (30 nm)/LiF (1 nm)/Al (200 nm) in this order on the thus prepared ITO transparent electrode.

DS-H522 and DS-501, which were used in the manufacture of the device, were products manufactured by Doosan Corporation Electro-Materials BG, and the structures of m-MTDATA, TCTA, CBP, Ir(ppy)$_3$, and BCP are as follows.

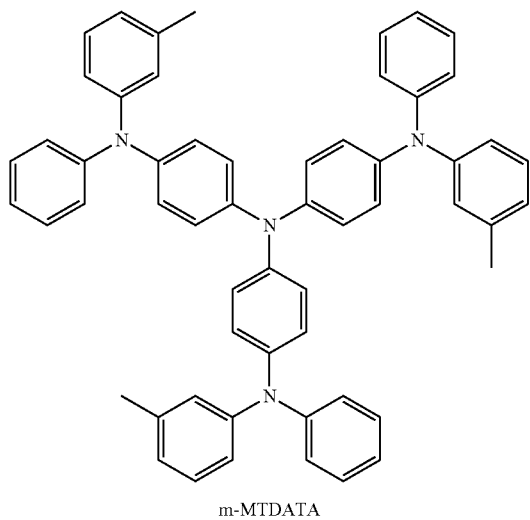

m-MTDATA

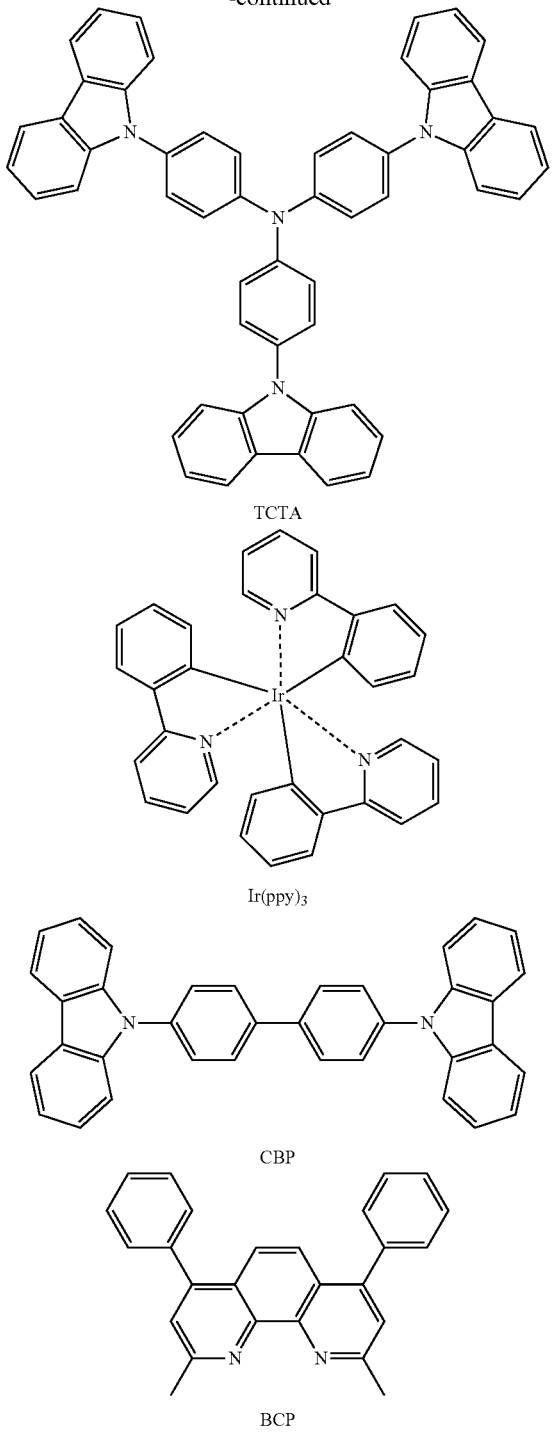

TCTA

Ir(ppy)$_3$

CBP

BCP

EXAMPLES 2 to 39

Manufacture of Organic EL Device

Organic EL devices were manufactured by performing the same procedure as in Example 1, except that Compounds Mat-2 to Mat-39 each synthesized in Synthesis Examples 2 to 39 were used instead of Compound Mat-1 used as a material for a hole transporting layer when a hole transporting layer is formed in Example 1.

COMPARATIVE EXAMPLE 1

Manufacture of Organic EL Device

An organic EL device was manufactured in the same manners as in Example 1, except that NPB was used as a material for a hole transporting layer instead of Compound Mat-1 used as a material for a hole transporting layer when a hole transporting layer is formed in Example 1. The structure of the NPB used is as follows.

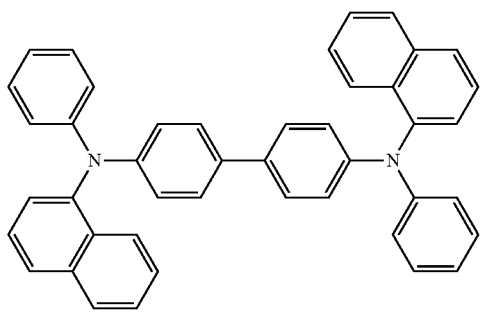

NPB

EXPERIMENTAL EXAMPLE

For each of the organic EL devices manufactured in Examples 1 to 39 and Comparative Example 1, the driving voltage and current efficiency were measured at a current density of 10 mA/cm$^2$, and the results are shown in the following Table 1.

TABLE 1

| Sample | Hole transporting layer | Driving voltage (V) | Current efficiency (cd/A) |
|---|---|---|---|
| Example 1 | Compound Mat-1 | 4.1 | 22.2 |
| Example 2 | Compound Mat-2 | 4.3 | 20.1 |
| Example 3 | Compound Mat-3 | 4.4 | 21.3 |
| Example 4 | Compound Mat-4 | 4.0 | 22.6 |
| Example 5 | Compound Mat-5 | 4.5 | 19.5 |
| Example 6 | Compound Mat-6 | 4.7 | 20.1 |
| Example 7 | Compound Mat-7 | 4.3 | 21.6 |
| Example 8 | Compound Mat-8 | 4.5 | 20.5 |
| Example 9 | Compound Mat-9 | 4.7 | 20.6 |
| Example 10 | Compound Mat-10 | 4.4 | 21.6 |
| Example 11 | Compound Mat-11 | 5.0 | 20.1 |
| Example 12 | Compound Mat-12 | 5.1 | 18.6 |
| Example 13 | Compound Mat-13 | 4.3 | 22.0 |
| Example 14 | Compound Mat-14 | 4.6 | 21.2 |
| Example 15 | Compound Mat-15 | 4.5 | 21.2 |
| Example 16 | Compound Mat-16 | 4.4 | 22.3 |
| Example 17 | Compound Mat-17 | 5.1 | 18.3 |
| Example 18 | Compound Mat-18 | 5.0 | 18.9 |
| Example 19 | Compound Mat-19 | 4.5 | 21.7 |
| Example 20 | Compound Mat-20 | 4.7 | 21.2 |
| Example 21 | Compound Mat-21 | 4.8 | 20.8 |
| Example 22 | Compound Mat-22 | 4.5 | 21.4 |
| Example 23 | Compound Mat-23 | 5.1 | 18.2 |
| Example 24 | Compound Mat-24 | 5.1 | 18.5 |
| Example 25 | Compound Mat-25 | 4.3 | 22.3 |
| Example 26 | Compound Mat-26 | 4.6 | 21.4 |
| Example 27 | Compound Mat-27 | 4.8 | 21.6 |
| Example 28 | Compound Mat-28 | 4.2 | 22.5 |
| Example 29 | Compound Mat-29 | 4.7 | 20.6 |
| Example 30 | Compound Mat-30 | 4.6 | 20.2 |
| Example 31 | Compound Mat-31 | 4.2 | 22.1 |
| Example 32 | Compound Mat-32 | 4.6 | 21.2 |
| Example 33 | Compound Mat-33 | 4.8 | 20.0 |
| Example 34 | Compound Mat-34 | 4.2 | 22.3 |
| Example 35 | Compound Mat-35 | 4.8 | 21.8 |
| Example 36 | Compound Mat-36 | 5.0 | 19.2 |
| Example 37 | Compound Mat-37 | 4.5 | 20.3 |
| Example 38 | Compound Mat-38 | 5.1 | 18.5 |
| Example 39 | Compound Mat-39 | 4.9 | 20.3 |
| Comparative Example 1 | NPB | 5.2 | 18.1 |

As shown in Table 1, it can be seen that the organic EL device (organic EL device each manufactured in Examples 1 to 39), in which the compounds (Mat 1 to Mat 39) according to the present disclosure are used as a hole transporting layer, exhibits excellent performance in terms of current efficiency and driving voltage as compared to the organic EL device (organic EL device of Comparative Example 1) in which the NPB in the related art is used.

The invention claimed is:

1. A compound of the following Formula 5, 6, 7, or 9:

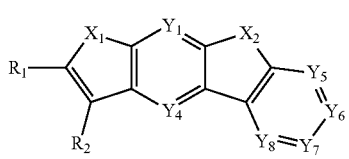

Formula 5

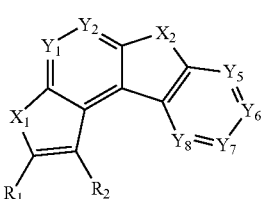

Formula 6

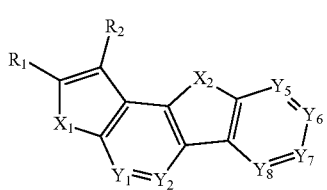

Formual 7

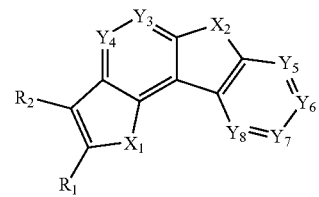

Formula 9 wherein, $Y_1$ to $Y_4$ are each independently N or $CR_3$, and, when $CR_3$ is present in a plural number, they are the same as or different from each other, $Y_5$ to $Y_8$ are each independently N or $CR_4$, and, when $CR_4$ is present in a plural number, they are the same as or different from each other, and provided that at least one of $Y_5$ to $Y_8$ is $CR_4$, and the at least one $R_4$ is a substituent of the following Formula 3;

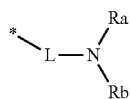

Formula 3 in Formula 3,

L is a single bond, or selected from the group consisting of a substituted or unsubstituted $C_6$ to $C_{60}$ arylene group, and a substituted or unsubstituted heteroarylene group having 5 to 60 nuclear atoms, and wherein one or more substituents each introduced into the arylene group and the heteroarylene group of L are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, and a $C_6$ to $C_{60}$ arylamine group, and provided that when the substituent is present in a plural number, they are the same as or different from each other;

$R_a$ and $R_b$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, and a substituted or unsubstituted heteroaryl group having 5 to 60 nuclear atoms, and wherein one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other;

provided that L, $R_a$, and $R_b$, taken with an adjacent substituent, optionally form a fused ring;

$X_1$ and $X_2$ are each $N(Ar_1)$, and are the same as or different from each other;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ to $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and wherein one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

2. The compound of claim 1, wherein the compound is selected from the group consisting of compounds represented by the following Formulae 11 to 13, and 15:

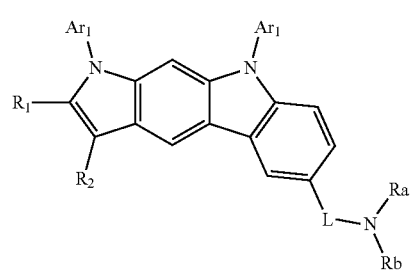

Formula 11

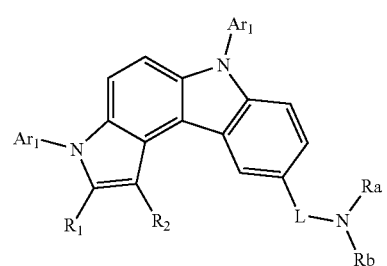

Formula 12

Formula 13

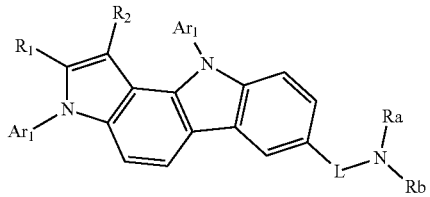

Formula 15

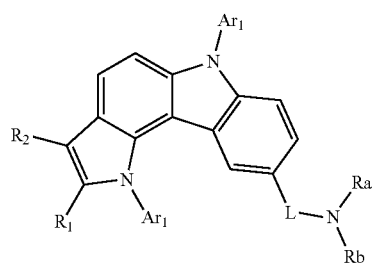

wherein,

R$_1$, R$_2$, Ar$_1$, R$_a$, R$_b$, and L are each the same as those defined in claim 1, and when Ar$_1$ is present in a plural number, they are the same as or different from each other.

3. The compound of claim 1, wherein Ar$_1$ is selected from the group consisting of a substituted or unsubstituted C$_6$ to C$_{60}$ aryl group, and a substituted or unsubstituted heteroaryl group having 5 to 60 nuclear atoms, wherein one or more substituents, which are optionally each introduced into the aryl group and the heteroaryl group of Ar$_1$, are each independently selected from the group consisting of deuterium, halogen, a nitrile group, a nitro group, a cyano group, a C$_1$ to C$_{40}$ alkyl group, a C$_2$ to C$_{40}$ alkenyl group, a C$_1$ to C$_{40}$ alkoxy group, a C$_1$ to C$_{40}$ amino group, a cycloalkyl group having 3 to 40 nuclear atoms, a C$_3$ to C$_{40}$ heterocycloalkyl group, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_1$ to C$_{40}$ alkylsilyl group, a C$_6$ to C$_{60}$ arylsilyl group, a C$_1$ to C$_{40}$ alkyl boron group, a C$_6$ to C$_{60}$ aryl boron group, a C$_6$ to C$_{60}$ arylphosphine group, a C$_6$ to C$_{60}$ arylphosphine oxide group, and a C$_6$ to C$_{60}$ arylamine group, and provided that when the substituent is present in a plural number, they are the same as or different from each other.

4. An organic electroluminescence device comprising: an anode; a cathode; and an organic material layer comprising one or more layers interposed between the anode and the cathode, wherein at least one of the one or more layers of the organic material layer comprises the compound of claim 1.

5. The organic electroluminescent device of claim 4, wherein the organic material layer comprising one or more layers, which comprises the compound, is selected from the group consisting of a hole injection layer, a hole transporting layer, and a light-emitting layer.

6. The organic electroluminescent device of claim 4, wherein the organic material layer comprising the compound is a hole transporting layer.

7. The organic electroluminescent device of claim 4, wherein the compound is selected from the group consisting of compounds of the following Formulae 11 to 13 and 15:

Formula 11

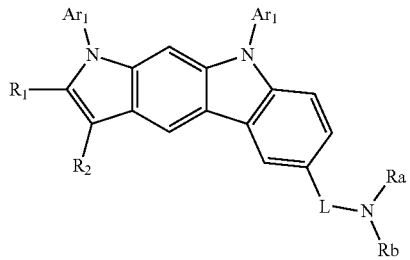

Formula 12

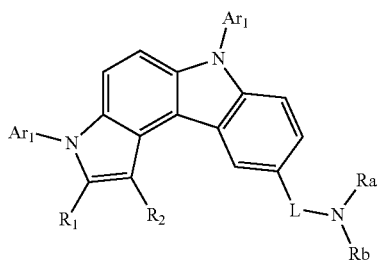

Formula 13

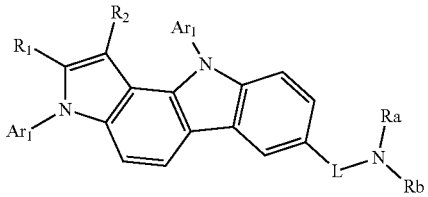

Formula 15

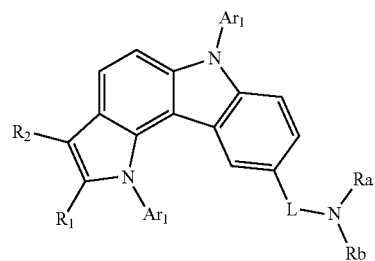

wherein,

L is a single bond, or selected from the group consisting of a substituted or unsubstituted C$_6$ to C$_{60}$ arylene group, and a substituted or unsubstituted heteroarylene group having 5 to 60 nuclear atoms, wherein one or more substituents each introduced into the arylene group and the heteroarylene group of L are each independently selected from the group consisting of deuterium, halogen, cyano, a C$_1$ to C$_{40}$ alkyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, and a C$_6$ to C$_{60}$ arylamine group, and provided that when the substituent is present in a plural number, they are the same as or different from each other;

R$_a$ and R$_b$ are each independently selected from the group consisting of a substituted or unsubstituted C$_1$ to C$_{40}$ alkyl group, a substituted or unsubstituted C$_3$ to C$_{40}$ cycloalkyl group, a substituted or unsubstituted heterocycloalkyl group having 3 to 40 nuclear atoms, a substituted or unsubstituted C$_6$ to C$_{60}$ aryl group, and a substituted or unsubstituted heteroaryl group having 5 to 60 nuclear atoms, and in this case, one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other;

provided that L, $R_a$, and $R_b$, taken together with an adjacent substituent, optionally form a fused ring;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ and $R_2$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and Ar1 are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other, in this case, when $Ar_1$ is present in a plural number, they are the same as or different from each other.

8. The organic electroluminescent device of claim 4, wherein $Ar_1$ is selected from the group consisting of a substituted or unsubstituted $C_6$ to $C_{60}$ aryl group, and a substituted or unsubstituted heteroaryl group having 5 to 60 nuclear atoms, wherein one or more substituents, which are optionally each introduced into the aryl group and the heteroaryl group of $Ar_1$, are each independently selected from the group consisting of deuterium, halogen, a nitrile group, a nitro group, a cyano group, a $C_1$ to $C_{40}$ alkyl group, a $C_2$ to $C_{40}$ alkenyl group, a $C_1$ to $C_{40}$ alkoxy group, a $C_1$ to $C_{40}$ amino group, a cycloalkyl group having 3 to 40 nuclear atoms, a $C_3$ to $C_{40}$ heterocycloalkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

* * * * *